US012102764B2

(12) United States Patent
Sims et al.

(10) Patent No.: US 12,102,764 B2
(45) Date of Patent: Oct. 1, 2024

(54) RESPIRATORY MASK SYSTEM
(71) Applicant: Fisher & Paykel Healthcare Limited, Auckland (NZ)
(72) Inventors: Christopher Gareth Sims, Auckland (NZ); Fadi Karim Moh'd Mashal, Auckland (NZ); Vitaly Kapelevich, Auckland (NZ); Mark Arvind McLaren, Auckland (NZ); Silas Sao Jin Siew, Auckland (NZ); Jonathan Mark Downey, Auckland (NZ); Christopher Michael Wong, Auckland (NZ); Matthew Aaron Bradley, Auckland (NZ); Janine Elizabeth Collins, Auckland (NZ); Dillan Patel, Auckland (NZ); Steve Thomas, Auckland (NZ); Chris Onin Limpin Hipolito, Auckland (NZ); Priyanka Ferdinand Pereira, Auckland (NZ); Matthew Robert Geoff Slight, Auckland (NZ); David Monroy Felix, Auckland (NZ); Xin Yue Zhu, Auckland (NZ); Jonathan Tong Lok Sng, Auckland (NZ); Arvin San Jose Gardiola, Auckland (NZ); Stephen Francis Heffernan, Auckland (NZ); Christine Marie Lynch, Auckland (NZ); Wen Dong Huang, Auckland (NZ); Bruce Michael Walls, Auckland (NZ); Jeremy Owen Young, Auckland (NZ); Tony William Spear, Auckland (NZ); Jake Baker Hocking, Auckland (NZ); Melissa Catherine Bornholdt, Auckland (NZ)
(73) Assignee: Fisher & Paykel Healthcare Limited, Auckland (NZ)
(*) Notice: Subject to any disclaimer, the term of this patent is extended or adjusted under 35 U.S.C. 154(b) by 729 days.
(21) Appl. No.: 16/625,177
(22) PCT Filed: Jun. 26, 2018
(86) PCT No.: PCT/IB2018/054685
§ 371 (c)(1),
(2) Date: Dec. 20, 2019
(87) PCT Pub. No.: WO2019/003094
PCT Pub. Date: Jan. 3, 2019

(65) Prior Publication Data
US 2020/0230343 A1 Jul. 23, 2020

Related U.S. Application Data
(60) Provisional application No. 62/654,802, filed on Apr. 9, 2018, provisional application No. 62/597,548, filed
(Continued)

(51) Int. Cl.
A61M 16/06 (2006.01)
(52) U.S. Cl.
CPC ..... *A61M 16/0683* (2013.01); *A61M 16/0622* (2014.02); *A61M 2205/0216* (2013.01);
(Continued)
(58) Field of Classification Search
CPC .......... A61M 16/0605; A61M 16/0683; A61M 16/0694; A44B 11/04; A44B 11/06–14; E06B 9/324; F16G 11/10–108
See application file for complete search history.

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| CA | 996301 | 9/1976 |
| CA | 1311662 | 12/1992 |

(Continued)

OTHER PUBLICATIONS

International Search Report; PCT/IB2018/054685; dated Oct. 16, 2018, 11 pages.
(Continued)

Primary Examiner — Valerie L Woodward
(74) Attorney, Agent, or Firm — Knobbe, Martens, Olson & Bear, LLP

(57) ABSTRACT

A respiratory mask system includes a mask interface and a headgear assembly. The headgear assembly is adjustable and
(Continued)

comprised of an elastic portion, a non-elastic portion and a restriction mechanism configured to provide a force resisting movement of the non-elastic portion when the elastic portion is extended. There is a support beam coupled to the non-elastic portion and extending along a portion of the headgear that is curved along its longitudinal extent. In this way particular seal modules can be comfortably fitted to a user and any blow off force is mitigated. A particular example of the respiratory mask system includes provision for removable attachment between the seal and a mask frame, the mask frame and a yoke of the headgear; and between a conduit and the mask frame.

18 Claims, 90 Drawing Sheets

Related U.S. Application Data on Dec. 12, 2017, provisional application No. 62/572,022, filed on Oct. 13, 2017, provisional application No. 62/525,643, filed on Jun. 27, 2017, provisional application No. 62/525,022, filed on Jun. 26, 2017.

(52) U.S. Cl.
CPC ............... *A61M 2210/0618* (2013.01); *A61M 2210/0625* (2013.01)

(56) References Cited

U.S. PATENT DOCUMENTS

| | | | |
|---|---|---|---|
| 577,926 A | 3/1897 | Miller | |
| 718,470 A | 1/1903 | Jones | |
| 751,091 A | 2/1904 | Moran | |
| 770,013 A | 9/1904 | Linn | |
| 1,364,104 A | 1/1921 | Geer | |
| 1,635,545 A | 7/1927 | Drager | |
| 1,942,442 A | 1/1934 | Motsinger | |
| 2,199,690 A | 5/1940 | Bullard | |
| 2,296,150 A | 9/1942 | Dockson et al. | |
| 2,353,643 A | 7/1944 | Bulbulian | |
| 2,359,506 A | 10/1944 | Battley et al. | |
| 2,388,604 A | 11/1945 | Eisenbud | |
| 2,390,233 A | 12/1945 | Akerman et al. | |
| 2,508,050 A | 5/1950 | Valente | |
| 2,586,851 A | 2/1952 | Monro et al. | |
| 2,611,897 A | 9/1952 | Adams | |
| 2,661,514 A | 12/1953 | Ada | |
| 2,693,800 A | 11/1954 | Caldwell | |
| 2,738,788 A | 3/1956 | Matheson et al. | |
| 2,843,121 A | 7/1958 | Hudson | |
| 2,859,748 A | 11/1958 | Hudson | |
| 3,045,672 A | 7/1962 | Croasdalle | |
| 3,156,922 A | 11/1964 | Anderson | |
| 3,295,529 A | 1/1967 | Corrigall et al. | |
| 3,416,521 A | 12/1968 | Humphrey | |
| 3,457,564 A | 7/1969 | Holloway | |
| 3,490,452 A | 1/1970 | Greenfield | |
| 3,500,474 A | 3/1970 | Austin | |
| 3,530,031 A | 9/1970 | Loew | |
| 3,792,702 A | 2/1974 | Delest | |
| 3,834,682 A | 9/1974 | McPhee | |
| 3,850,171 A | 11/1974 | Ball et al. | |
| 3,887,968 A | 6/1975 | Lynam | |
| 3,972,321 A | 8/1976 | Proctor | |
| 3,990,757 A | 11/1976 | Gill | |
| 3,992,720 A | 11/1976 | Nicolinas | |
| 3,994,022 A | 11/1976 | Villari et al. | |
| 4,051,556 A | 10/1977 | Davenport et al. | |
| 4,062,068 A | 12/1977 | Davenport et al. | |
| 4,090,510 A | 5/1978 | Segersten | |
| 4,106,165 A | 8/1978 | Clowers et al. | |
| D250,047 S | 10/1978 | Lewis et al. | |
| D250,131 S | 10/1978 | Lewis et al. | |
| 4,127,130 A | 11/1978 | Naysmith | |
| D252,322 S | 7/1979 | Johnson | |
| 4,167,185 A | 9/1979 | Lewis | |
| 4,201,205 A | 5/1980 | Bartholomew | |
| 4,266,540 A | 5/1981 | Panzik et al. | |
| 4,278,082 A | 7/1981 | Blackmer | |
| 4,288,891 A | 9/1981 | Boden | |
| 4,313,437 A | 2/1982 | Martin | |
| 4,328,605 A | 5/1982 | Hutchison et al. | |
| 4,354,488 A | 10/1982 | Bartos | |
| 4,367,735 A | 1/1983 | Dali | |
| 4,402,316 A | 9/1983 | Gadberry | |
| 4,413,382 A | 11/1983 | Siegmann | |
| 4,437,462 A | 3/1984 | Piljay | |
| 4,453,292 A | 6/1984 | Bakker | |
| 4,458,373 A | 7/1984 | Maslow | |
| 4,477,928 A | 10/1984 | Graff | |
| 4,606,077 A | 8/1986 | Phillips | |
| D293,613 S | 1/1988 | Wingler | |
| 4,734,940 A | 4/1988 | Galet et al. | |
| 4,753,233 A | 6/1988 | Grimes | |
| 4,782,832 A | 11/1988 | Trimble et al. | |
| 4,817,596 A | 4/1989 | Gallet | |
| 4,848,334 A | 7/1989 | Bellm | |
| 4,853,275 A * | 8/1989 | Tracy | D04D 9/04 428/178 |
| 4,856,508 A | 8/1989 | Tayebi | |
| 4,915,105 A | 4/1990 | Lee | |
| 4,941,467 A | 7/1990 | Takata | |
| 4,944,310 A | 7/1990 | Sullivan | |
| 4,947,488 A | 8/1990 | Ashinoff | |
| D310,431 S | 9/1990 | Bellm | |
| 4,971,051 A | 11/1990 | Toffolon | |
| 4,986,269 A | 1/1991 | Hakkinen | |
| 5,010,925 A | 4/1991 | Atkinson et al. | |
| 5,016,625 A | 5/1991 | Hsu et al. | |
| 5,042,478 A | 8/1991 | Kopala et al. | |
| D320,677 S | 10/1991 | Kumagai et al. | |
| 5,052,084 A | 10/1991 | Braun | |
| D321,419 S | 11/1991 | Wallace | |
| 5,065,756 A | 11/1991 | Rapoport | |
| 5,074,297 A | 12/1991 | Venegas | |
| 5,094,236 A | 3/1992 | Tayebi | |
| 5,113,857 A | 5/1992 | Dickerman et al. | |
| 5,148,578 A | 9/1992 | Clarke et al. | |
| 5,148,802 A | 9/1992 | Sanders et al. | |
| 5,191,882 A | 3/1993 | Vogliano | |
| 5,231,979 A | 8/1993 | Rose | |
| 5,245,995 A | 9/1993 | Sullivan et al. | |
| D340,317 S | 10/1993 | Cole | |
| 5,269,296 A | 12/1993 | Landis et al. | |
| D354,128 S | 1/1995 | Rinehart | |
| D355,484 S | 2/1995 | Rinehart | |
| 5,388,743 A | 2/1995 | Silagy | |
| 5,438,979 A | 8/1995 | Johnson et al. | |
| 5,477,852 A | 12/1995 | Landis et al. | |
| 5,488,948 A | 2/1996 | Dubruille | |
| 5,513,634 A | 5/1996 | Jackson | |
| 5,529,062 A | 6/1996 | Byrd | |
| 5,533,506 A | 7/1996 | Wood | |
| 5,546,605 A | 8/1996 | Mallardi | |
| 5,551,419 A | 9/1996 | Froehlich et al. | |
| 5,566,395 A | 10/1996 | Nebeker | |
| 5,595,174 A | 1/1997 | Gwaltney | |
| 5,601,078 A | 2/1997 | Schaller et al. | |
| D378,610 S | 3/1997 | Reischel et al. | |
| 5,657,752 A | 8/1997 | Landis et al. | |
| 5,724,965 A | 3/1998 | Handke et al. | |
| 5,752,510 A | 5/1998 | Goldstein | |
| 5,755,578 A | 5/1998 | Contant et al. | |
| 5,774,901 A | 7/1998 | Minami | |
| 5,823,020 A | 10/1998 | Benda | |
| 5,884,624 A | 3/1999 | Barnett et al. | |
| 5,921,239 A | 7/1999 | McCall et al. | |
| 5,941,245 A | 8/1999 | Hannah et al. | |
| 5,941,856 A | 8/1999 | Kovacs et al. | |
| 6,017,315 A | 1/2000 | Starr et al. | |
| 6,019,101 A | 2/2000 | Cotner et al. | |

(56) References Cited

U.S. PATENT DOCUMENTS

| | | | |
|---|---|---|---|
| 6,044,844 A | 4/2000 | Kwok et al. |
| 6,050,260 A | 4/2000 | Daniell et al. |
| 6,119,694 A | 9/2000 | Correa et al. |
| 6,192,886 B1 | 2/2001 | Rudolph |
| D440,302 S | 4/2001 | Wolfe |
| 6,256,798 B1 | 7/2001 | Egolf et al. |
| 6,272,690 B1 | 8/2001 | Carey et al. |
| 6,282,725 B1 | 9/2001 | Vanidestine, Jr. |
| 6,298,850 B1 | 10/2001 | Argraves |
| 6,338,342 B1 | 1/2002 | Fecteau et al. |
| 6,347,631 B1 | 2/2002 | Hansen et al. |
| D455,891 S | 4/2002 | Biedrzycki |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,470,886 B1 | 10/2002 | Jestrabek-Hart |
| 6,478,026 B1 | 11/2002 | Wood |
| 6,491,034 B1 | 12/2002 | Gunaratnam et al. |
| 6,536,435 B1 | 3/2003 | Fecteau et al. |
| 6,561,188 B1 | 5/2003 | Ellis |
| 6,561,191 B1 | 5/2003 | Kwok |
| 6,571,854 B1 | 6/2003 | Palmer |
| 6,581,594 B1 | 6/2003 | Drew et al. |
| 6,581,601 B2 | 6/2003 | Ziaee |
| 6,588,424 B2 | 7/2003 | Bardel |
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,659,102 B1 | 12/2003 | Sico |
| 6,662,803 B2 | 12/2003 | Gradon et al. |
| 6,679,257 B1 | 1/2004 | Robertson et al. |
| 6,679,265 B2 | 1/2004 | Strickland et al. |
| 6,772,761 B1 | 8/2004 | Rucker, Jr. |
| 6,851,425 B2 | 2/2005 | Jaffre et al. |
| 6,883,519 B2 | 4/2005 | Schmidtke et al. |
| 6,886,564 B2 | 5/2005 | Sullivan et al. |
| 6,892,729 B2 | 5/2005 | Smith et al. |
| 6,907,882 B2 | 6/2005 | Ging et al. |
| 6,951,218 B2 | 10/2005 | Gradon et al. |
| 7,004,165 B1 | 2/2006 | Salcido |
| D520,140 S | 5/2006 | Chaggares |
| 7,036,508 B2 | 5/2006 | Kwok |
| 7,062,795 B2 | 6/2006 | Skiba et al. |
| 7,066,179 B2 | 6/2006 | Eaton et al. |
| D526,094 S | 8/2006 | Chen |
| 7,096,864 B1 | 8/2006 | Mayer et al. |
| 7,096,867 B2 | 8/2006 | Smith et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,318,437 B2 | 1/2008 | Gunaratnam et al. |
| 7,353,826 B2 | 4/2008 | Sleeper et al. |
| 7,353,827 B2 | 4/2008 | Geist |
| 7,814,911 B2 | 10/2010 | Bordewick et al. |
| 7,845,352 B2 | 12/2010 | Sleeper et al. |
| 7,861,715 B2 | 1/2011 | Jones et al. |
| 7,870,860 B2 | 1/2011 | McCormick et al. |
| 7,896,003 B2 | 3/2011 | Matula et al. |
| 7,913,692 B2 | 3/2011 | Kwok |
| 7,967,014 B2 | 6/2011 | Heidmann |
| 8,042,539 B2 | 10/2011 | Chandran et al. |
| 8,047,893 B2 | 11/2011 | Fenske |
| 8,074,651 B2 | 12/2011 | Bierman et al. |
| 8,104,473 B2 | 1/2012 | Woodard et al. |
| 8,132,270 B2 | 3/2012 | Lang et al. |
| 8,136,524 B2 | 3/2012 | Ging et al. |
| 8,209,995 B2 | 7/2012 | Kieling et al. |
| 8,297,285 B2 | 10/2012 | Henry et al. |
| 8,371,302 B2 | 2/2013 | Ging et al. |
| 8,443,807 B2 | 5/2013 | McAuley et al. |
| D686,313 S | 7/2013 | Matula et al. |
| 8,479,741 B2 | 7/2013 | McAuley et al. |
| 8,505,538 B2 | 8/2013 | Amarasinghe |
| 8,522,785 B2 | 9/2013 | Berthon-Jones et al. |
| 8,573,201 B2 | 11/2013 | Rummery et al. |
| 8,596,271 B2 | 12/2013 | Matula, Jr. et al. |
| 8,596,274 B2 | 12/2013 | Hieber et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,636,008 B2 | 1/2014 | Flory et al. |
| 8,757,157 B2 | 6/2014 | Price et al. |
| 8,783,257 B2 | 7/2014 | McAuley et al. |
| 8,794,239 B2 | 8/2014 | Gunaratnam |
| 8,857,435 B2 | 10/2014 | Matula, Jr. et al. |
| 8,915,251 B2 | 12/2014 | Lubke et al. |
| 8,997,742 B2 | 4/2015 | Moore et al. |
| 9,032,955 B2 | 5/2015 | Lubke et al. |
| 9,044,564 B2 | 6/2015 | Dravitzki et al. |
| 9,103,161 B2 | 8/2015 | Mader |
| 9,138,555 B2 | 9/2015 | McAuley et al. |
| 9,149,596 B2 | 10/2015 | Valcic et al. |
| 9,265,909 B2 | 2/2016 | Ho et al. |
| 9,302,065 B2 | 4/2016 | Smith et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,480,809 B2 | 11/2016 | Guney et al. |
| 9,517,320 B2 | 12/2016 | Barlow et al. |
| 9,550,038 B2 | 1/2017 | McAuley et al. |
| 9,555,943 B2 | 1/2017 | Breen, IV et al. |
| 9,592,336 B2 | 3/2017 | Nielsen et al. |
| 9,656,038 B2 | 5/2017 | Rummery et al. |
| 9,744,385 B2 | 8/2017 | Henry |
| 9,782,554 B2 | 10/2017 | Mazzone et al. |
| 9,878,118 B2 | 1/2018 | Formica |
| D810,277 S | 2/2018 | Amarasinghe |
| 9,884,160 B2 | 2/2018 | McAuley |
| 9,901,700 B2 | 2/2018 | McAuley et al. |
| 9,925,349 B2 | 3/2018 | Jablonski |
| 9,974,914 B2 | 5/2018 | McAuley |
| 9,993,606 B2 | 6/2018 | Gibson et al. |
| 10,039,665 B2 | 8/2018 | Blaszczykiewicz et al. |
| 10,065,010 B2 | 9/2018 | Smith et al. |
| 10,071,217 B2 | 9/2018 | Grashow |
| 10,080,856 B2 | 9/2018 | McLaren |
| 10,137,319 B2 | 11/2018 | Carr et al. |
| 10,207,072 B2 | 2/2019 | Dunn et al. |
| 10,279,138 B2 | 5/2019 | Ovzinsky |
| 10,456,546 B2 | 10/2019 | McLaren et al. |
| 10,646,680 B2 | 5/2020 | Huddart et al. |
| 10,675,428 B2 | 6/2020 | Guney et al. |
| 10,792,451 B2 | 10/2020 | Allan et al. |
| 10,828,449 B2 | 11/2020 | Higgins et al. |
| 10,828,452 B2 | 11/2020 | Huddart et al. |
| 10,874,814 B2 | 12/2020 | Huddart et al. |
| 11,000,663 B2 | 5/2021 | Felix et al. |
| 11,419,999 B2 | 8/2022 | Patel et al. |
| 11,701,486 B2 | 7/2023 | Mashal et al. |
| 11,819,620 B2 | 11/2023 | Hammer |
| 11,850,365 B2 | 12/2023 | Freestone et al. |
| 2002/0005198 A1 | 1/2002 | Kwok et al. |
| 2002/0020416 A1 | 2/2002 | Namey |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0096178 A1 | 7/2002 | Ziaee |
| 2002/0157668 A1 | 10/2002 | Bardel |
| 2003/0005933 A1 | 1/2003 | Izuchukwu |
| 2003/0051732 A1 | 3/2003 | Smith et al. |
| 2003/0079749 A1 | 5/2003 | Strickland et al. |
| 2003/0084903 A1 | 5/2003 | Fecteau et al. |
| 2003/0111080 A1 | 6/2003 | Olsen et al. |
| 2003/0121519 A1 | 7/2003 | Estes et al. |
| 2003/0164170 A1 | 9/2003 | Drew et al. |
| 2003/0172936 A1 | 9/2003 | Wilkie et al. |
| 2003/0196656 A1 | 10/2003 | Moore |
| 2003/0196659 A1 | 10/2003 | Gradon et al. |

(56) References Cited

U.S. PATENT DOCUMENTS

| | | |
|---|---|---|
| 2003/0196664 A1 | 10/2003 | Jacobson |
| 2003/0200970 A1 | 10/2003 | Stenzler et al. |
| 2004/0067333 A1 | 4/2004 | Amarasinghe |
| 2004/0211427 A1 | 10/2004 | Jones et al. |
| 2004/0226566 A1 | 11/2004 | Gunaratnam et al. |
| 2005/0011524 A1 | 1/2005 | Thomlinson et al. |
| 2005/0016067 A1 | 1/2005 | Pettit |
| 2005/0028822 A1 | 2/2005 | Sleeper et al. |
| 2005/0033247 A1 | 2/2005 | Thompson |
| 2005/0066976 A1 | 3/2005 | Wondka |
| 2005/0076913 A1 | 4/2005 | Ho et al. |
| 2005/0098183 A1 | 5/2005 | Nash et al. |
| 2005/0150497 A1 | 7/2005 | Eifler et al. |
| 2005/0161049 A1 | 7/2005 | Wright |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2006/0060200 A1 | 3/2006 | Ho et al. |
| 2006/0081250 A1 | 4/2006 | Bordewick et al. |
| 2006/0096596 A1 | 5/2006 | Occhialini et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0137690 A1 | 6/2006 | Gunaratnam et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1* | 6/2007 | Lang .................. B29C 45/1676 2/9 |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reier et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1 | 9/2008 | Valcic et al. |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2011/0048425 A1 | 3/2011 | Chang |
| 2011/0197341 A1 | 8/2011 | Formica |
| 2011/0220113 A1 | 9/2011 | Newman |
| 2011/0247628 A1 | 10/2011 | Ho |
| 2011/0259335 A1 | 10/2011 | Sullivan |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0285464 A1 | 11/2012 | Birch et al. |
| 2012/0304999 A1 | 12/2012 | Swift et al. |
| 2013/0000648 A1 | 1/2013 | Madaus et al. |
| 2013/0074845 A1 | 3/2013 | Smith et al. |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1 | 8/2013 | Barlow et al. |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0216452 A1 | 8/2014 | Miller et al. |
| 2014/0305439 A1 | 10/2014 | Chodkowski |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0283349 A1* | 10/2015 | McLaren ............... A61M 16/06 128/206.21 |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0074614 A1* | 3/2016 | Huddart ............ A61M 16/0866 128/204.18 |
| 2016/0082214 A1 | 3/2016 | Barlow et al. |
| 2016/0082217 A1* | 3/2016 | McLaren .......... A61M 16/0683 128/207.11 |
| 2016/0144146 A1 | 5/2016 | Huddart et al. |
| 2016/0166793 A1 | 6/2016 | McLaren et al. |
| 2016/0178027 A1 | 6/2016 | Wetzel |

(56) References Cited

U.S. PATENT DOCUMENTS

| | | |
|---|---|---|
| 2016/0278463 A1 | 9/2016 | Stevenson |
| 2016/0375214 A1 | 12/2016 | Chodkowski et al. |
| 2017/0136269 A1 | 5/2017 | Jacotey et al. |
| 2017/0182276 A1 | 6/2017 | Hammer |
| 2017/0189636 A1 | 7/2017 | Gibson et al. |
| 2017/0216548 A1 | 8/2017 | Gerhardt |
| 2018/0214655 A1 | 8/2018 | Kooij et al. |
| 2018/0264218 A1 | 9/2018 | Chodkowski |
| 2018/0339123 A1 | 11/2018 | Smith et al. |
| 2019/0083734 A1 | 3/2019 | Hammer et al. |
| 2019/0111227 A1 | 4/2019 | Veliss et al. |
| 2019/0151592 A1 | 5/2019 | Bornholdt |
| 2020/0129720 A1 | 4/2020 | McLaren et al. |
| 2020/0171260 A1 | 6/2020 | McLaren et al. |
| 2020/0230344 A1 | 7/2020 | Huddart et al. |
| 2020/0338294 A1 | 10/2020 | McLaren et al. |
| 2021/0008316 A1 | 1/2021 | McLaren et al. |
| 2021/0016041 A1 | 1/2021 | Huddart et al. |
| 2022/0126049 A1 | 4/2022 | Amarasinghe |
| 2022/0331542 A1 | 10/2022 | McLaren et al. |
| 2023/0347090 A1 | 11/2023 | Huddart et al. |
| 2024/0024606 A1 | 1/2024 | McLaren et al. |
| 2024/0033461 A1 | 2/2024 | Felix et al. |

FOREIGN PATENT DOCUMENTS

| | | |
|---|---|---|
| CN | 2172538 | 7/1994 |
| CN | 2504493 Y | 8/2002 |
| CN | 2562067 Y | 7/2003 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 202822396 U | 3/2013 |
| CN | 103536996 | 1/2014 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 060 294 | 5/2009 |
| EP | 2 130 563 | 12/2009 |
| EP | 2 517 757 | 10/2012 |
| EP | 2 022 528 | 3/2016 |
| EP | 2988814 | 11/2019 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/039185 | 5/2004 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/038918 | 3/2009 |
| WO | WO 09/052560 | 4/2009 |
| WO | WO 09/059353 | 5/2009 |
| WO | WO 09/092057 | 7/2009 |
| WO | WO 09/108994 | 9/2009 |
| WO | WO 09/108995 | 9/2009 |
| WO | WO 09/139647 | 11/2009 |
| WO | WO 09/148956 | 12/2009 |
| WO | WO 10/066004 | 6/2010 |
| WO | WO 2010/066004 | 6/2010 |
| WO | WO 10/081295 | 7/2010 |
| WO | WO 2010/073142 | 7/2010 |
| WO | WO 10/131189 | 11/2010 |
| WO | WO 10/139014 | 12/2010 |
| WO | WO 2011/060479 | 5/2011 |
| WO | WO 11/072739 | 6/2011 |
| WO | WO 11/077254 | 6/2011 |
| WO | WO-2011077254 A2 * | 6/2011 ............ A61M 16/00 |
| WO | WO 11/112401 | 9/2011 |
| WO | WO 12/07300 | 1/2012 |
| WO | WO 12/045127 | 4/2012 |
| WO | WO 12/069951 | 5/2012 |
| WO | WO 12/071300 | 5/2012 |
| WO | WO 12/143822 | 10/2012 |
| WO | WO 12/154883 | 11/2012 |
| WO | WO 12/177152 | 12/2012 |
| WO | WO 13/006913 | 1/2013 |
| WO | WO 13/026091 | 2/2013 |
| WO | WO 13/026092 | 2/2013 |
| WO | WO 13/064930 | 5/2013 |
| WO | WO 14/020469 | 2/2014 |
| WO | WO 14/025267 | 2/2014 |
| WO | WO 14/031673 | 2/2014 |
| WO | WO 14/075141 | 5/2014 |
| WO | WO 14/077708 | 5/2014 |

(56) References Cited

FOREIGN PATENT DOCUMENTS

| WO | WO 14/110622 | 7/2014 |
| WO | WO 14/110626 | 7/2014 |
| WO | WO 14/129913 | 8/2014 |
| WO | WO 14/175752 | 10/2014 |
| WO | WO 14/175753 | 10/2014 |
| WO | WO 15/033287 | 3/2015 |
| WO | WO 15/043229 | 4/2015 |
| WO | WO 15/070289 | 5/2015 |
| WO | WO 15/079396 | 6/2015 |
| WO | WO 15/083060 | 6/2015 |
| WO | WO 15/151019 | 10/2015 |
| WO | WO 15/187986 | 12/2015 |
| WO | WO 2016/043603 | 3/2016 |
| WO | WO 2017/030447 A1 | 2/2017 |
| WO | WO 17/150990 | 9/2017 |
| WO | WO 17/158474 | 9/2017 |
| WO | WO 17/158544 | 9/2017 |
| WO | WO 17/160166 | 9/2017 |
| WO | WO 2017/216708 A1 | 12/2017 |
| WO | WO 19/003094 | 1/2019 |

OTHER PUBLICATIONS

European Search Report for Application No. 18822623.7 dated Feb. 22, 2021, 13 pages.
UK Examination Report in GB 2103410.3 dated Mar. 26, 2021 in 6 pages.
cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.
Pad A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-series-cpap-humidifier-manual.pdf.
Chinese Second Office Action for Application No. 201810366796.0 dated Feb. 9, 2021, 7 pages.

* cited by examiner

Headgear in neutral position (minimum length)

Headgear during elongation (maximum length) – High force

Headgear under retraction (balanced fit length) – Low force

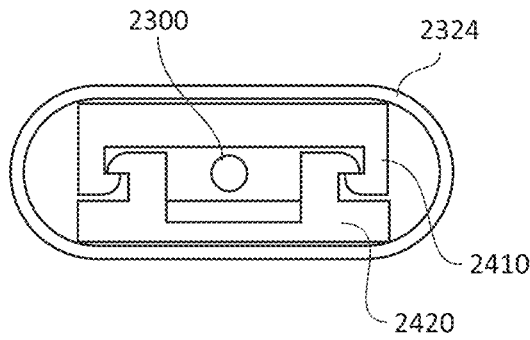
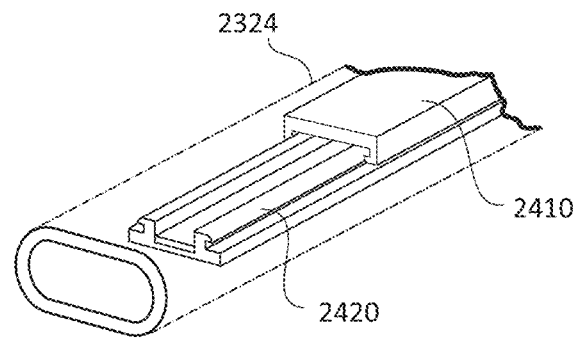
Fig. 78A
Fig. 78B
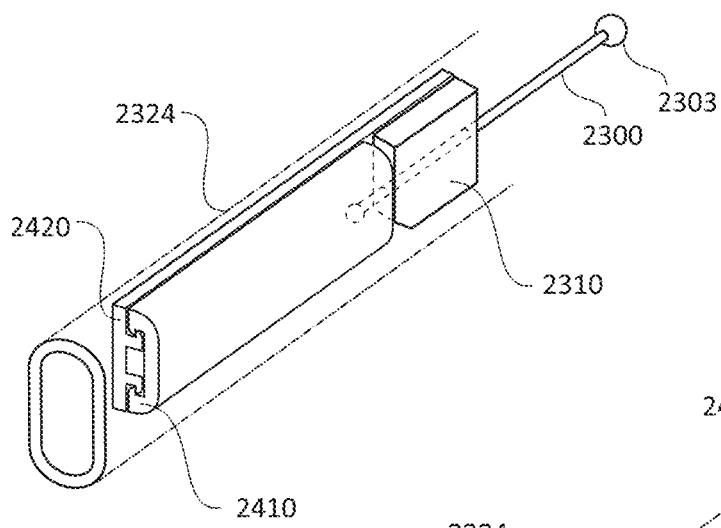
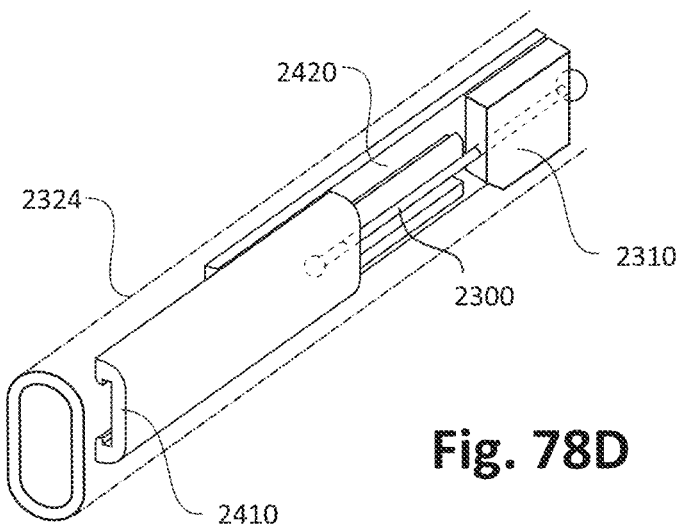
Fig. 78C
Fig. 78D

Headgear in neutral position (minimum length)

Headgear during elongation (maximum length) – High force

Headgear under retraction (balanced fit length) – Low force

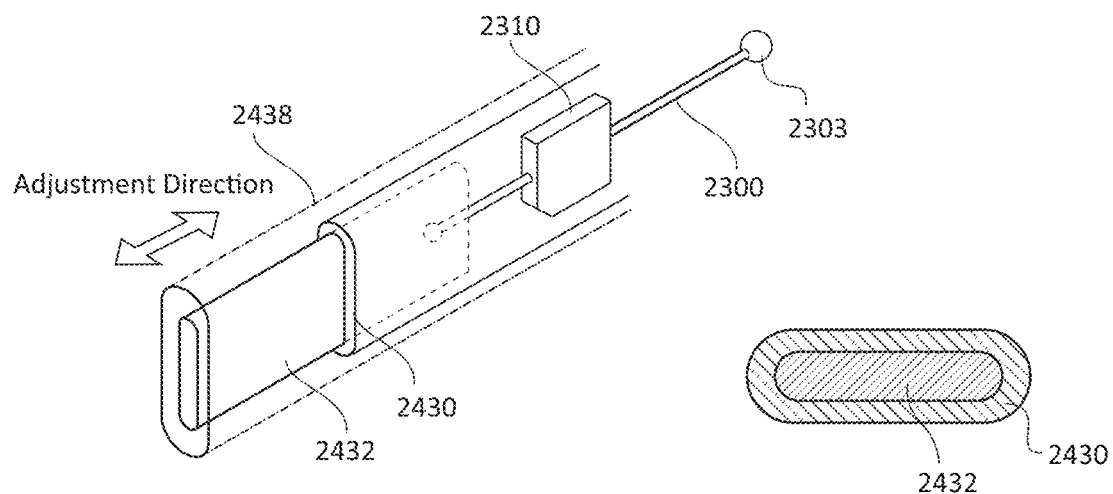
Fig. 80A
Fig. 80B
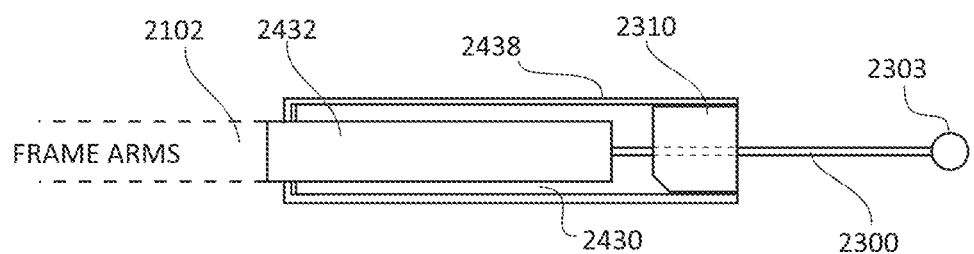
Fig. 80C
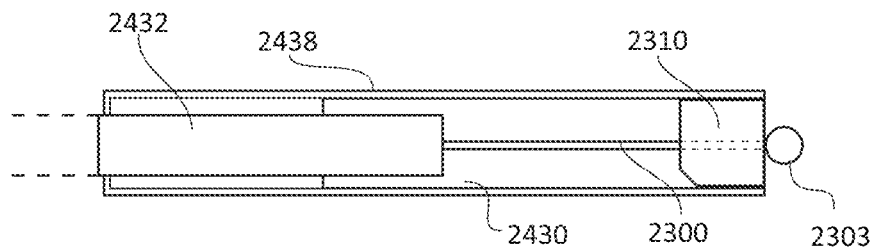
Fig. 80D

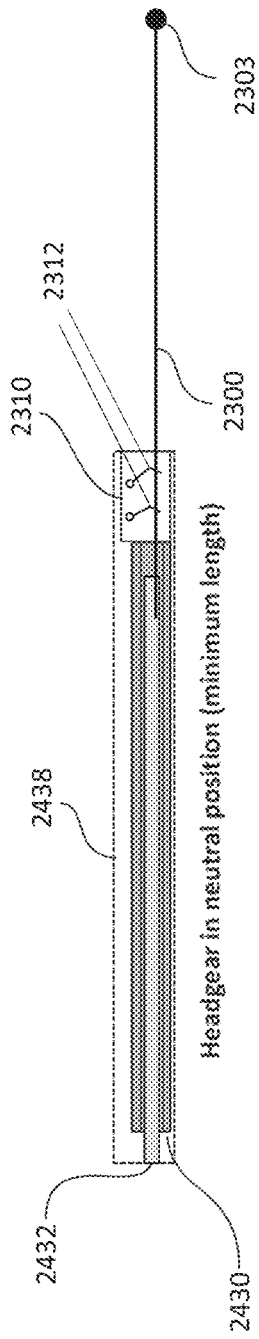
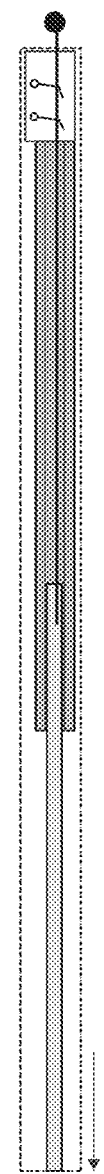
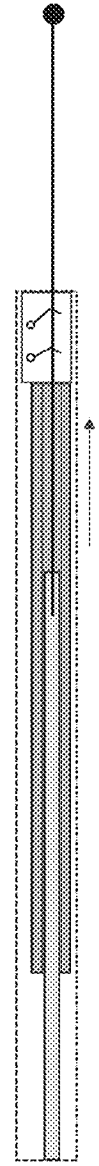
Fig. 81A  Headgear in neutral position (minimum length)
Fig. 81B  Headgear during elongation (maximum length) – High force
Fig. 81C  Headgear under retraction (balanced fit length) – Low force

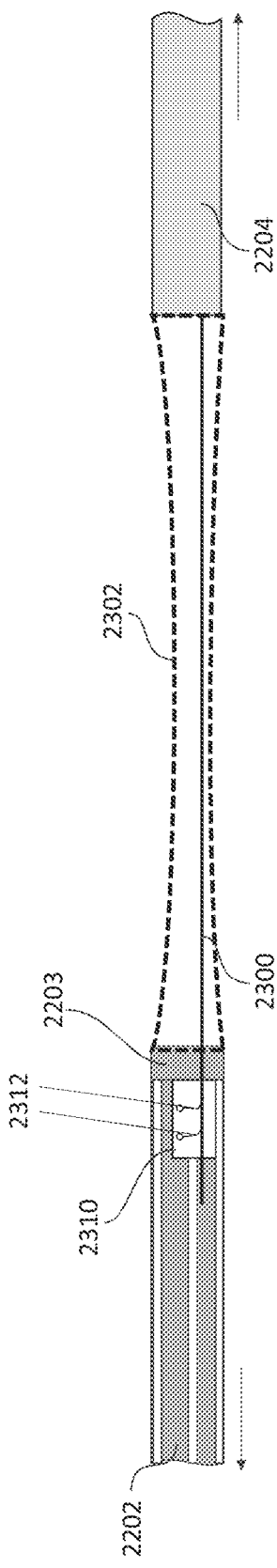
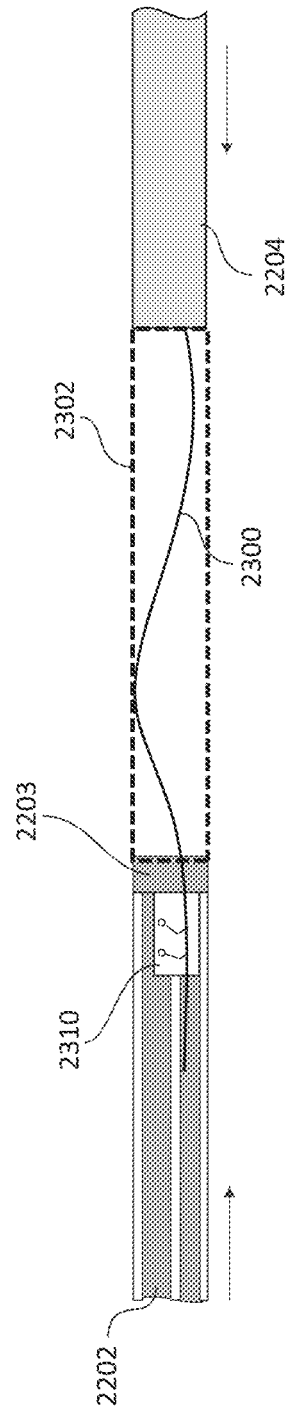
Fig. 82A
Fig. 82B

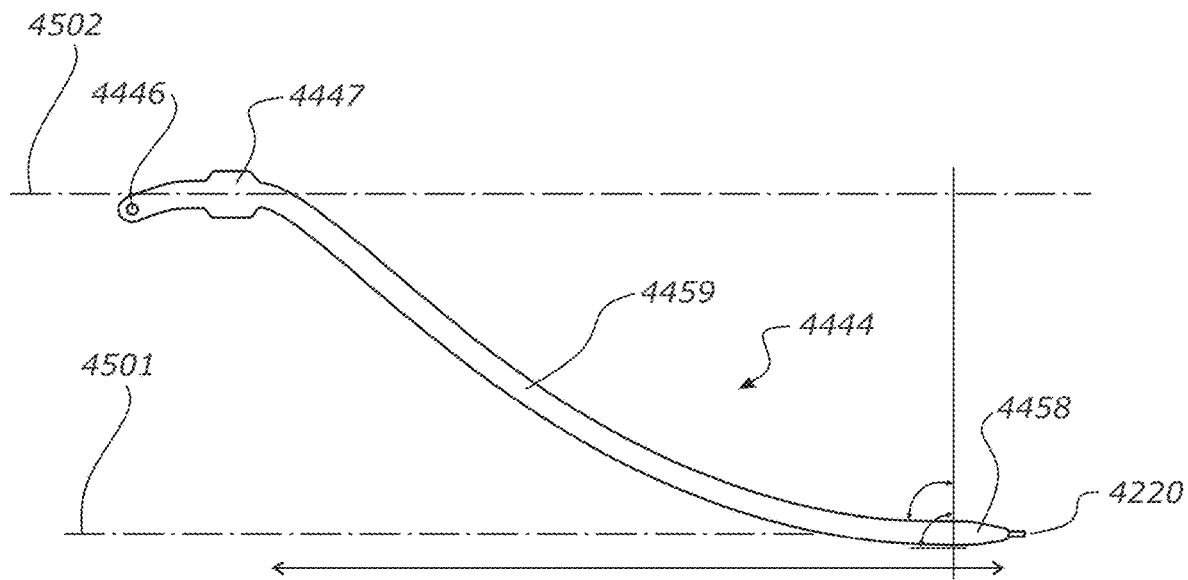
Fig. 123
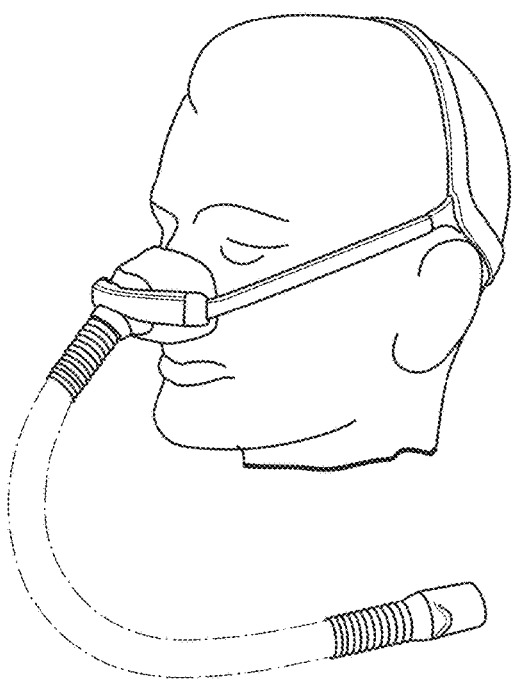 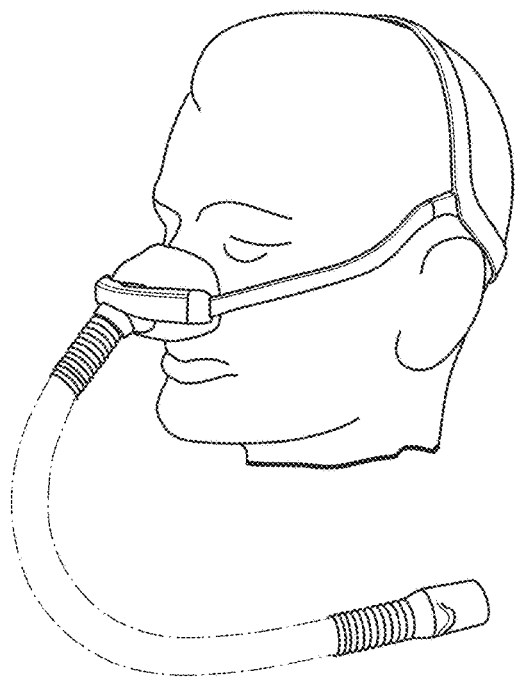
Fig. 124A    Fig. 124B

RESPIRATORY MASK SYSTEM

BACKGROUND

Technical Field

The present disclosure generally relates to a respiratory mask system for the delivery of respiratory therapy to a patient. More particularly, the present disclosure relates to various components of a respiratory mask system.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that forms an airtight seal in or around the patient's nose and/or mouth. Respiratory masks are available in a range of styles including full-face, nasal, direct nasal and oral masks, which create an airtight seal with the nose and/or mouth. The seal or cushion is held in place on the patient's face by the headgear. In order to maintain an airtight seal the headgear should provide support to the patient interface such that it is held in a stable position relative to the patient's face during use. Such respiratory masks may also be used to deliver NIV and other therapies including NIV in combination with nasal high flow.

The seal of an indirect nasal interface or nasal mask contacts the upper lip, the face on either side of the nose, and the bridge of the nose, and substantially encloses the nose. Such nasal interfaces are often secured to the head of the user with headgear. Often the nasal mask assembly comprises a T-piece frame for connecting to headgear that include a pair of upper side straps and lower side straps that extend generally substantially horizontally across the side of the users head. The upper straps extend above the user's ears and connect to an upper part of the T-piece frame in the user's forehead region, and the lower straps extend under the user's ears and connect to a lower part of the T-piece frame at or toward the nasal interface, or from the nasal interface itself. While such headgear tends to provide a relative stable securement of the nasal interface to the user, it can be obstructive or uncomfortable in use. Single side strap headgears are known that are less bulky, but also tend to be less stable in securing the nasal interface in a sealing engagement during use.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY

The systems and devices described herein have innovative aspects, no single one of which is indispensable or solely responsible for their desirable attributes. Without limiting the scope of the claims, some of the advantageous features will now be summarized. However, further combinations of features will be possible, even if not explicitly described by way of example herein.

In one embodiment an adjustable headgear is comprised of an elastic portion, a non-elastic portion and a restriction mechanism configured to provide a force resisting movement of the non-elastic portion when the elastic portion is extended. A support beam is coupled to the non-elastic portion and extends along a portion of the headgear. The support beam is curved along its longitudinal extent.

A first portion of the support beam can be connected to the non-elastic portion, the first portion being configured to extend along a first axis. A second portion can be connected to a top and/or rear strap of the headgear, the second portion being configured to extend along a second axis that is substantially parallel to the first axis. There can be a transition portion extending along a curve between the first and second portions. The transition portion can extend downwardly from the second portion and the first portion can extend from the transition portion towards a mask to be connected to the headgear. Also, the second portion can be connected to the top and/or rear strap at a position above a user's ear.

In one form the first and second axes are spaced apart by 20-60 mm, preferably 30-50 mm, preferably about 40 mm, and a width of the support beam can be substantially constant along its longitudinal extent. Preferably the width is 1-15 mm, preferably less than 10 mm, preferably less than 7 mm, preferably less than 5 mm, preferably about 3 mm. A thickness of the support beam can substantially constant along its longitudinal extent while that thickness can be 0.5-1 mm, preferably about 0.8 mm.

In one form the second portion connects to a halo strap that provides top and rear straps of the headgear. The elastic portion and support beam can comprise a side strap of the headgear.

In a further example there is a nasal mask interface assembly comprising a seal housing, a flexible nasal seal connected or connectable to the seal housing to define a mask cavity, the nasal seal extending between a face-contacting side and an outer side. The nasal seal may comprise an under-nose support fixedly connected into the nasal seal and which is configured to extend within the mask cavity and having a contact surface that is oriented to contact at least a portion of the under-nose surface of the user. There also can be a mask frame removably attachable with the seal housing and a yoke for a headgear, removably attachable with the mask frame.

The mask frame may comprise a collar for removably attaching a conduit, wherein the collar of the mask frame includes a plurality of bias flow holes.

The mask frame in one example may comprise a recessed region extending longitudinally across the mask frame in a front wall thereof; and two overhanging portions extending forward from the wall to form an upper boundary of the recessed region, the two overhanging portions separated from each other by a gap; and wherein the yoke is configured to be at least partially disposed in the recessed region.

The nasal mask interface assembly may further comprise an adjustable headgear extending from the yoke. The adjustable headgear can comprise a head engaging portion and an adjustment mechanism of adjustable length and configured to couple the head engaging portion to the mask frame via the yoke. The adjustment mechanism can comprise an elastic portion configured to provide a retraction force, a non-elastic filament that is relatively inelastic compared to the elastic portion, a restriction mechanism configured to provide a force resisting movement of the non-elastic filament when the elastic portion is extended in the direction of its longitudinal axis and a core disposed within the elastic portion and coupled to the non-elastic filament.

In one form the elastic portion can comprises an elastic braid. The core can be relatively more rigid than the non-elastic filament. Preferably the core is curved, forming a curved side strap with the elastic portion, extending from the yoke to the head engaging portion at a position above an ear of a user. The seal housing and flexible nasal seal can be connected by an overmold portion. The seal housing includes a channel that becomes occupied with overmold material of the overmold portion, causing the seal housing to be permanently attached to the seal.

In some further examples, a respiratory mask system includes a mask frame and a yoke. The mask frame includes an inlet collar defining an aperture and configured to be coupled to a gas conduit in use, an outlet collar defining an outlet aperture, a gas pathway formed through the mask frame between the inlet aperture and the outlet aperture, a wall disposed between the inlet collar and the outlet collar, a recessed region extending longitudinally across the mask frame in a front surface of the wall, and two overhanging portions extending forward from the wall to form an upper boundary of the recessed region, the two overhanging portions separated from each other by a gap. The yoke is configured to be at least partially disposed in the recessed region.

The yoke can include a yoke locating feature projecting upward and rearward from upper and rear surfaces of the yoke. The yoke locating feature is configured to be disposed in the gap between the two overhanging portions when the yoke and mask frame are coupled together. An upper surface of the yoke locating feature can form a continuous surface with upper surfaces of the overhanging portions when the yoke and mask frame are coupled together. The yoke locating feature can be curved.

The mask frame can include at least two protrusions, at least one of the at least two protrusions extending into the recessed region from a lower wall of the recessed region, and at least one of the at least two protrusions extending into the recessed region from at least one of the overhanging portions, and the yoke can include at least two recesses, at least one of the at least two recesses disposed in the upper surface of the yoke and at least one of the at least two recesses disposed in a lower surface of the yoke, Each of the at least two protrusions is configured to be disposed in a respective recess when the yoke and mask frame are coupled together.

The mask frame can include two protrusions extending from the lower wall of the recessed region and a protrusion extending from each of the overhanging portions, and the yoke can include two recesses in the upper surface of the yoke and two recesses disposed in the lower surface of the yoke. A distance between the two recessed in the upper surface of the yoke can be greater than a distance between the two recesses in the lower surface of the yoke. A distance between the protrusions extending from the overhanging portions can be greater than a distance between the protrusions extending from the lower wall of the recessed region. A distance between the overhanging portions can be greater than a distance between the protrusions extending from the lower wall of the recessed region.

The overhanging portions can extend upward from the wall. The overhanging portions can have concave inner surfaces. A lower wall of the recessed region can be upwardly-facing convex along a longitudinal axis of the recessed region and concave in a front-to-back direction. In a front-to-back direction, or depth direction, of the recessed region, the lower wall can be upwardly-facing concave. The recessed region can have a surface that is forward-facing convex along a longitudinal axis of the recessed region and planar extending between the overhanging portions and a lower wall of the recessed region. A height of the recessed region can be greater than a depth of the recessed region.

In some examples, a yoke configured to be coupled to a mask frame of a respiratory mask system includes a yoke front extending from a first lateral end to a second lateral end, a yoke rear extending from a first lateral end to a second lateral end, the yoke front and the yoke rear coupled together and defining an inner cavity therebetween, and a filament divider disposed in the cavity and at least partially defining a first line path configured to receive a first filament of an automatically adjusting headgear mechanism and a second line path configured to receive a second filament of the automatically adjusting headgear mechanism, the first line path at least partially defined by a front of the filament divider and the yoke front, and the second line path at least partially defined by a rear of the filament divider and the yoke rear.

The yoke front can include at least one protrusion, the yoke rear can include at least one recess, and the at least one protrusion can be received in the at least one recess when the yoke front and yoke rear are coupled together.

The yoke can include a first lock disposed in the cavity adjacent or proximate the first lateral ends and acting on the first filament and a second lock disposed in the cavity adjacent or proximate the second lateral ends and acting on the second filament. The first lock can be disposed in a first washer housing, the second lock can be disposed in a second washer housing, and the first and second washer housings can be oriented in the same direction. The yoke can further include a first end cap coupled to the first lateral ends of the yoke front and the yoke rear and a second end cap coupled to the second lateral ends of the yoke front and the yoke rear, the first end cap comprising an aperture configured to receive the first filament and the second end cap comprising an aperture configured to receive the second filament. The yoke rear can include a protrusion proximate each lateral end, each end cap can include a recess, and the protrusions can be received in the recesses when the end caps are coupled to the yoke rear.

The filament divider can be a separate component from the yoke front and yoke rear. The first line path can extend from an upper right portion of the yoke at an angle with respect to a longitudinal axis of the yoke. The first line path can widen as the first line path extends from the upper right portion. The second line path can extend from an upper left portion of the yoke at an angle with respect to a longitudinal axis of the yoke. The second line path can widen as the second line path extends from the upper left portion. The first and second line paths can extend laterally beyond the first and second lateral ends of the yoke front and the yoke rear.

In some examples, a yoke configured to be coupled to a mask frame of a respiratory mask system includes a yoke front extending from a first lateral end to a second lateral end, a yoke rear extending from a first lateral end to a second lateral end, the yoke front and the yoke rear coupled together and defining an inner cavity therebetween, a first line path configured to receive a first filament of an automatically adjusting headgear mechanism, and a second line path configured to receive a second filament of the automatically adjusting headgear mechanism. The first and second line paths are located between the yoke front and the yoke rear such that the first line path is forward of the second line path.

The first line path and second line path can be separated by a wall. The wall can be formed in the yoke front or the yoke rear. The yoke can include a divider disposed between the yoke front and the yoke rear, the divider defining the wall separating the first and second line paths. The divider can at least partially define the first and second line paths.

In some examples, an adjustable headgear for a respiratory mask includes a head engaging portion and an adjustment mechanism of adjustable length. The adjustment mechanism is configured to couple the head engaging portion to the respiratory mask. The adjustment mechanism can include a first elongate member, a second elongate member slidably engaged with the first elongate member, a restriction mechanism, and a retraction means. The first elongate member and the second elongate member are configured to enable adjustment of the length of the adjustment mechanism by changing an amount of overlap between the first and second elongate members. The restriction mechanism is configured to provide resistance against decreasing the amount of overlap between the first and second elongate members. The retraction means is configured to apply a retraction force to the first elongate member that increases the amount of overlap between the first and second elongate members.

In some examples, the first elongate member is an inner member, the second elongate member is an outer member, and the first elongate member telescopingly slides within the second elongate member. In some embodiments, the first elongate member includes at least one outer rail, and the second elongate member includes at least one inner rail. In some embodiments, the first elongate member includes at least one inner rail, and the second elongate member includes at least one outer rail. In some embodiments, the retraction means comprises a portion of elastic material. In some embodiments, the portion of elastic material is coupled to an inelastic filament that extends through the restriction mechanism and is coupled to the first elongate member. In some embodiments, the retraction means comprises an elastic tube surrounding the first and second elongate members.

In some examples, an adjustable headgear for a respiratory mask includes a head engaging portion and an adjustment mechanism of adjustable length. The adjustment mechanism is configured to couple the head engaging portion to the respiratory mask. The adjustment mechanism can include a first elongate member, a second elongate member slidably engaged with the first elongate member, a restriction mechanism, and a biasing element. The first elongate member and the second elongate member are configured to enable adjustment of the length of the adjustment mechanism by changing an amount of overlap between the first and second elongate members. The restriction mechanism is configured to provide resistance against decreasing the amount of overlap between the first and second elongate members. The biasing element is configured to apply a retraction force to the first elongate member that increases the amount of overlap between the first and second elongate members.

In some examples, an adjustable headgear for a respiratory mask includes an elastic portion having a longitudinal axis, a non-elastic portion, a restriction mechanism, and a support beam. The non-elastic portion is relatively inelastic compared to the elastic portion and has a longitudinal axis that is aligned with the longitudinal axis of the elastic portion. The elastic portion is configured to provide a retraction force to the non-elastic portion in the direction of the elastic portion's longitudinal axis. The restriction mechanism is configured to provide a force resisting movement of the non-elastic portion when the elastic portion is extended in the direction of its longitudinal axis. The support beam is coupled to the non-elastic portion and extends along a portion of the headgear. The support beam exhibits greater resistance to buckling in a direction perpendicular to the support beam's length than the non-elastic portion in a direction perpendicular to the non-elastic portion's longitudinal axis.

In some examples, the resistance to buckling is greater in a superior-inferior direction than in a medial-lateral direction in use. In some embodiments, the elastic portion comprises a tube and the support beam is disposed within the tube. In some embodiments, the support beam comprises inter-engaging rails. In some examples, the support beam comprises telescoping inner and outer members. In some examples, the elastic portion comprises an elastic braid and the support beam comprises a body disposed within the elastic braid. In some examples, the non-elastic portion extends from the body and partially extends within the elastic braid when the elastic braid is extended in the direction of its longitudinal axis. In some examples, the body is tapered. In some examples, an end of the body coupled to the non-elastic portion is narrower than an opposite end of the body.

In some examples, an adjustable headgear for a respiratory mask includes an elastic portion configured to provide a retraction force, a non-elastic filament, a restriction mechanism, and a core. The non-elastic filament is relatively inelastic compared to the elastic portion. The restriction mechanism is configured to provide a force resisting movement of the non-elastic filament when the elastic portion is extended in the direction of its longitudinal axis. The core is disposed within the elastic portion and coupled to the non-elastic filament. The core is configured to limit buckling of the non-elastic filament under the retraction forces of the elastic portion.

In some examples, the elastic portion comprises an elastic braid. In some embodiments, the core is relatively more rigid than the non-elastic filament. In some embodiments, the core is tapered. In some embodiments, an end of the core coupled to the non-elastic filament is narrower than an opposite end of the core.

In some examples, an adjustable headgear for a respiratory mask includes an elastic portion having a longitudinal axis, a non-elastic component, and a restriction mechanism. The elastic portion is configured to provide a retraction force in the direction of its longitudinal axis. The non-elastic component is relatively inelastic compared to the elastic portion. The non-elastic component has first and second portions, the second portion being wider than the first portion. The restriction mechanism is configured to provide a force resisting movement of the non-elastic component when the elastic portion is extended in the direction of its longitudinal axis.

In some examples, the second portion is substantially contained within the elastic portion when the elastic portion is extended in the direction of its longitudinal axis, and the first portion partially moves into the elastic portion when the elastic portion is extended in the direction of its longitudinal axis. In some examples, the second portion is joined to the first portion. In some embodiments, the second portion is joined to the first portion by overmolding. In some embodiments, the first and second portions are a unitary body. In some embodiments, the first portion is a filament and the second portion is a body.

Examples of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made.

Terms such as "top", "bottom', "upper", "lower", "front", "back", "left", "right", "rear", and "side" describe the orientation and/or location of portions of the components or elements within a consistent but arbitrary frame of reference which is made clear by reference to the text and the associated drawings describing the components or elements under discussion. Moreover, terms such as "first", "second", "third", and so on may be used to describe separate components. Such terminology may include the words specifically mentioned above, derivatives thereof, and words of similar import.

BRIEF DESCRIPTION OF THE DRAWINGS

FIG. 28B shows an example of a filament extending through a washer housing of the yoke.

FIGS. 28C, D and E show cross-sectional views of a filament extending through an example of lock washers disposed within a washer housing, with a locked position of the washers shown in dashed lines.

FIG. 78A is a transverse cross-section view of another example embodiment of an adjustment mechanism;

FIG. 78B is a perspective view of the adjustment mechanism of FIG. 78A;

FIG. 78C is a perspective view of the adjustment mechanism of FIG. 78A in a neutral position;

FIG. 78D is a perspective view of the adjustment mechanism of FIG. 78A at a maximum length during elongation;

FIG. 80A is a perspective view of another example embodiment of an adjustment mechanism;

FIG. 80B is a transverse cross-section of the adjustment mechanism of FIG. 80A;

FIG. 80C is a perspective view of the adjustment mechanism of FIG. 80A in a neutral position;

FIG. 80D is a perspective view of the adjustment mechanism of FIG. 80A at a maximum length during elongation;

FIG. 81A is a schematic showing the adjustment mechanism of FIG. 80A in a neutral position;

FIG. 81B is a schematic showing the adjustment mechanism of FIG. 80A at a maximum length during elongation;

FIG. 81C is a schematic showing the adjustment mechanism of FIG. 80A during retraction;

FIG. 82A shows another example embodiment of an adjustment mechanism during elongation;

FIG. 82B shows the adjustment mechanism of FIG. 82A including a filament kinking during retraction;

FIG. 97 is a cross-sectional view of the first embodiment nasal seal through a central line A-A of FIG. 13;

FIG. 98 is a front or face-contacting side view of the nasal seal of the fourth embodiment nasal mask interface;

FIG. 99 is a rear view of the nasal seal of the fourth embodiment nasal mask interface;

FIG. 100 is a underside perspective view from the outer side of the nasal seal of the fourth embodiment nasal mask interface;

FIG. 101 is an upper perspective view from the outer side of the nasal seal of the fourth embodiment nasal mask interface;

FIG. 102 is a side elevation view of the nasal seal of the fourth embodiment nasal mask interface;

FIG. 103 is a top view of the nasal seal of the fourth embodiment nasal mask interface;

FIG. 104 is an underside view of the nasal seal of the fourth embodiment nasal mask interface;

FIG. 105 is a cross-sectional view of the nasal seal of the fourth embodiment nasal mask interface through line AB of FIG. 103;

FIG. 106 is a perspective cross-sectional view of the nasal seal of the fourth embodiment nasal mask interface through line AC of FIG. 98;

FIG. 107 is a cross-sectional view of the nasal seal of the fourth embodiment nasal mask interface through line AC of FIG. 98;

FIG. 108 is a cross-sectional view of the nasal seal of the fourth embodiment nasal mask interface through line AG of FIG. 98;

Figure 107:
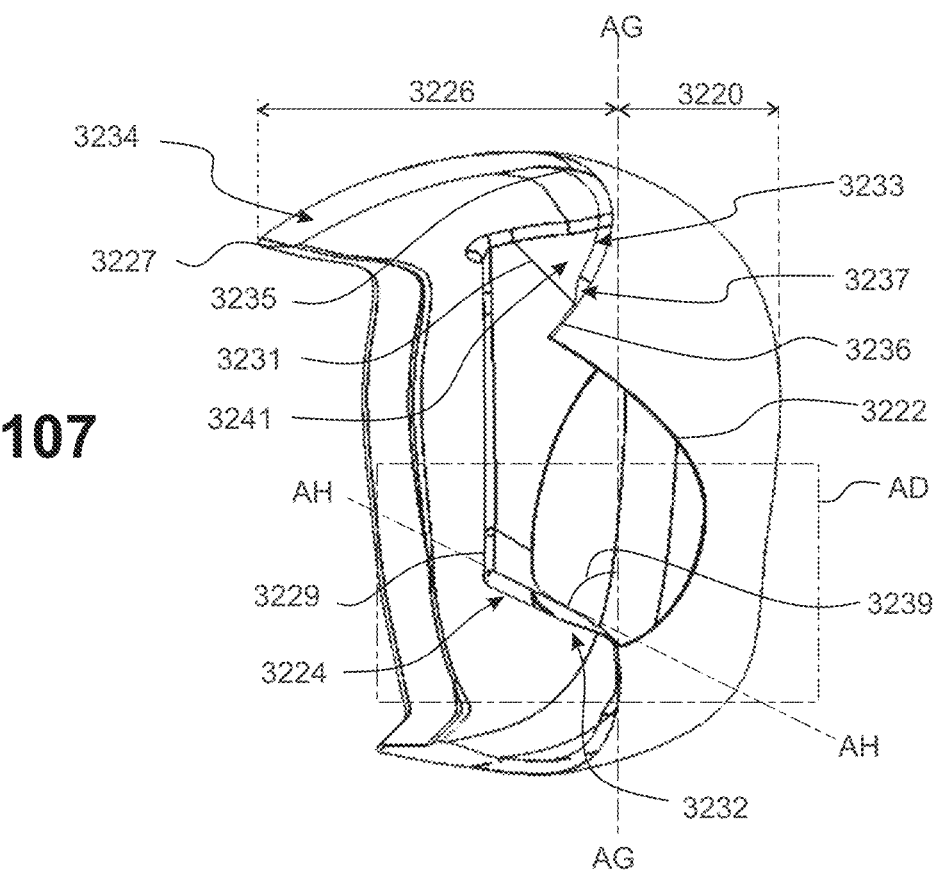
Figure 109:
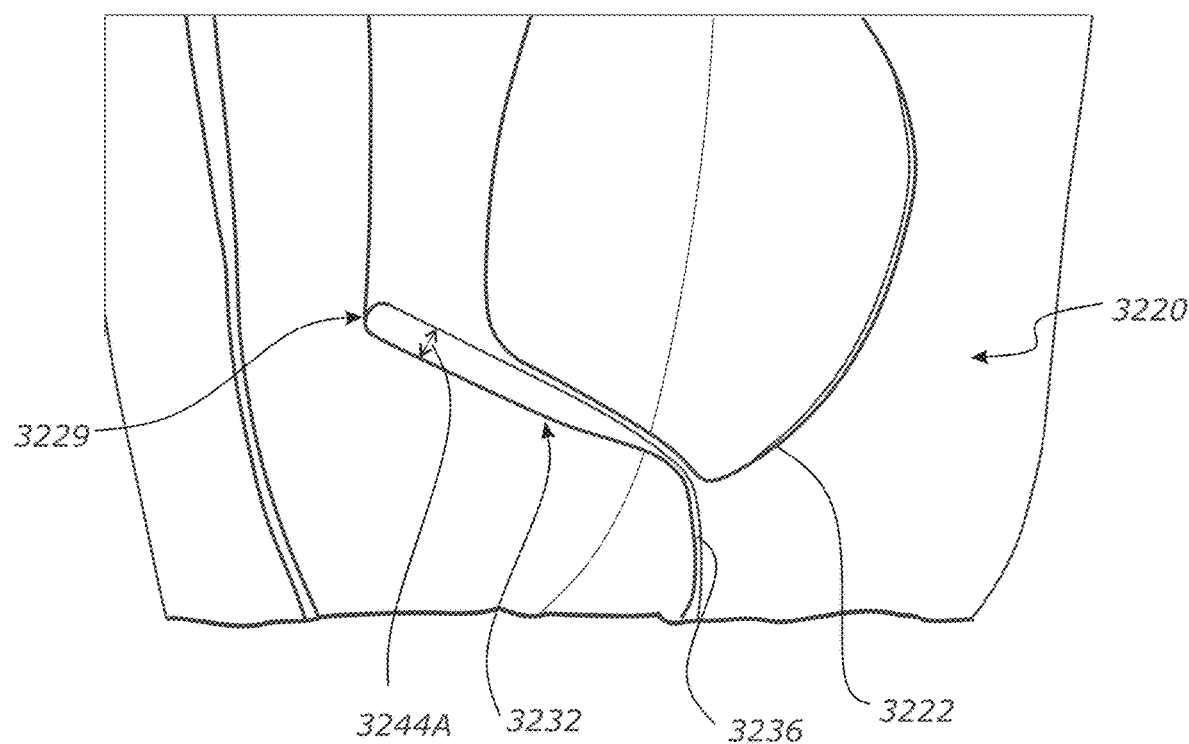
Figure 110:
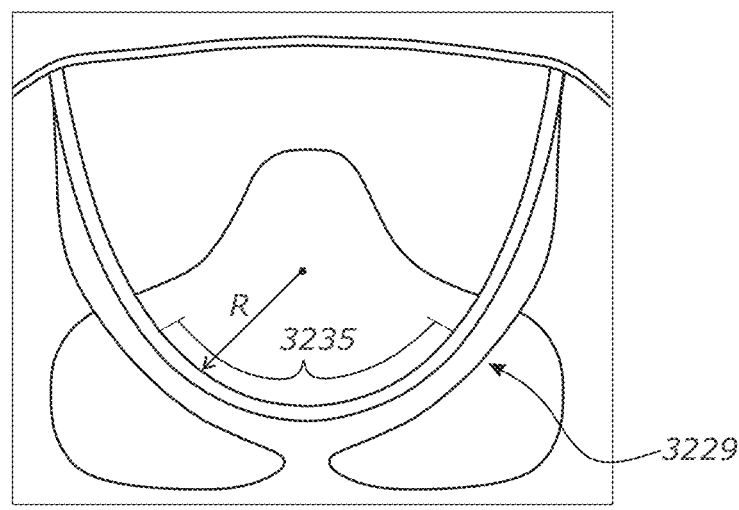
Figure 111:
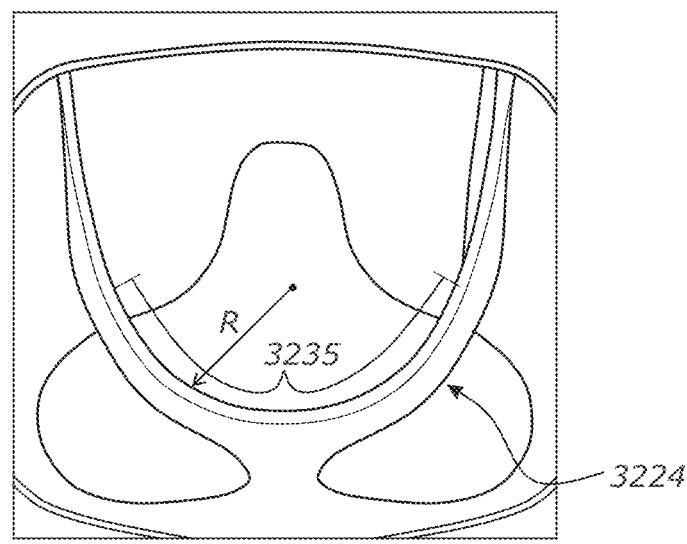
Figure 112:
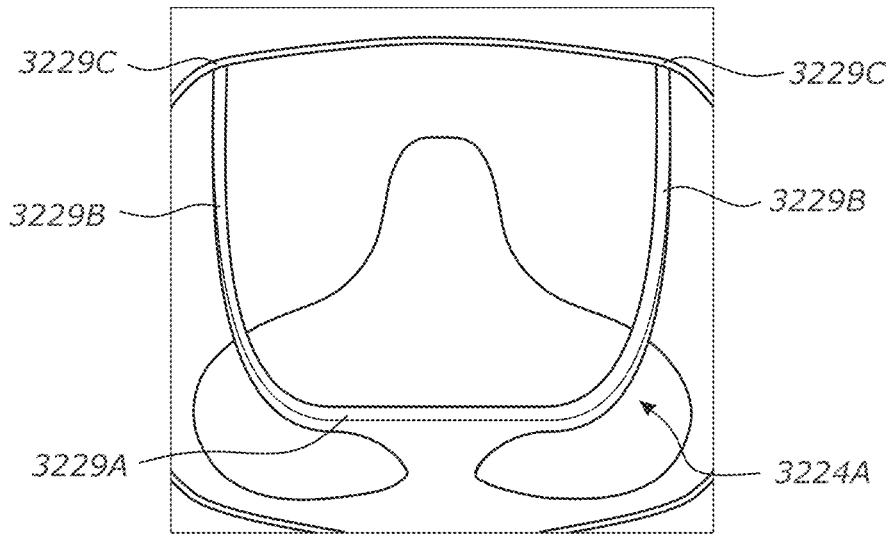
Figure 113:
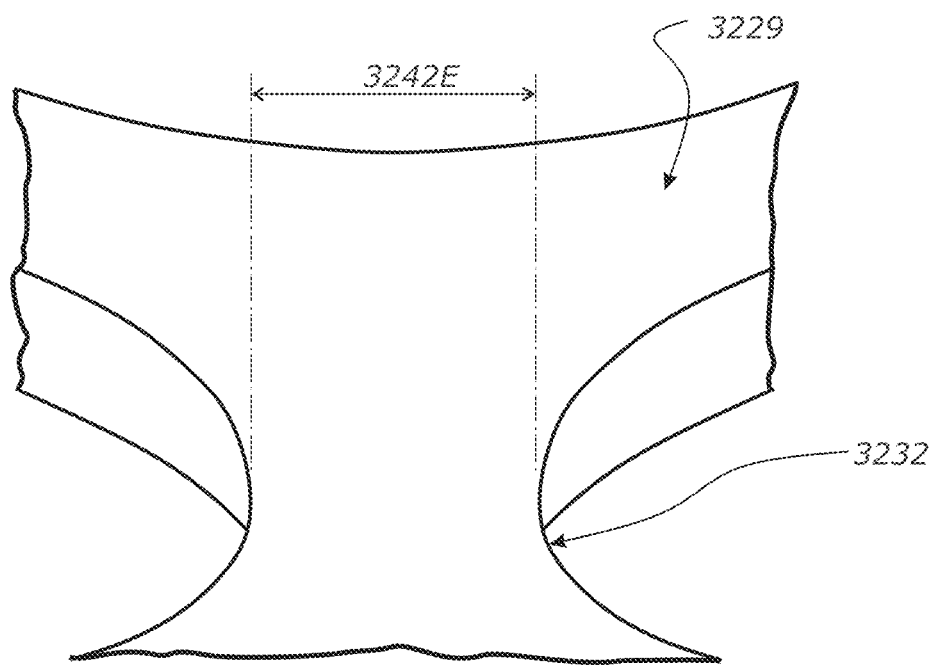
Figure 114:
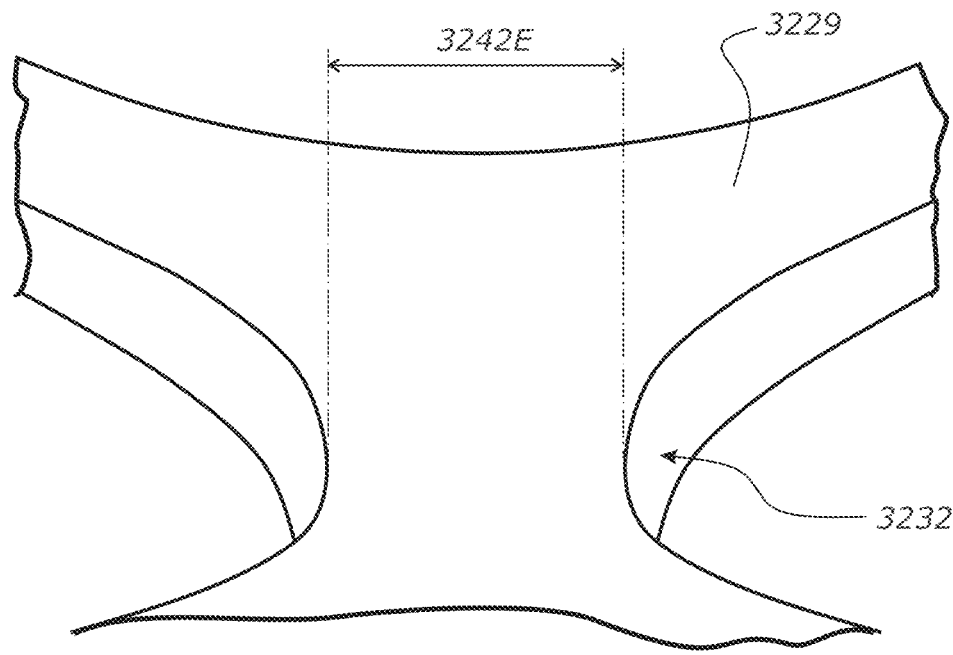
Figure 115:
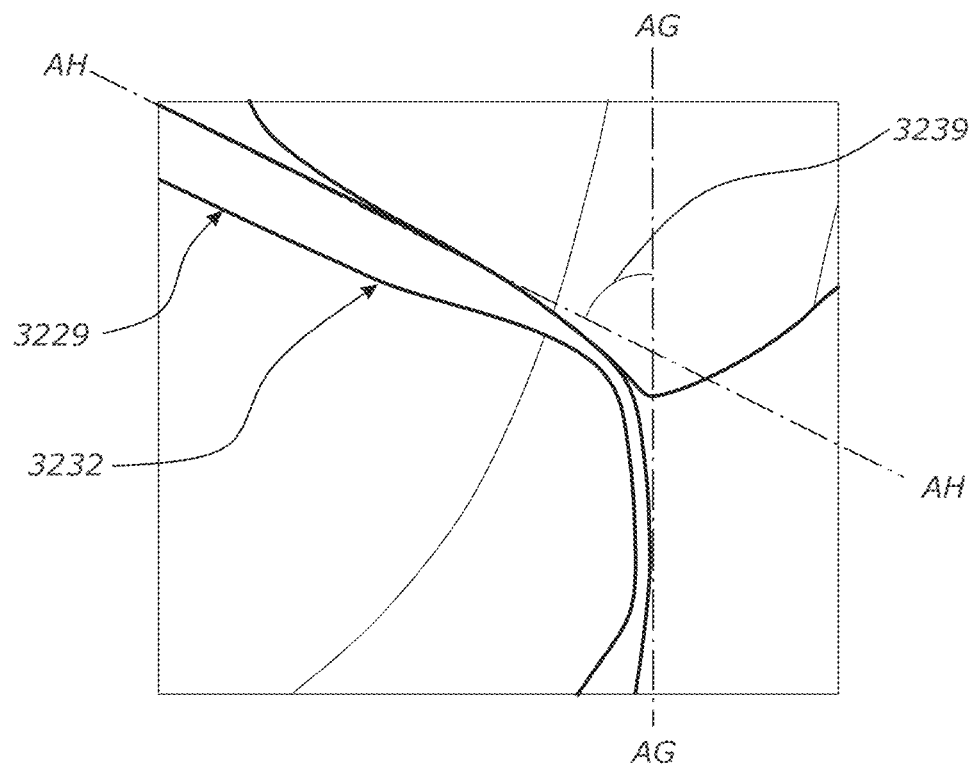
Figure 116:
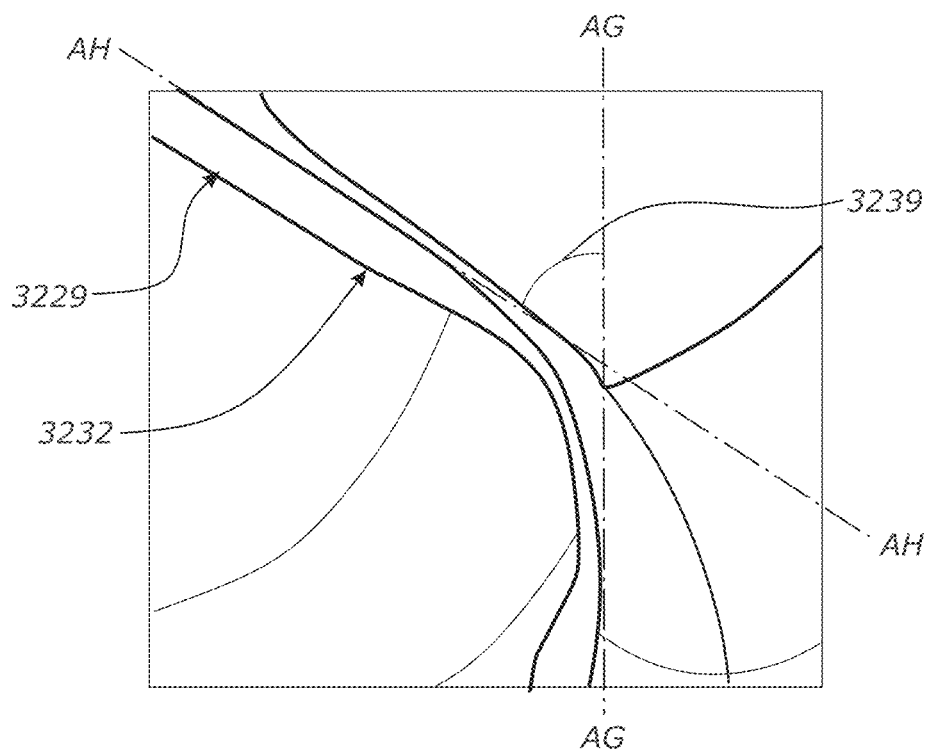
Figure 117:
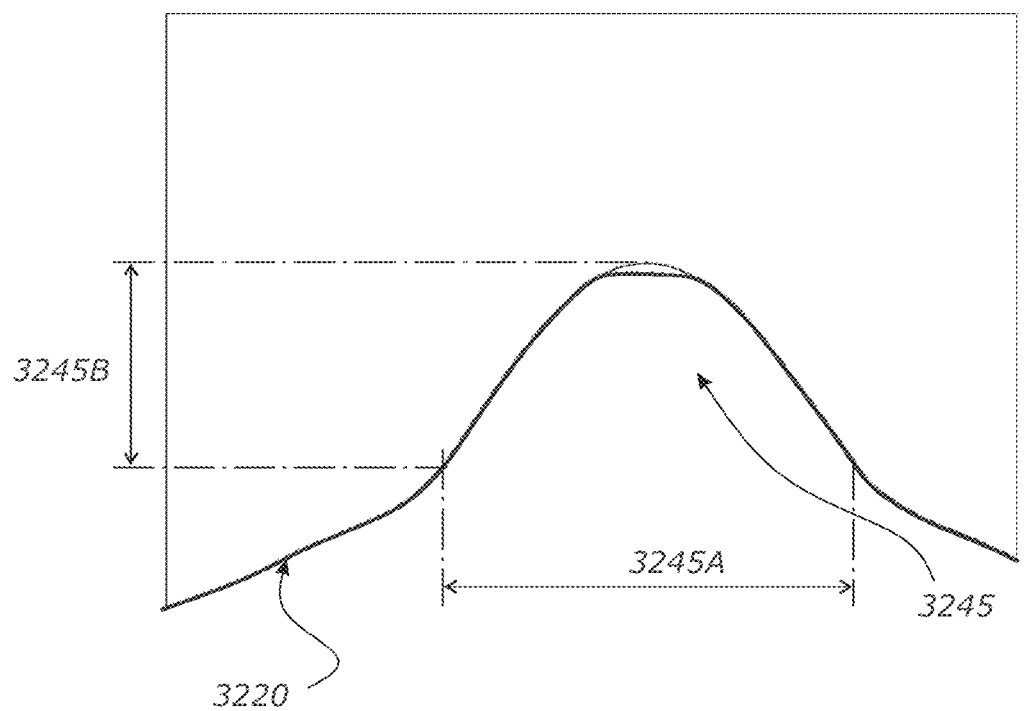
Figure 118:
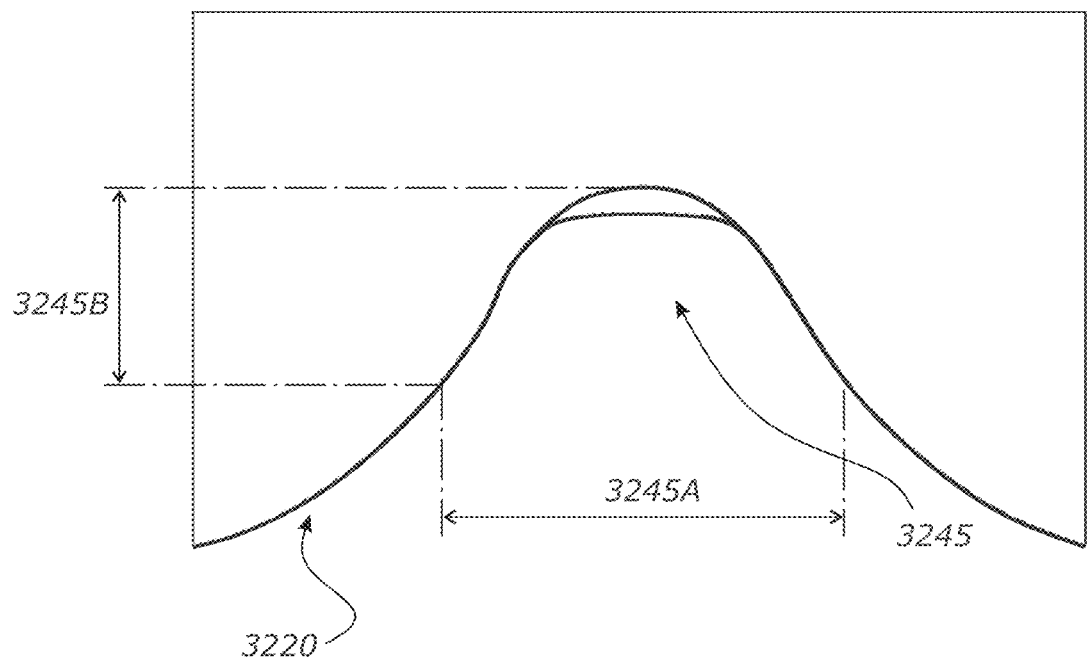
Figure 119:
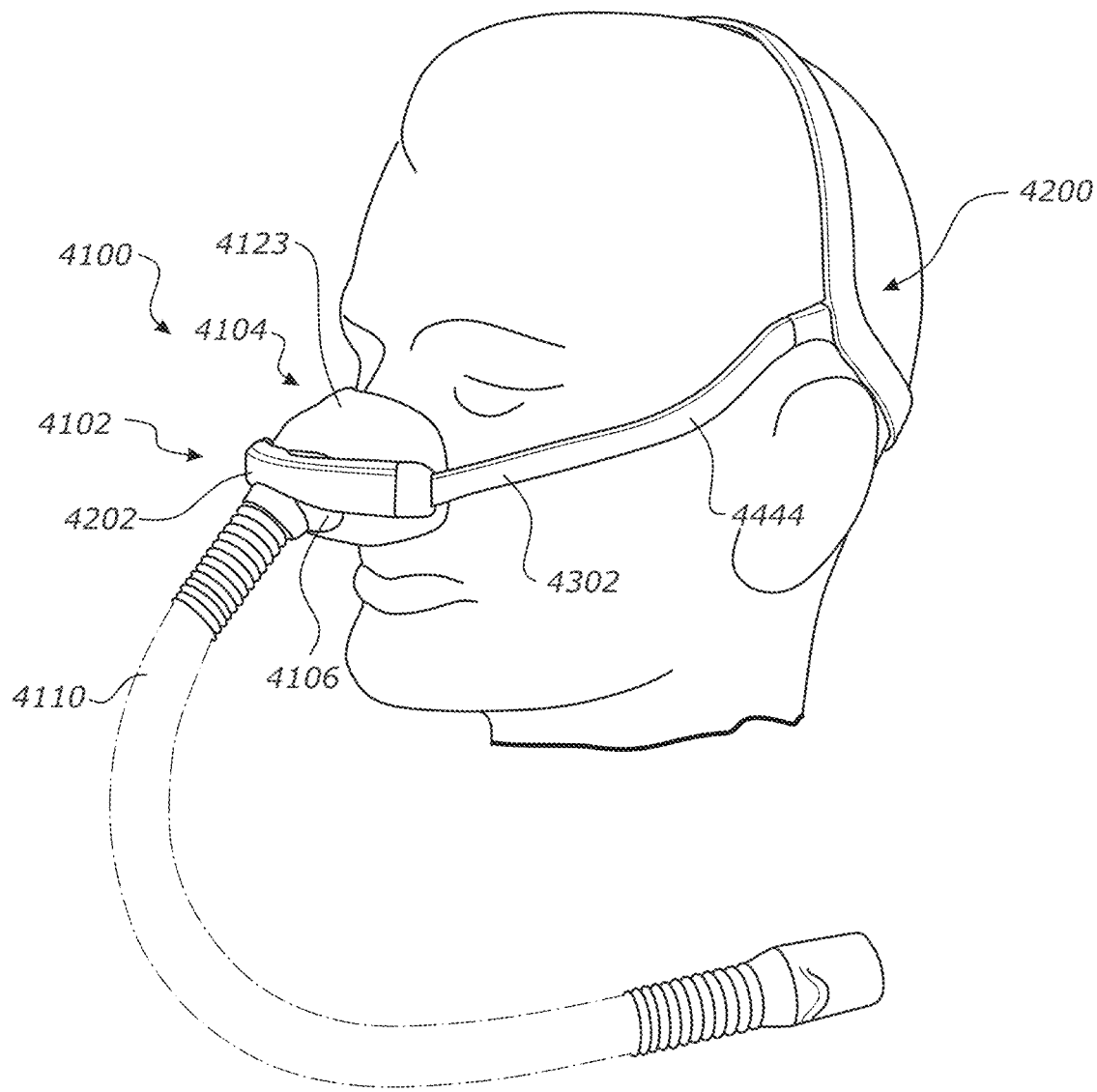
Figure 120:
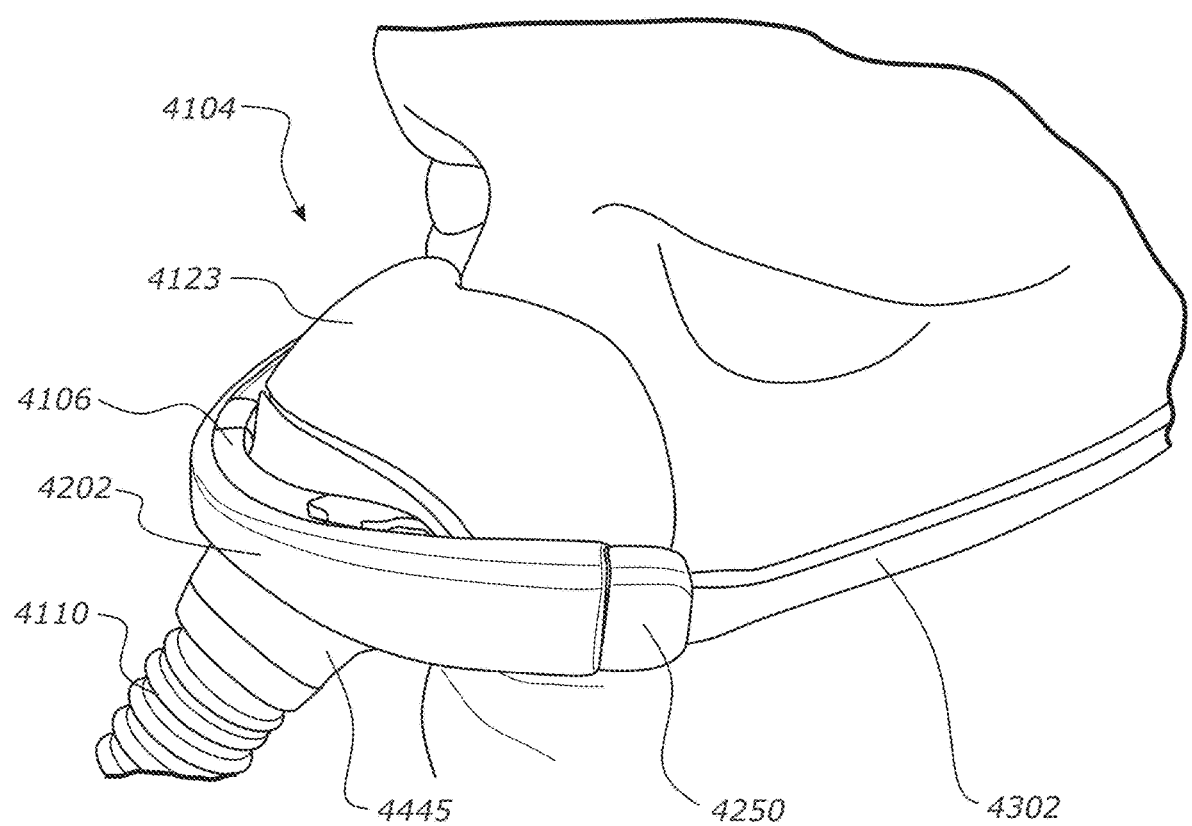
Figure 121:
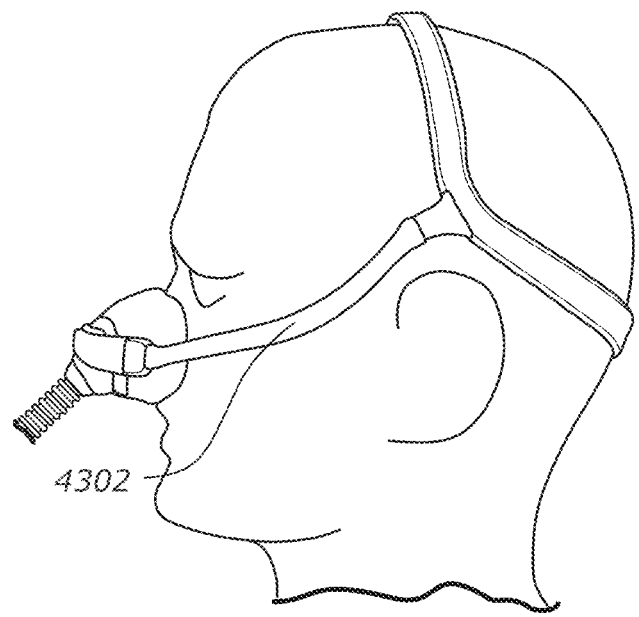
Figure 122:
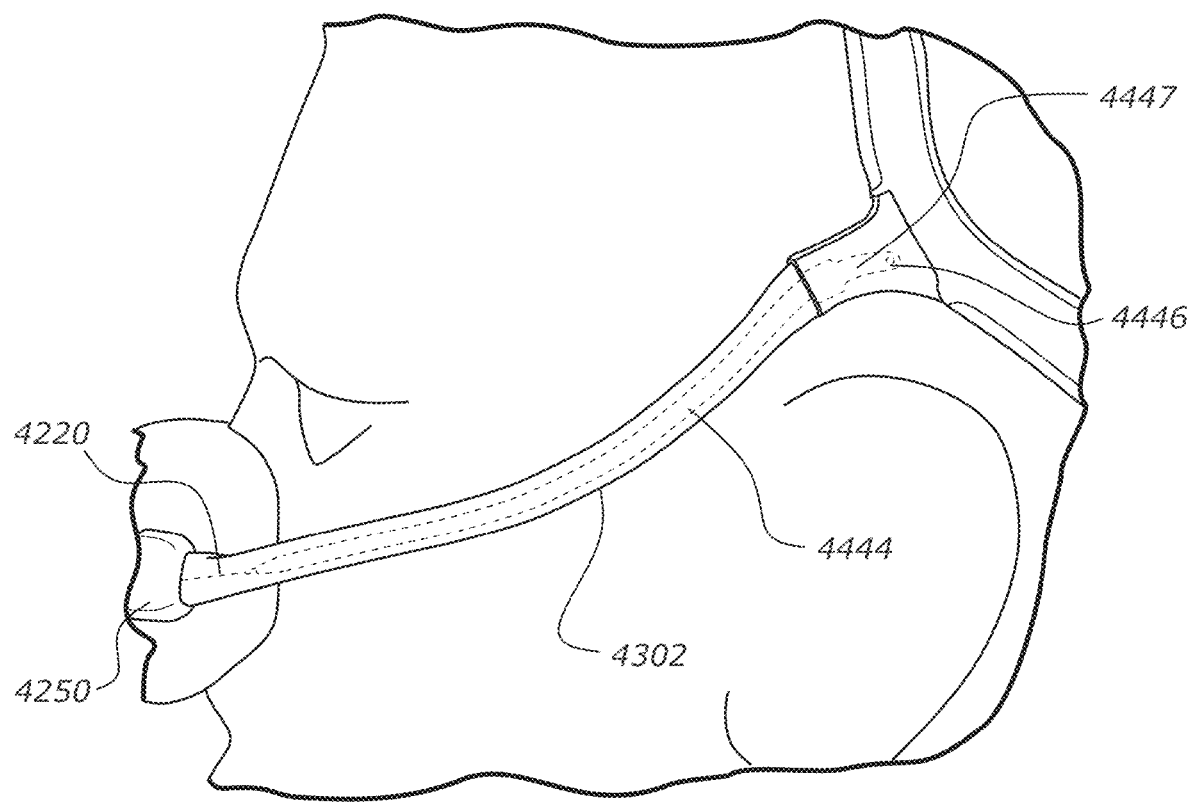
Figure 125A:
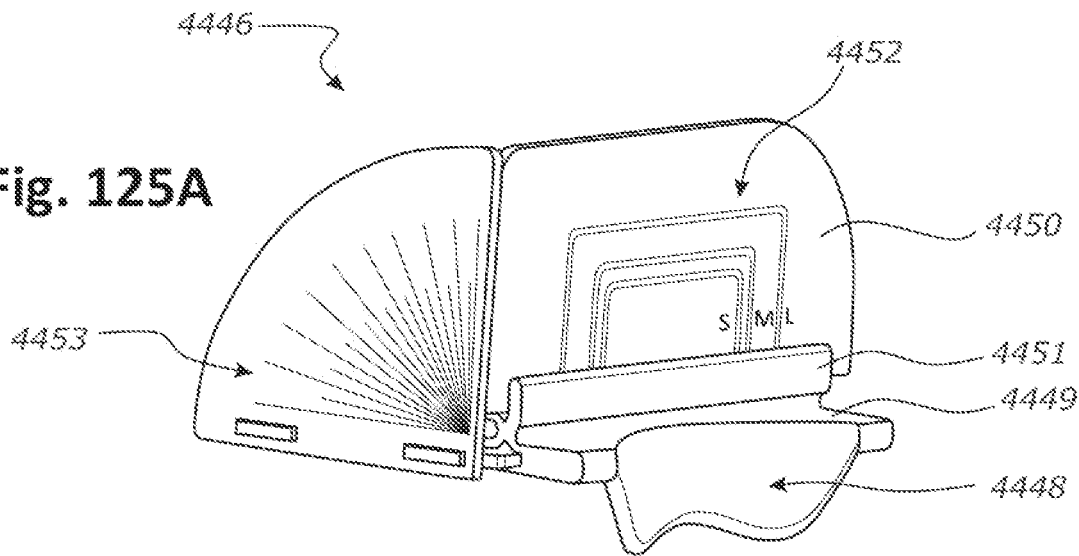
Figure 125B:
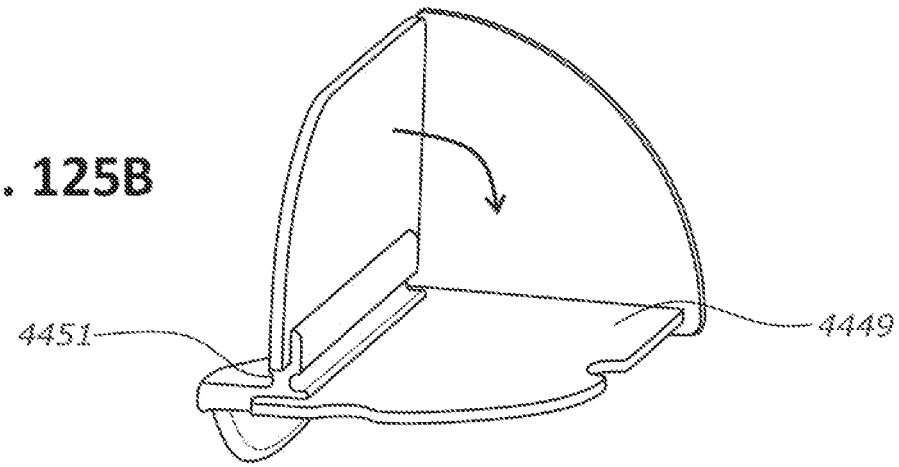
Figure 125C:
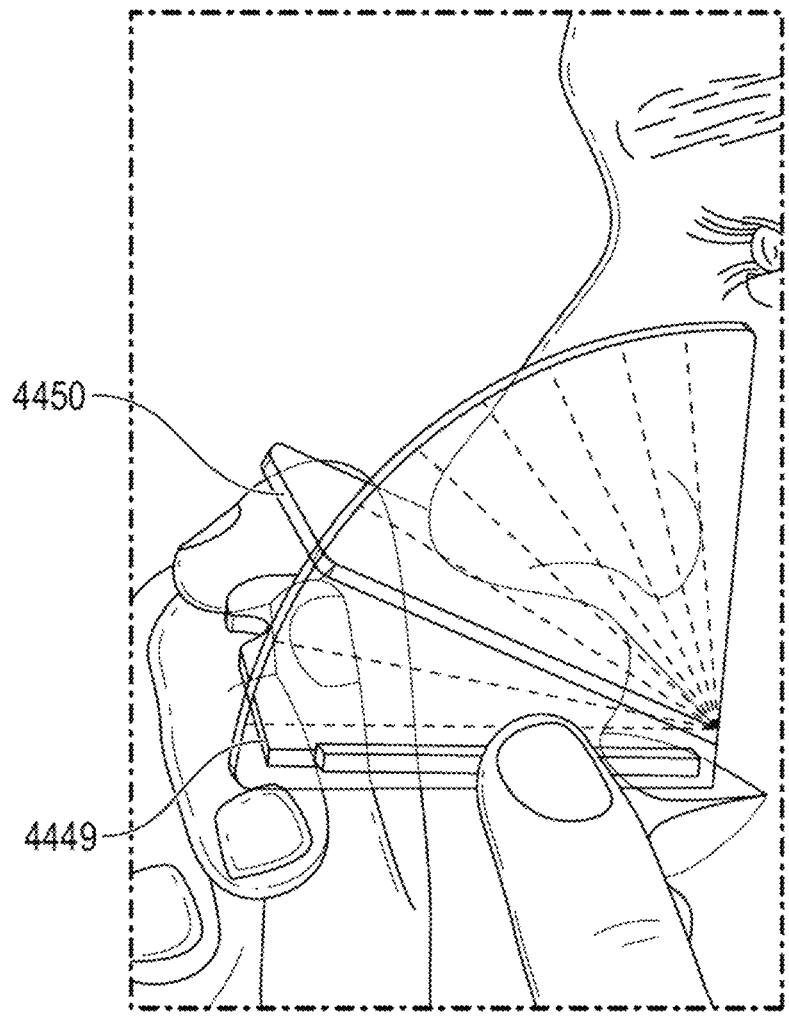
Figure 126A:
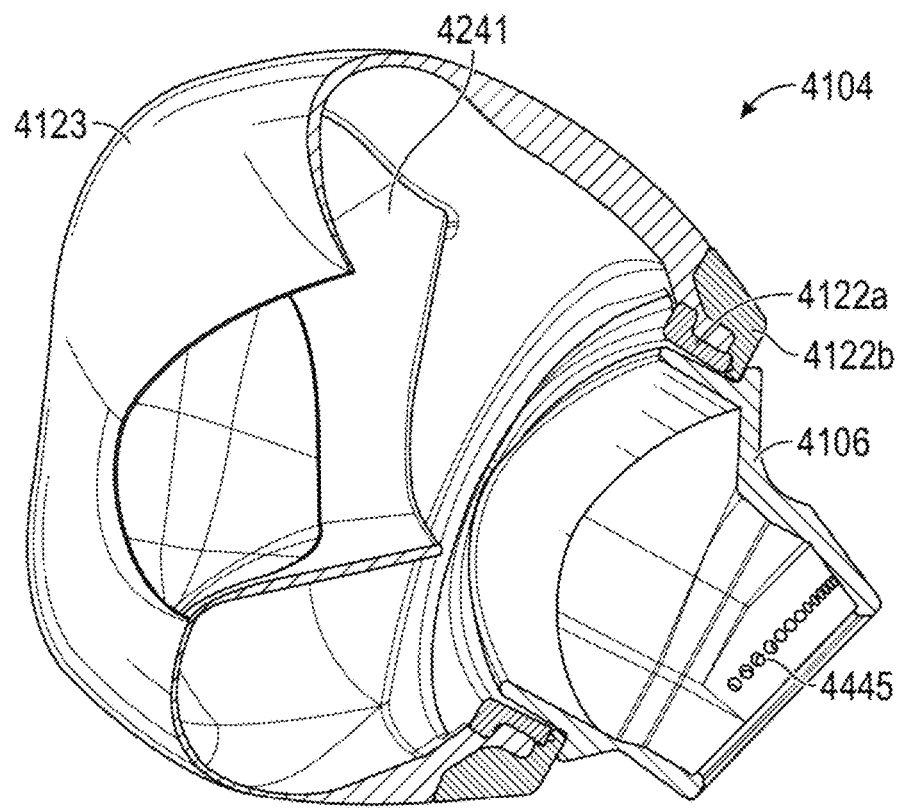
Figure 126B:
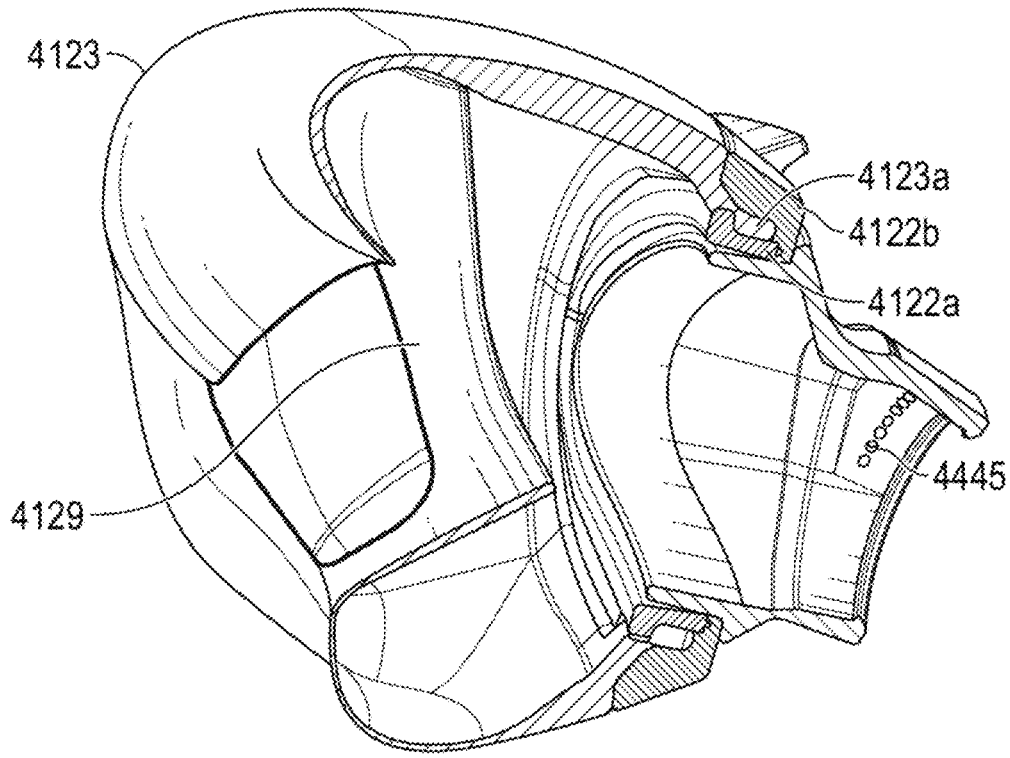
Figure 127:
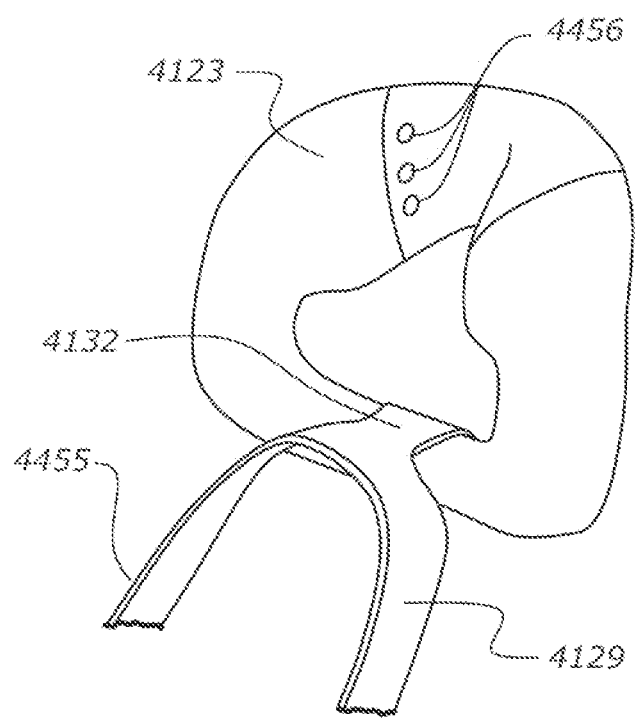
Figure 128A:
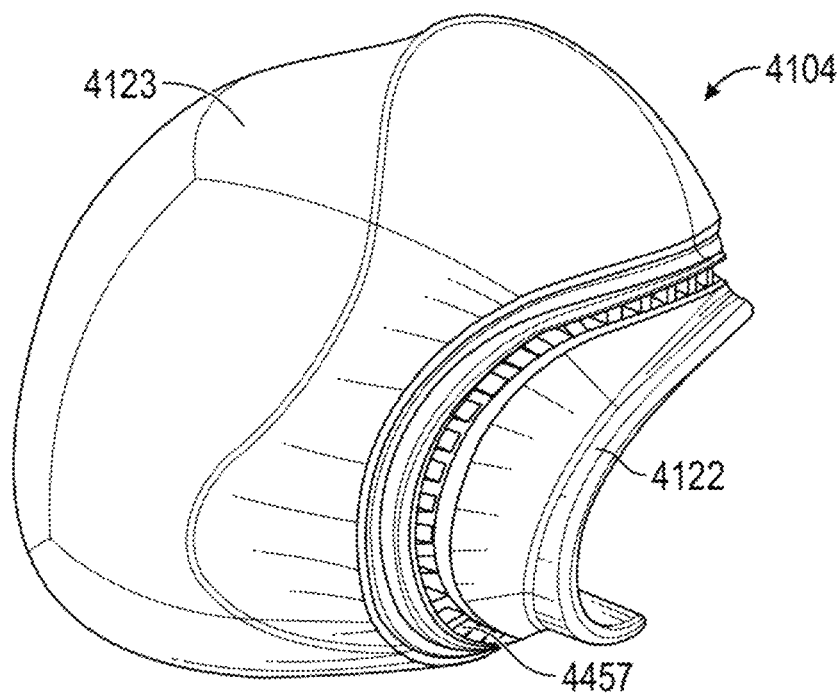

FIG. 109 is a close-up view of area AD of FIG. 107, and in particular showing the angular dimensional profile of a portion of the under-nose support of the nasal seal of the fourth embodiment nasal mask interface;

FIG. 110 is a rear close-up view of the under-nose support of the fourth embodiment nasal mask interface configured for a small-medium sized seal configuration, and in particular showing the radius of curvature of a central portion of the under-nose support;

FIG. 111 is a rear close-up view of the under-nose support of the fourth embodiment nasal mask interface configured for a medium-large sized seal configuration, and in particular showing the radius of curvature of a central portion of the under-nose support;

FIG. 112 shows a rear close-up view of another form of under-nose support of the fourth embodiment nasal mask interface, the under-nose support having a modified alternative squarish-shape;

FIG. 113 shows a close-up upper perspective view of a central region of the under-nose support of the nasal seal of the fourth embodiment nasal mask interface, and in particular identifies a width dimension of a portion of the under-nose support for a small-medium sized seal configuration;

FIG. 114 shows a close-up upper perspective view of a central region of the under-nose support of the nasal seal of the fourth embodiment nasal mask interface, and in particular identifies a width dimension of a portion of the under-nose support for a medium-large sized seal configuration;

FIG. 115 shows a close-up cross-sectional view of a portion of the central connecting portion of the under-nose support of the nasal seal of the fourth embodiment nasal mask interface, and in particular an angular dimension of the central connecting portion for a small-medium sized seal configuration;

FIG. 116 shows a close-up cross-sectional view of a portion of a central connecting portion of the under-nose support of the nasal seal of the fourth embodiment nasal mask interface, and in particular an angular dimension of the central connecting portion for a medium-large sized seal configuration;

FIG. 117 shows a close-up upper view of a nasal bridge region of the nasal seal of the fourth embodiment nasal mask interface, and in particular a valley region of the contacting surface for a small-medium sized seal configuration;

FIG. 118 shows a close-up upper view of a nasal bridge region of the nasal seal of the fourth embodiment nasal mask interface, and in particular a valley region of the contacting surface for a medium-large sized seal configuration;

FIG. 119 shows a perspective view of a mask assembly, including a headgear assembly, a seal assembly, and a frame assembly;

FIG. 120 shows a more detailed view of the seal and frame assembly from FIG. 119;

FIG. 121 shows a side elevation view of the mask assembly, including headgear assembly, seal assembly, and frame assembly of FIG. 119;

FIG. 122 shows a more detailed side elevation view of the headgear assembly;

FIG. 123 shows a side elevation view of a curved linked member, within a side strap of the headgear assembly;

FIG. 124A shows a perspective view of an example with a straight side strap;

FIG. 124B shows a perspective view of an example with a curved side strap;

FIG. 125A shows a rear perspective view of a size guide device;

FIG. 125B shows a front perspective view of the size guide device;

FIG. 125C shows a pictorial perspective view of the size guide device;

FIG. 126A shows a partial cutaway view of a seal module and mask frame;

FIG. 126B shows a further partial cutaway view of the seal module and mask frame;

FIG. 127 shows a perspective view of a molded seal component prior to assembly in a seal module;

FIG. 128A shows front perspective view of a section of a seal module; and

Figure 128B:
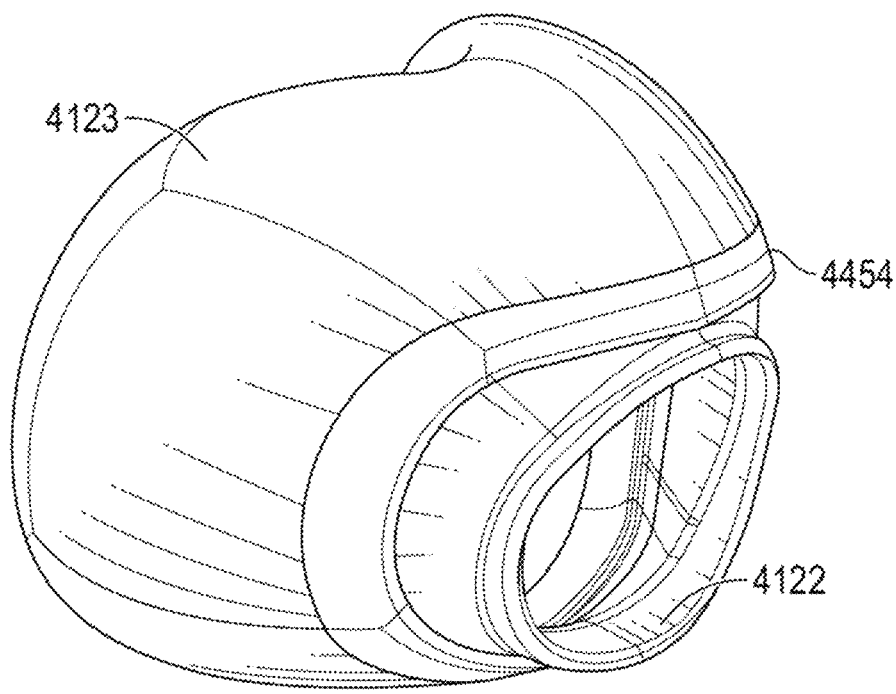

FIG. 128B shows a front perspective view of an assembled seal module.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Figure 1:
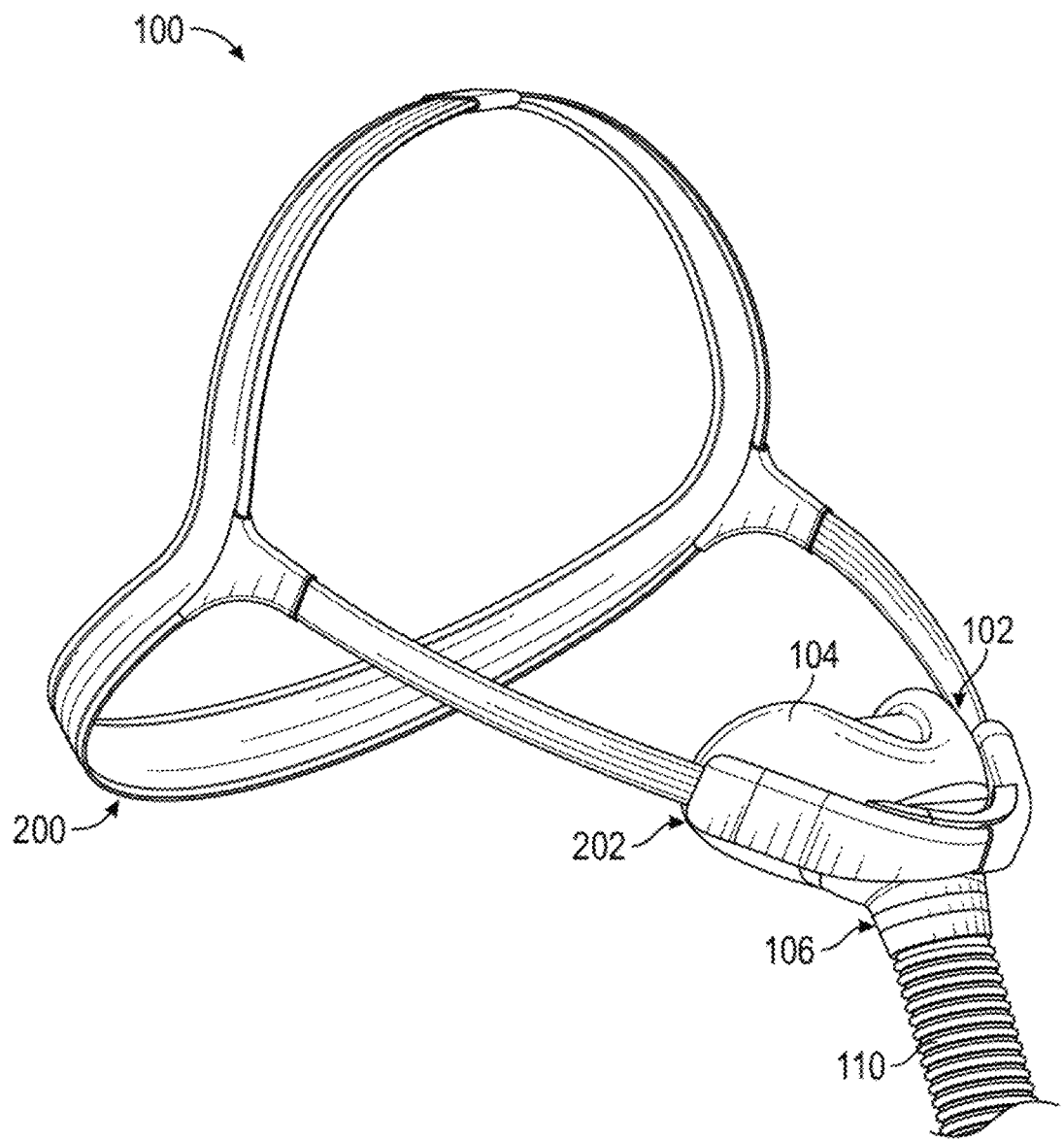
FIG. 1 is a perspective view of a mask assembly, including a headgear assembly, a seal assembly, and a frame assembly.
Figure 2:
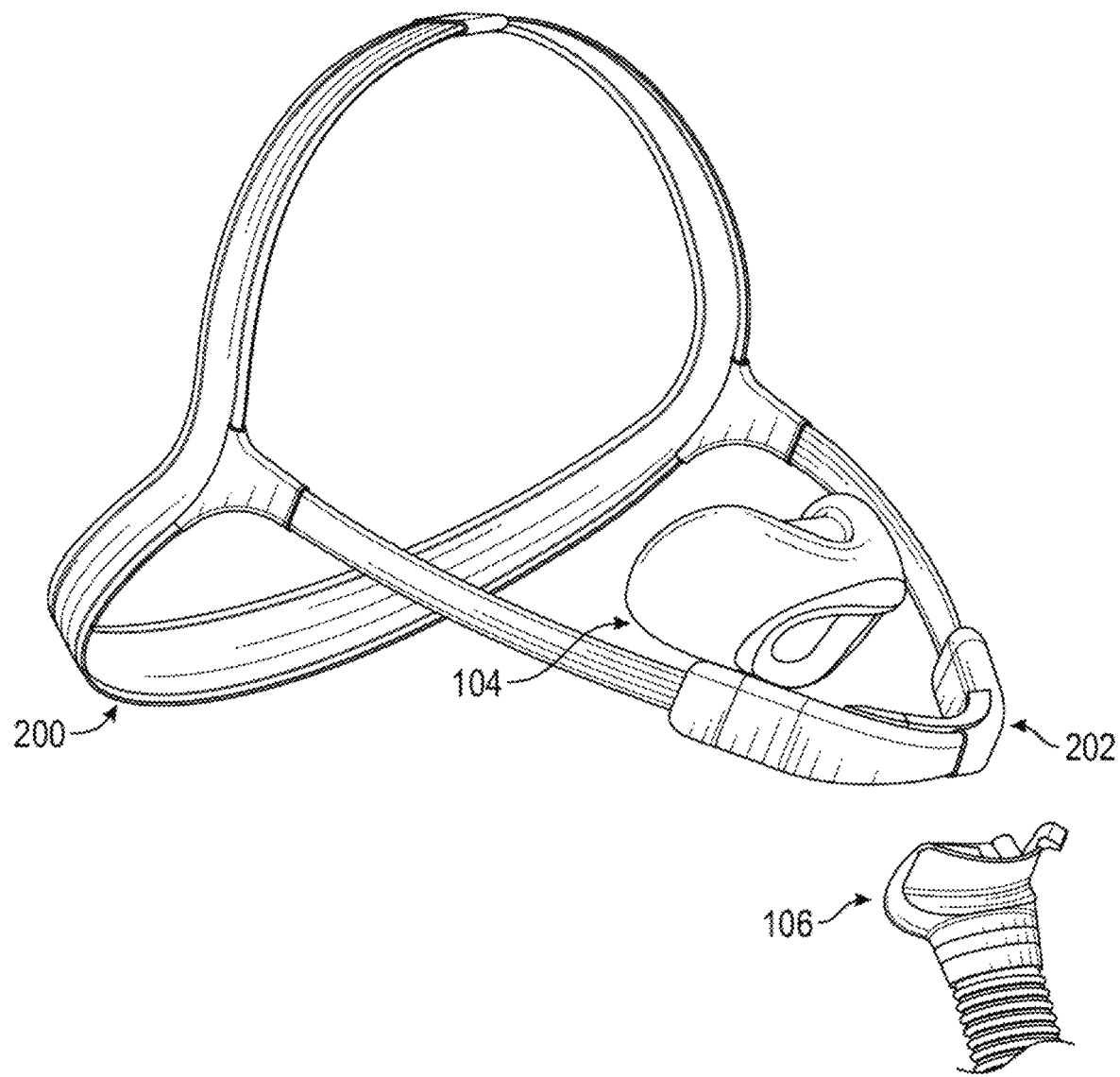
FIG. 2 is a perspective exploded view of the mask assembly of FIG. 1.

The present disclosure relates to a respiratory mask system or mask assembly 100 for the delivery of respiratory therapy to a patient. For example, FIGS. 1 and 2 illustrate an example embodiment of a mask assembly 100 including a mask interface 102, such as a seal and frame assembly, and a headgear assembly 200. The mask interface 102 includes a seal or cushion 104 that seals around the user's nose and/or mouth and/or inside the user's nares in use and a frame 106 that supports the seal 104 and couples the seal 104 to the headgear 200 and/or a gas delivery conduit 110. The seal 104 can be removably coupled to the frame 106 in use. The headgear 200 supports the mask interface 102 in a suitable position on the user's face in use.

In the illustrated example, the seal 104 is a nasal mask, in particular a pillows mask that seals inside the nares of the patient in use. In the illustrated arrangement, the seal 104 includes a secondary under-nose or sub-nasal seal portion that seals on the lower surfaces of a patient's/user's nose. The seal 104 is configured to form a secondary seal under the nose of the patient/user, along a portion of the face extending lateral to the nose, as well as along the upper lip of the user.

The headgear 200 includes a halo portion or halo strap 204 (FIG. 3) configured to wrap around the back and top of the user's head in use, a pair of front or side straps 208, each configured to extend along one of the user's cheeks in use, and a yoke or collector 202. A first end of each front strap 208 is attached to the halo strap 204. In the illustrated example, each front strap 208 is attached to the halo strap 204 at and/or via a joint 207. A second, opposite end of each front strap 208 extends from and/or is coupled to one end of the yoke 202. The yoke 202 couples, e.g., removably couples, to the frame 106 to couple the headgear 200 to the mask interface 102, such as in a manner described in greater detail herein.

The headgear 200 can be automatically adjustable and/or can incorporate one or more directional locks that allow the headgear to reduce in length with a relatively low amount of resistance and resist an increase in length of the headgear with a greater amount of resistance. Preferably, the directional lock(s) are configured to resist at least the blow-off force produced by the mask assembly 100 and, in some configurations, may also resist some amount of hose pull force. In some configurations, a locking force of the directional locks can be overcome to allow lengthening of the headgear for donning/doffing of the interface assembly. In some forms the yoke 202 may form a collector for filaments used in an automatically adjustable headgear system. The filaments can extend within the side arms 208. The side arms 208 or portions thereof can form or include braided elements of an automatic headgear adjustment mechanism, and the filaments can extend within the braided elements. One or more elastic elements (or other suitable biasing arrangements) can be provided and configured to apply a retraction force to the headgear 200, which tends to reduce a circumference of the headgear 200 or reduce a length of a portion of the headgear 200, such as the braided elements. In some configurations, elastic elements are incorporated in the braided elements. The yoke 202 may incorporate one or more directional locks, each of which can comprise one or more lock members. Each lock member may be generally in the form of a washer and referred to as "lock washers" or "washers" herein. That is, the lock washers can be relatively flat members defining an aperture through which the filament passes. The lock washers can be configured to frictionally engage with the filament during elongation of the headgear, but allow reduced-friction or relatively friction-free movement during retraction of the headgear. The directional lock or washer mechanism may be incorporated into the ends of the yoke/collector 202 and the body of the yoke/collector 202 may be substantially hollow to receive the filaments within the body. The headgear or any portion thereof can be configured in accordance with any of the embodiments disclosed in Applicant's U.S. Publication No. 2016/0082217, U.S. application Ser. No. 14/856,193, filed Sep. 16, 2015, and PCT Publication No. WO2016/043603, the entireties of which are incorporated by reference herein.

Figure 3:
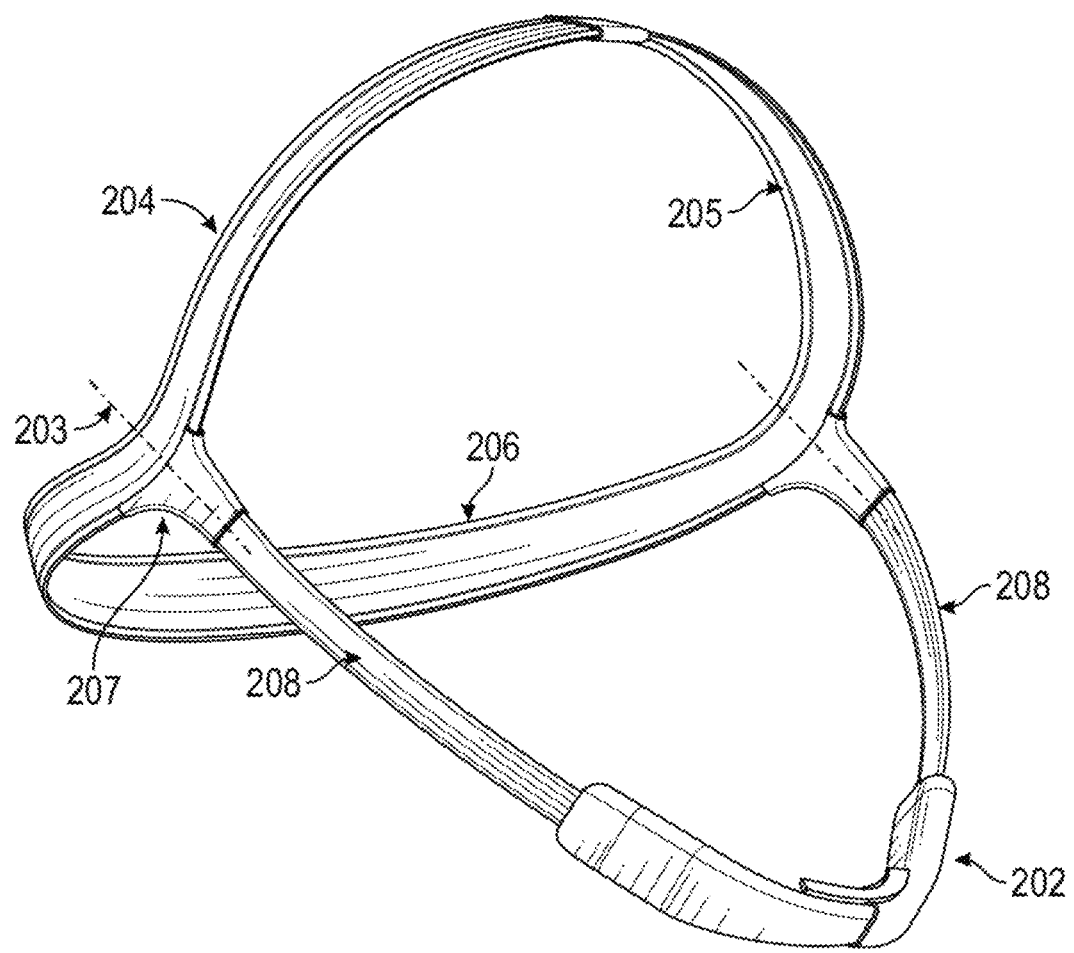
FIG. 3 is a perspective view of the headgear assembly of FIG. 1.

As shown in FIG. 3, the halo strap 204 includes a top portion 205 and a rear portion 206. Boundary lines 203 between the top portion 205 and the rear portion 206 can extend through the joints 207, for example, generally parallel to or along a longitudinal axis of the side straps 208, as shown. In the illustrated arrangement, the top portion 205 extends over the top of the user's head in use. The rear portion 206 extends across the back of the user's head in use. The top portion 205 and rear portion 206 are integrally formed and form a continuous (loop) strap. The side straps 208 extend above the user's ears and along the user's cheeks to the yoke 202 in use. The side straps 208 pass below the user's eyes in use. In the illustrated embodiment, the side straps 208 are permanently connected to the halo strap 204.

Figure 4:
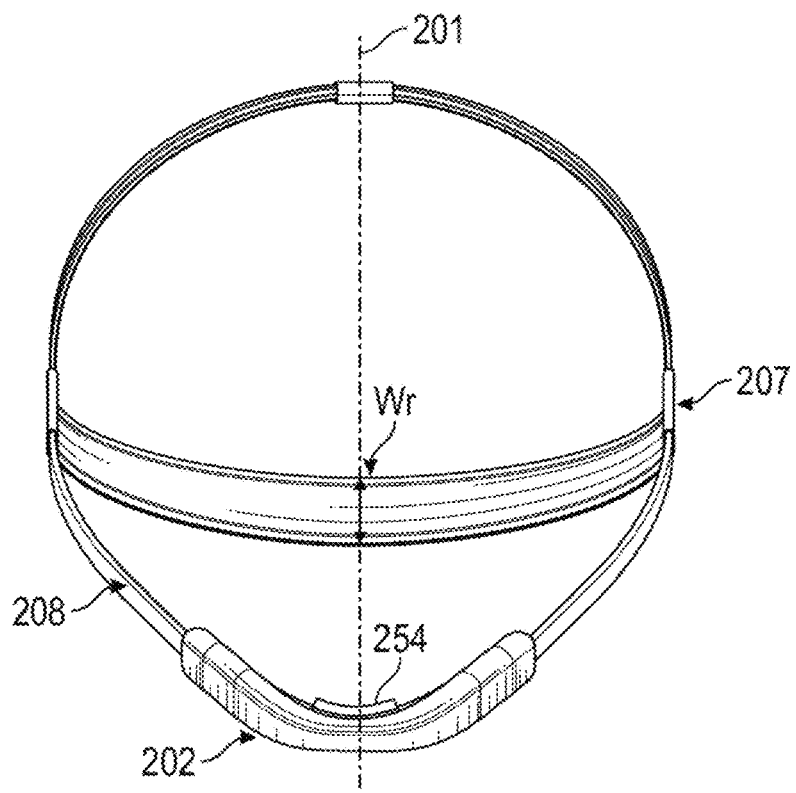
FIG. 4 is a front view of the headgear assembly of FIG. 3.
Figure 5:
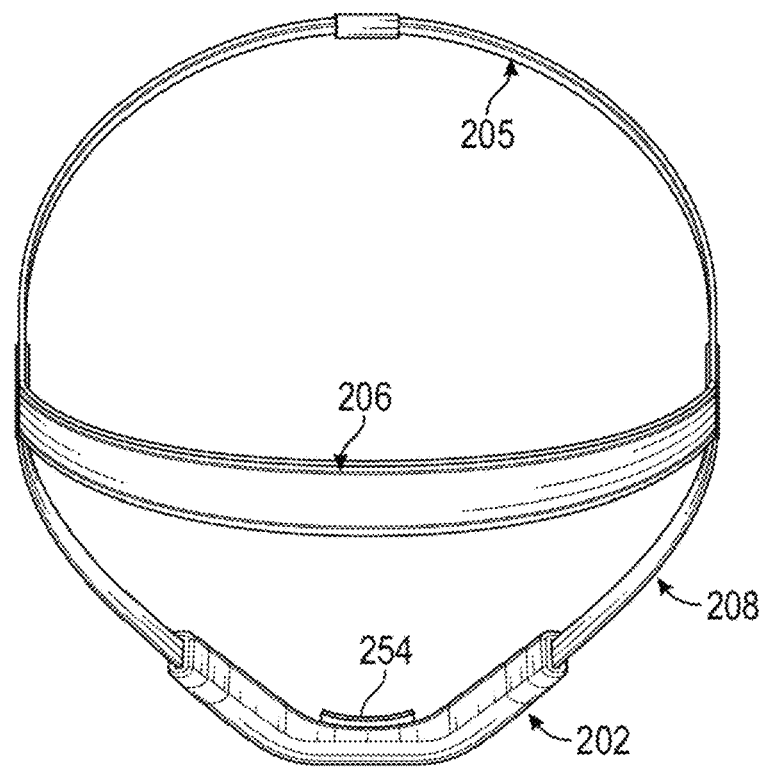
FIG. 5 is a rear view of the headgear assembly of FIG. 3.

A width of the rear portion 206 of the halo strap 204 increases toward a center line 201 (when viewed from the front, as shown in FIG. 4, or a rear of the headgear 200) of the headgear 200, as shown in FIG. 4. A width Wr of the rear portion 206 extending along or parallel to the center line 201 (in other words, a most distal or most rearward point of the rear portion 206 that contacts the back of the user's head when the headgear 200 is disposed on the user's head in use) is therefore a maximum width of the rear portion 206 and greater than a width of the rear portion 206 adjacent the joints 207. The greater width toward the back of the user's head can advantageously provide a greater contact area between the halo strap 204 and the user's head to help secure the headgear 200 to the user's head in use and to provide increased comfort compared to a narrower strap. The greater width toward the back of the user's head can also or alternatively provide a gripping location that is easier and/or more intuitive for the user to grasp when donning and/or doffing the mask assembly 100. The functionality and aesthetics of this gripping location can be further improved with the addition of additional layers of material to provide tactile feedback.

Figure 11:
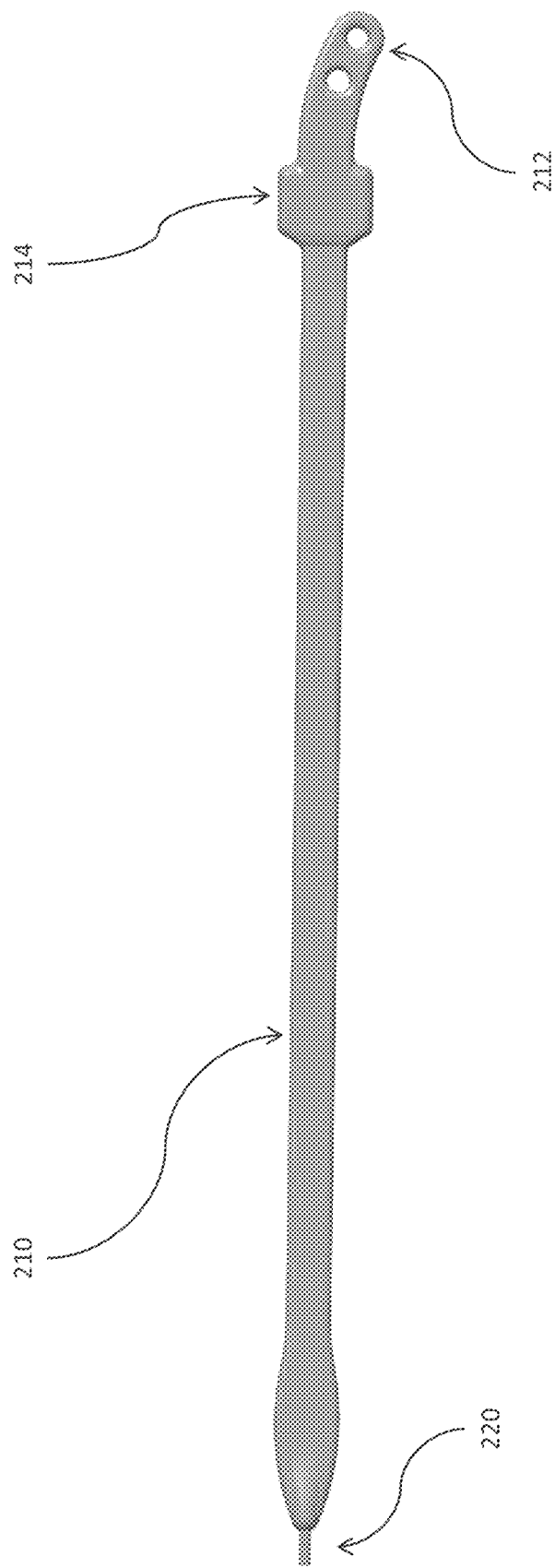
FIG. 11 shows a braid core of the side straps of the headgear assembly of FIG. 3.

Each side strap 208 can include a braid core 210 as shown in FIG. 11. A first end of the braid core 210 is coupled to one of the filaments 220 of the automatically adjustable headgear system. A second, opposite end of the braid core 210 includes a locating feature 212 positioned and designed to assist location of the side strap 208 in an overmold tool 300 as described in greater detail herein. The second end of the braid core 210 including the locating feature 212 is coupled to the halo strap 204 as described in greater detail herein. The braid core 210 can include a widened area 214 proximate the second end and/or locating feature 212 as shown. The widened area 214 can provide a location for connection of a braided element 216 of the automatically adjustable headgear system to the braid core 210.

The braid core 210 can act as a support beam for the side strap 208. The braid core 210 can be flexible but relatively more rigid than the filament 220 due to, for example, the braid core 210 being made of or including a relatively harder or rigid material than the filament 220 and/or relative dimensions of the braid core 210 and filament 220 (e.g., the braid core 210 can be thicker than the filament 220, which can provide greater rigidity to the braid core 210 compared to the filament 220). The braid core 210 advantageously increases stability of the adjustment mechanism by providing additional structure to at least a portion of the adjustment length of the adjustment mechanism compared to the filament 220 alone. For example, the braid core 220 provides structure and support to the braided element 216 and improves the braided element's 216 ability to transfer loads applied to the mask interface 102 via the yoke 202 to the headgear 200, thereby improving the stability of the mask on the user's face. Reduced buckling of the filament can help reduce or minimize the activation length of the adjustment mechanism. Additional details regarding the braid core 210 can be found in Applicant's U.S. Provisional Application No. 62/525,643, which is hereby incorporated by reference herein in its entirety.

Figure 12:
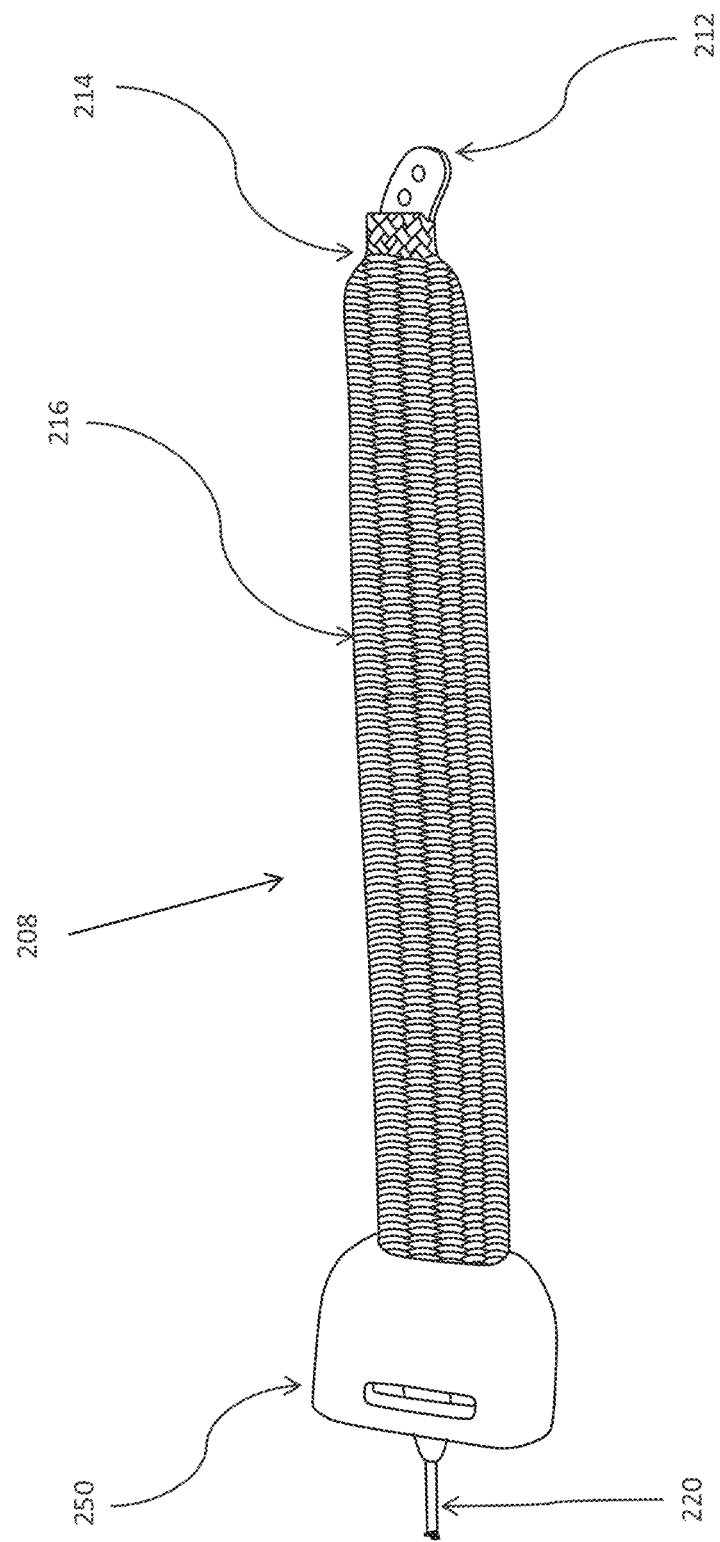
FIG. 12 shows the side strap coupled to an end cap.
Figure 13:
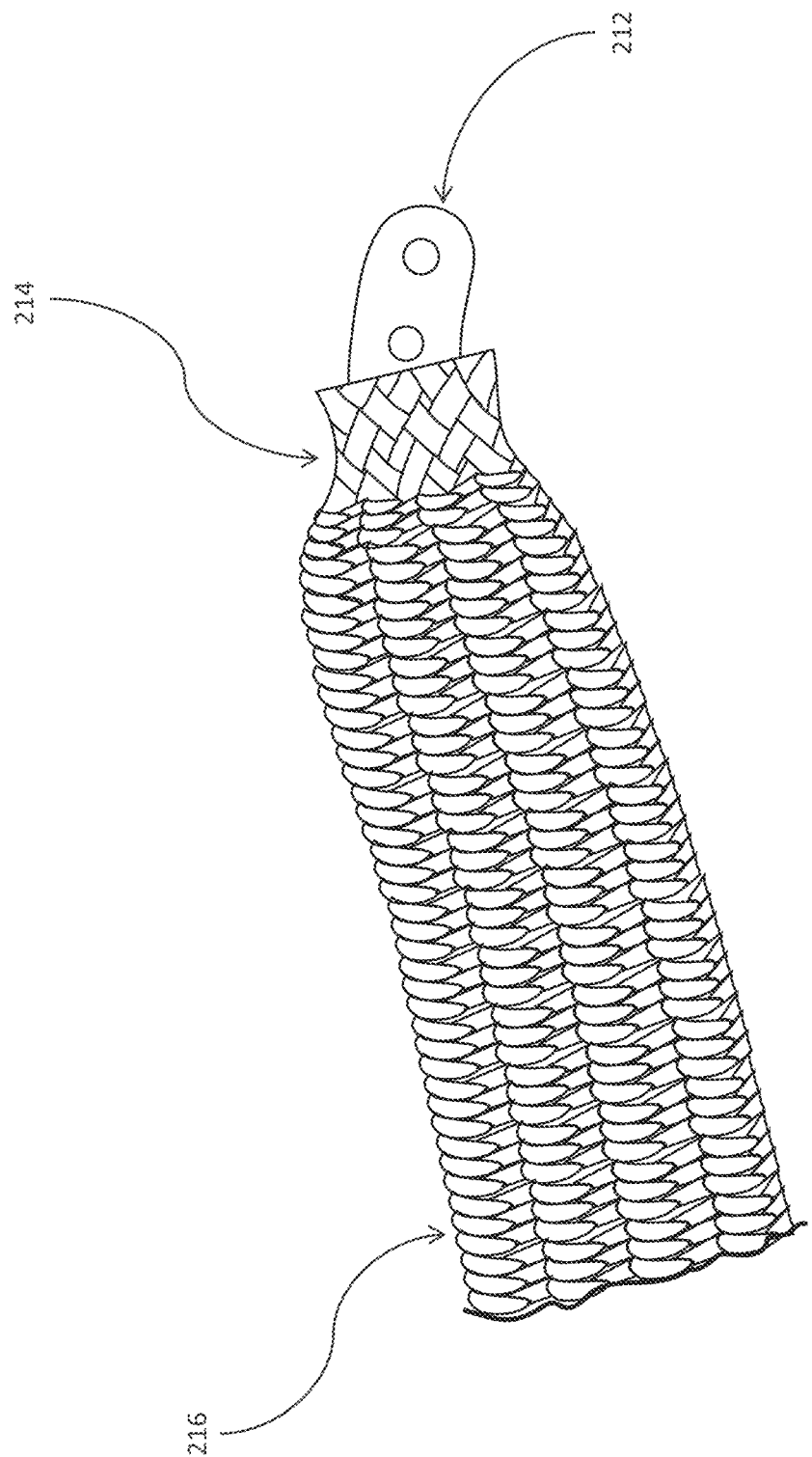
FIG. 13 shows a detail view of one end of the side strap.

As shown in FIGS. 12 and 13, the illustrated braided element 216 is tubular in shape and surrounds the braid core 210 (excluding the locating feature 212). The braided element 216 can also surround part of the filament 220. The braided element 216 is connected, e.g., permanently connected, to the braid core 210. In the illustrated embodiment, a first end of the braided element 216 is connected to the braid core 210 at the widened area 214. The braided element 216 is not connected to a remainder of the braid core 210 or filament 220 such that the braided element 216 can stretch and therefore translate relative to the remainder of the braid core 210 and the filament 220. As shown in FIG. 12, a second end of the braided element 216 opposite the first end connected to the braid core 210 at the widened area 214 is connected to, e.g., overmolded onto, an end cap 250 of the yoke 202.

Figure 7:
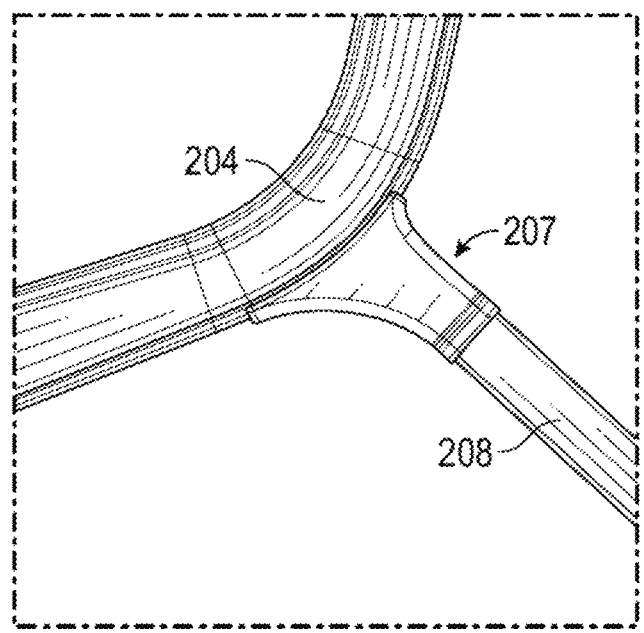
FIG. 7 is a detailed view of a joint between a halo strap and a side strap of the headgear assembly of FIG. 3.
Figure 8:
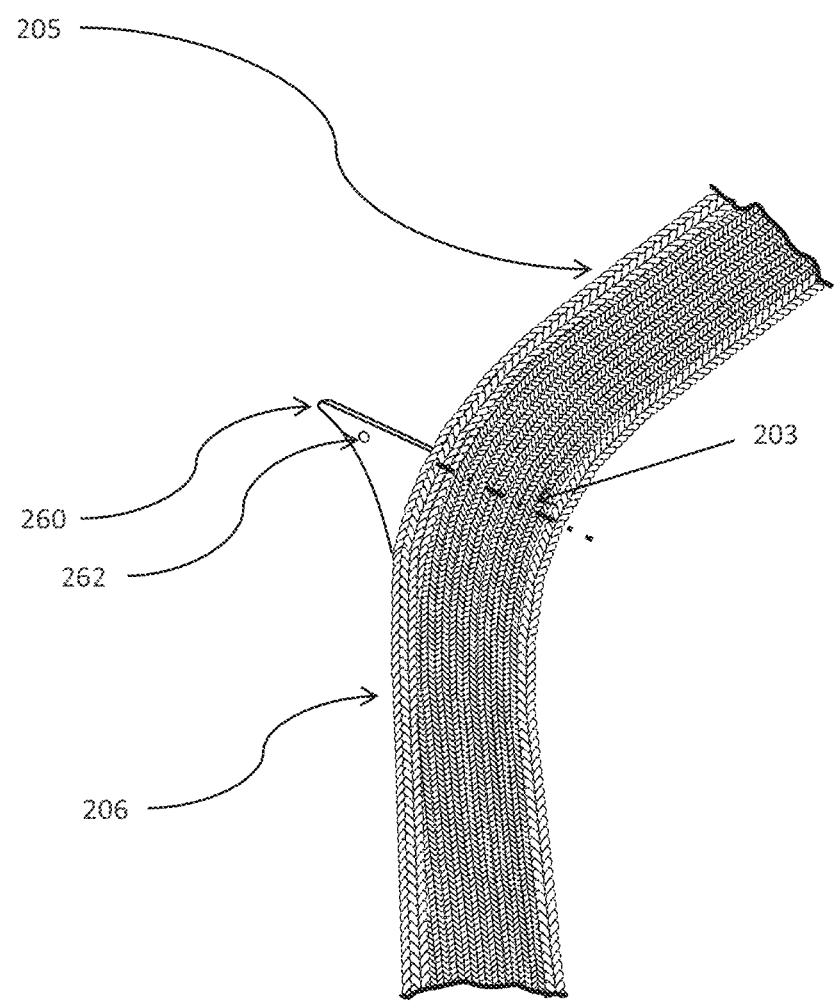
FIG. 8 is a detailed view of a portion of the halo strap including a burst through protrusion that helps form the joint between the halo strap and the side strap.

In the illustrated example, the joints 207 between the halo strap 204 and the side straps 208, shown in FIG. 7, can be formed by or include an over-molded section that permanently connects the side straps 208 to the halo strap 204. The halo strap 204 can be formed via an intramolding process, examples of which are described in the Applicant's PCT Publication No. 2016/043603, the entirety of which is incorporated herein. "Intra-molding" comprises forming a component as a plastic core and a textile casing as an integral structure by the application of molten plastic into the textile casing. A strap or any other component that has been "intra-molded" is a component formed by the application of molten plastic into the textile casing. Burst through protrusions 260 are formed during the intramolding process to extend from the halo strap 204 at or adjacent the boundary lines 203 between the top 205 and rear 206 portions of the halo strap 204, as shown in FIG. 8. "Burst-through molding" is described in the Applicant's PCT Publication No. WO2017/158476, the entirety of which is incorporated by reference herein. Burst-through molding is a variation of intra-molding as described above. The burst-through molding process comprises introducing molten plastic into a textile casing and pushing the molten plastic through a portion of the textile casing. A component formed by the burst-through molding process comprises a unitary plastic core that is integrally formed with a textile casing and the unitary plastic core has a portion that extends through the textile casing. Each of the burst through protrusions 260 includes a locating feature 262 positioned and designed to assist location of the halo strap 204 in the overmold tool 300.

Figure 6:
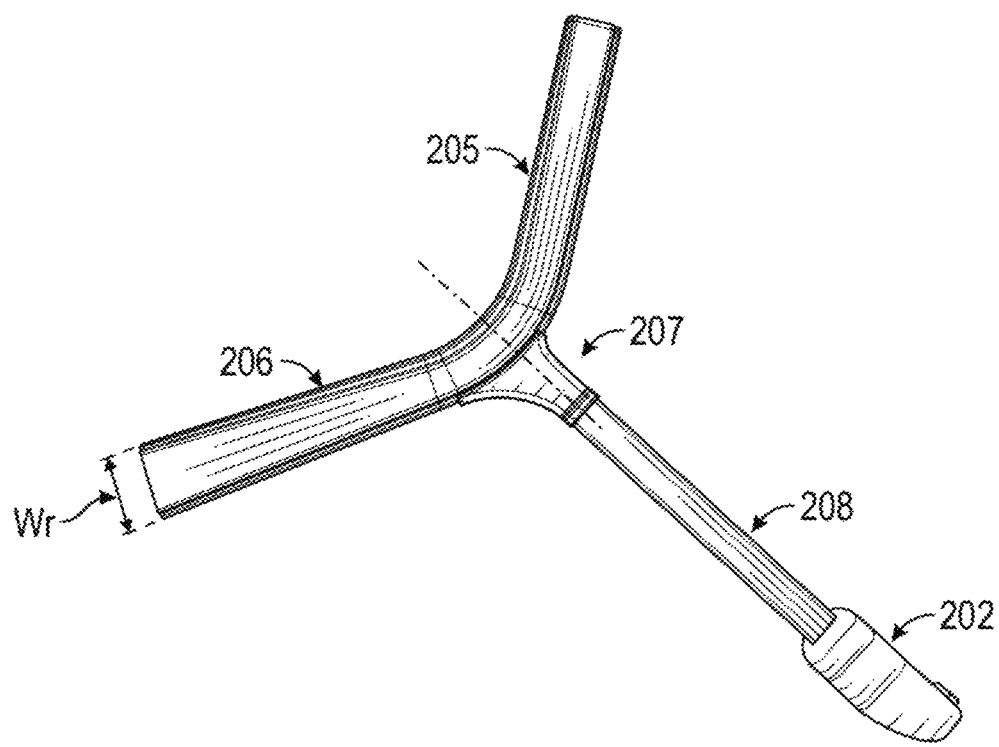
FIG. 6 is a side view of the headgear assembly of FIG. 3.
Figure 9:
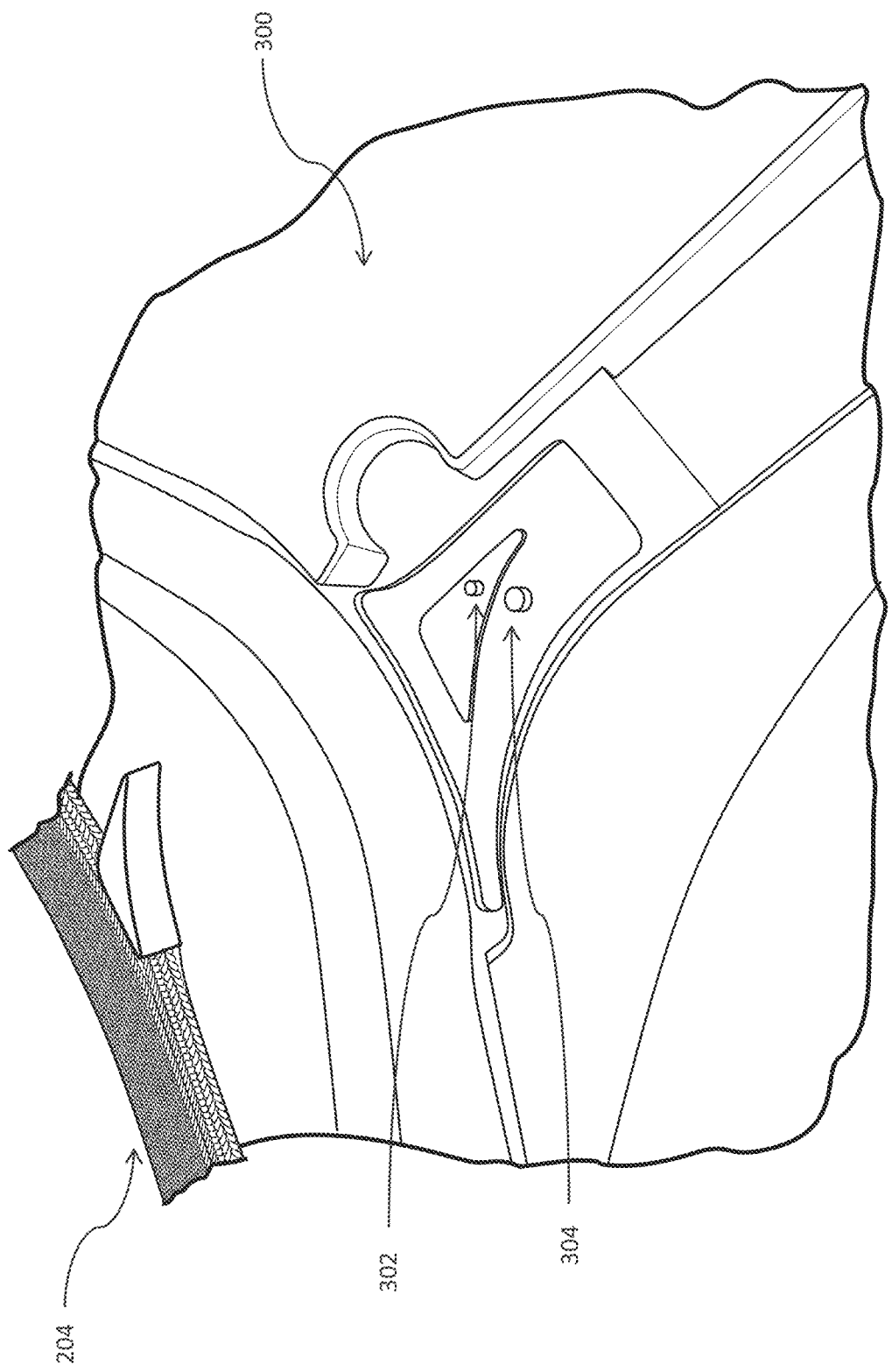
FIG. 9 shows part of an overmold tool for forming the joint between the halo strap and the side strap.
Figure 10:
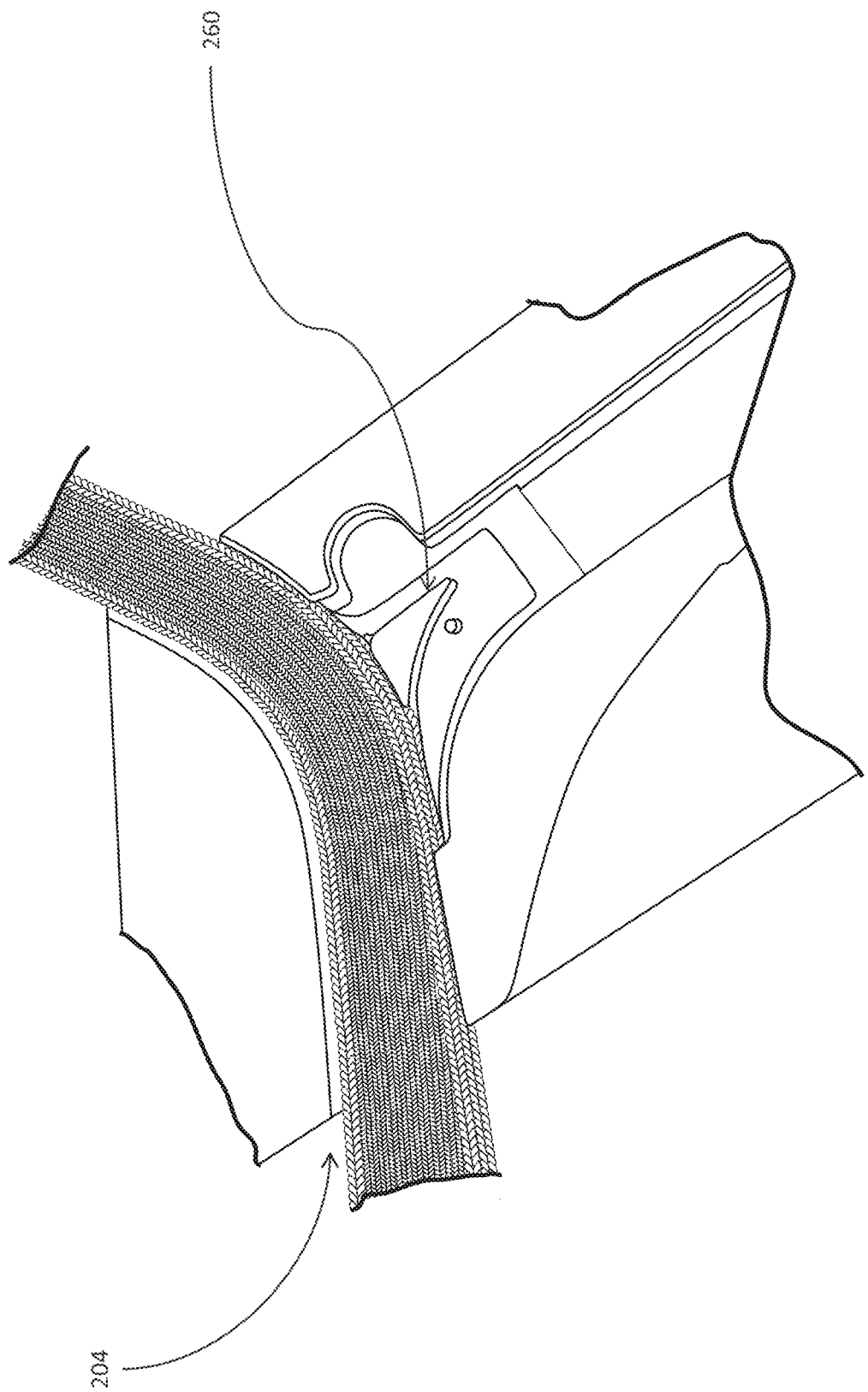
FIG. 10 shows the halo strap and burst through protrusion of FIG. 8 positioned in the overmold tool of FIG. 9.
Figure 14:
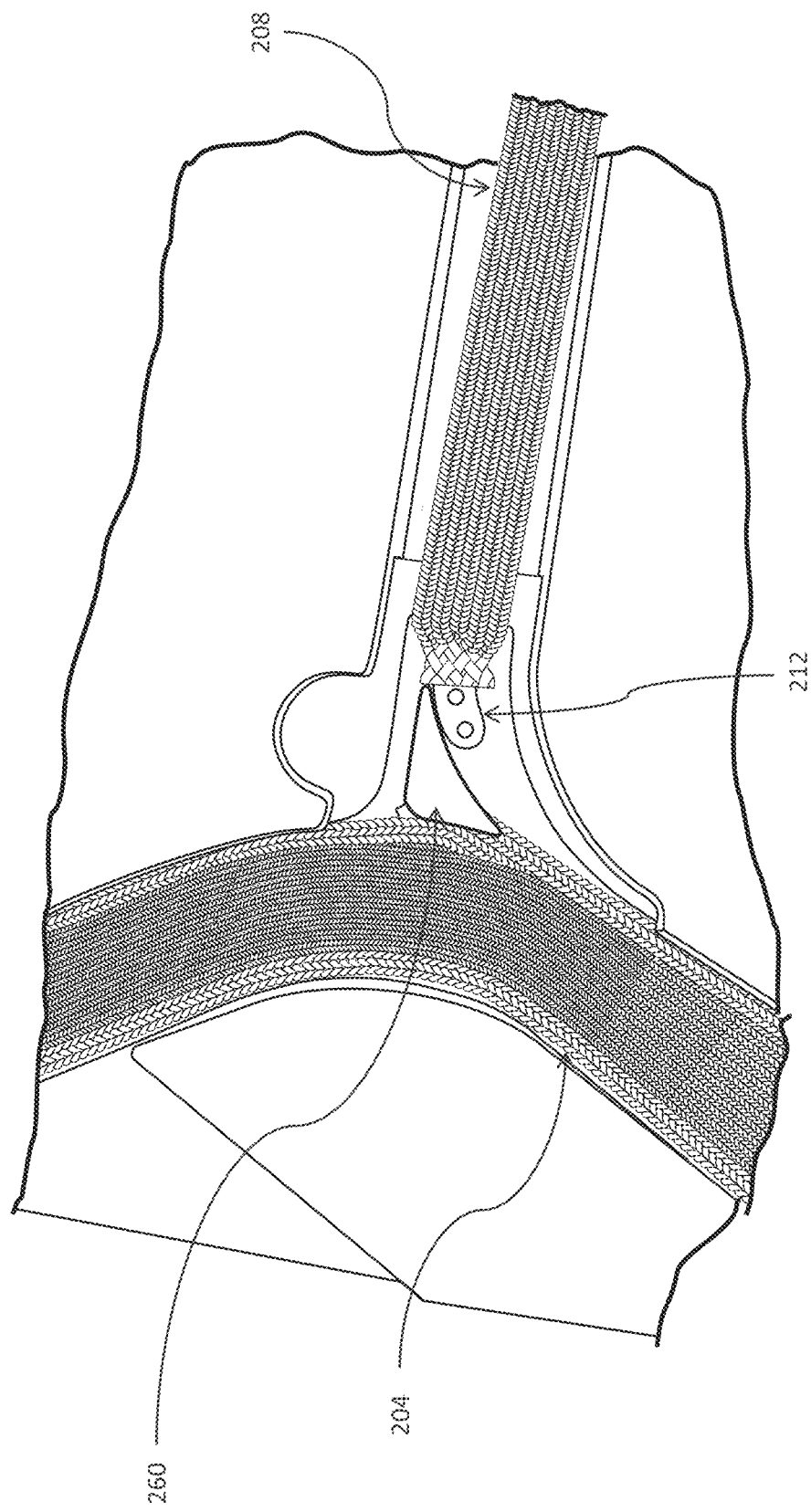
FIG. 14 shows the halo strap and side strap positioned in the overmold tool of FIG. 9.
Figure 15:
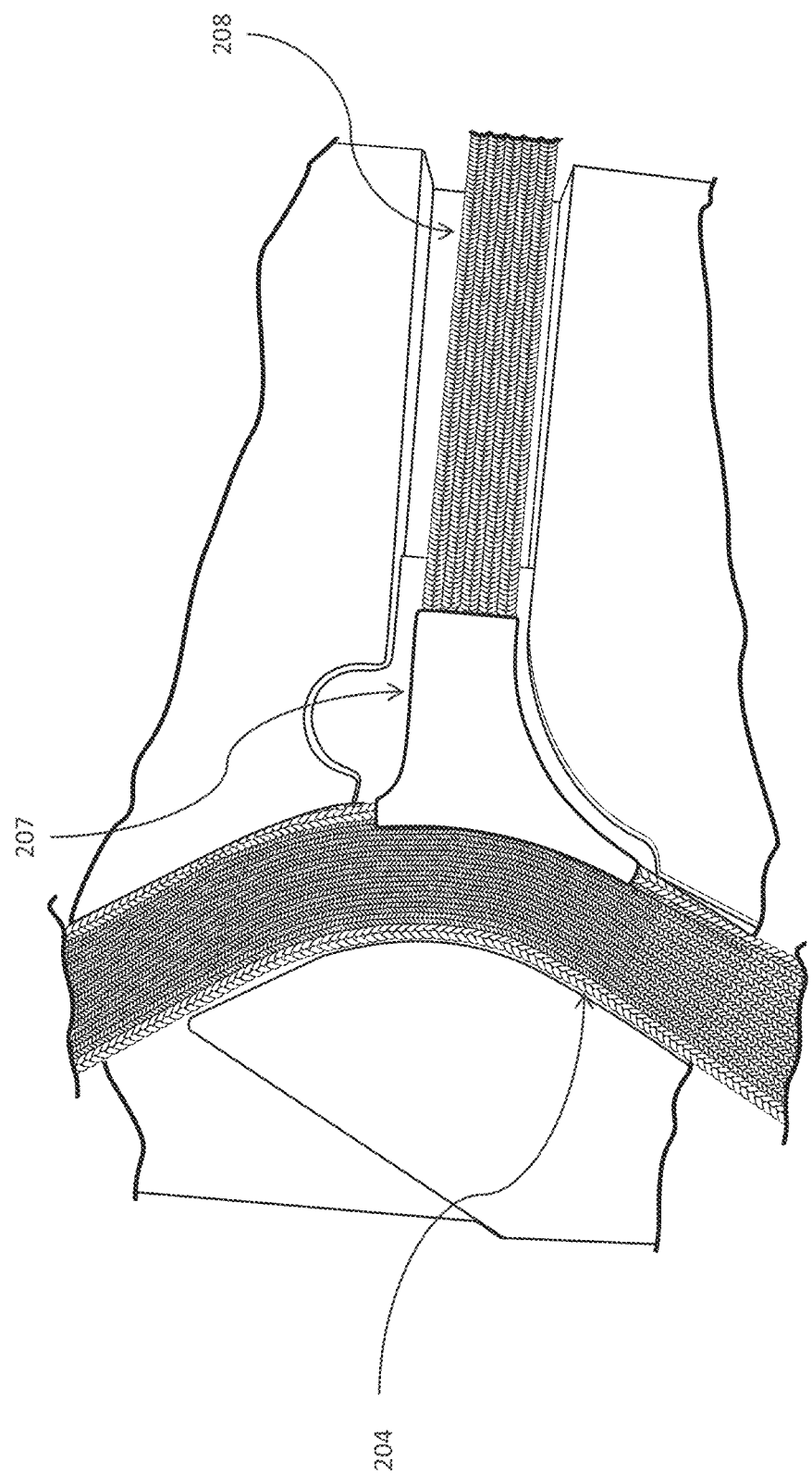
FIG. 15 shows the halo strap and side strap positioned in the overmold tool after overmolding to form the joint between the halo strap and the side strap.
Figure 16:
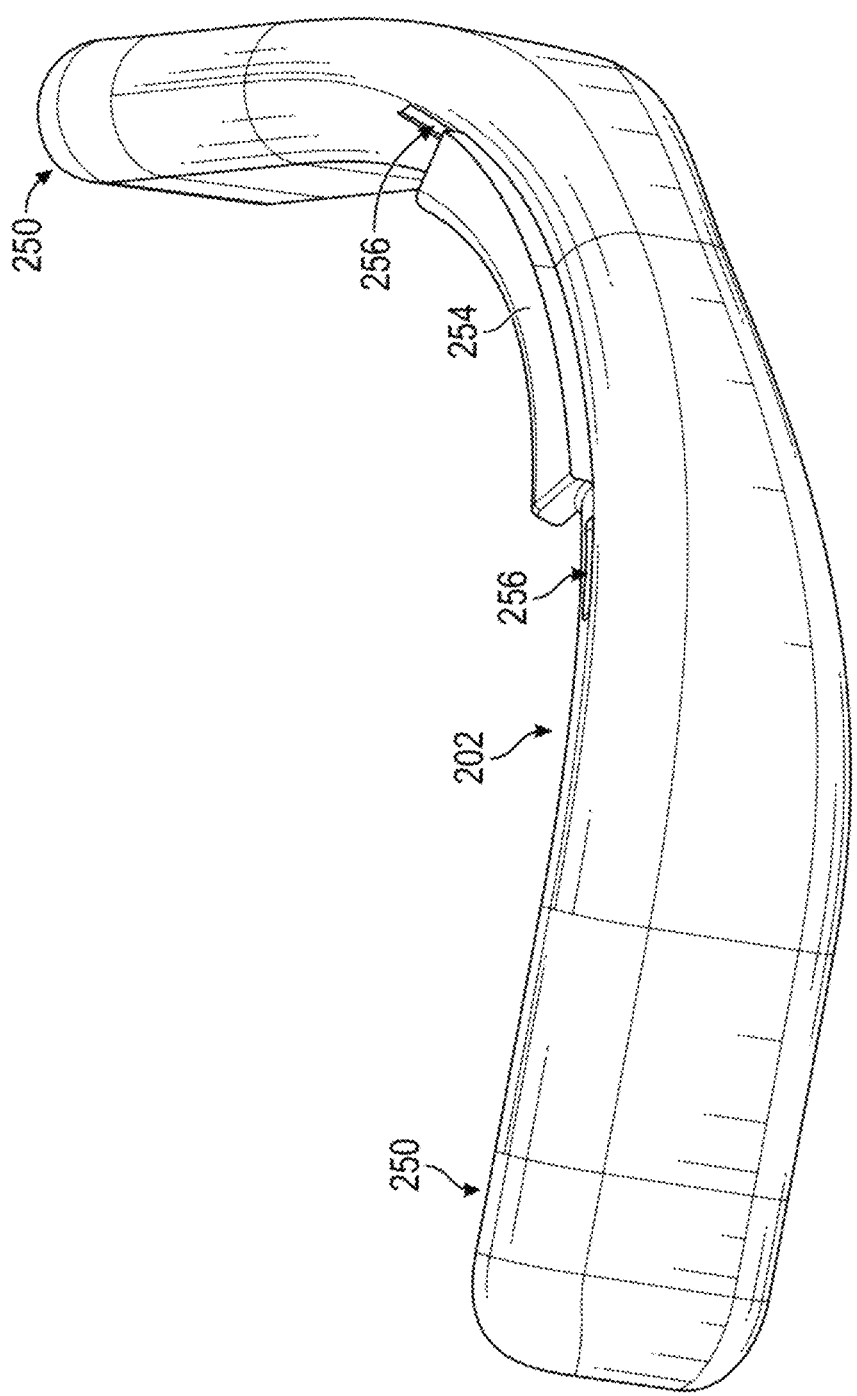
FIG. 16 is a perspective view of a yoke of the headgear assembly of FIG. 3.

As shown in FIG. 9, the overmold tool 300 includes two locating features 302, 304. A first locating feature 302 engages, interlocks with, or interacts with the locating feature 262 of the halo strap 204 as shown in FIGS. 10 and 14. The second locating feature 304 engages, interlocks with, or interacts with the locating feature 212 of the braid core 210 of the side strap 208 as shown in FIG. 14. With the halo strap 204 and side strap 208 properly positioned in the overmold tool 300, the burst through protrusion 260 and end portion of the braid core 210 of the side strap 208 including the locating feature 212 are overmolded to form the joint 207, as shown in FIG. 15. The overmold material of the joint 207 can cover the portion of the braided element 216 connected to the widened portion 214 of the braid core 210 as shown to further secure the braided element 216 to the braid core 210. Alternatively, the overmold material of the joint 207 can be the only or primary connection of the braided element 216 to the braid core 210. The overmold creates a permanent connection between the halo strap 204 and side strap 208 such that the two are not separable. As shown in FIGS. 6-7 and 15, the overmolded joint 207 is asymmetrical. A lower edge of the joint 207 (that is, an edge of the joint 207 positioned toward and facing the rear portion 206 of the halo strap 204 can be curved or contoured as shown to help guide the user to place the joint 207 above the user's ear. In the illustrated embodiment, the lower edge of the joint 207 is longer than an opposite, upper edge of the joint. The lower edge has a greater radius of curvature than the upper edge. An edge of the joint 207 extending along or adjacent the halo strap 204 extends further along the rear portion 206 of the halo strap 204 than it extends along the top portion 205.

The yoke 202 couples, e.g., removably couples, to the frame 106 in use. In the illustrated example, the yoke 202 has a curved or forward-facing convex profile. As shown in FIGS. 16-20, the yoke 202 includes a yoke locating feature 254. The yoke locating feature 254 is designed to align with corresponding feature(s) of the frame 106 to help guide and/or indicate correct alignment of the yoke 202 with the frame 106 in use. The interaction between the yoke locating feature 254 and corresponding feature(s) of the frame 106 can also or alternatively help secure the yoke 202 to the frame 106 by resisting relative lateral forces between the yoke 202 and frame 106. In the illustrated example, the yoke locating feature 254 extends along an upper rear surface or edge of the yoke 202. The yoke 202 can include connection recesses 256 that align and interact with corresponding yoke connection protrusions 160 (shown in FIGS. 21-25) on the frame 106 to removably connect the yoke 202 to the frame 106. In the illustrated example, the yoke 202 includes four connection recesses 256—two in a top or upper surface of the yoke 202 and two in a bottom or lower surface of the yoke 202. In the illustrated example, a distance between the connection recesses 256 in the upper surface of the yoke 202 is greater than a distance between the connection recesses 256 in the lower surface of the yoke 202.

Figure 17:
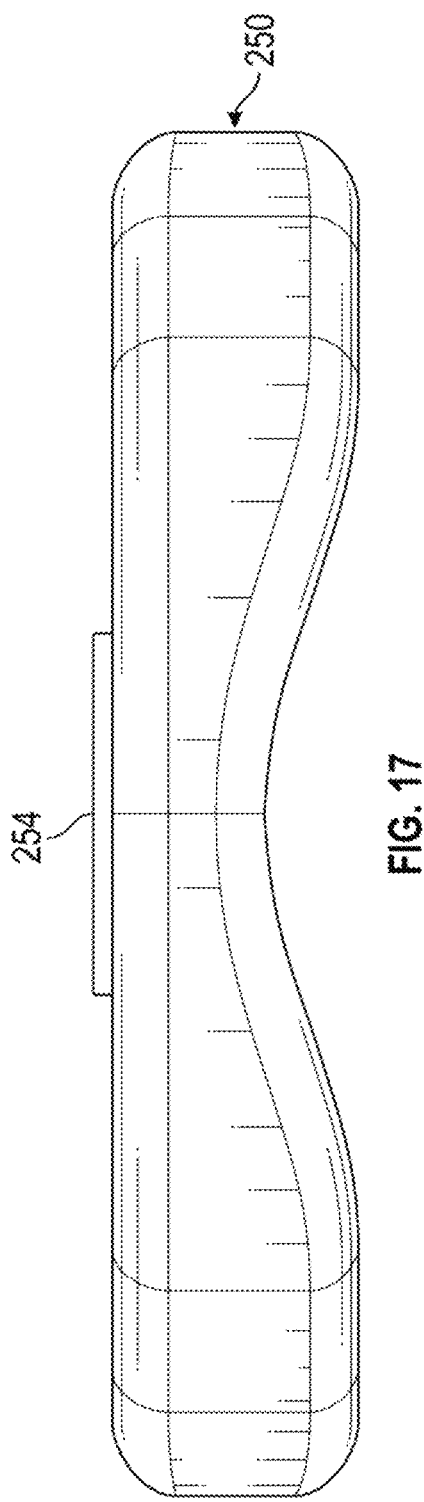
FIG. 17 is a front view of the yoke of FIG. 16.
Figure 18:
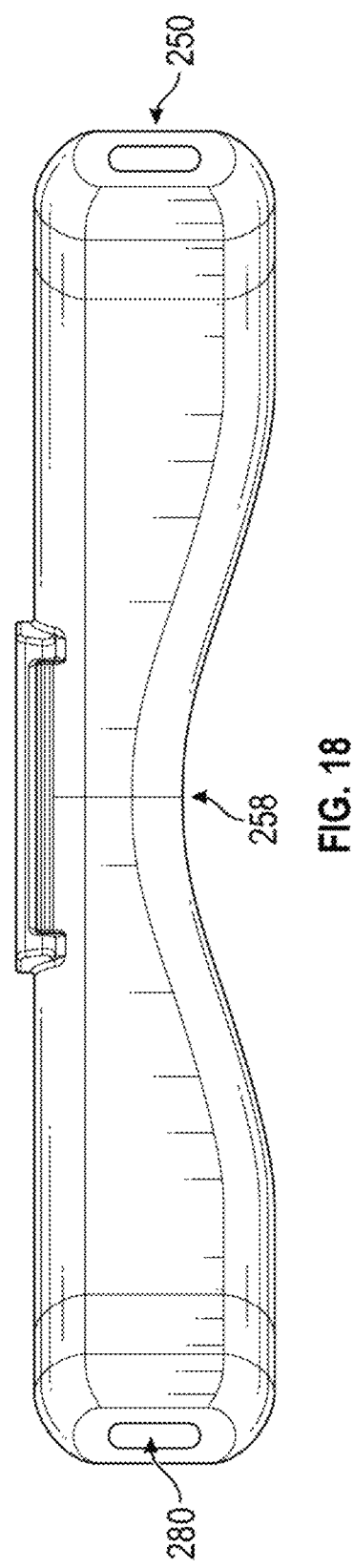
FIG. 18 is a rear view of the yoke of FIG. 16.
Figure 19:
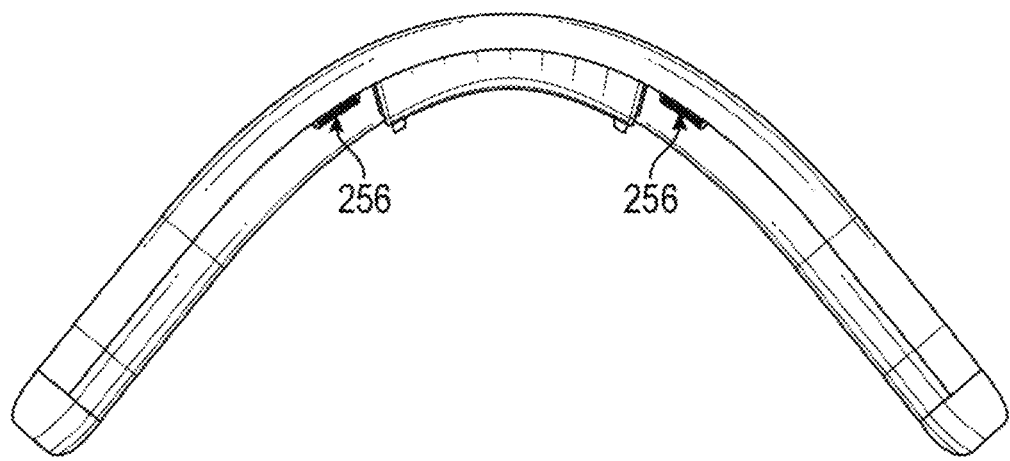
FIG. 19 is a top view of the yoke of FIG. 16.
Figure 20:
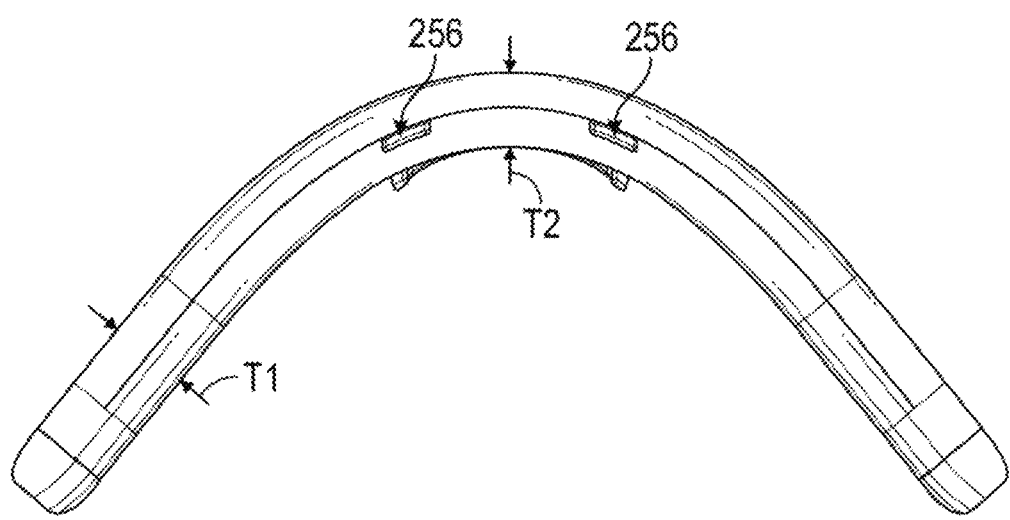
FIG. 20 is a bottom view of the yoke of FIG. 16.
Figure 21:
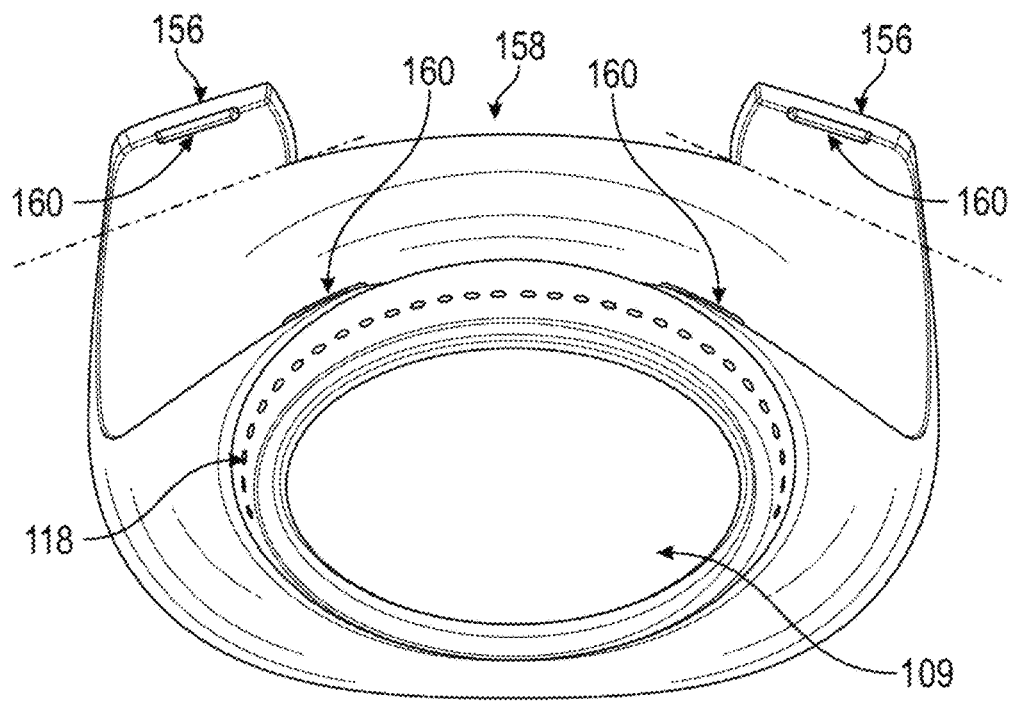
FIG. 21 is a front view of a frame of the mask assembly of FIG. 1.
Figure 22:
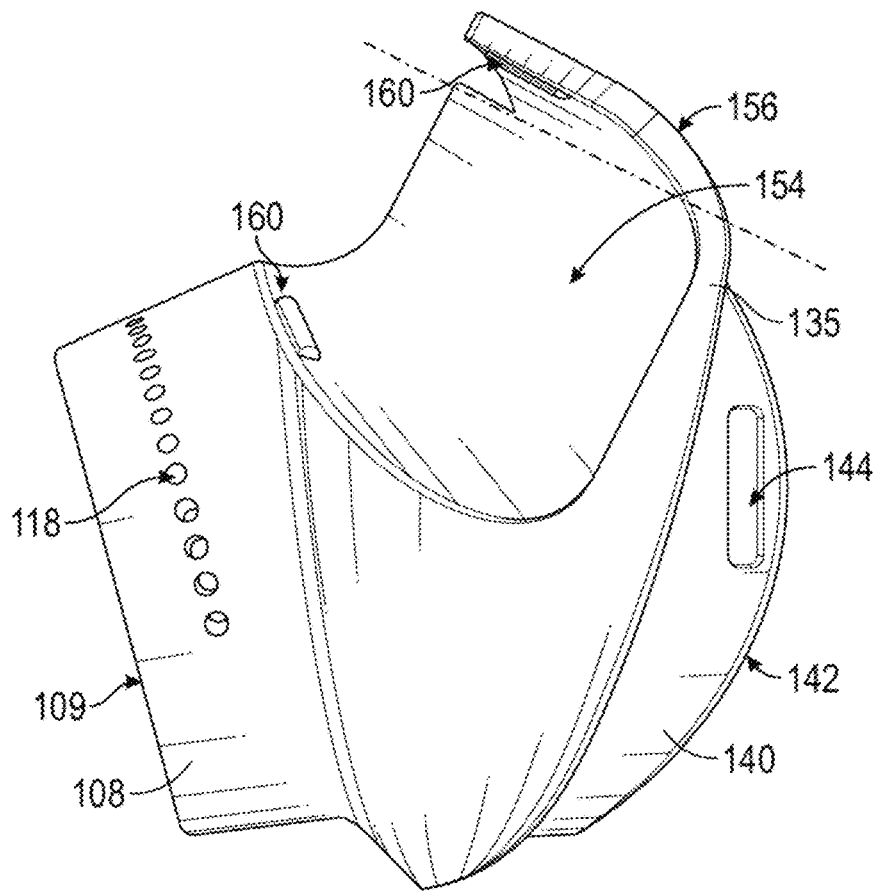
FIG. 22 is a side view of the frame of FIG. 21.
Figure 23:
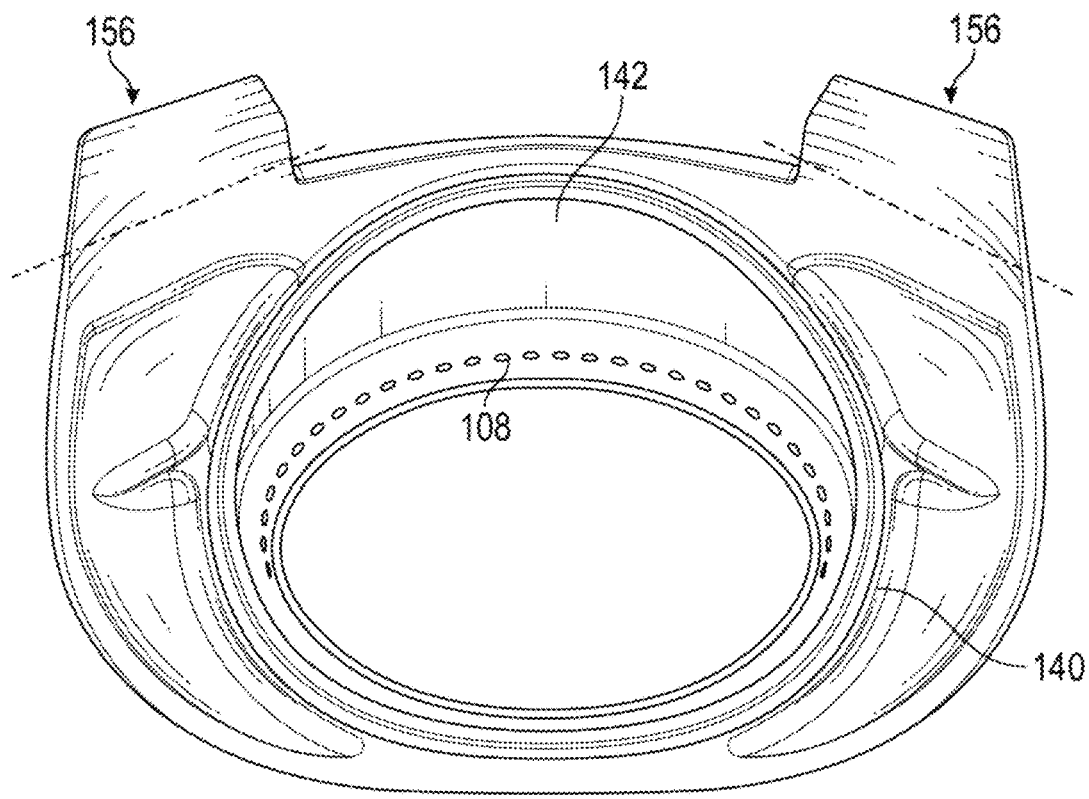
FIG. 23 is a rear view of the frame of FIG. 21.
Figure 24:
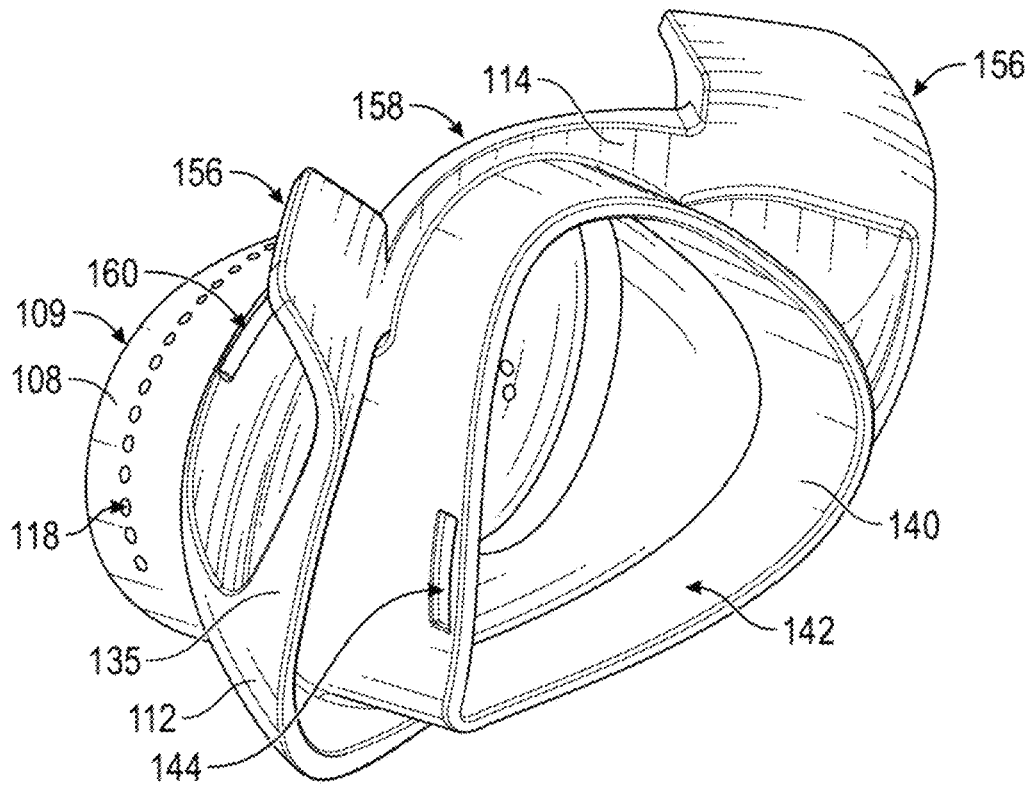
FIG. 24 is a rear perspective view of the frame of FIG. 21.
Figure 25:
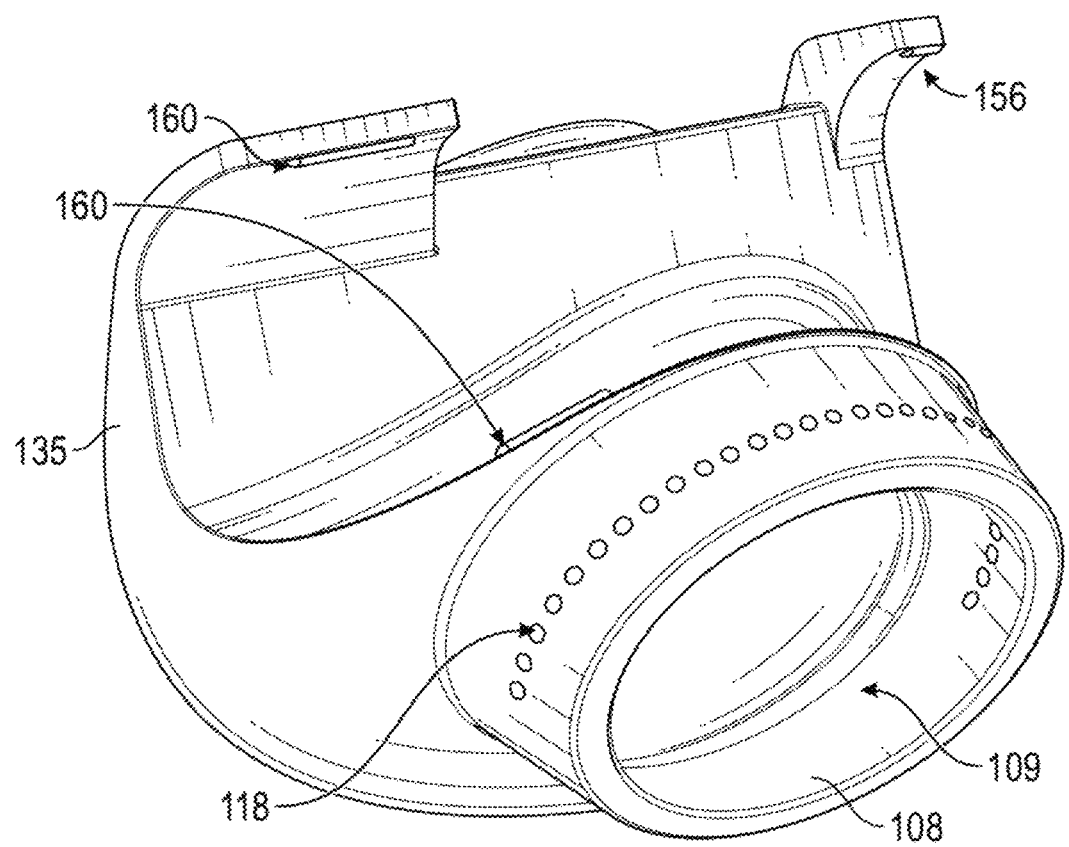
FIG. 25 is a front perspective view of the frame of FIG. 21.
Figure 26:
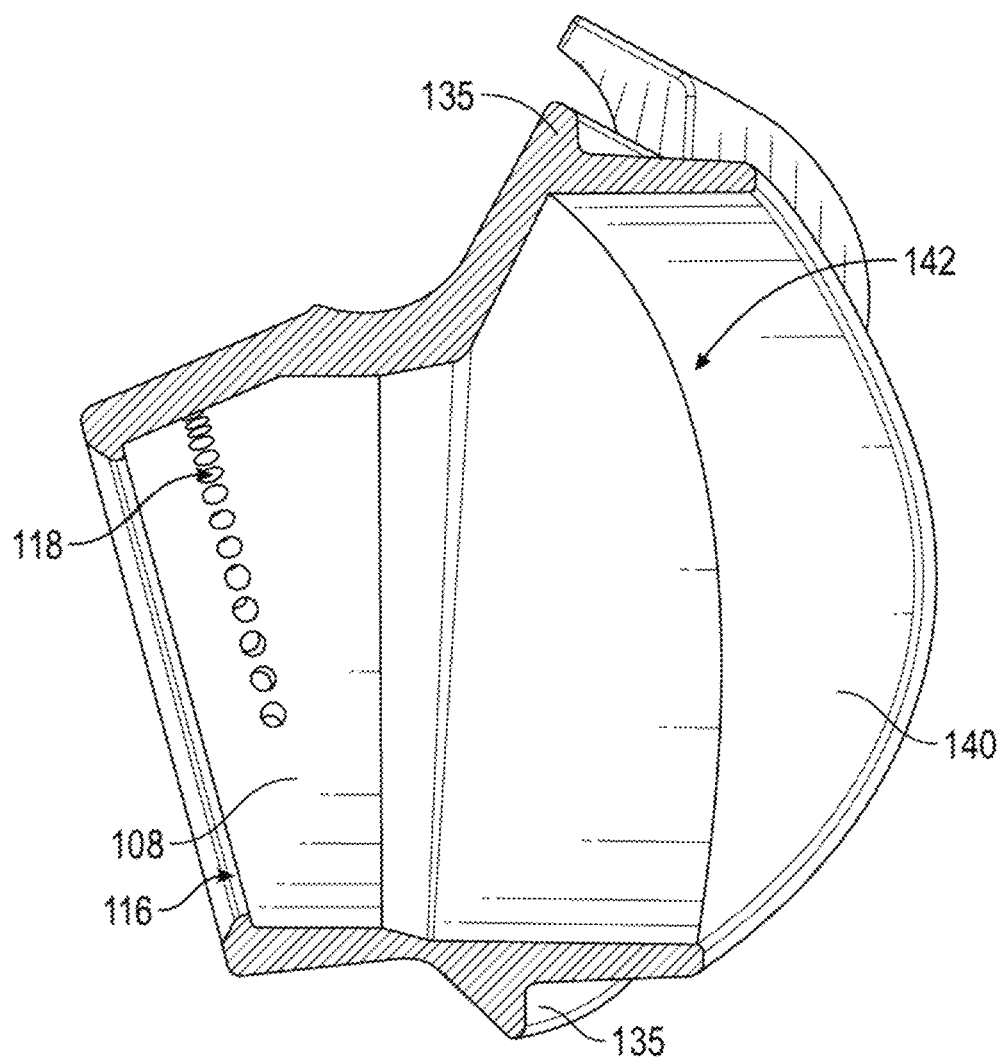
FIG. 26 is a side cross-sectional view of the frame of FIG. 21.

As shown in FIGS. 17 and 18, the bottom surface of the yoke 202 has a curved profile such that a central portion of the bottom surface is concave. In other words, the yoke 202 has a region of reduced height 258 in a central or mid-portion of the yoke 202 such that a height (measured from the top surface to the bottom surface) of the yoke 202 at a midline of the yoke 202 is less than a height of the yoke 202 at lateral ends of the yoke 202 (i.e., at and/or adjacent the end caps 250). The asymmetrical height of the yoke 202 can help indicate the correct orientation of the yoke 202 for connection to the frame 106 and/or provide aesthetic appeal. The region of reduced height 258 can also accommodate the frame 106, in particular, a portion of the frame 106 that connects to the gas delivery conduit 110. As shown in FIGS. 19-20, a thickness (measured from a front surface to a rear surface) of the yoke 202 is substantially uniform or constant across the length of the yoke 202 (measured from one lateral end to the other lateral end) such that a thickness T1 proximate the lateral ends is equal or approximately equal to a thickness T2 along a midline of the yoke 202.

As shown in FIGS. 21-26, the frame 106 includes a body 134 and a protruding or radial structure 135 extending from the body. The protruding structure 135 may be in the form of a flange, skirt, or wall, e.g., a surrounding wall, that can partially or completely circumferentially surround the frame body. The protruding structure 135 has a front surface 112 and a rear surface 114. The frame comprises an inlet collar 108 and an outlet collar 140. The inlet and outlet collars, at least in part, define the frame body. The inlet collar 108 protrudes from the front surface 112, and the outlet collar 140 protrudes from the rear surface 114. Thus, the wall 135 extends generally or substantially in a radial direction relative to the inlet collar 108 and/or the outlet collar 140. The inlet collar 108 defines an inlet aperture 109, and the outlet collar 140 defines an outlet aperture 142. In use, the conduit 110 is coupled to the inlet collar 108 and the seal 104 is coupled to the outlet collar 140. The inlet and outlet collars are in the form of tubes that are in fluid communication. Gases supplied by the conduit 110 to the frame 106 via the inlet aperture 109, pass through the frame 106 from the inlet collar 108 to the outlet collar 140, and are delivered to the seal 104 via the outlet aperture 142 to be delivered to the user. The inlet and outlet collars have different cross-sectional shapes. The inlet and outlet collars extend along respective longitudinal axis that are disposed at an angle to each other. The frame body is thus provided with a bent tube configuration. The front surface 112 includes a recessed region 154 extending in a lateral direction across the front surface 112. The recessed region 154 receives the yoke 202 when the yoke 202 is coupled to the frame 106. In the illustrated embodiment, the recessed region 154 is positioned above the inlet collar 108. The yoke 202 therefore contacts the frame 106 above the inlet collar 108 when the yoke 202 is coupled to the frame 106.

Figure 27:
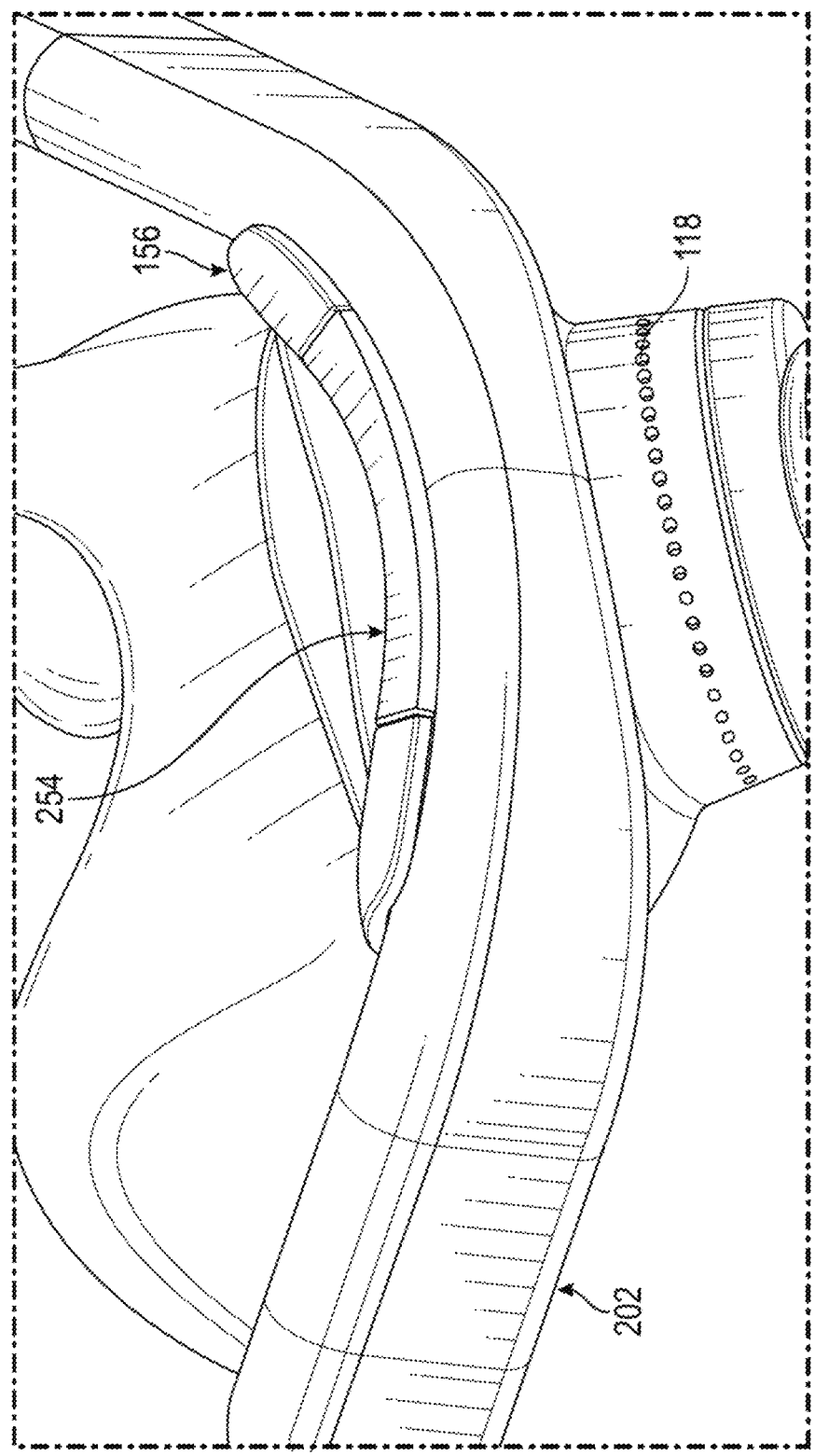
FIG. 27 is a front perspective view of a portion of the mask assembly of FIG. 1 showing connection of the yoke to the frame.

In the illustrated example, the frame 106 includes two clips or overhanging portions 156 formed as portions of the wall 135 that extend upward from the recessed region 154 and then curve forward to overhang the recessed region 154. The overhanging portions 156 form an upper boundary of the recessed region 154 that receives the yoke 202. To couple the yoke 202 to the frame 106, the yoke 202 can be clipped or snapped into the recessed region 154 horizontally, i.e., in a front to back direction. In some examples, to remove the yoke 202 from the frame 106, the yoke can be rolled or pivoted out of the recessed region 154 leading with the bottom edge of the yoke 202. Alternatively, the yoke 202 could be pivoted or pulled out of the recessed region 154 leading with one lateral end of the yoke 202. In the illustrated form, the overhanging portions 156 are separated by a gap 158. When the yoke 202 is received in the recessed region 154, the yoke locating feature 254 is received in the gap 158 as shown in FIG. 27. In some configurations, the yoke locating feature 254 is tightly received in the gap 158. This helps properly align the yoke 202 with the frame 106 and/or can help couple the yoke 202 to the frame 106. As shown, the yoke locating feature 254 and overhanging portions 156 are sized and shaped such that the yoke locating feature 254 is flush with the overhanging portions 156 along upper and/or rear and/or front surfaces of the yoke locating feature 254 and overhanging portions 156 when the yoke 202 is coupled to the frame 106. The overhanging portions 156 can help inhibit or restrict relatively lateral movement between the yoke 202 and the frame 106 due to the positioning of the yoke locating feature 254 in the gap 158.

Each overhanging portion 156 includes a yoke connection protrusion 160 protruding toward the recessed region 154 from a lower surface of the forwardly-curved portion of the overhanging portion 156. The frame 106 includes two additional yoke connection protrusions 160 extending into the recessed region 154 from a lower wall or boundary of the recessed region 154. When the yoke 202 is received in the recessed region 154, the yoke connection protrusions 160 of the frame 106 are received in the connection recesses 256 of the yoke 202. In the illustrated example, a distance between the yoke connecting protrusions 160 extending from the overhanging portions 156 is greater than a distance between the yoke connecting protrusions 160 extending from the lower wall of the recessed region 154. The spacing of the yoke connecting protrusions 160 extending from the overhanging portions 156 and the yoke connecting protrusions 160 extending from the lower wall of the recessed region 154 corresponds to the spacing between the connection recesses 256 in the top surface of the yoke 202 and the connection recesses 256 in the bottom surface of the yoke 202, respectively. The yoke connecting protrusions 160 of the overhanging portions 156 are received in the connection recesses 256 in the top surface of the yoke 202, and the yoke connecting protrusions 160 positioned along the lower wall or boundary of the recessed region 154 are received in the connection recesses 256 in the bottom surface of the yoke 202. Engagement of the yoke connecting protrusions 160 with the connection recesses 256 allows for a removable connection between the yoke 202 and the frame 106. In other examples, the frame, e.g., the overhanging portions 156 and lower wall of the recessed region 154, can include connection recesses and the yoke 202 can include connecting protrusions.

In the illustrated form, the inlet collar 108 extends from the front surface 112 at an angle downward rather than directly or perpendicularly outward. Such a configuration causes the conduit 110 to point somewhat downward (when the user's head is in an upright position) rather than directly outward, which can help reduce possible hose drag forces from the conduit 110 on the frame 106. Such a configuration can also or alternatively provide a less intrusive feel to the patient as the downward angle allows the conduit 110 to be somewhat out of the patient's sight in use. The inlet collar 108 includes a projection 116 that retains and/or allows for the connection of the conduit 110 to the inlet collar 108. In the illustrated example, the projection 116 projects inwardly from an inner surface of the inlet collar 108 proximate or adjacent an edge of the inlet collar 108 (i.e., an edge positioned away from the wall 135). The projection 116 can extend circumferentially around an entirety of the circumference of the inner surface, or can extend only partially around the circumference of the inner surface in one or more segments. The conduit 110 can be coupled, for example, irreversibly or permanently coupled, to the inlet collar 108 via or with the aid of the projection 116. The inlet collar 108 can include a plurality of bias vent holes 118. In the illustrated example, the plurality of bias vent holes 118 are arranged around the circumference of the inlet collar 108, but do not extend around the entire circumference of the inlet collar 108. The bias vent holes 118 may not extend around or may be omitted on the bottom of the inlet collar 108. This arrangement can help prevent or inhibit flow through the bias vent holes 118 from being directed toward the user; which can cause discomfort during use, due to the downward angle of the inlet collar 108 and therefore conduit 110.

The outlet collar 140 includes one or more connection features 144, such as recesses, that help connect and retain the seal 104 (or seal clip as described herein) to the outlet collar 140. The seal 104 or seal clip can couple to the outlet collar 140 via the connection features 144 and/or an interference fit. As the seal 104 or seal clip is pushed onto the outlet collar 140, the wall 135 acts as a stop for the seal 104 or seal clip and indicates to the user, e.g., by providing tactile and/or visual cues, that the seal 104 or seal clip has been fully coupled to the frame 106.

Figure 29:
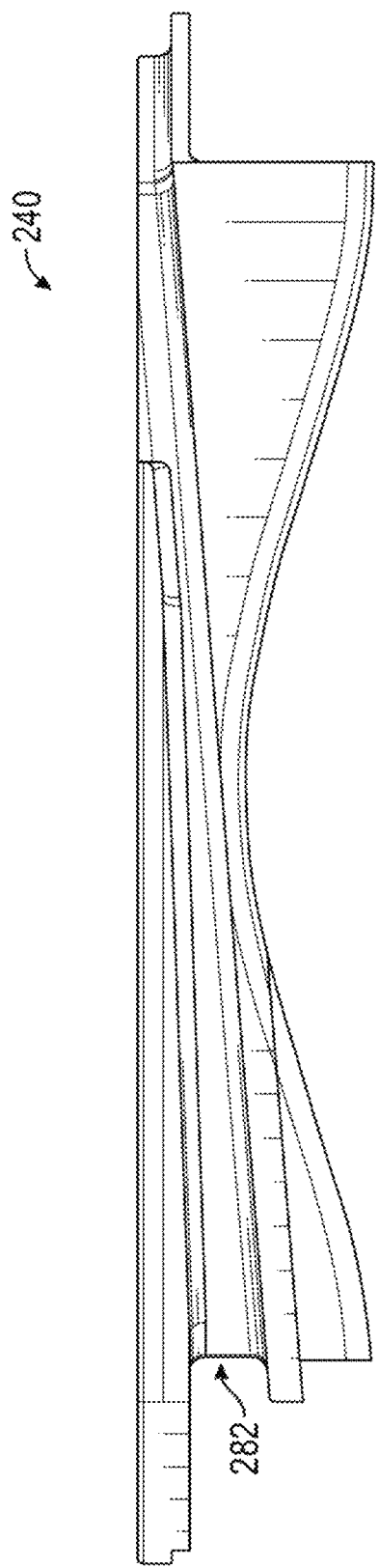
FIG. 29 is a front view of a filament divider insert of the yoke of FIG. 16.
Figure 30:
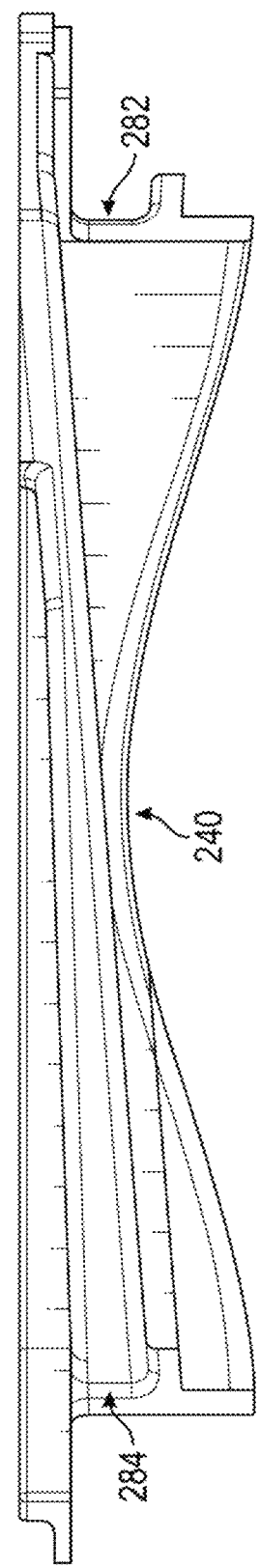
FIG. 30 is a rear view of the filament divider insert of FIG. 29.
Figure 31:
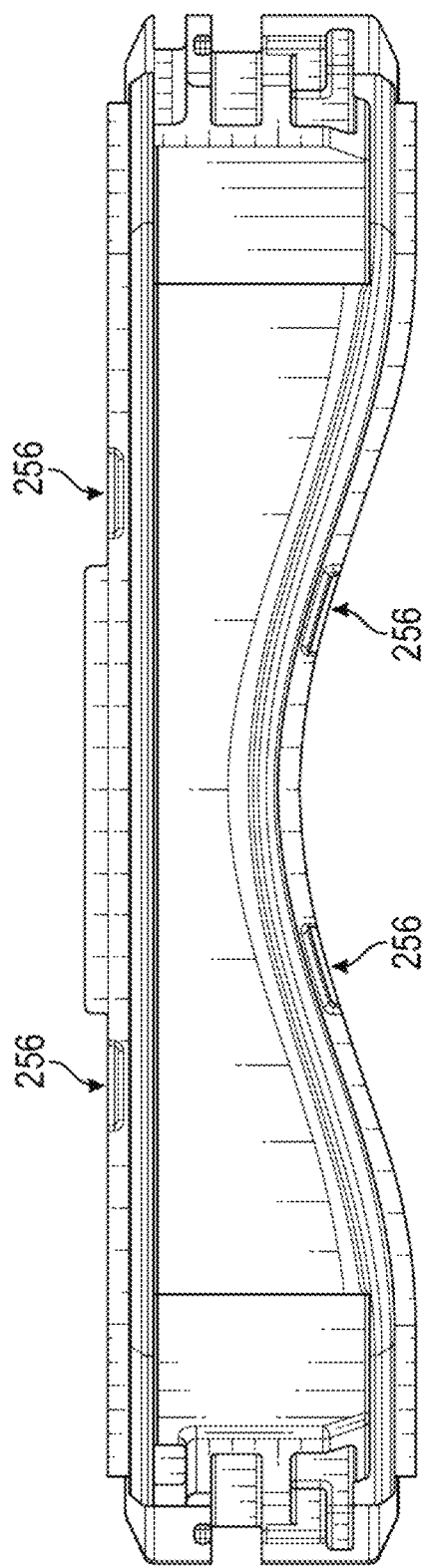
FIG. 31 is a front view of a yoke back of the yoke of FIG. 16.
Figure 32:
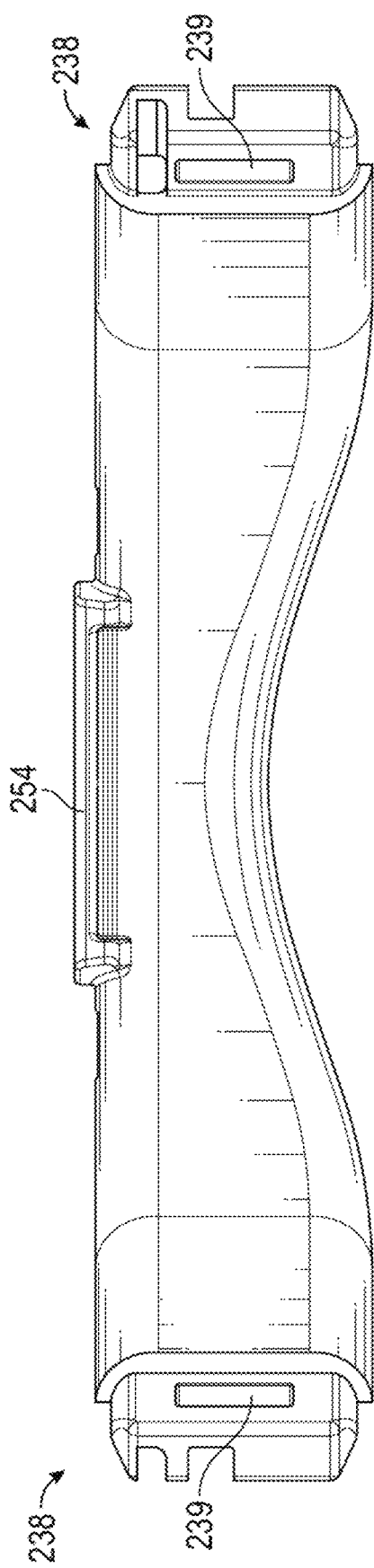
FIG. 32 is a rear view of the yoke back of FIG. 31.
Figure 33:
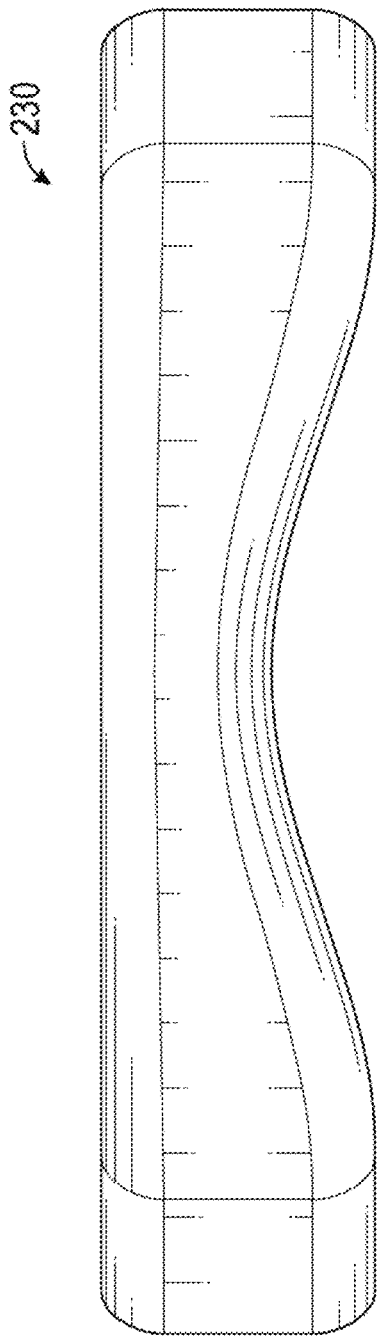
FIG. 33 is a front view of a yoke front of the yoke of FIG. 16.
Figure 36:
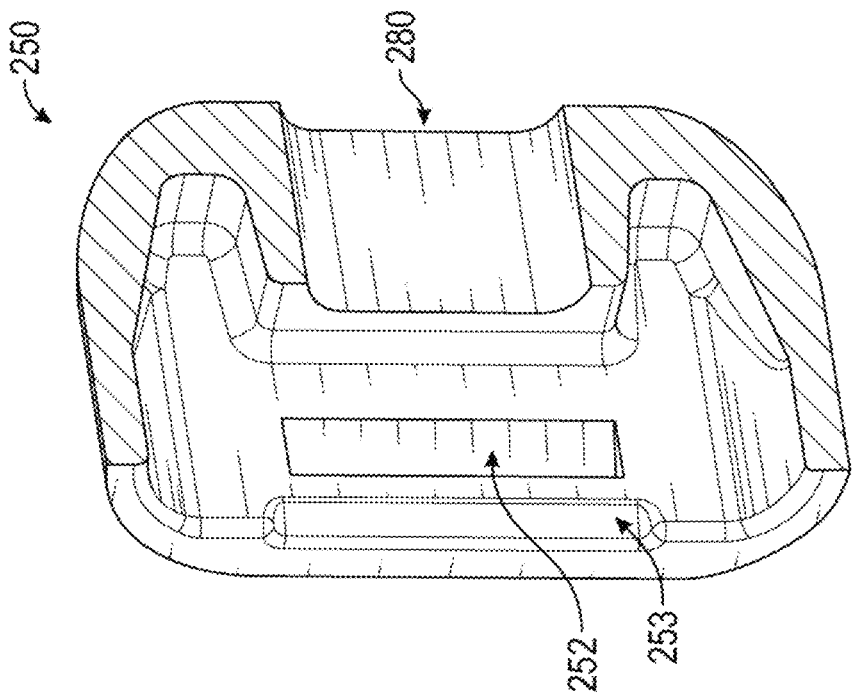
FIG. 36 is a cross sectional view of the end cap of FIG. 35.
Figure 37:
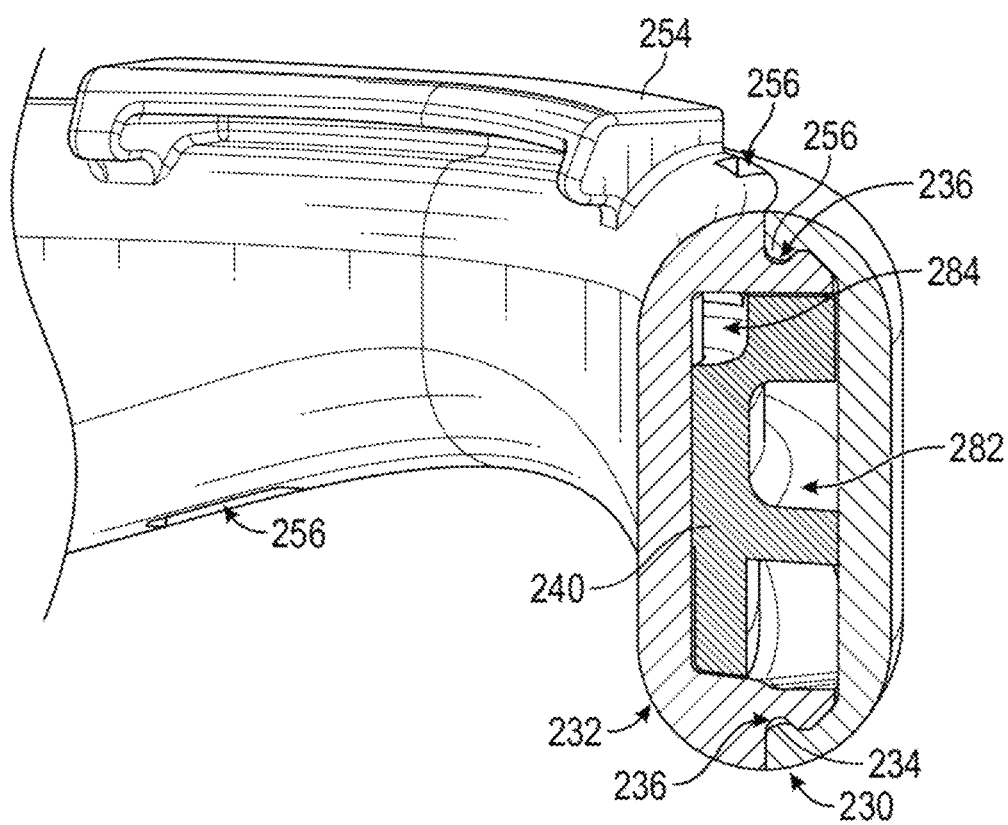
FIG. 37 is a cross sectional view of the yoke of FIG. 16.
Figure 38:
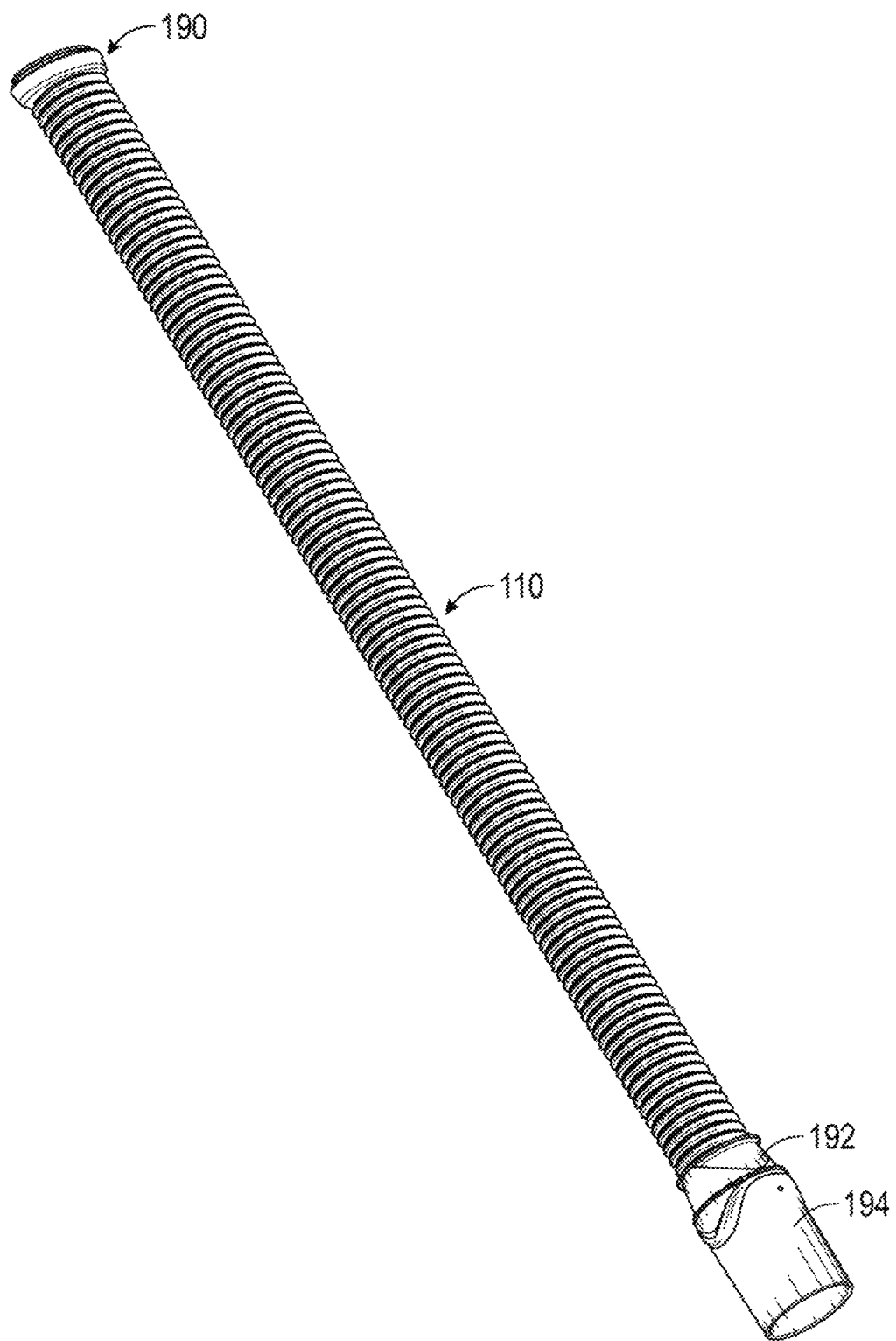
FIG. 38 is a perspective view of a conduit of the mask assembly of FIG. 1.
Figure 39:
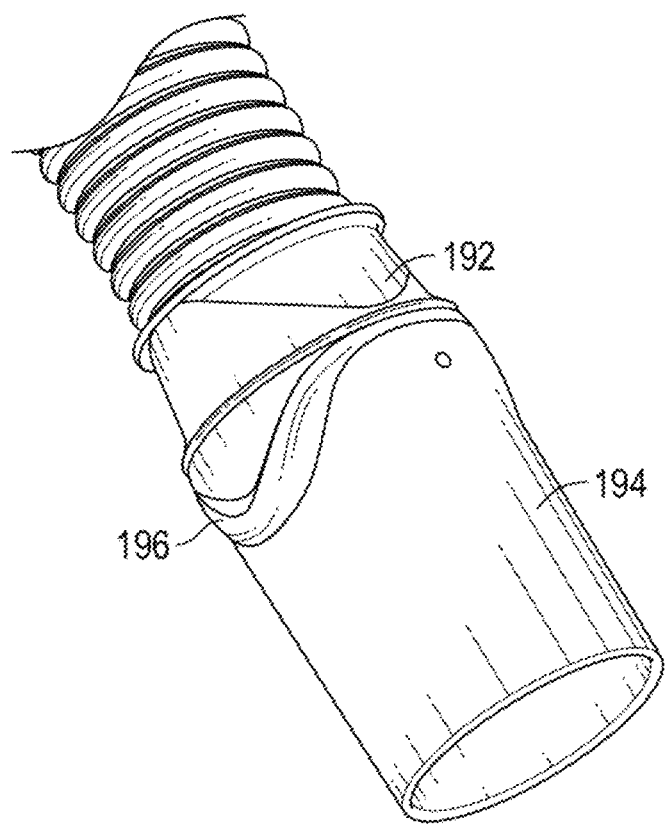
FIG. 39 is a perspective view of a swivel connector of the conduit of FIG. 38.

As described herein, the yoke 202 couples the headgear 200 to the frame 106 and can serve as a collector or housing for filaments 220 of an automatically adjustable headgear system. As shown in FIGS. 28-37, the yoke 202 includes a yoke front 230, a yoke back 232, a filament divider insert 240, two washer housings 270, and two end caps 250, one at each lateral end of the yoke 202. The yoke front 230 and yoke back 232 can have a generally C-shaped cross-section with the yoke front 230 being rearwardly-facing concave and the yoke back 232 being forwardly-facing concave, for example as shown in FIG. 37, to create a space therebetween when coupled. In the illustrated example, the lateral ends of the yoke back 232 include or are formed by end cap inserts 238. Each end cap insert 238 includes an end cap connection protrusion 239 protruding from a rear surface of the end cap insert 238 as shown in FIG. 32. In the illustrated example, the yoke rear 232 includes the yoke locating feature 254 and the connection recesses 256 as shown in FIGS. 31-32.

Figure 34:
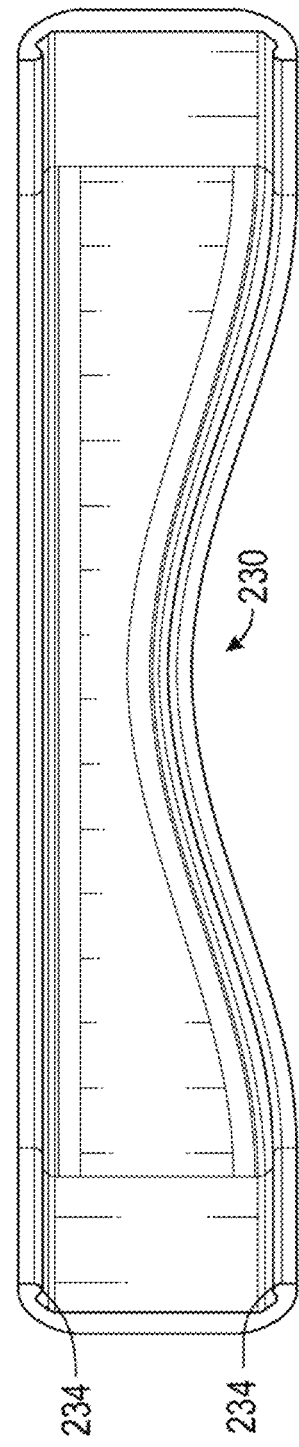
FIG. 34 is a rear view of the yoke front of FIG. 33.

The yoke front 230 and yoke back 232 can be coupled together, for example, via an interference fit or snap fit. In the illustrated example, the yoke front 230 includes a protrusion 234 protruding downward from an inner surface of an upper wall of the yoke front 230 and a protrusion 234 protruding upward from an inner surface of a lower wall of the yoke front 230, as shown in FIG. 34. The protrusions 234 can extend along a portion of or an entire length of the yoke front 230. The yoke back 232 includes a recess 236 in an outer surface of an upper wall of the yoke back 232 and a recess 236 in an outer surface of a lower wall of the yoke back 232, as shown in FIG. 37. As also shown in FIG. 37, when the yoke front 230 and yoke back 232 are coupled together, the protrusions 234 of the yoke front 230 are received in the recesses 236 of the yoke back 232 to secure the yoke front 230 and yoke back 232 together.

Each washer housing 270 houses one or more washers 272, as shown in FIGS. 28B, 28C, 28D, and 28E, that act as part of a locking mechanism for the automatically adjustable headgear system. The filament 220 extends through the washer(s) 272 as shown. The washers 272 may be the same (FIGS. 28D and E) or different (FIG. 28C). When the washers 272 are in the position illustrated in solid lines with an axis of the washer apertures aligned or more closely aligned with a longitudinal axis of the filament 220, the filament 220 is able to move through the apertures of the washers 272 with a relatively low amount of resistance in a direction from right to left in FIG. 28C, D, or E or in a direction tending to reduce a circumference of the associated headgear or a length of a portion of the headgear. This can be referred to as a released or unlocked position of the washers 272 or the directional lock. In response to movement of the filament 220 in the opposite direction (left to right in FIG. 28C, D, or E or in a direction tending to increase the circumference of the associated headgear or length of a portion of the headgear), the washers 272 move with the filament 220 to or toward a position shown in dashed lines in which the resistance to movement is relative greater than the released position as a result of frictional contact between the washers 272 and the filament 220. This can be referred to as a locked position of the washers 272 or the directional lock. Preferably, the resistance to movement of the filament 220 in the locked position is sufficient to resist blow-off forces created by the pressurized gas within the interface for a given therapy taking into account the overall arrangement of the headgear (e.g., the number of directional locks employed). Other variations of the illustrated directional lock or other types of directional locks could also be employed. An example of such locking mechanisms are shown and described in PCT Publication No. WO2017/158544 and U.S. Publication No. 2016/0082217, the entireties of which are incorporated by reference herein.

Figure 35:
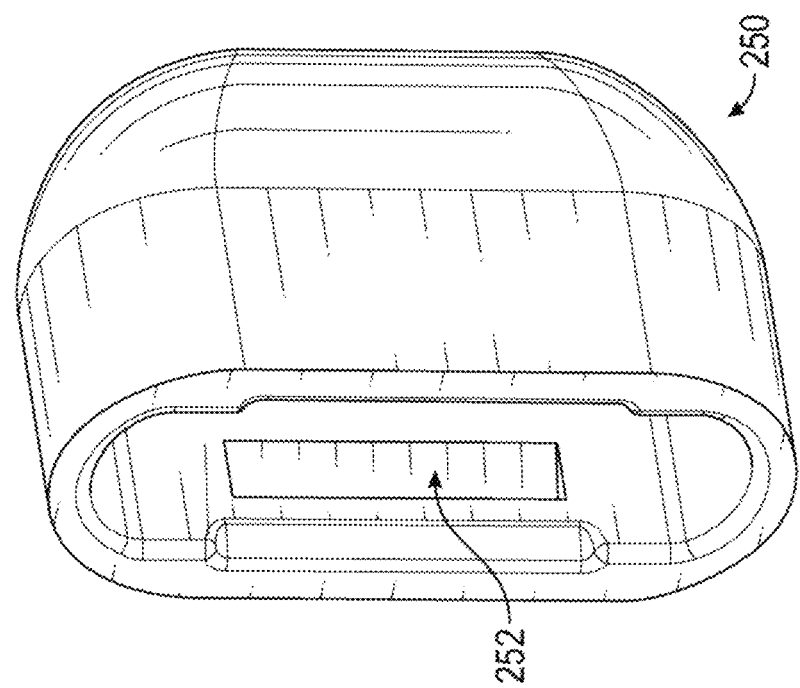
FIG. 35 is a perspective view of an end cap of the yoke of FIG. 16.

The end caps 250 can help secure the yoke front 230 and yoke back 232 together, couple the side straps 208 to the yoke 202, and/or provide an entrance for the filaments 220 into the yoke 202. As shown in FIGS. 35-36, an inner surface of a rear wall of each end cap 250 includes a connection recess 252. The connection recess 252 receives the end cap connection protrusion 239 when the end cap 250 is coupled to the end cap insert 238 to help secure the end cap 250 to the end cap insert 238. A medial edge (that is, an edge of the end cap 250 positioned medially relative to a remainder of the end cap 250 when the end cap 250 is coupled to the yoke front 230 and/or yoke back 232) of the rear wall of each end cap 250 can include a recessed leading edge 253 to help guide the end cap 250 into place such that the connection recess 252 receives the end cap connection protrusion 239 of the end cap insert 238. In the illustrated embodiment, the recessed leading edge 253 is positioned along a corner between the medial edge and the inner surface of the rear wall of the end cap 250. A lateral end or wall (that is, an end or wall of the end cap 250 that forms a lateral end of the yoke 202 when the end cap 250 is coupled to the yoke 202) of each end cap 250 includes an aperture 280 as shown in FIG. 36. Each aperture 280 receives one of the filaments 220 to allow the filament 220 to pass from the side strap 208, through the end cap 250, and into the yoke 202.

To assemble the yoke 202, the filament divider insert 240 and two washer housings 270 are disposed in the yoke back 232, and the yoke front 230 is coupled to the yoke back 232. Each end cap 250 can be coupled to one of the end cap inserts 238. When the yoke front 230 and yoke back 232 are coupled together, the filament divider insert 240 and two washer housings 270 are disposed and secured between the yoke front 230 and the yoke back 232.

A filament 220 from each side strap 208 extends into the yoke 202 such that there are two filaments 220 passing through the yoke 202. The filament divider insert 240 separates the interior of the yoke 202 to create separate line paths for the two filaments 220. As shown in FIGS. 29-30, a first line path 282 is at least partially defined by a front of the filament divider insert 240 and the yoke front 230, and a second line path 284 is at least partially defined by a rear of the filament divider insert 240 and the yoke back 232. One filament 220 therefore resides in the first line path 282 in front of the filament divider insert 240, and the other filament 220 resides in the second line path 284 behind the filament divider insert 240. A first filament 220 passes through a first of the end caps 250 and washer(s) in a first of the washer housings 270 into the first line path 282. A second filament 220 passes through a second of the end caps 250 and washer(s) in a second of the washer housings 270 into the second line path 284.

As shown in FIGS. 29-39, the first and second line paths 282, 284 have greater heights or widths at the end at which the filament 220 enters the line path. This can advantageously help prevent or inhibit sharp bends from forming in the filament 220 immediately or soon after the filament 220 exits the washer housing 270, which can help the washer(s) properly engage with the filament 220. This can also or alternatively help prevent or inhibit the filament 220 from getting caught on internal geometry of the yoke 202 during retraction of the filament 220 and headgear.

Figure 28:
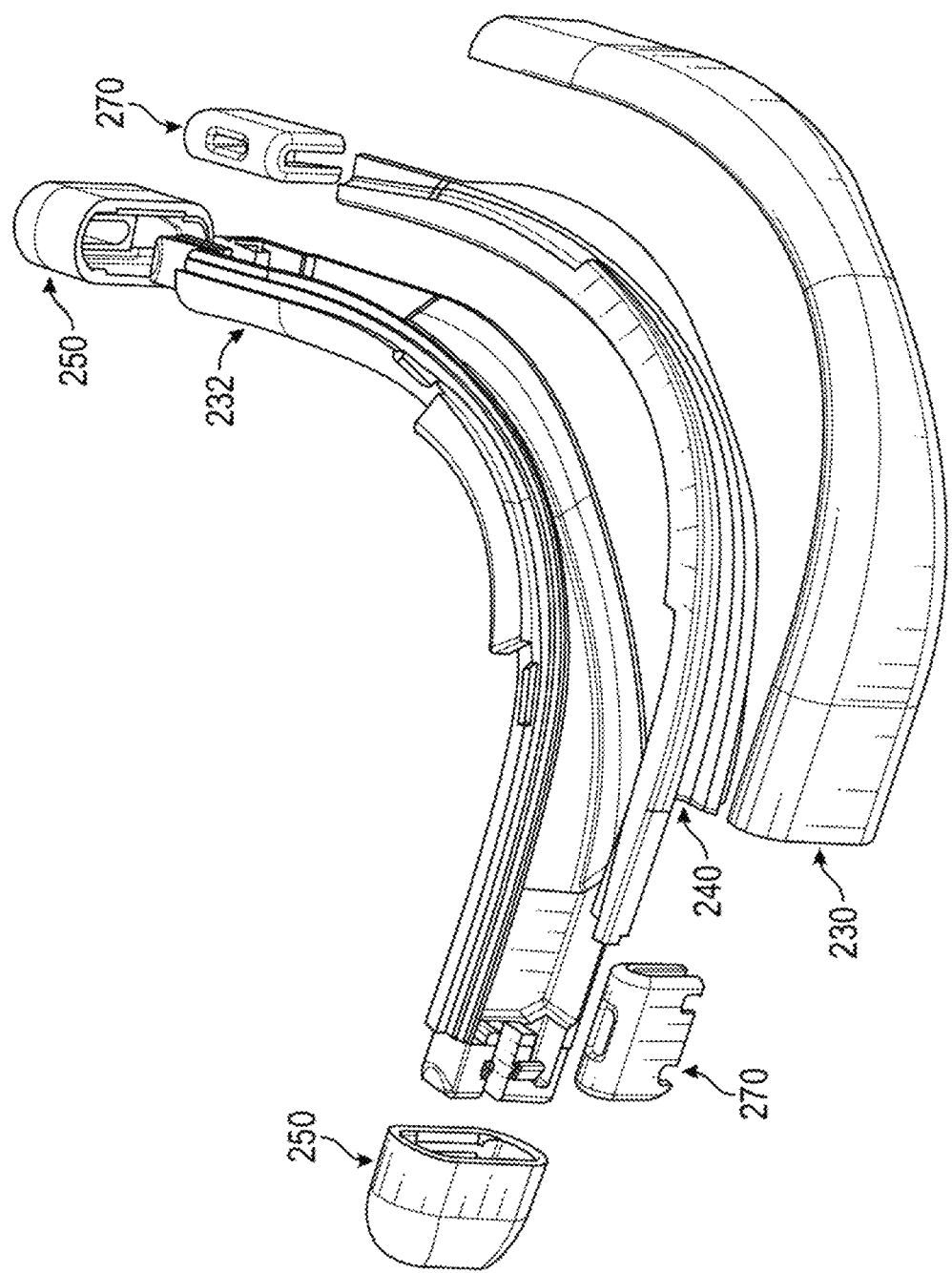
FIG. 28 is an exploded view of the yoke of FIG. 16.

The separated line paths prevent or inhibit interference between the two filaments 220. Because the line paths 282, 284 are separated in a front to back direction, both washer housings 270 and the washers housed therein can be oriented in the same direction, as shown in FIG. 28. Orienting the washer housings 270 and washers in the same direction advantageously helps provide consistency between the operation of the two side straps 208. If the line paths were not separated in a front to back direction and both washer housings 270 were oriented in the same direction, the two filaments 220 could interfere with each other and cause, for example, bucking, jamming, and/or tangling, which could inhibit smooth operation of the automatically adjustable headgear mechanism. Orienting the washer housings 270 and washers opposite each other (e.g., one upside down with respect to the other), which can allow the line paths to be separated in a top to bottom direction, could cause uneven operation and/or wear between the side straps 208 and/or directional locks.

Figure 42:
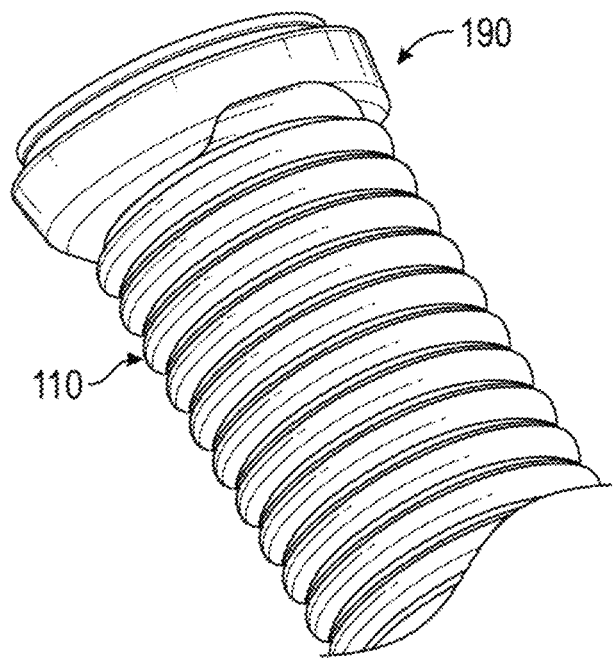
FIG. 42 is a perspective view of a conduit frame connector of the conduit of FIG. 38.

FIGS. 38-42 show an example embodiment of a conduit 110 that can be coupled to the frame 106. A conduit frame connector 190 is coupled, e.g., overmolded, to a first end of the conduit 110 as shown in FIG. 42. The conduit frame connector 190 couples, e.g., permanently couples, the conduit 110 to the frame 106. The conduit frame connector 190 can couple to the frame 106 via an interference fit. A swivel connector 192 is coupled, e.g., overmolded, to a second, opposite end of the conduit 110. The swivel connector 192 couples the conduit 110 to a swivel 194 that allows for rotatable and removable connection to a CPAP hose or other gas supply tube. In the illustrated example, the swivel connector 192 includes an enlarged ring 191 and a protrusion 193 extending distally (away from the conduit 110) from the enlarged ring 191. The swivel 194 is coupled to the protrusion 193. The swivel 194 can be coupled to the swivel connector 192 by pushing the swivel 194 onto the protrusion 193 until the swivel 194 abuts the enlarged ring 191.

Figure 40:
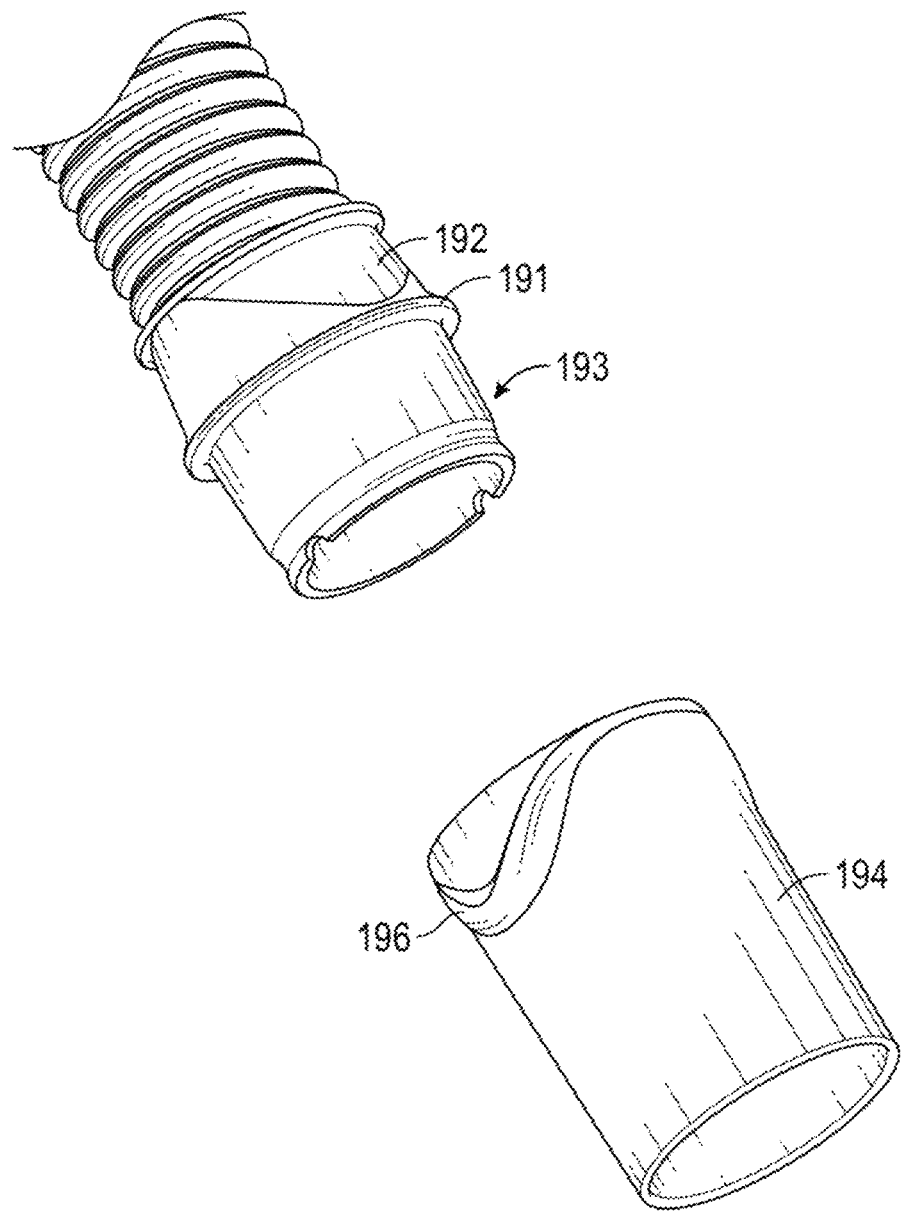
FIG. 40 is an exploded view of the swivel connector of FIG. 39.
Figure 41:
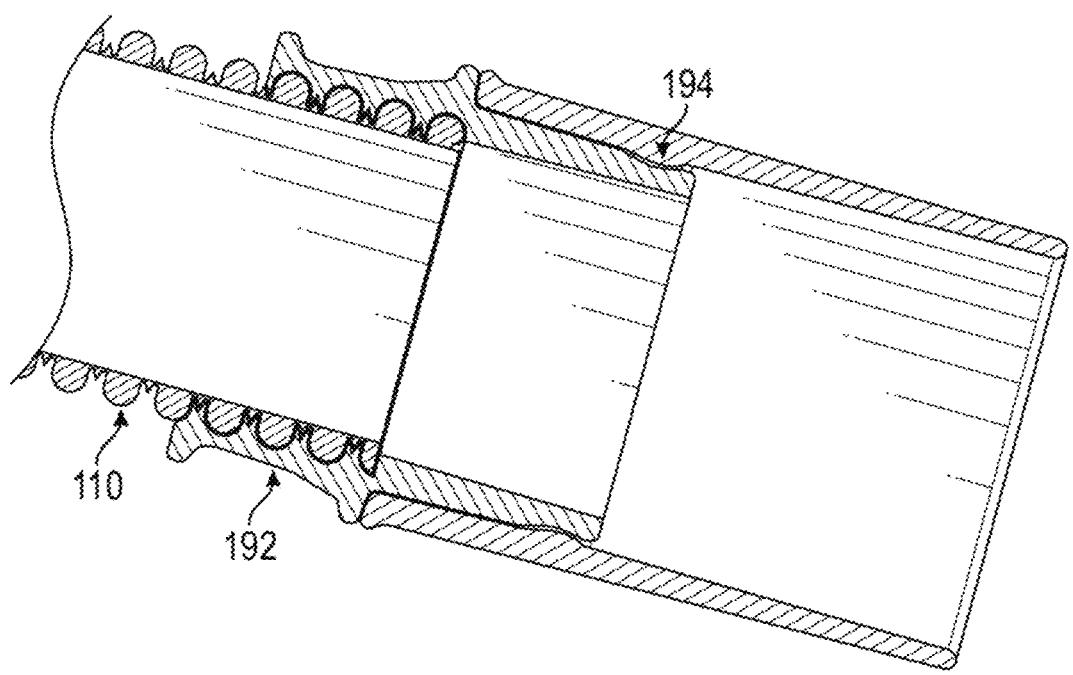
FIG. 41 is a cross-sectional view of the swivel connector of FIG. 39.

The swivel 194 can at least partially decouple the CPAP hose or other gas supply tube from the frame 106 and seal 104. As shown in FIG. 40, the swivel 194 can be separated from the swivel connector 192 and conduit 110 to detach the frame 106 and seal 104 from the CPAP hose or gas supply tube. The swivel 194 can include grips 196, e.g., scalloped protrusions, to provide the user with improved grip and/or tactile feedback as to where to grip the swivel 196 to separate the swivel 196 from the swivel connector 192 and conduit 110. The swivel 194 can pivot relative to the swivel connector 192, which can help decouple forces on the CPAP hose or gas supply tube from the conduit 110.

Figure 51:
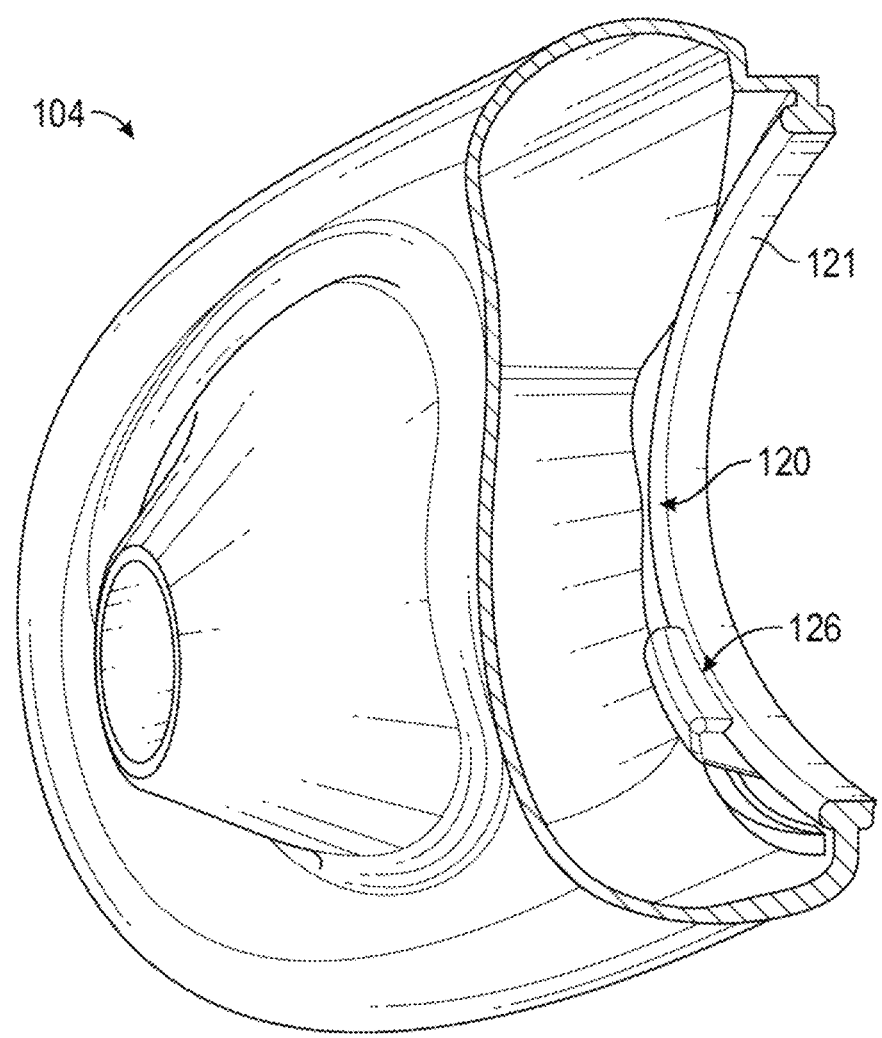
FIG. 51 is a side cross-sectional view of the seal of FIG. 47.

As shown in FIG. 43-51, the mask interface 102 can include a seal assembly including the seal 104 and a seal clip assembly or seal clip 122. In the illustrated arrangement, the seal clip 122 includes a pair of seal clip members 122a, 122b. The seal assembly attaches to the outlet collar 140 of the frame 106. The seal 104 includes a gas inlet opening 120 surrounded by a base portion 121 of the seal 104 as shown in FIG. 51. The seal 104 may be formed of a stretchable, resilient material, such as an elastomer, silicone or rubber for example, that can stretch under tension but will substantially return to its original shape after removal of the tension force. The seal clip 122 can provide a rigid component that allows or helps couple the seal 104 to the frame 106. Alternatively, the base portion 121 of the seal 104 may be configured to stretch around the outlet collar 140 of the frame 106 so that an inner face of the base portion 121 (or another suitable sealing structure) substantially surrounds and seals against an outer surface of the outlet collar 140. The clip could also be formed of an elastomer (preferably more rigid than the seal) that is configured to stretch over the outlet collar.

Figure 43:
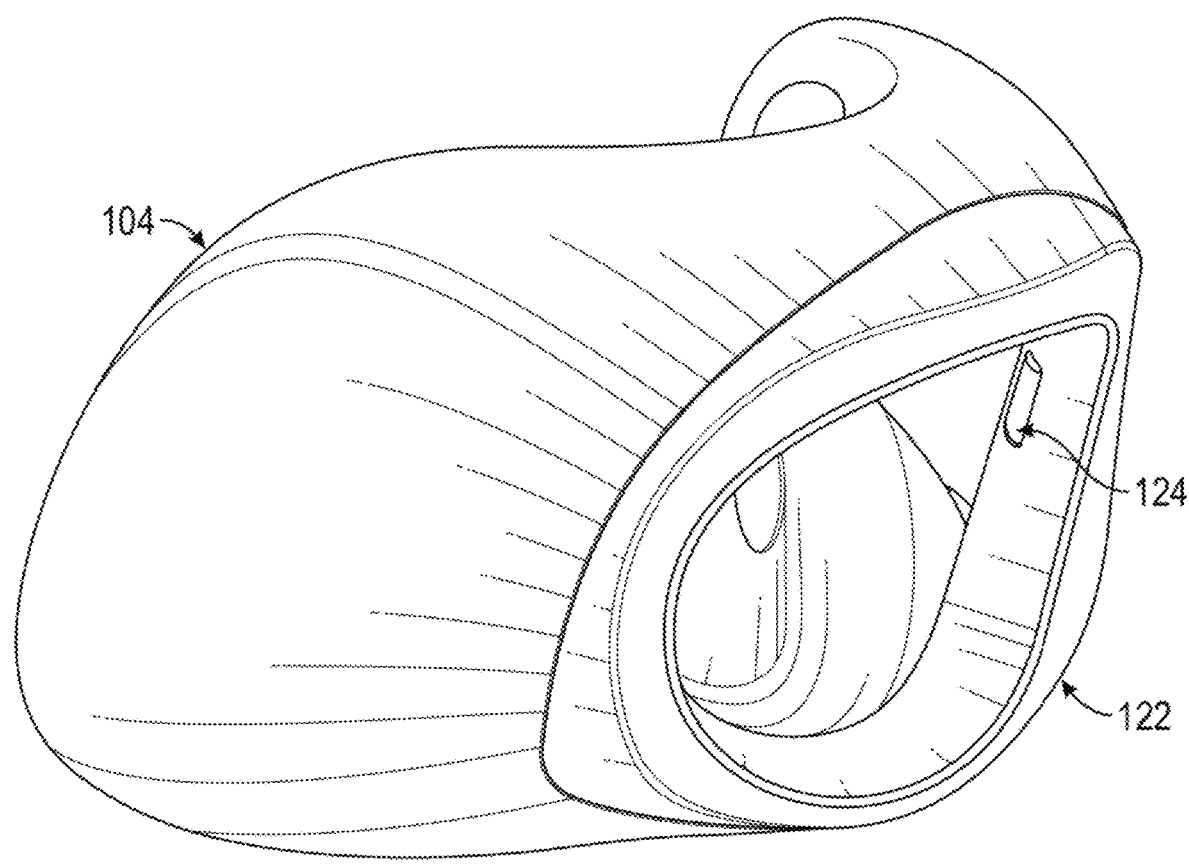
FIG. 43 is a perspective view of a seal assembly of the mask assembly of FIG. 1 including a seal and a seal clip having two seal clip portions.
Figure 45:
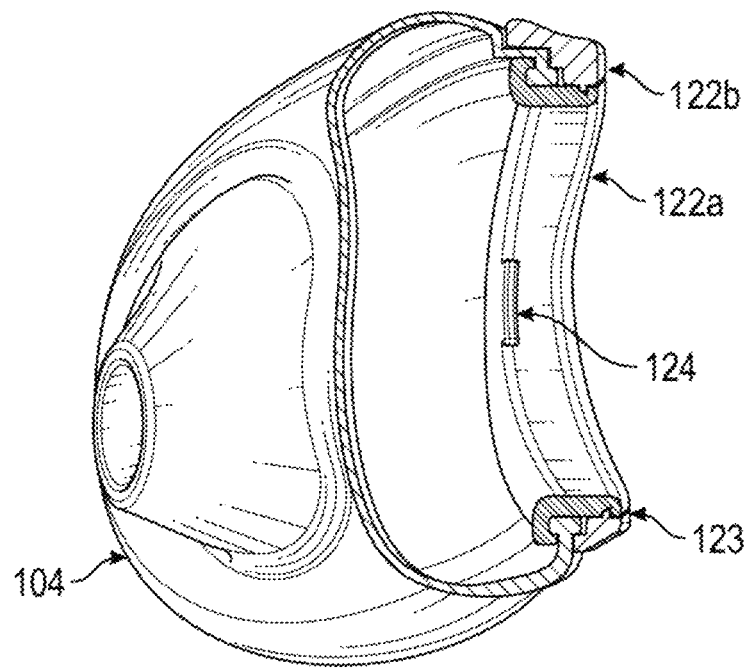
FIG. 45 is a side cross-sectional view of the seal assembly of FIG. 43.
Figure 46:
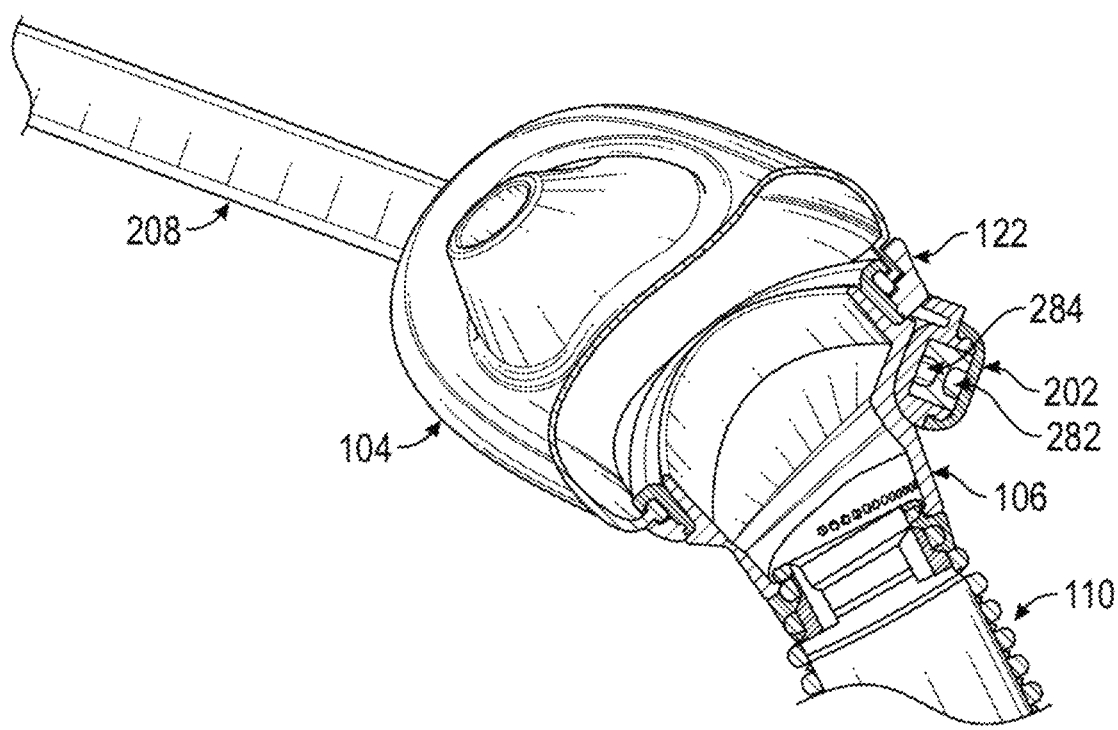
FIG. 46 is a side cross-sectional view of the mask assembly of FIG. 1 illustrating the seal assembly of FIG. 43 coupled to the headgear, frame, and conduit of the mask assembly.
Figure 47:
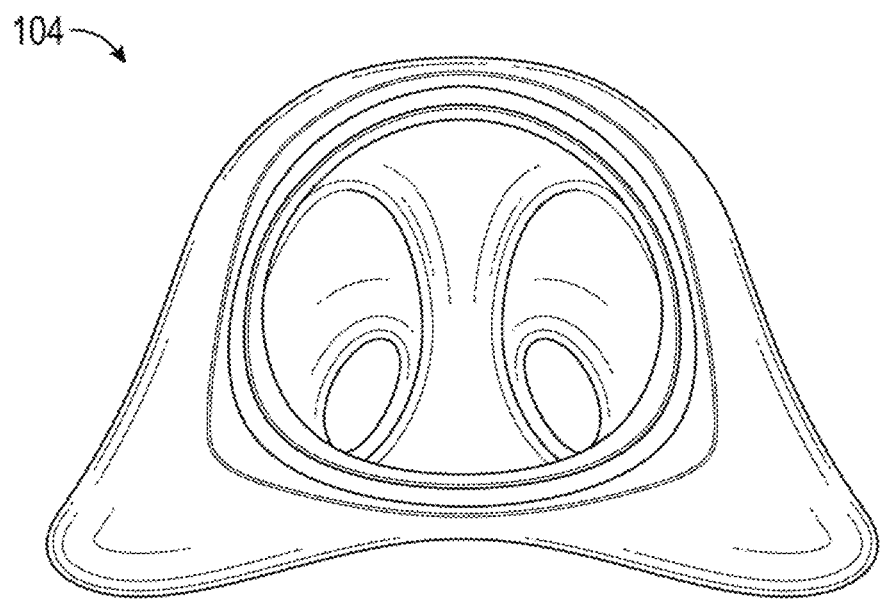
FIG. 47 is a front view of the seal of FIG. 43.
Figure 48:
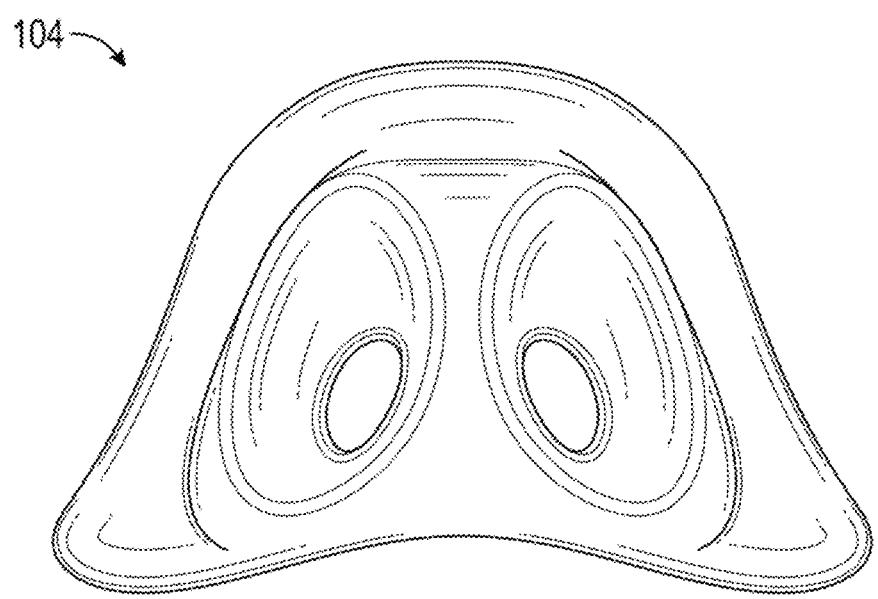
FIG. 48 is a rear view of the seal of FIG. 47.
Figure 49:
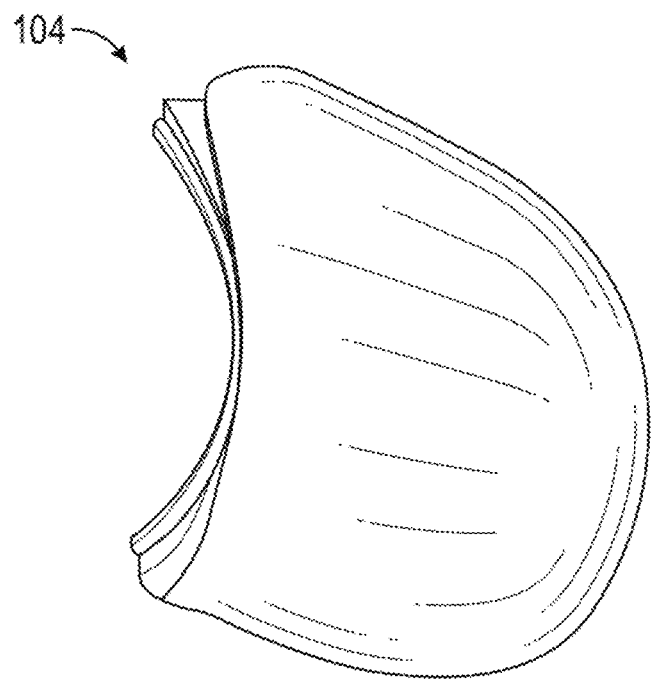
FIG. 49 is a side view of the seal of FIG. 47.
Figure 50:
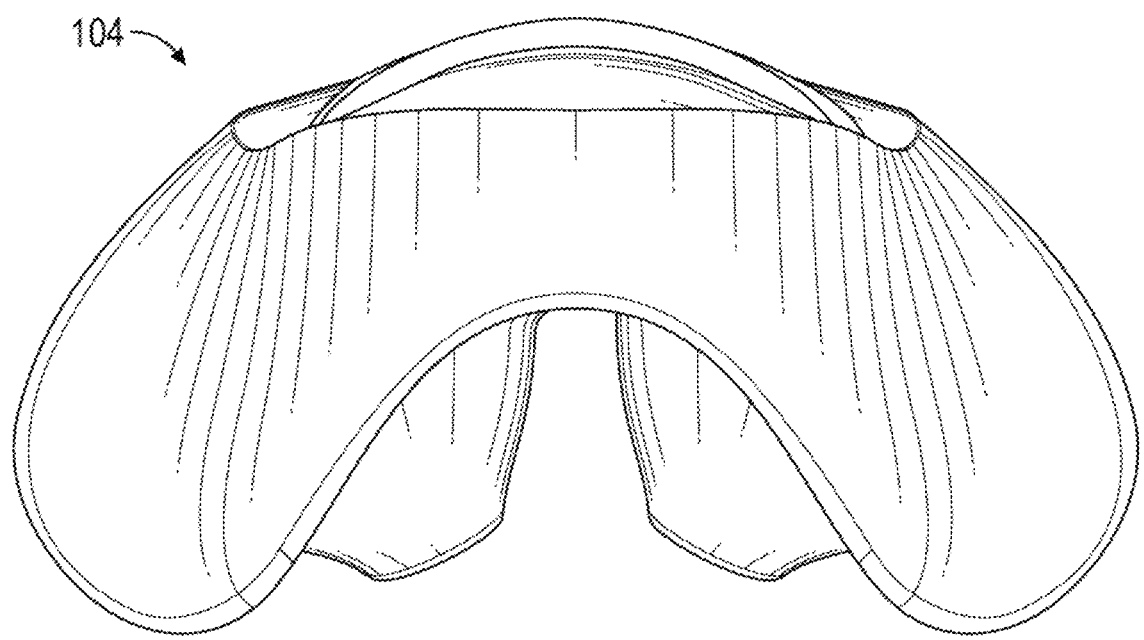
FIG. 50 is a top view of the seal of FIG. 47.

As described herein, an outer surface of the outlet collar 140 can include one or more connection features 144, such as recesses. The seal clip 122 can include one or more corresponding connection features 124, such as corresponding projections as shown in FIGS. 43 and 45, that help couple and secure the seal 104 via the seal clip 122 to the outlet collar 140. When the seal 104 and/or seal clip 122 are pushed onto the outlet collar 140, the corresponding connection features 144, 124 can engage each other to help inhibit the seal and/or seal clip 122 from being pulled off of the outlet collar 140 and/or from rotating relative to the outlet collar 140. The outlet collar 140 and seal 104 and/or seal clip 122 can have an asymmetrical geometry, which can help prevent or inhibit the seal 104 and seal clip 122 from rotating on or relative to the outlet collar 140.

Figure 44:
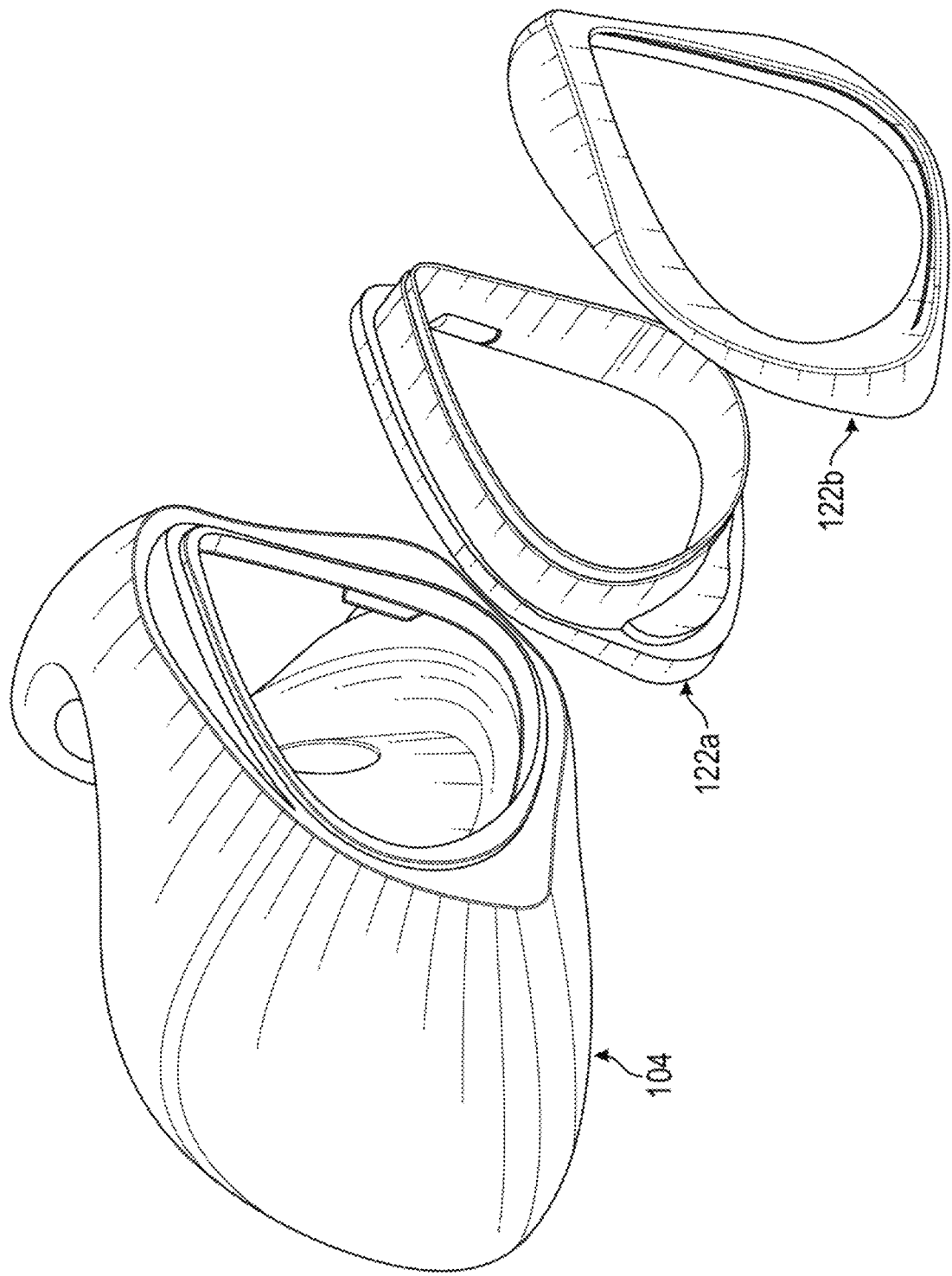
FIG. 44 is an exploded view of the seal assembly of FIG. 43.

As shown in FIG. 44, in the illustrated example, the seal assembly includes a seal 104, an inner clip portion or member 122a and an outer clip portion or member 122b. The inner 122a and outer 122b clip members may form a collar or ring that defines an opening forming the gas inlet 120. The gas inlet 120 may be substantially the same shape (e.g., non-circular) and dimensions as the outlet collar 140 of the frame 106. The inner clip member 122a may comprise an inner surface configured to substantially surround and seal against the outer surface of the outlet collar 140. The inner clip member 122a can be disposed within an internal cavity of the seal 104, e.g., around an interior of the base portion 121. The outer clip member 122b can be positioned on an external surface of the seal, e.g., around an exterior of the base portion 121. When the inner clip member 122a and outer clip member 122b are connected to each other, e.g., via an interference fit connection 123, the seal 104, e.g., the base portion 121, is therefore clamped between the inner 122a and outer 122b clip members as shown in FIG. 45. The seal 104 can include an alignment feature 126 to help proper alignment and positioning of the clip 122 on the seal 104. As shown in FIG. 51, the alignment feature 126 can be positioned along the interior of the base portion 121.

As described above, in the illustrated example, the seal 104 is a pillows mask that seals inside the nares of the patient in use and includes a secondary under-nose or sub-nasal portion that seals on the lower surfaces of a patient's/user's nose. The seal 104 is configured to form an airtight seal under the nose of the patient/user, along a portion of the face extending lateral to the nose, as well as along the upper lip of the user. The seal 104 includes projections or nasal pillows that substantially seal inside the patient's/user's nares. A remainder of the seal 104 inflates and conforms around the user's nose to help properly locate or position the seal 104, support the seal 104, and/or act as a secondary seal should the seal between the nasal pillows and the user's nares leak during movement. Additional information regarding seals as described herein and/or that can be used in the mask assemblies described herein can be found in Applicant's PCT Publication WO 2017/160166, which is hereby incorporated by reference herein.

Figure 53:
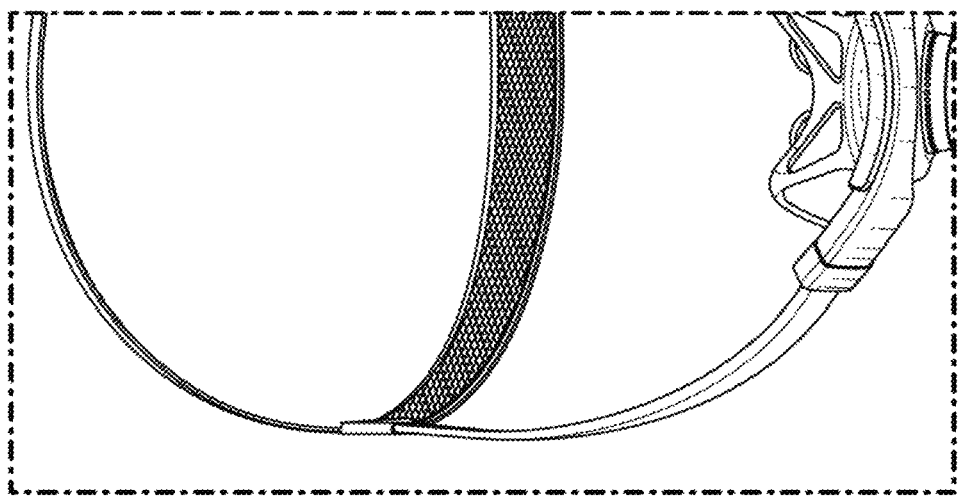
FIG. 53 is a partial front view of the mask assembly of FIG. 52.
Figure 52:
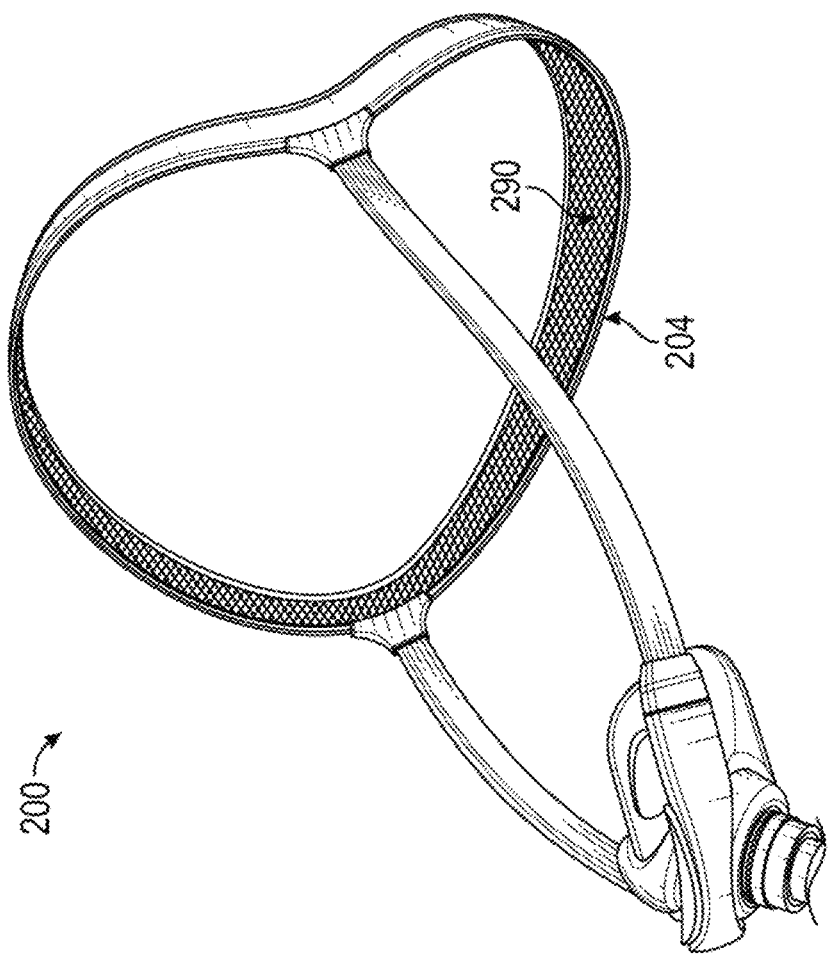
FIG. 52 is a perspective view of a mask assembly, including a headgear assembly having a textured surface, a seal assembly, and a frame assembly.
Figure 55:
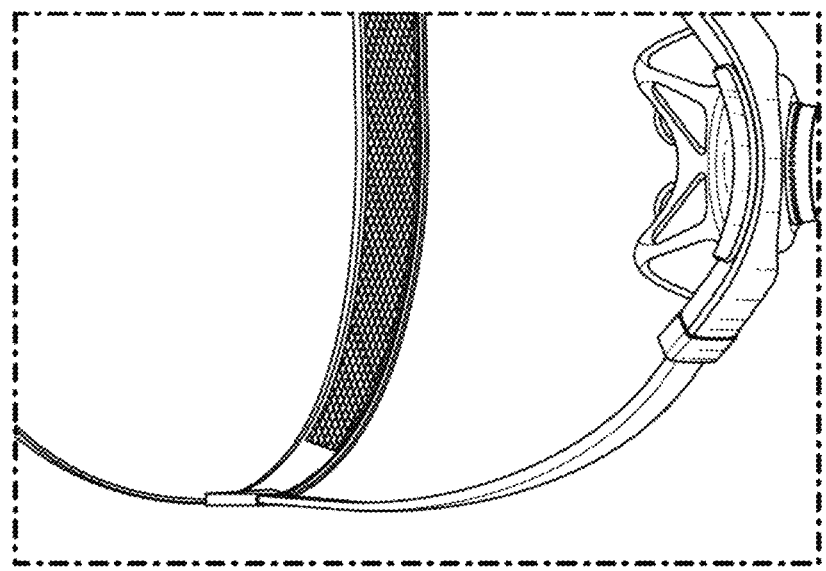
FIG. 55 is a partial front view of the mask assembly of FIG. 54.
Figure 54:
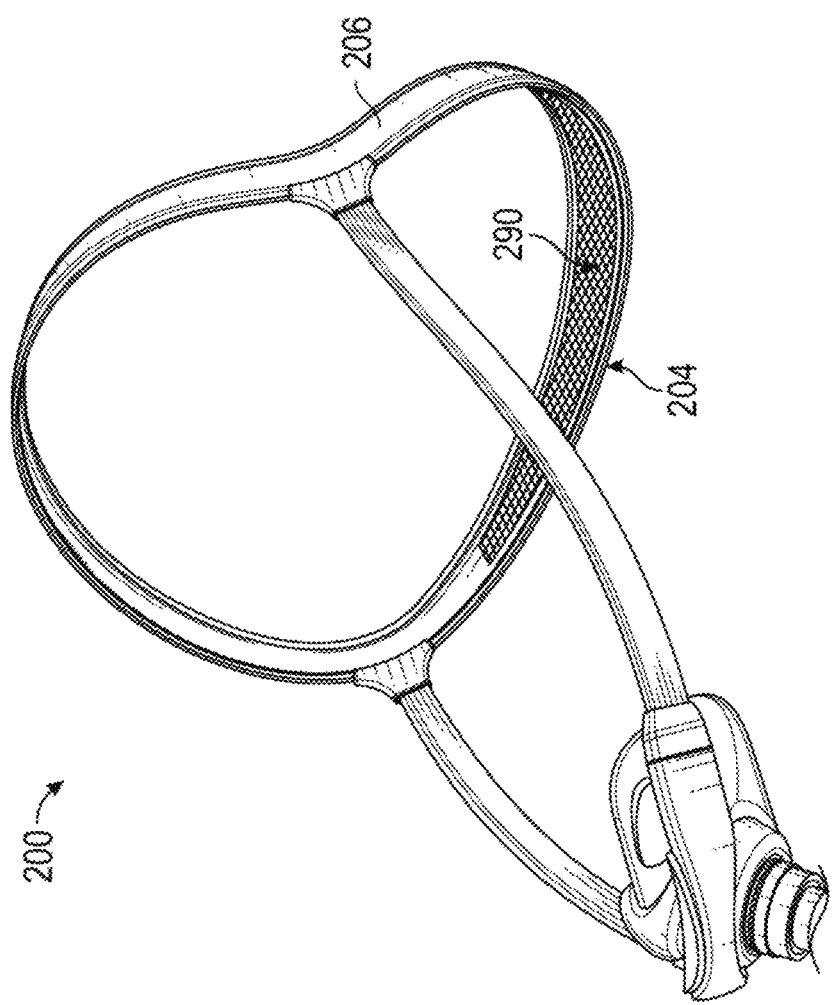
FIG. 54 is a perspective view of a mask assembly, including a headgear assembly having a textured surface, a seal assembly, and a frame assembly.
Figure 57:
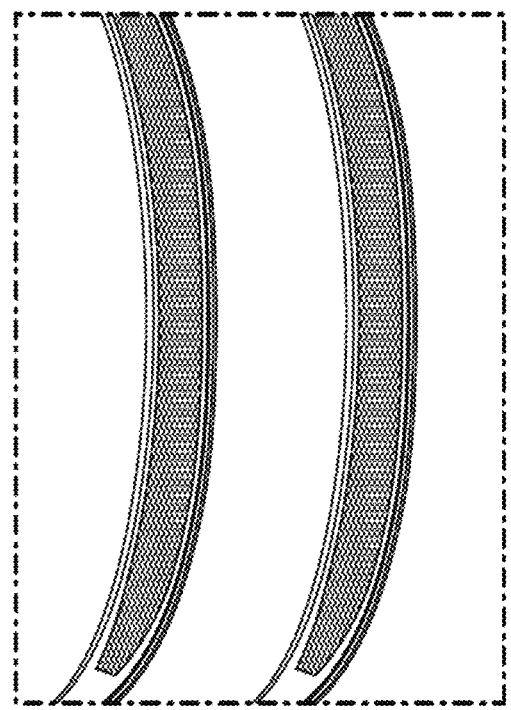
FIG. 57 shows an inner surface of a rear portion of the headgear assembly of FIG. 56.
Figure 56:
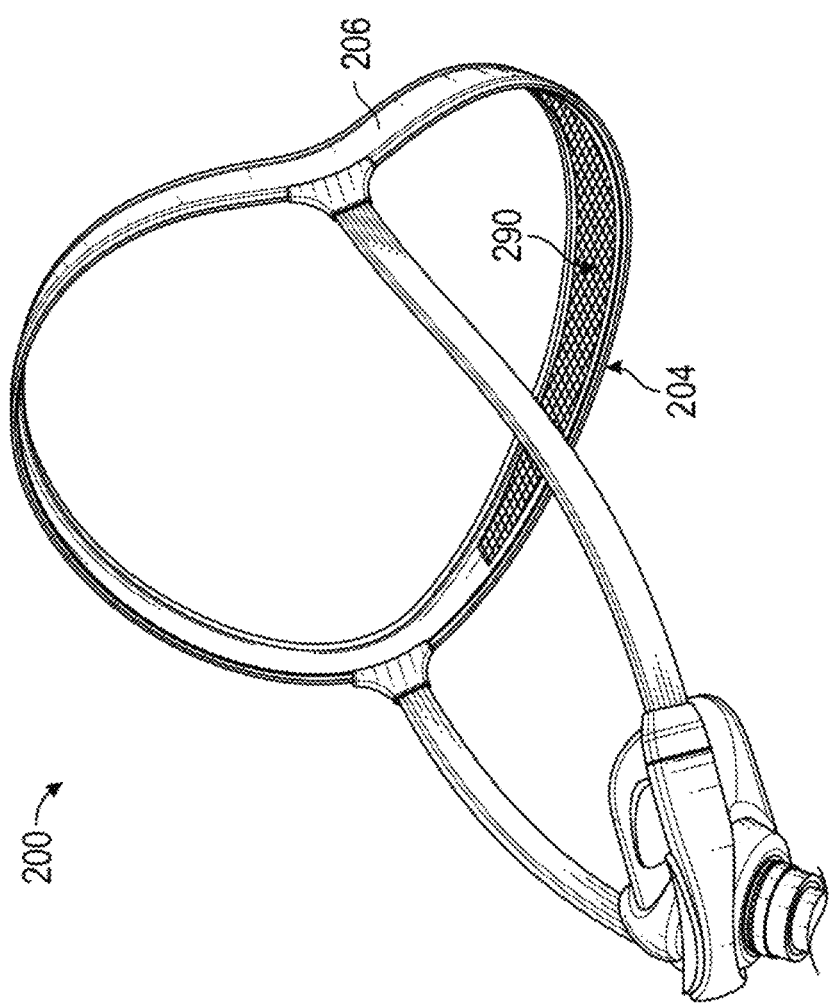
FIG. 56 is a perspective view of a mask assembly, including a headgear assembly having a textured surface, a seal assembly, and a frame assembly.

As described herein, the headgear 200 can be automatically adjustable. To don and/or doff the mask assembly 100, the user can pull the halo strap 204 away from or relative to the yoke 202, frame 106, and seal 104. This stretches the braided elements 216 of the side straps 208 and causes the filaments 220 (which are secured relative to the halo strap 204 via the braid cores 210 and the joints 207) to slide within and relative to the yoke 202 to increase the overall length or size of the headgear 200. When the mask assembly 100 is positioned on the user's head and face, the user releases the halo strap 204 to allow the overall length or size of the headgear 200 to decrease or retract to automatically adjust or size itself to the user's head. To help encourage and guide the user to grip and pull on the rear portion 206 of the halo strap 204, rather than the side straps 208, to don the mask assembly 100, the halo strap 204 can include a textured inner surface 290 as shown in FIGS. 52 and 53. In this example, the textured inner surface 290 extends around an entirety of the halo strap 204. FIGS. 54 and 55 illustrate a variation in which the textured inner surface 290 covers only a portion of the inside surface of the halo strap 204. In this example, the textured inner surface 290 is disposed on only a portion of the rear portion 206 of the halo strap 204. In this example, there is a relatively sharp boundary between the textured 290 and non-textured portions of the halo strap 204. FIGS. 56 and 57 illustrate another variation in which the textured inner surface 290 covers only a portion of the inside surface of the halo strap 204, e.g., a portion of the rear portion 206 of the halo strap 204 as illustrated. However, in this example, the textured surface 290 portion has a faded edge. In other words, the textured surface 290 or pattern slowly or gradually fades out and blends into the non-textured portion such that the textured surface 290 portion does not have a sharp defined edge or clear transition point. The textured surface 290, whether extended around the entire inner surface of the halo strap 204 or only a portion thereof, can include one or more of dimples (as illustrated), ribs, crosses, spirals, and/or other designs or textures.

Figure 58:
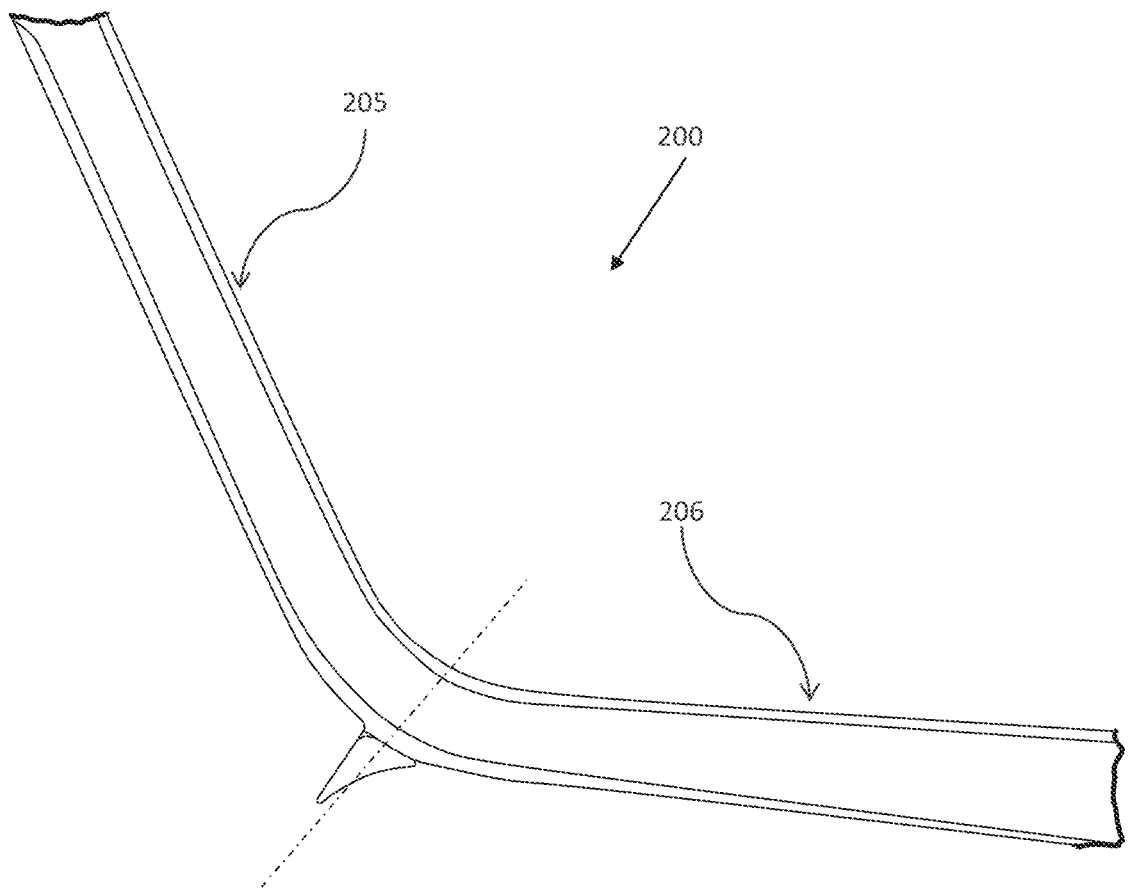
FIG. 58 shows a portion of a headgear assembly having color variation.

The top portion 205 and rear portion 206 of the halo strap 204 can be different colors, for example as shown in FIG. 58. The side straps 208 can be the same color as the rear portion 206. Having the side straps 208 and rear portion 206 the same color can help emphasize the correct orientation of the headgear 200 to the user, as the same color side straps 208 and rear portion 206 form a loop from the yoke 202 around the back of the user's head. In some examples, the top portion 205 and rear portion 206 can be interwoven, knitted in one piece, and/or otherwise configured such that the two colors fade or blend into each other as shown.

Figure 59:
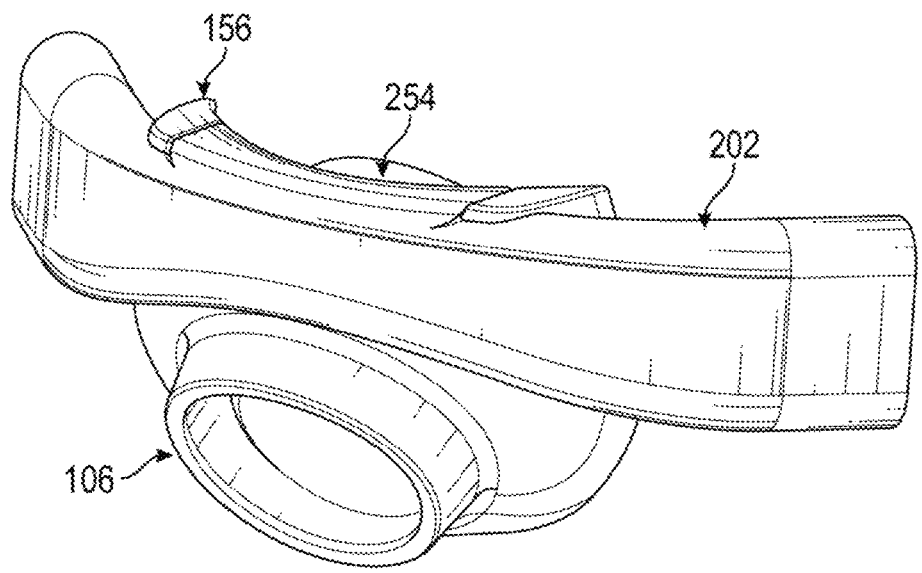
FIG. 59 is a front perspective view of an alternative of a frame and yoke.
Figure 60:
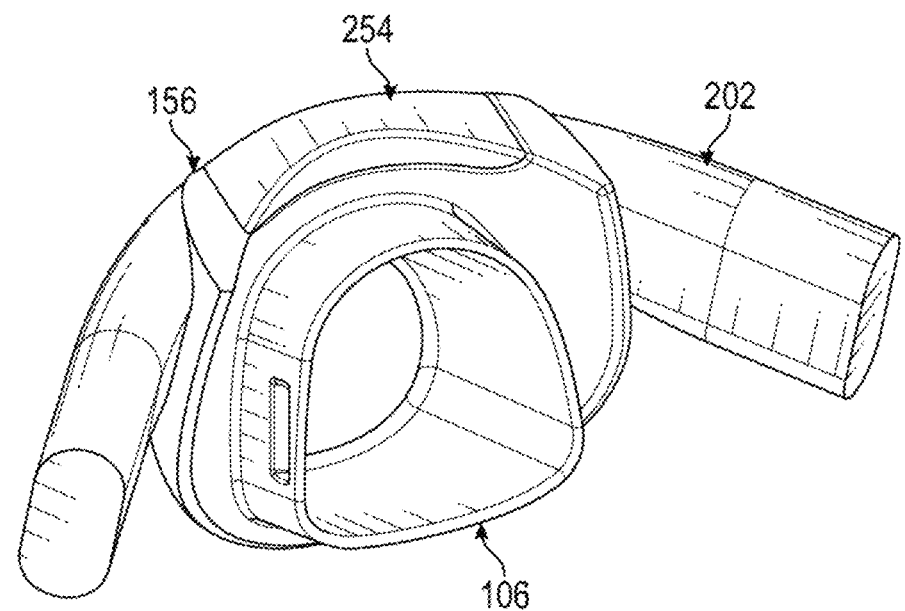
FIG. 60 is a rear perspective view of the frame and yoke of FIG. 59.
Figure 61:
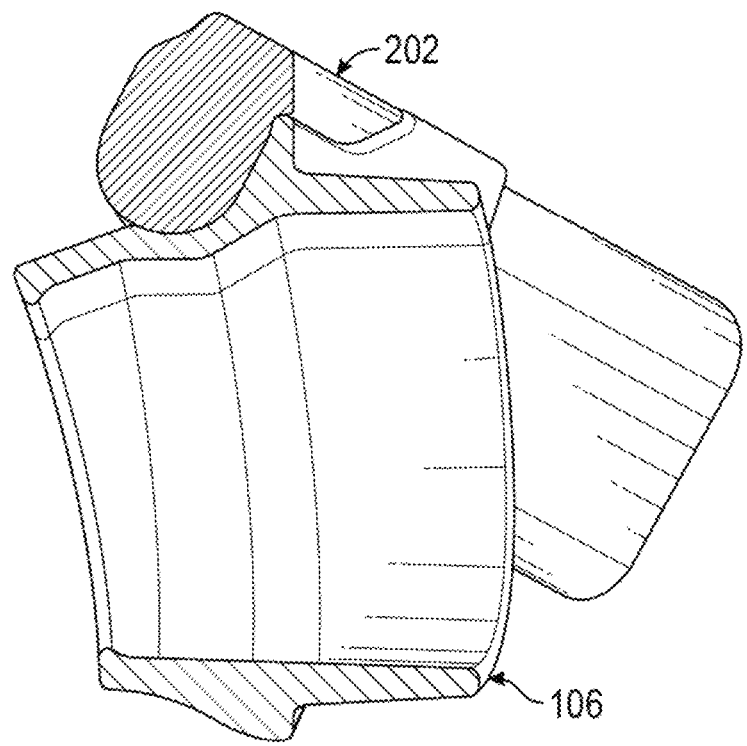
FIG. 61 is a side cross-sectional view of the frame and yoke of FIG. 59.
Figure 62:
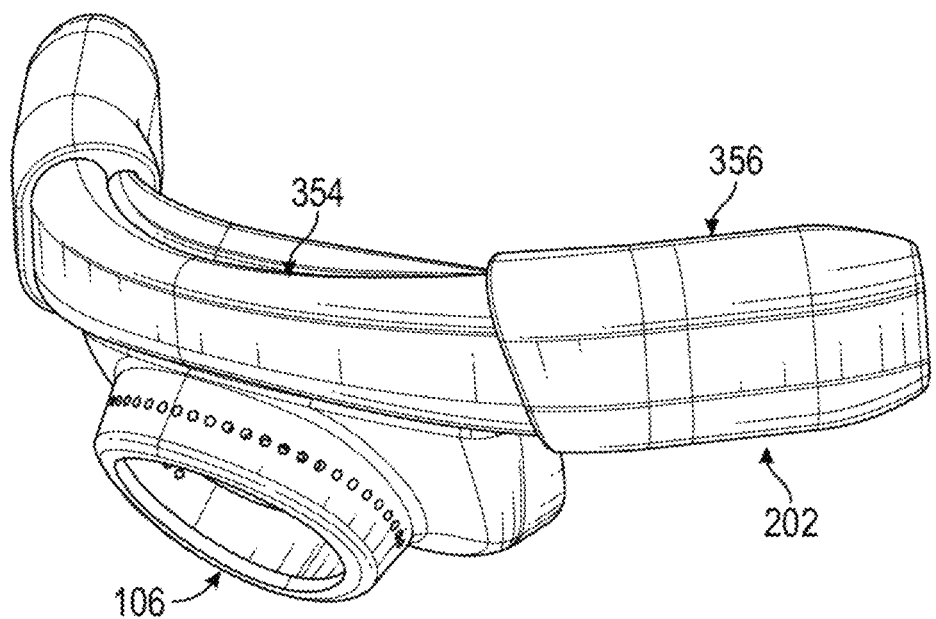
FIG. 62 is a front perspective view of an alternative frame and yoke.

FIGS. 59-61 show a variation of the yoke 202 and frame 106. As described above, the illustrated yoke 202 includes a yoke locating feature 254. The frame 106 includes two overhanging portions 156 separated by a gap. When the yoke 202 is coupled to the frame 106, the frame locating feature 254 is disposed in the gap between the overhanging portions 156. The frame locating feature 254 and overhanging portions 156 are sized and shaped such that the yoke locating feature 254 lies flush with the overhanging portions 156 along upper and rear surfaces of the yoke locating feature 254 and overhanging portions 156. In this example, the yoke locating feature 254 is relatively larger or longer than the yoke locating feature 254 of the example of FIG. 27, and the overhanging portions 156 are relatively smaller or shorter than the overhanging portions 156 of the example of FIG. 27.

Figure 63:
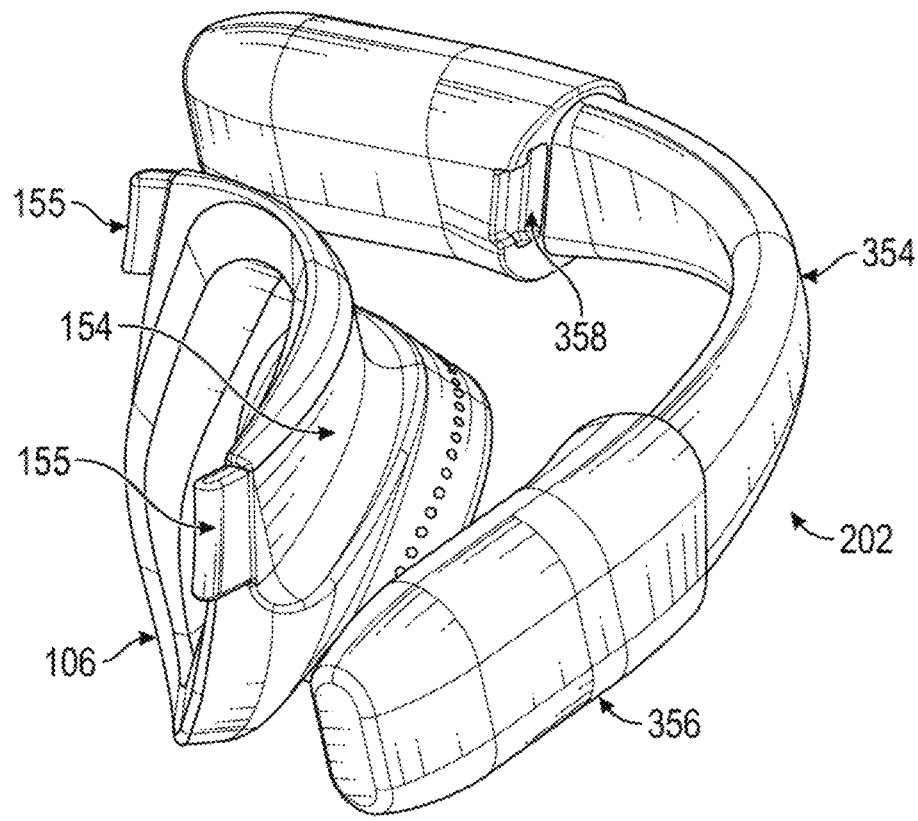
FIG. 63 is an exploded view of the frame and yoke of FIG. 62.
Figure 64:
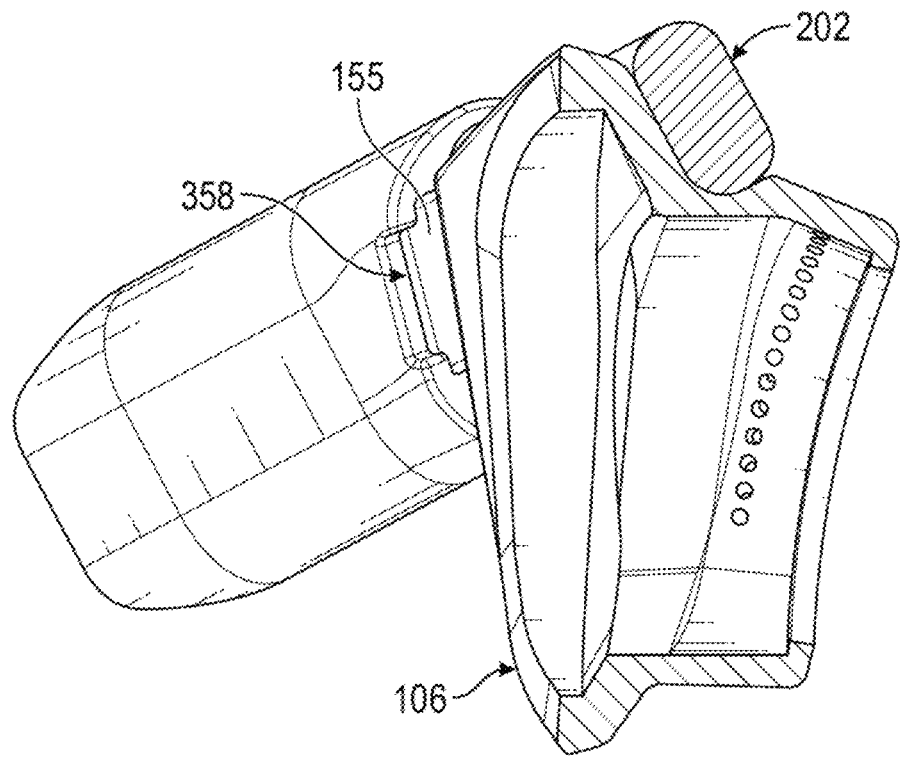
FIG. 64 is a side cross-sectional view of the frame and yoke of FIG. 62.
Figure 65:
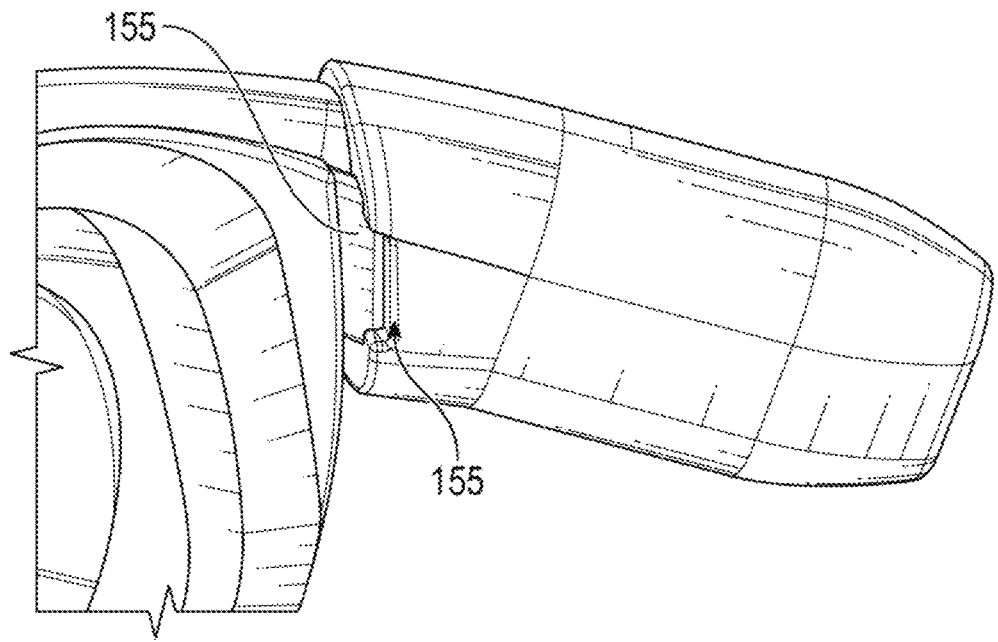
FIG. 65 shows a detailed view of an interaction between the yoke and frame of FIG. 62.

FIGS. 62-65 show another variation of the yoke 202 and frame 106. In this example, the yoke 202 includes a central portion 354 and two lateral portions 356, one extending from each lateral end of the central portion 354. The lateral portions 356 have a greater thickness and height than the central portion 354. Each lateral portion 356 includes a recess 358 in a medial end or surface of the lateral portion 356 on a rear or back side of the lateral portion 356 relative to the central portion 354, as shown in FIG. 63. The frame 106 includes two lateral protrusions 155, one extending outward or laterally from each lateral end or edge of the recessed region 154 that receives the yoke 202. When the yoke 202 is coupled to the frame 106, the lateral protrusions 155 are received in the recesses 358 in the lateral portions 356 of the yoke 202 as shown in FIGS. 64-65 to secure the yoke 202 to the frame 106.

Figure 66:
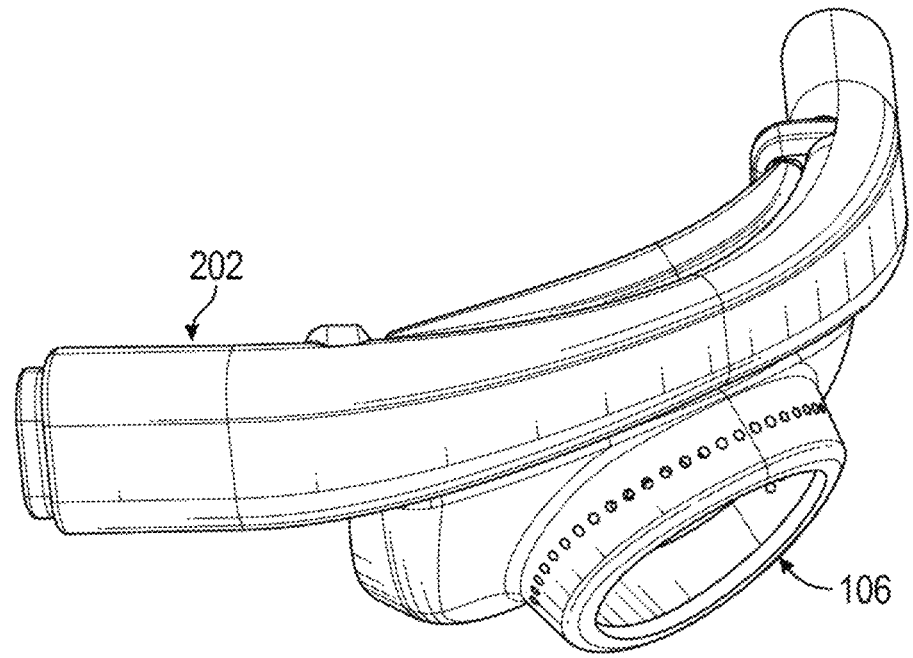
FIG. 66 is a front perspective view of an alternative frame and yoke.
Figure 67:
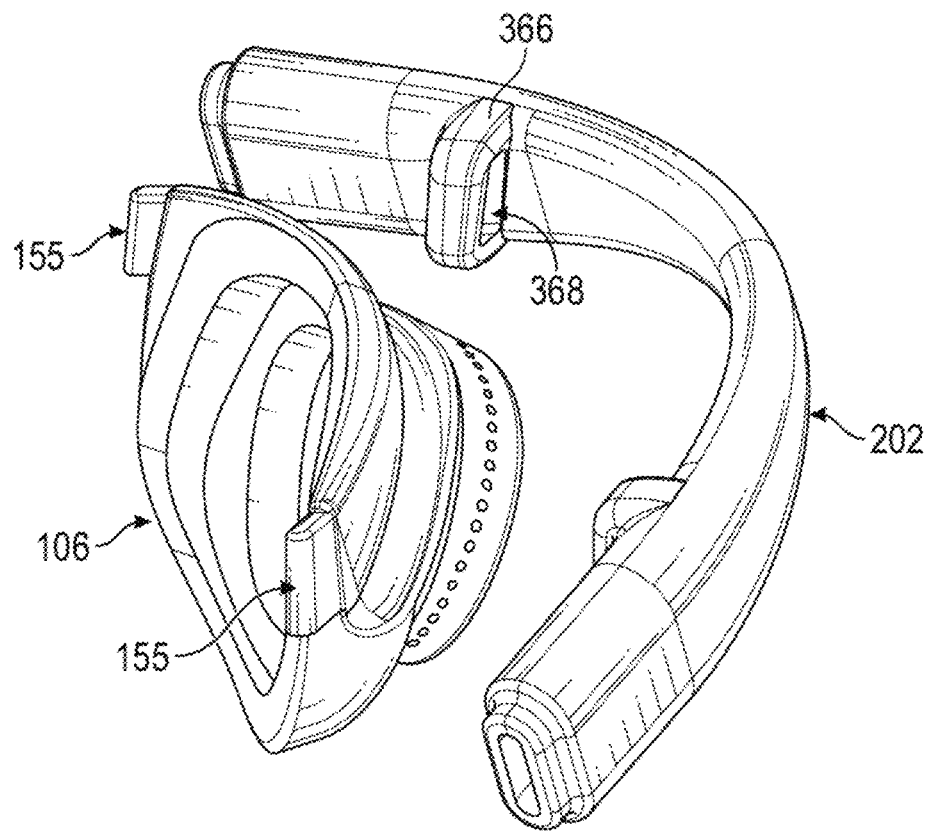
FIG. 67 is an exploded view of the frame and yoke of FIG. 66.
Figure 68:
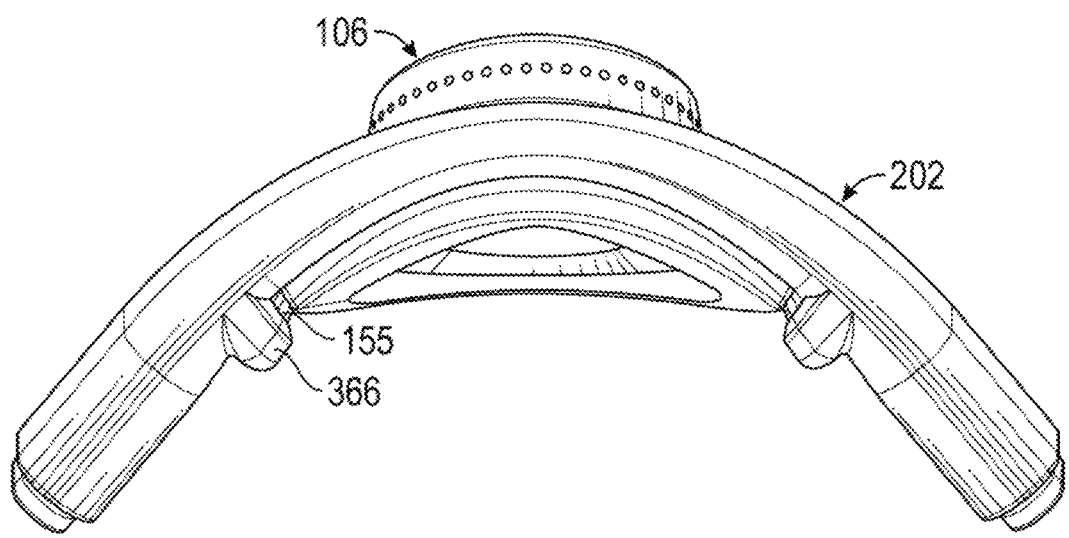
FIG. 68 is a top view of the frame and yoke of FIG. 66.
Figure 69:
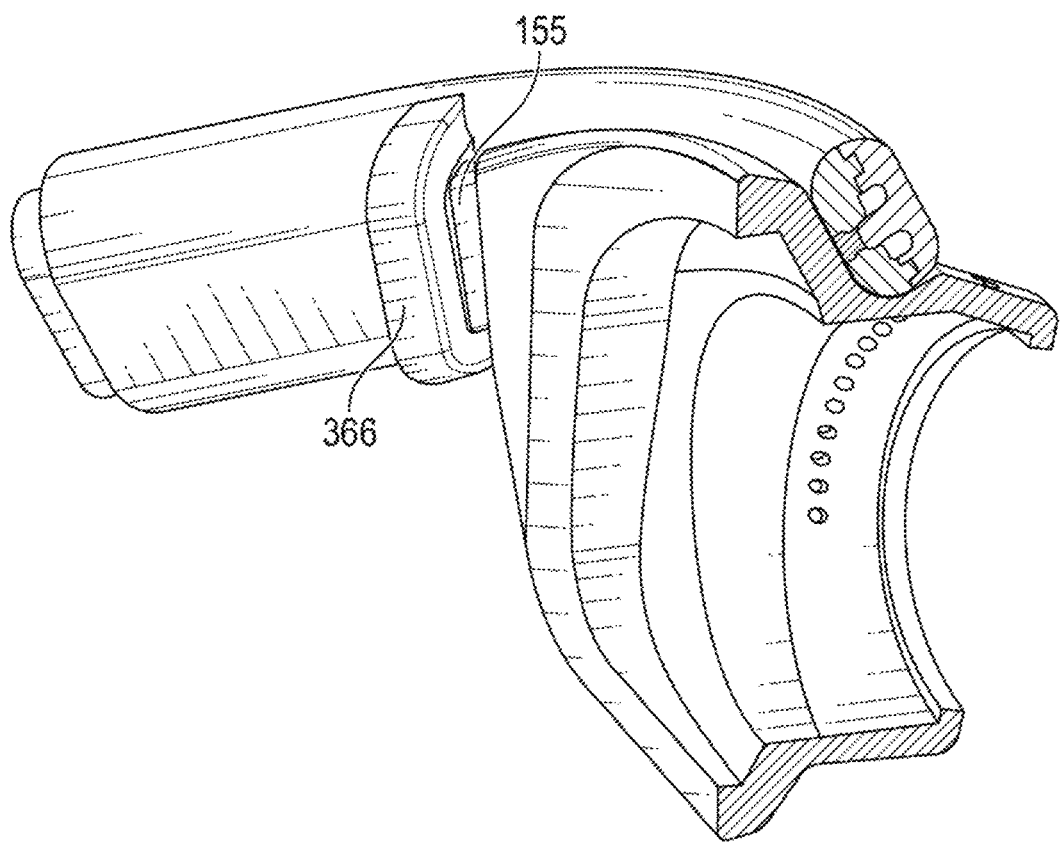
FIG. 69 is a side cross-sectional view of the frame and yoke of FIG. 66.
Figure 70:
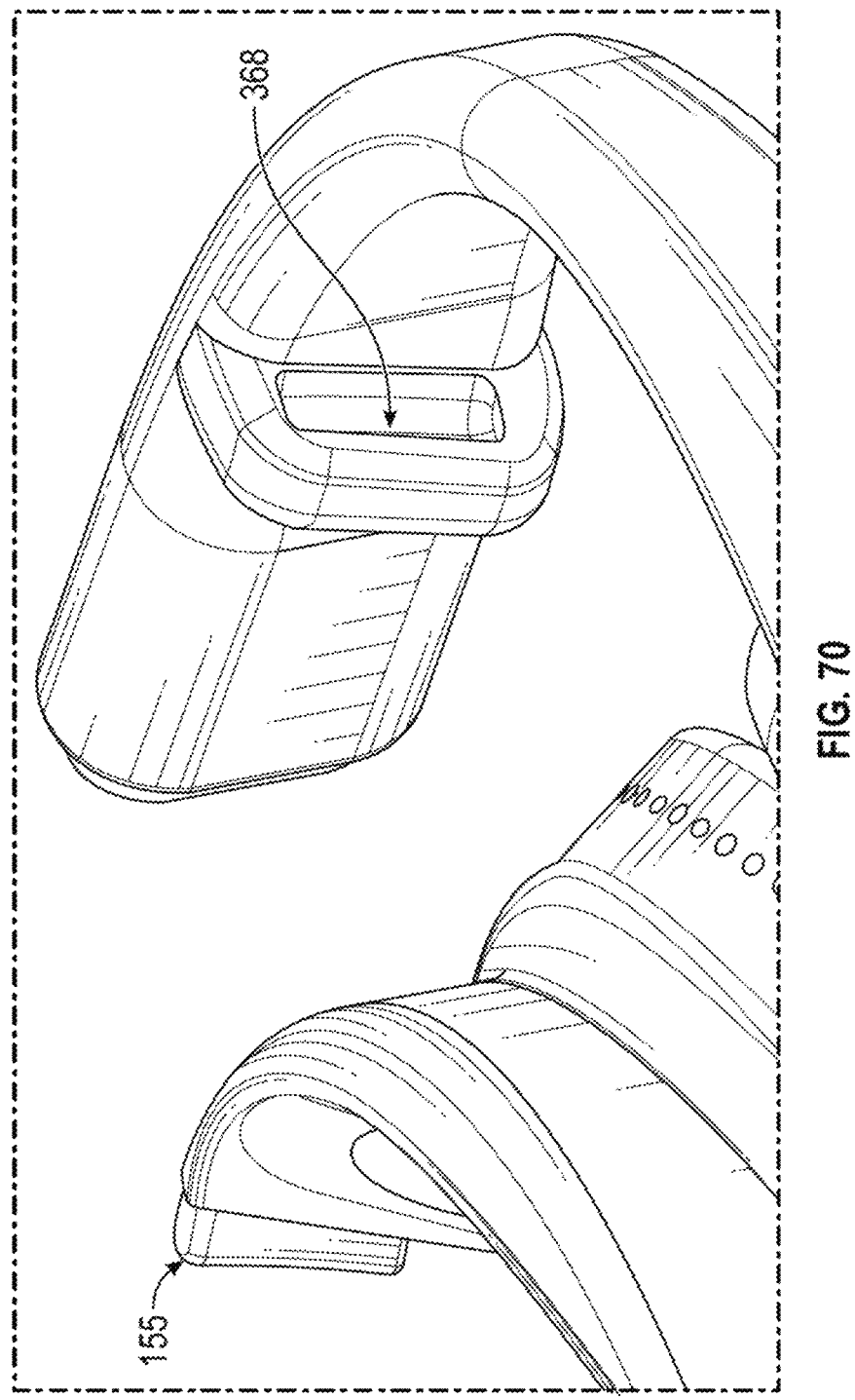
FIG. 70 is a detailed exploded view of the frame and yoke of FIG. 66.

FIGS. 66-70 show another variation of the yoke 202 and frame 106. In this example, the frame 106 includes two lateral protrusions 155 like the example of FIGS. 62-65. The yoke 202 includes two recesses or apertures 368. In the illustrated example, each recess or aperture 368 is formed in or by a loop 366 projecting from a rear surface of the yoke as shown in FIG. 67. When the yoke 202 is coupled to the frame 106, the lateral protrusions 155 are received in the recesses 368 of the yoke 202 as shown in FIGS. 66 and 68-69 to secure the yoke 202 to the frame 106.

Figure 71:
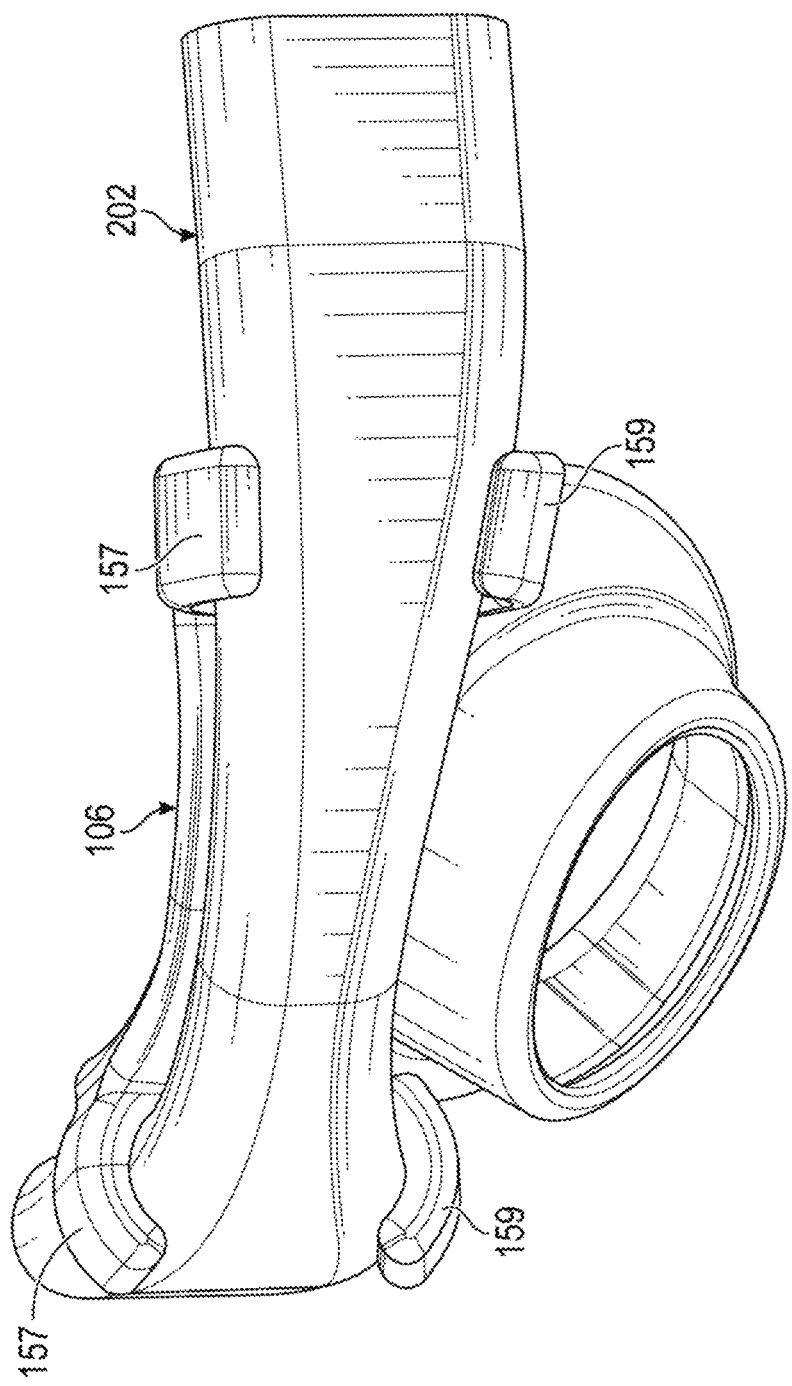
FIG. 71 is a front perspective view of an alternative frame and yoke.
Figure 72:
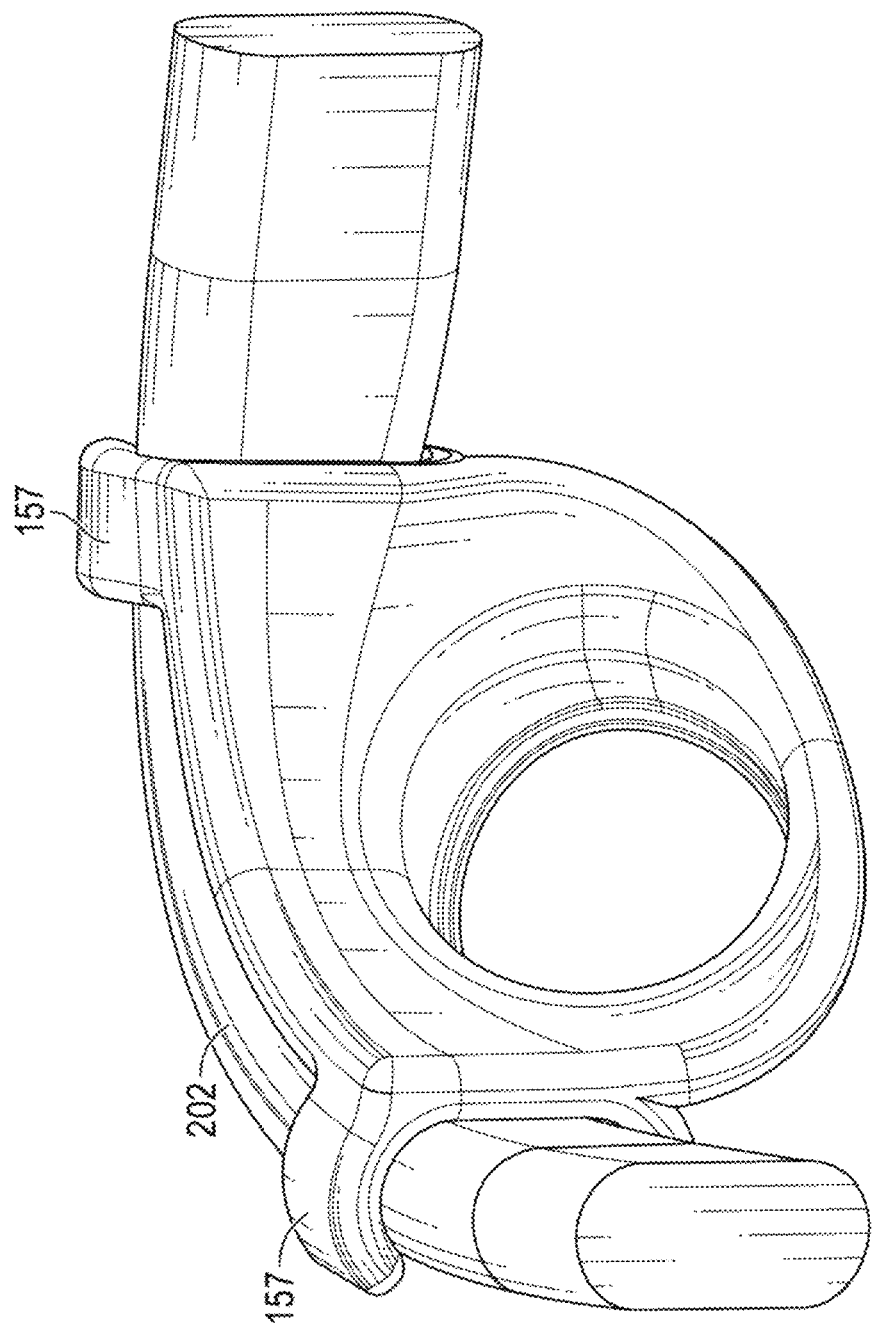
FIG. 72 is a rear perspective view of the frame and yoke of FIG. 71.
Figure 73:
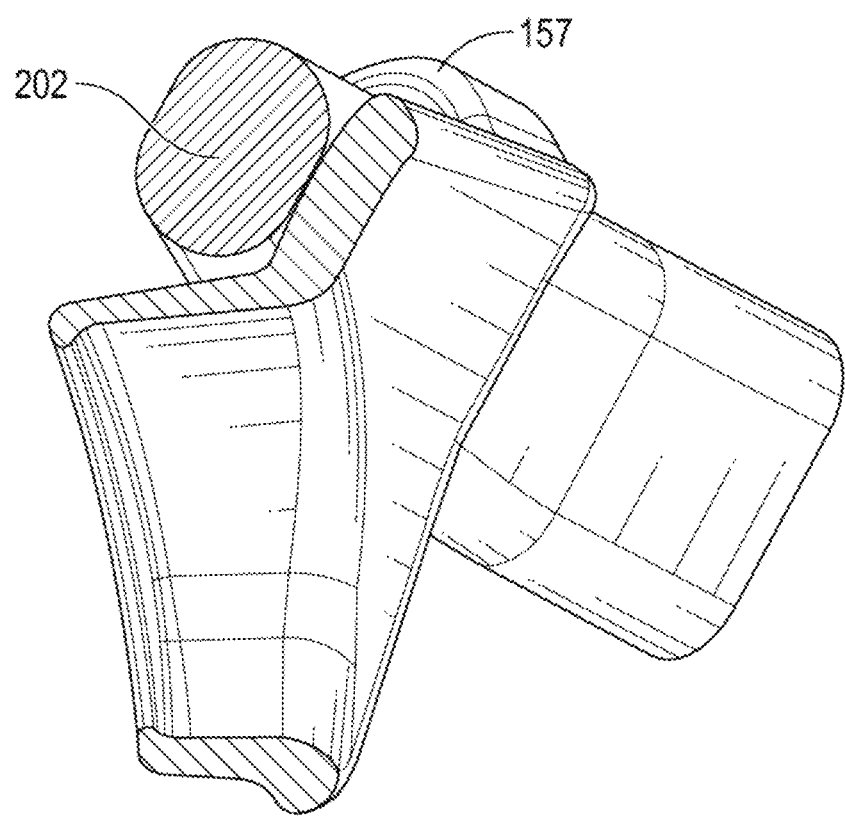
FIG. 73 is a side cross-sectional view of the frame and yoke of FIG. 71.

FIGS. 71-73 show another variation of the yoke 202 and frame 106. In this example, the frame 106 includes two upper overhanging portions 157 and two lower overhanging portions 159 extending forward from the frame 106. The upper overhanging portions 157 are downwardly-facing concave, and the upper overhanging portions 159 are upwardly-facing concave. The yoke 202 is received in an area between the upper overhanging portions 157 and the lower overhanging portions 159. An interference fit between the yoke 202 and upper 157 and lower 159 overhanging portions holds the yoke 202 in place. The yoke 202 and/or frame 106 can include one or more locating features (e.g., yoke locating feature 254) to help properly center the yoke 202 with respect to the frame 106.

Figure 74:
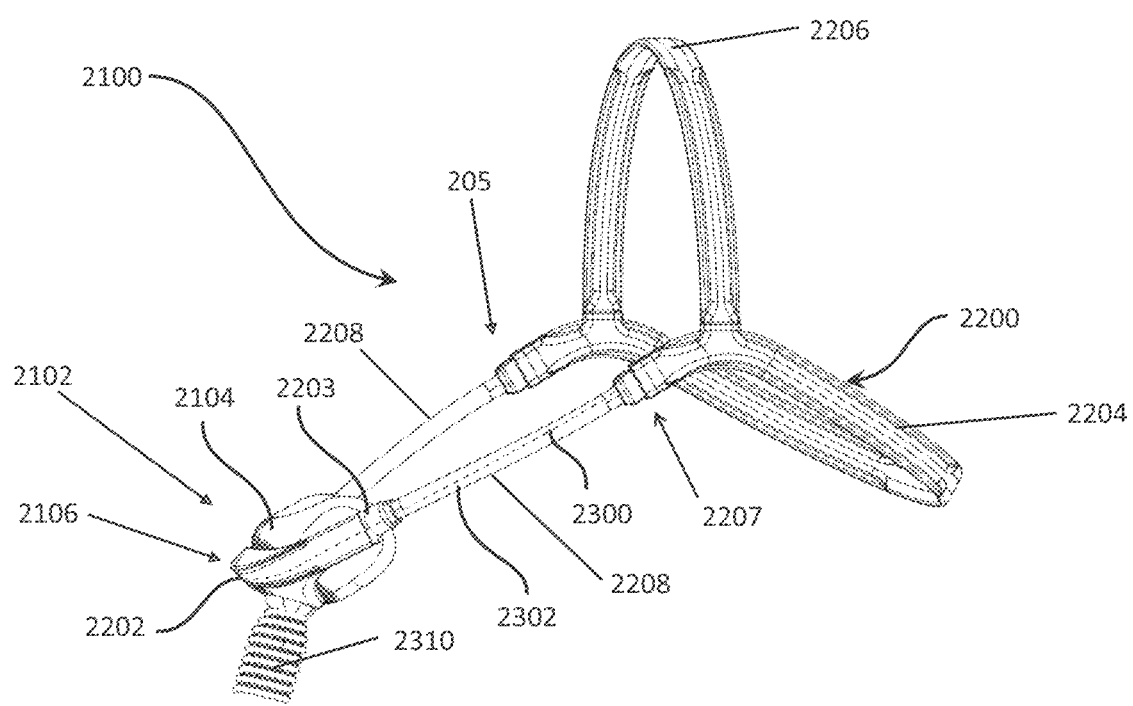
FIG. 74 is a perspective view of a mask assembly, including a headgear assembly, a seal assembly, and a frame assembly.

FIG. 74 illustrates a further example of a respiratory mask system or mask assembly 2100 for the delivery of respiratory therapy to a patient. Any features of this system may be substituted with or for features as described above or below to result in new combinations that may not be explicitly illustrated.

A mask system can include a mask interface, such as a seal and frame assembly 2102, and a headgear assembly 2200. The mask interface 2102 and headgear assembly 2200 can include a connection system to attach the headgear 2200 to the mask interface 2102. Various forms of connection systems may be used to attach the headgear 2200 to the mask interface 2102. The mask interface 2102 can be used with various types of headgear. The headgear 2200 can be used with various mask interfaces.

The mask interface or seal and frame assembly 2102 can include a seal 2104, for sealing around and/or underneath a patient's mouth and/or nose, and a frame 2106 for supporting the seal 2104 and attaching the seal 2104 to the headgear 2200. The frame 2106 can include a gas inlet configured to attach to a gas conduit 2110 for delivering a gas to the patient via the mask interface 2102.

The headgear 2200 of the respiratory mask system holds the mask interface 2102 to the patient's face in use. The headgear 2200 is typically attached to the mask interface 2102 and wraps around the rear of the patient's head to seal the mask interface 2102 against the patient's face.

In some examples, the headgear assembly 2200 includes a yoke or collector 2202, which is configured to attach to the mask interface 2102. In some examples, the mask interface 2102 includes a recessed region that receives at least a portion of the yoke 2202 therein when the yoke 2202 and mask interface 2102 are attached together.

The yoke 2202 can attach to straps of the headgear 2200. In the example shown in FIG. 74, the headgear 2200 includes an assembly of straps, including a rear strap 2204 configured to wrap behind a patient's head, an upper strap 2206 configured to wrap over the top of a patient's head, and a pair of front straps 2208 configured to extend along the patient's cheeks during use. In some examples, each front strap 2208 is attached to the rear strap 2204 of the headgear assembly 2200, e.g., to a free end 2207 of the rear strap 2204 or a connector coupled to the free end 2207, by a rear connector 2205. Each front strap 2208 may comprise a free end to which may be attached a connector. Each connector may engage with a complementary strap connector located on the yoke 2202. The connection between the front straps 2208 and yoke 2202 may be any suitable form of connection, such as a snap-fit connection, a screw and thread type connection, or a hooked connection. In some examples, the yoke 2202 includes an end cap 2203 at each lateral end of the yoke 2202. Each end cap 2203 can act as a connector and can be coupled to one of the front straps 2208 as shown in FIG. 74.

In some examples, the headgear can be automatically adjustable and/or can incorporate one or more directional locks that allow the headgear to reduce in length with a relatively low amount of resistance and resist an increase in length of the headgear. In some configurations, a locking force of the directional locks can be overcome to allow lengthening of the headgear for donning and doffing of the interface assembly. In some examples, the yoke 2202 forms a collector for filaments used in an automatically adjustable headgear system.

Figure 83A:
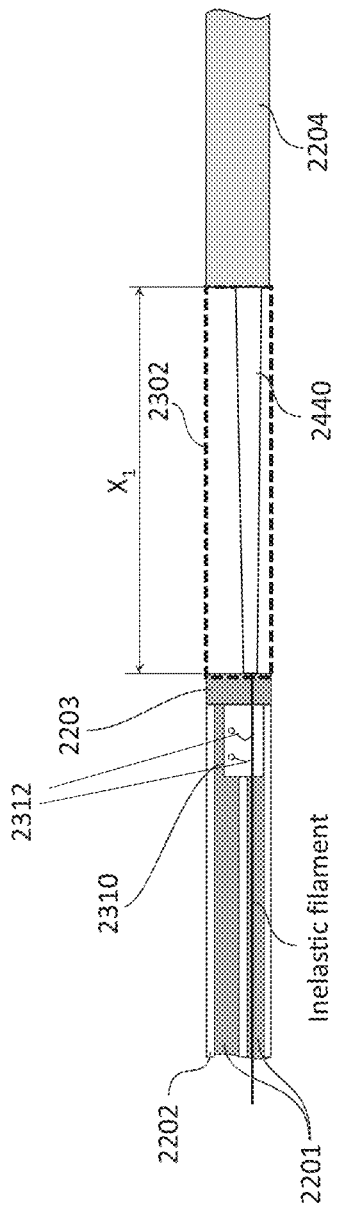
FIG. 83A shows another example embodiment of an adjustment mechanism in a neutral position.

In some examples, for example as shown in FIG. 74, each front strap 2208 includes a filament 2300, which can be inelastic, extending within and/or covered by an elastic covering 2302, such as an elastic braid. As shown, a longitudinal axis of the filament 2300 can be aligned with (e.g., parallel to or coaxial with) a longitudinal axis of the elastic braid. The elastic braid can act as a retraction means or biasing element to retract the headgear or cause the headgear to reduce in length after being stretched or increased in length. Other retraction means or biasing elements can be used instead of or in addition to an elastic braid, for example an elastic filament or other member, a spring of any suitable type, a recoil mechanism or any other suitable biasing element including but not limited to any as described herein. In some examples, the end caps 2203 are over-molded onto ends of the elastic braids 2302. The yoke 2202 or another portion of the headgear can incorporate one or more restriction mechanisms or directional locks, each of which can comprise a washer mechanism 2312 (as shown in, for example, FIG. 75A), which may be configured to frictionally engage with the filament 2300 during elongation of the headgear, but allows relatively friction-free movement during retraction of the headgear. The washer mechanism may be incorporated into the ends of the yoke/collector 2202, for example, the end caps 2203 or portions of the yoke/collector 2202 adjacent or near the end caps 2203. The body of the yoke/collector 2202 may be substantially hollow to receive the filaments 2300 within the body. In some examples, the yoke 2202 includes upper and lower line tracks 2201 as shown in FIG. 83A to accommodate the filaments 2300 extending within the yoke 2202 from each side of the headgear.

Figure 75A:
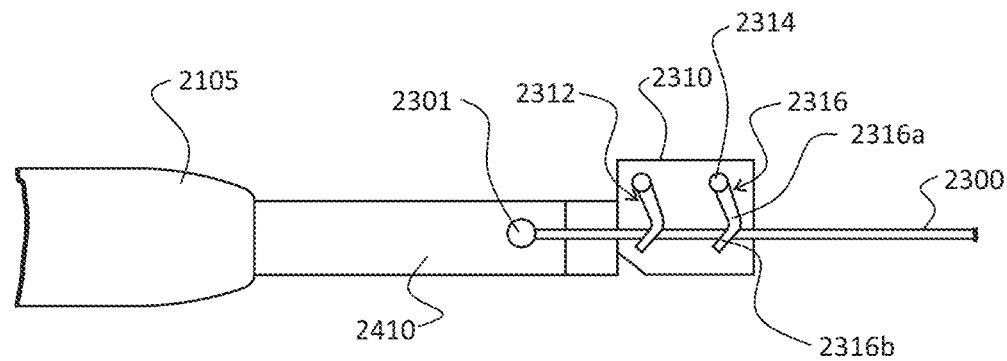
FIG. 75A is a partial schematic side view of an example embodiment of an adjustment mechanism for an automatically adjusting headgear.

Each washer mechanism 2312 can include a cylindrical shaft 2314 and an arm 2316 that extends from the shaft (as shown in FIG. 75A). The cylindrical shaft 2314 is substantially the same width as a washer housing 2310, which can house the washer mechanisms 2312, and the arm 2316 is narrower. In the illustrated arrangement, the arm 2316 comprises a first section 2316a and a second section 2316b, wherein the first section 2316a extends radially or perpendicularly from the cylindrical shaft 2314 and the second section 2316b extends at an obtuse angle from the end of the first section 2316a. The second section 2316b of the arm 2316 comprises a centrally located aperture configured to receive the filament 2300. Application of a tension force to the filament 2300 causes the washer 2312 to pivot back and/or forward between a locked position and/or open position. For example, FIGS. 77B, 79B, and 81B show the directional lock in a locked configuration in which a force is applied to the filament 2300 in a direction towards the left side of the figure. The force applied to the filament 2300 in this configuration causes the washers 2312 to pivot such that the path of the filament 2300 through the directional lock is non-linear or tortuous and movement of the filament is restricted. FIGS. 77C, 79C, and 81C show the directional lock in an open configuration in which a force is applied to the filament 2300 in a direction towards the right side of the figure. In this configuration, the washers 2312 are pivoted such that the path of the filament 2300 is a substantially straight line. This provides a smooth path for the filament 2300 to be pulled substantially freely through the directional lock. The headgear or any portion thereof can be configured in accordance with any of the embodiments disclosed in Applicant's U.S. Publication No. 2016/0082217, U.S. application Ser. No. 14/856,193, filed Sep. 16, 2015, and PCT Publication No. WO2016/043603, the entireties of which are incorporated by reference herein.

In some examples, a frame 2106 and/or headgear 2200 according to the present disclosure includes one or more features, for example, a support beam, that help stabilize the joint or connection between the headgear 2200 and the mask interface 2102 and/or frame 2106, which in turn can help stabilize the seal of the mask to the patient's face in use.

For example, FIGS. 75A-77C illustrate an example in which a support beam in the form of elongate inter-engaging members or arms provides structure and support to the automatically adjustable headgear system, which can help resist rotation of the seal 2104 relative to the user's face. In the illustrated example, the inter-engaging members or arms include inner rails 2420 and outer rails 2410 that can extend or retract relative to one another to vary a length of the overall assembly of the inner rails 2420 and outer rails 2410 (and, thus, to vary a length of the associated headgear). The outer rails 2410 and inner rails 2420 interlock with each other as shown in FIGS. 76A-76B. In some examples, the inner rails 2420 and/or outer rails 2410 are semi-rigid. The inner rails 2420 and outer rails 2410 can be incorporated into a frame or side arms 2105 of the mask interface 2102, for example, frame 2106, yoke 2202, and/or extensions of the frame 2106 and/or yoke 2202, that extend over the user's cheeks in use. In the illustrated example, the outer rails 2410 extend from and/or are coupled to the side arms 2105. In the illustrated example, the inner rails 2420 extend from and/or are coupled to the headgear 2200, for example, the rear strap 2204. In other examples, the inner rails 2420 can extend from and/or be coupled to the side arms 2105, and the outer rails 2410 can extend from and/or be coupled to the headgear 2200, e.g. at the rear strap 2204. The inner 2420 and outer rails 410 can be included in, act as part or all of, or replace the front straps 2208 of the headgear 2200. The headgear 2200 includes two sets of inner rails 2420 and outer rails 2410, one on each side of the user's face in use.

Figure 76A:
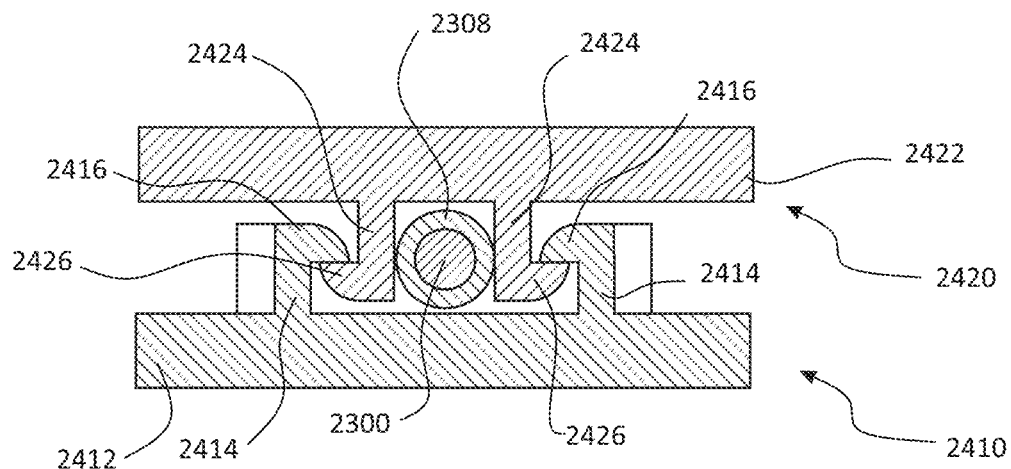
FIG. 76A is a transverse cross-section view of the adjustment mechanism of FIG. 75A.
Figure 76B:
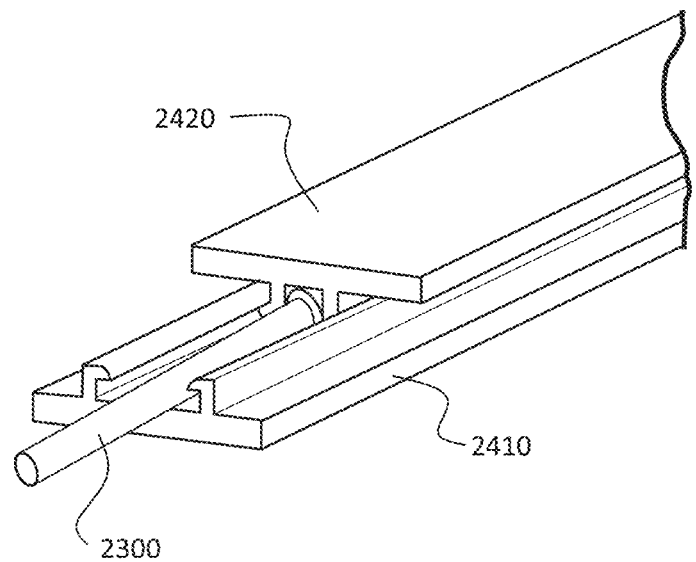
FIG. 76B is a perspective view of a portion of the adjustment mechanism of FIG. 75A.

As shown in FIG. 76A, the inner rails 2420 include two elongate projections 2424 protruding perpendicularly or substantially perpendicularly from an elongate base 2422. The projections 2424 are spaced apart from each other. The outer rails 2410 include two elongate projections 2414 protruding perpendicularly or substantially perpendicularly from an elongate base 2412. The projections 2414 of the outer rails 2410 are spaced apart from each other by a distance that is wider or greater than the spacing of the projections 2424 of the inner rails 2420. The projections 2424 of the inner rails 2420 are positioned inwardly of, or between, the projections 2414 of the outer rails 2410. In the illustrated example, the outer and inner rails 2410, 2420 include a flange 2416, 2426 at an end of each projection 2414, 2424 opposite the base 2412, 2422. The flanges 2426 of the inner rails 2420 project outwardly, and the flanges 2416 of the outer rails 2410 project inwardly. As shown in FIG. 76A, the flanges 2416 of the outer rails 2410 engage with or contact the flanges 2426 of the inner rails 2420. The engagement or contact of the flanges 2416, 2426 forms a retaining feature that helps secure the inner 2420 and outer 2410 rails together. The inner 2420 and outer 2410 rails can slide relative to each other (e.g., lengthwise, toward and away from each other, and/or along axes extending parallel to longitudinal axes of the bases 2412, 2422) in use.

Figure 75B:
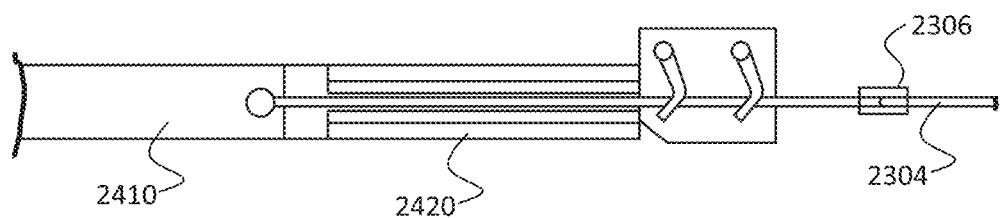
FIG. 75B is a partial longitudinal section view of the adjustment mechanism of FIG. 75A.
Figure 75C:
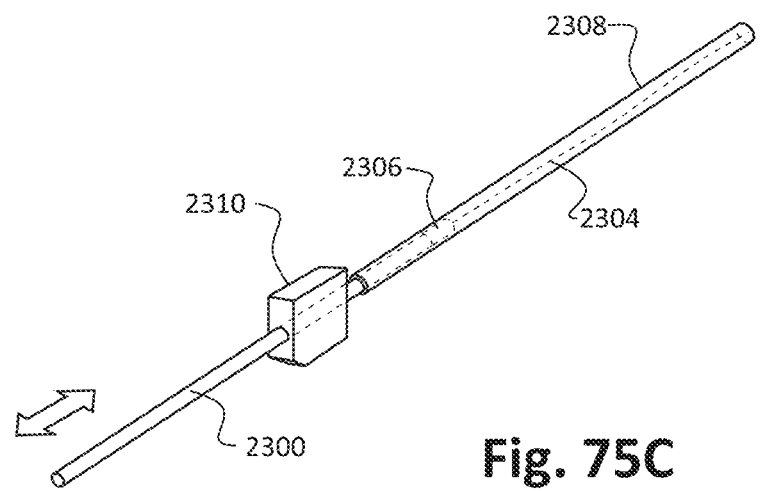
FIG. 75C is a perspective view of the adjustment mechanism of FIG. 75A.

A washer housing 2310, which can house the restriction or washer mechanism(s) 2312, can be coupled to the inner rails 2420 or outer rails 2410. In the illustrated example, a washer housing 2310 is fixed to an end of each of the inner rails 2420 (i.e., one on each side of the user's face in use). In the illustrated example, the automatic adjustment mechanism includes an inelastic filament 2300 and a recoil elastic 2304. One end 2301 of the filament 2300 can be fixed or secured to or relative to the inner 2420 or outer 2410 rails. The opposite end of the inelastic filament 2300 can be joined to the recoil elastic 2304 by, for example, a crimp or shuttle 2306, as shown in FIG. 75B. A longitudinal axis of the inelastic filament 2300 can be aligned with (e.g., parallel to or coaxial with) a longitudinal axis of the recoil elastic 2304. At least a portion of the inelastic filament 2300, recoil elastic 2304, and/or shuttle 2306 can be housed and/or slide within a housing or tube 2308. The tube 2308 provides a low or relatively low friction housing for the filament 2300 and recoil elastic 2304 to slide within. The tube 2308 helps protect the filament 2300 and recoil elastic 2304 from interference from external forces, for example, contact with a pillow, that may reduce the functionality of the automatic adjustment mechanism.

Figure 77A:
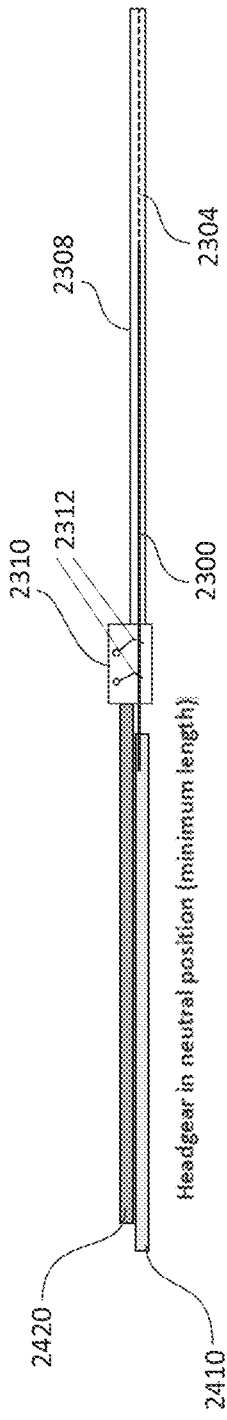
FIG. 77A is a schematic showing the adjustment mechanism of FIG. 75A in a neutral position.
Figure 77B:
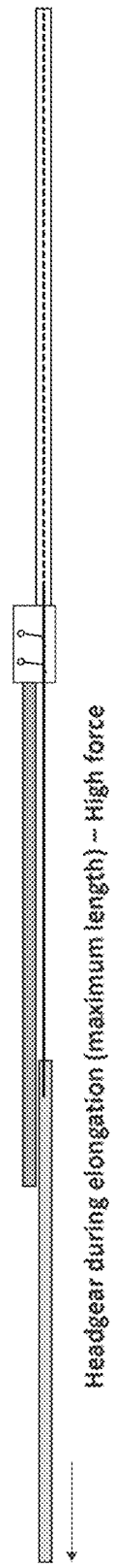
FIG. 77B is a schematic showing the adjustment mechanism of FIG. 75A at a maximum length during elongation.
Figure 77C:
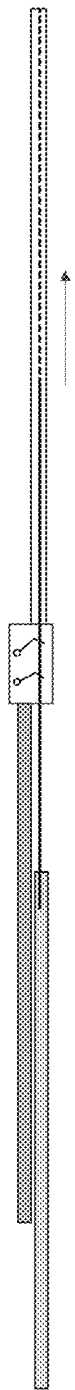
FIG. 77C is a schematic showing the adjustment mechanism of FIG. 75A during retraction.

FIGS. 77A-77C illustrate operation of a headgear 2200 including the inner 2420 and outer 2410 rails in use. As shown in FIG. 77A, in a neutral position, the inner 2420 and outer 2410 rails overlap to their full or greatest extent, and the headgear is at its minimum size or length. The headgear 2200 can be stretched or elongated, for example, for donning and/or doffing, by pulling the mask interface 2102 away from the headgear 2200, thereby applying an elongation force. As the mask interface 2102 is pulled away from the headgear 2200, the inner 2420 and outer 2410 rails slide relative to each other, reducing the overlap between the inner 2420 and outer 2410 rails and increasing the length of the headgear 2200. As the inner rails 2420 and outer rails 2410 slide away from each other, the filament 2300 is drawn through the washer housing 2310, the washers 2312 engage to provide resistance to elongation, and the recoil elastic 2304 is stretched and put under tension, as shown in FIG. 77B. When the elongation force is released, the headgear 2200 automatically retracts as shown in FIG. 77C. The internal forces of the recoil elastic 2304 cause the recoil elastic 2304 to recoil and/or retract. The retraction force provided by the recoil elastic 2304 draws the filament 2300 back through the washer housing 2310 (in the opposite direction as during elongation), which releases the washers 2312 to reduce or minimize resistance to the filament 2300 moving through the washer housing 2310. As the filament 2300 is drawn back through the washer housing 2310, the outer rails 2410 and inner rails 2420 are drawn back toward each other, reducing the length of the headgear 2200.

FIGS. 78A-79C illustrate another example embodiment of an automatic headgear adjustment mechanism including a support beam in the form of inner 2420 and outer 2410 rails and an inelastic filament 2300. A headgear can include two such adjustment mechanisms, one on each side of the user's face in use. In the illustrated example, the outer rails 2410 extend from, are coupled to, and/or are positioned relatively closer to the frame 2106, and the inner rails 2420 extend from, are coupled to, and/or are positioned relatively closer to the headgear or washer housing 2310. In other examples, the inner rails 2420 extend from, are coupled to, and/or are positioned relatively closer to the frame 2106, and the outer rails 2410 extend from, are coupled to, and/or are positioned relatively closer to the headgear or washer housing 2310. The embodiment of FIGS. 78A-79C also includes an elastic tube 2324 surrounding the inner rails 2420, outer rails 2410, and washer housing 2310. The elastic tube 2324 can be made of or include, for example, a textile such as a knitted or braided material, silicone, or TPE (thermoplastic elastomer). In the illustrated example, a first end of the elastic tube 2324 is fixed to the outer rails 2410, and the other end of the elastic tube 2324 is fixed to the washer housing 2310 or another headgear component. In examples in which the inner rails 2420 and outer rails 2410 are reversed, the first end of the elastic tube 2324 is fixed to the inner rails 2420. One end of the filament 2300 can be fixed or secured to or relative to the inner 2420 or outer 2410 rails. The opposite end of the inelastic filament 2300 forms or includes an end stop 2303. A longitudinal axis of the inelastic filament 2300 can be aligned with (e.g., parallel to or coaxial with) a longitudinal axis of the elastic tube 2324.

Figure 79A:
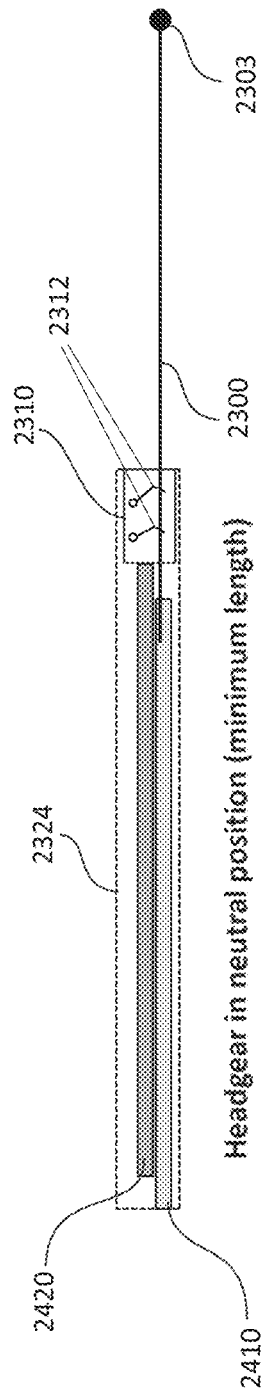
FIG. 79A is a schematic showing the adjustment mechanism of FIG. 78A in a neutral position.
Figure 79B:
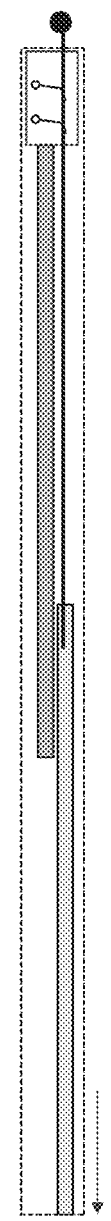
FIG. 79B is a schematic showing the adjustment mechanism of FIG. 78A at a maximum length during elongation.
Figure 79C:
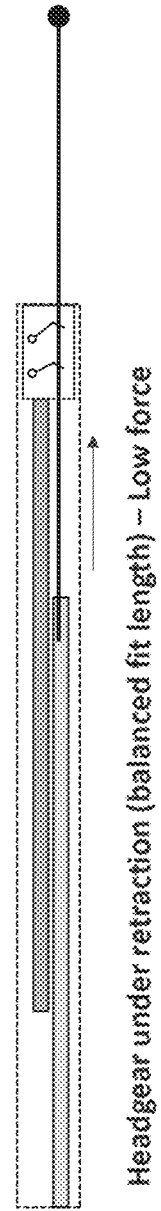
FIG. 79C is a schematic showing the adjustment mechanism of FIG. 78A during retraction.

FIGS. 78C and 79A illustrate a neutral position of the headgear in which the inner 2420 and outer 2410 rails overlap to their full or greatest extent and the headgear is at its minimum size or length. When the headgear 2200 is stretched or elongated, for example, for donning and/or doffing, the inner rails 2420 and outer rails 2410 slide away from each other along axes extending parallel to longitudinal axes of the inner rails 2420 and outer rails 2410 such that the overlap between them is reduced, the filament 2300 is drawn through the washer housing 2310, the washers 2312 engage with the filament to provide resistance to elongation, and the elastic tube 2324, which resists elongation, is stretched and put under tension, as shown in FIGS. 78D and 79B. The end stop 2303 provides a stop or limit to the amount the elastic tube 2324 is allowed to stretch. The washer housing 2310 contacts the end stop 2303 when the headgear has reached its maximum length during elongation, and the end stop 2303 prevents, inhibits, or reduces the likelihood of further movement or travel of the washer housing 2310 and filament 2300 relative to each other. When the elongation force is released, the headgear 2200 automatically retracts, as shown in FIG. 79C, to or towards a fitted position, which can be a balanced fit position that can match or substantially match the circumference of the user's head. The balanced fit position can be a position or length (size) of the headgear at which the retention force of the headgear balances with the force induced by the therapy (e.g., blow-off force) and/or other forces (e.g., hose pull forces) attempting to elongate the headgear. The internal forces of the elastic tube 2324 cause the elastic tube 2324 to recoil and/or retract. The retraction force provided by the elastic tube 2324 pushes the outer rails 2410 back towards the washer housing 2310 and/or pushes the filament 2300 back through the washer housing 2310 and washers 2312 (in the opposite direction as during elongation), which releases the washers 2312 to reduce or minimize resistance to the filament 2300 moving through the washer housing 2310.

FIGS. 80A-81C illustrate an example embodiment of an automatic headgear adjustment mechanism including telescoping members. A headgear can include two such adjustment mechanisms, one on each side of the user's head in use. As shown, the adjustment mechanism includes an outer member 2430, an inner member 2432, an inelastic filament 2300, a washer housing 2310, and an elastic tube 2438. The inner member 2432 is disposed within the outer member 2430, and the inner member 2432 and outer member 2430 can slide relative to each other. The telescoping inner member 2432 and outer member 2430 can act as a support beam. The elastic tube 2438 surrounds the inner member 2432, outer member 2430, and washer housing 2310. In the illustrated example, the outer member 2430 is coupled to the washer housing 2310, a first end of the elastic tube 2438 is fixed to the inner member 2432, and the other end of the elastic tube 2438 is fixed to the washer housing 2310 or another headgear component. In other examples, the inner member 2432 can be coupled to the washer housing 2310, and the first end of the elastic tube 2438 can be fixed to the outer member 2430. The elastic tube 2438 can be made of or include, for example, a textile such as a knitted or braided material, silicone, or TPE (thermoplastic elastomer). One end of the filament 2300 can be fixed or secured to or relative to the inner 2432 or outer 2430 members. The opposite end of the inelastic filament 2300 forms or includes an end stop 2303. A longitudinal axis of the filament 2300 can be aligned with (e.g., parallel to or coaxial with) a longitudinal axis of the elastic tube 2438.

In a neutral position, shown in FIGS. 80C and 81A, the inner member 2432 and outer member 2430 overlap to their full or greatest extent and the headgear is at its minimum size or length. When the headgear 2200 is stretched or elongated, for example, for donning and/or doffing, the inner member 2432 and outer member 2430 slide relative to each other such that the overlap between them is reduced, the filament 2300 is drawn through the washer housing 2310, the washers 2312 engage with the filament to provide resistance to elongation, and the elastic tube 2438, which resists elongation, is stretched and put under tension, as shown in FIGS. 80D and 81B. The end stop 2303 can provide a stop or limit to the sliding of the inner member 2432 and outer member 2430 relative to each other and/or the amount the elastic tube 2438 is allowed to stretch. The washer housing 2310 contacts the end stop 2303 when the headgear has reached its maximum length during elongation, and the end stop 2303 prevents, inhibits, or reduces the likelihood of further movement or travel of the washer housing 2310 and filament 2300 relative to each other. When the elongation force is released, the headgear 2200 automatically retracts as shown in FIG. 81C. The internal forces of the elastic tube 2438 cause the elastic tube 2438 to recoil and/or retract. The retraction force provided by the elastic tube 2438 pushes the outer member 2430 and inner member 2432 back toward each other such that the overlap between the outer member 2430 and inner member 2432 is increased and/or pushes the filament 2300 back through the washer housing 2310 (in the opposite direction as during elongation), which releases the washers to reduce or minimize resistance to the filament 2300 moving through the washer housing 2310.

In some situations, a filament in an automatically adjustable headgear mechanism may buckle or bend during retraction. This can prevent, inhibit, or reduce the likelihood of the adjustment mechanism and/or headgear from retracting smoothly to a smaller size to fit the user, which may compromise the seal between the mask interface and user's face, and/or reduce comfort to the user. The filament may buckle if the force required to bend or buckle the filament is less than the resistance forces that are applied to the filament by the washer mechanism. The filament can then bend or buckle before the filament enters the washer housing and washers. For example, FIGS. 82A-82B illustrate an example of an automatically adjustable headgear mechanism including an inelastic filament 2300 disposed and extending within an elastic braid 2302. One end of the braid 2302 is coupled to an end of the yoke 2202, and the other end of the braid 2302 is coupled to the rear strap 2204 of the headgear. FIG. 82B shows the filament 2300 buckled. The problem of the filament potentially bending or buckling can be accentuated in an embodiment in which the braid 2302 has an increased neutral or minimum length to provide a greater range of size adjustment.

Figure 83B:
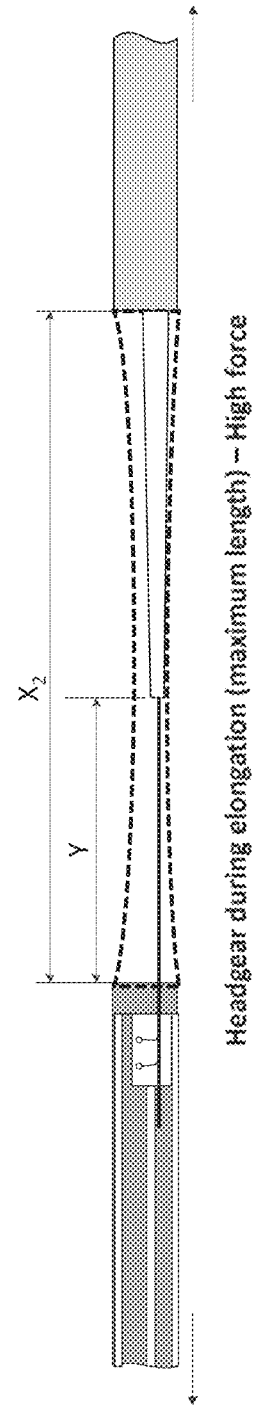
FIG. 83B shows the adjustment mechanism of FIG. 83A at a maximum length during elongation.
Figure 83C:
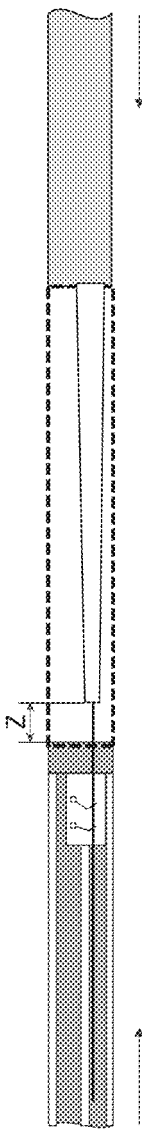
FIG. 83C shows the adjustment mechanism of FIG. 83A during retraction.

To address this problem, in some examples, an automatically adjustable headgear mechanism includes a support beam in the form of a braid core 2440 that is housed and slides within the braid 2302, as shown in FIGS. 83A-83C. The filament 2300 can be permanently joined to the braid core 2440, for example, by overmolding. The braid core 2440 can be integrally formed with a plastic headgear or headgear component and/or permanently joined to a headgear strap, for example, the rear strap 2204, for example, by intramolding as described above. Examples of an intramolding process and intramolded products are described in PCT Publication No. WO 2016/043603 and U.S. Publication No. 2016/0074614, which are hereby incorporated by reference herein. An intramolded headgear strap in some embodiments comprises a tube of fabric with an integrated plastic core. The braid core in these embodiments may comprise an extension of that plastic core beyond the fabric layers. That is, the braid core comprises plastic with no integrated fabric layers. The braid core 2440 can be flexible but relatively more rigid than the filament 2300 due to, for example, the braid core 2440 being made of or including a relatively harder or rigid material than the filament 2300 and/or relative dimensions of the braid core 2440 and filament 2300 (e.g., the braid core 2440 can be thicker than the filament 2300, which can provide greater rigidity to the braid core 2440 compared to the filament 2300). The elastic braid 2302 can have a minimum length X1 that is substantially equal to a length of the braid core 2440. The braid core 2440 advantageously increases stability of the adjustment mechanism by providing additional structure to at least a portion of the adjustment length of the adjustment mechanism compared to the filament 2300 alone. For example, the braid core 2440 provides structure and support to the braid 2302 and improves the braid's 2302 ability to transfer loads applied to the mask interface 2102 via the yoke 2202 to the headgear 2200, thereby improving the stability of the mask on the user's face. Reduced buckling of the filament can help reduce or minimize the activation length of the adjustment mechanism. In the illustrated example, the washer housing 2310 is included in a yoke 2202 that couples to the mask interface in use, and the filament 2300 extends through the washer housing 2310 into a line track 2201 within the yoke 2202. A headgear can include two such adjustment mechanisms, one on each side of the user's head in use.

Figure 87:
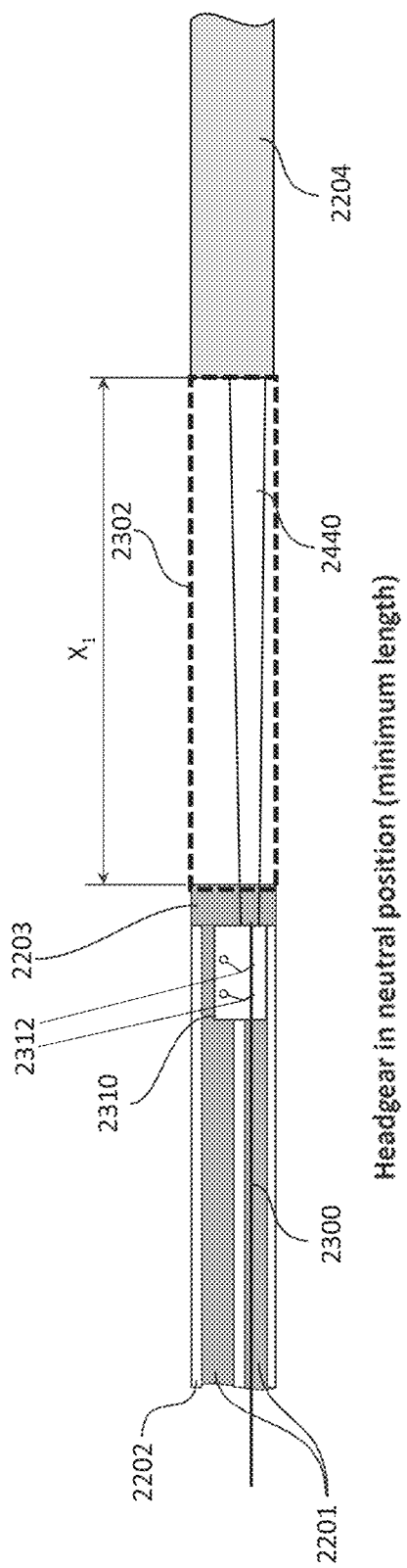
FIG. 87 shows another example embodiment of an adjustment mechanism.

In a neutral position, for example as shown in FIG. 83A, the braid core 2440 abuts the end cap 2203 (e.g., as illustrated) or the washer housing 2310 (e.g., by extending through the end cap 2203 as illustrated in FIG. 87 and described in greater detail herein or in an example that does not include a yoke 202 and/or examples shown in FIGS. 75A-81C). When the headgear 2200 is stretched or elongated, for example, for donning and/or doffing, the elastic braid 2302 is stretched, the braid core 2440 and inelastic filament 2300 slide within the elastic braid 2302, the filament 2300 is drawn through the washer housing 2310, and the washers engage to provide resistance to elongation, as shown in FIG. 83B. The elastic braid 2302 has a maximum extended length X2. When elastic braid 2302 is stretched, the elastic braid 2302 is partially supported by the braid core 2440, and a length of the elastic braid 2302 is supported only by the filament 2300. When the elastic braid 2302 is stretched to its greatest or fullest extent and at its maximum length, a length Y of the elastic braid 2302 unsupported by the braid core 2440 is equal to the difference between $X_2$ and $X_1$. When the elongation force is released, the headgear 2200 automatically retracts as shown in FIG. 83C. The internal forces of the elastic braid 2302 cause the elastic braid 2302 to recoil and/or retract. The retraction force provided by the elastic braid 2302 pushes the filament 2300 back through the washer housing 2310 (in the opposite direction as during elongation), which releases the washers to reduce or minimize resistance to the filament 2300 moving through the washer housing 2310. When the headgear is fitted to the user, the headgear settles at a balanced-fit length, as shown in FIG. 83C. The balanced-fit length can match or substantially match the circumference of the user's head. In the balanced-fit length, the elastic braid 2302 can have a length between the minimum length $X_1$ and the maximum length $X_2$, depending on the size of the user's head, and a length Z of the elastic braid 2302 unsupported by the braid core 2440 can be less than Y.

Figure 84A:
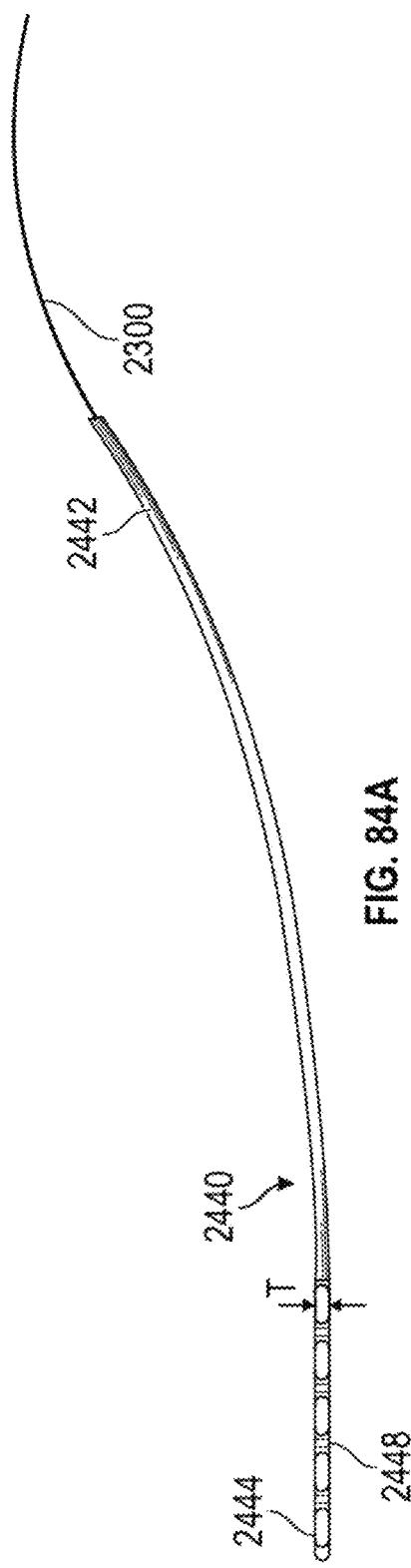
FIG. 84A is a top view of an example embodiment of a braid core of the adjustment mechanism of FIG. 83A.
Figure 84B:
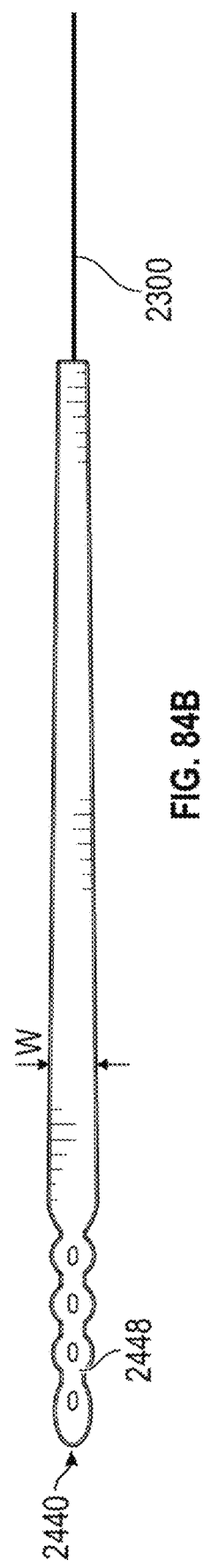
FIG. 84B is a side view of the braid core of FIG. 84A.

FIGS. 84A-84B illustrate an example embodiment of a braid core 2440. The filament 2300 can be permanently joined to a free end 2442 of the braid core 2440, for example, by overmolding. A fixed end 2444 of the braid core 2440 can be permanently joined to a headgear strap, for example, the rear strap 2204, for example, by overmolding or intramolding. A portion of the braid core 2440 at, adjacent, or near the fixed end 2444 can include a geometry 2448 designed to help improve the strength of the mechanical connection between the braid core 2440 and headgear strap. The geometry 2448 can include ribbed edges and/or apertures as shown. Any other appropriate geometry can be used. The apertures can help form a mechanical bond between the overmold material of the headgear strap and the braid core 440.

In the illustrated example, the braid core 2440 is curved, which can allow the braid core 2440 to follow the curvature of the user's head in use. The curvature of the braid core 2440 can also or alternatively help hold the headgear 2200 open (e.g., such that the headgear 2200 can hold or maintain a hoop-like structure or shape) when not in use and/or during donning and doffing, which can help improve the ease of fitting the headgear 2200 to the user. The braid core 2440 can help prevent, inhibit, or reduce the likelihood of the headgear straps or braid twisting or tangling with themselves and/or other parts of the headgear. The curvature of the braid core 2440 can help guide the filament 2300 into the washer housing 2310 in the correct direction, which can help reduce or minimize kinks in the filament 2300 which could prevent the adjustment mechanism from functioning effectively.

Figure 85A:
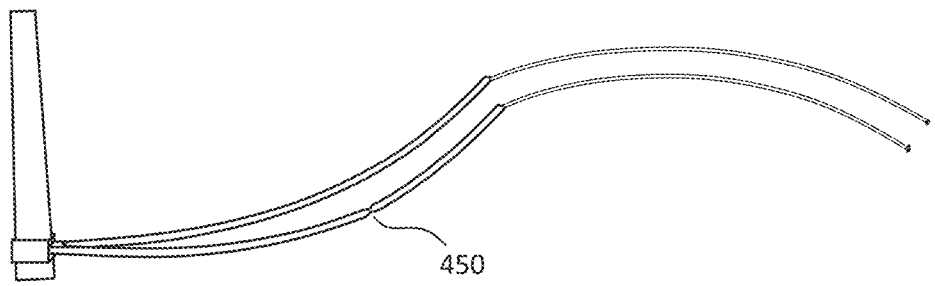
FIG. 85A is a top view of an example embodiment of a braid core during manufacturing.

The braid core 2440 has a width W that is narrower or less than a width of the braid 2302 when the braid 2302 is fully extended as shown in FIG. 83B. This difference in width can help reduce or prevent friction between the braid core 2440 and the braid 2302 from limiting extension of the braid 2302. The width W of the braid core 2440 is greater than a thickness T of the braid core 2440. The lesser thickness T compared to the width W allows the braid core 2440 to flex in the direction of the thickness T and/or curvature, which can allow the headgear to adapt more easily to the shape of the user's head. The increased width W compared to the thickness T helps provide stability for the mask interface 2102 in superior-inferior direction relative to the user in use. The width of the braid core 2440 can be tapered toward the free end 2442 (i.e., such that the free end 2442 is narrower than a portion of the braid core 2440 closer to the fixed end 2444). The tapered width can help prevent, inhibit, or reduce the likelihood of the free end 2442 from snagging or catching on the inside of the elastic braid 2302 when the headgear is retracting in size. The tapered width can allow forces to be distributed evenly along the length of the braid core 2440. The tapered width can make the free end 2442 more flexible than the fixed end 2444, which can reduce the difference in flexibility between the free end 2442 and the filament 2300. If the braid core 2440 was instead significantly more rigid than the filament 2300, a hinge point could be created at or near the joint between the filament 2300 and braid core 2440. The filament 2300 could therefore be more likely to bend or kink at the hinge point as a result of forces applied by the restriction mechanism, which could reduce the functionality of the adjustment mechanism. In some examples, the braid core 2440 includes a notch 2450, i.e., a region of reduced thickness, as shown in FIG. 85A. The notch 2450 can be positioned near the free end 2442, or relatively closer to the free end 2442 than the fixed end 2444. The notch 2450 can provide increased flexibility near the filament 2300, which can help guide the filament 2300 into the washer housing 2310. The notch 2450 can help prevent, inhibit, or reduce the likelihood of the joint between the braid core 2440 and the filament 2300 from becoming a hinge point at which the filament 2300 bends or kinks as a result of a sudden change in rigidity.

Figure 85B:
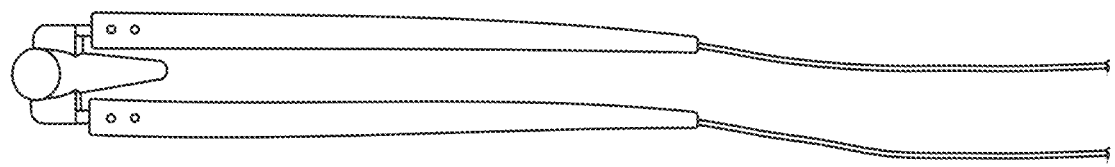
FIG. 85B is a side view of the braid core of FIG. 85A during manufacturing.

In some examples, two braid cores 2440 can be formed in a single injection molding process shot, for example as shown in FIGS. 85A and 85B, which can improve ease and efficiency of manufacturing.

Figure 86A:
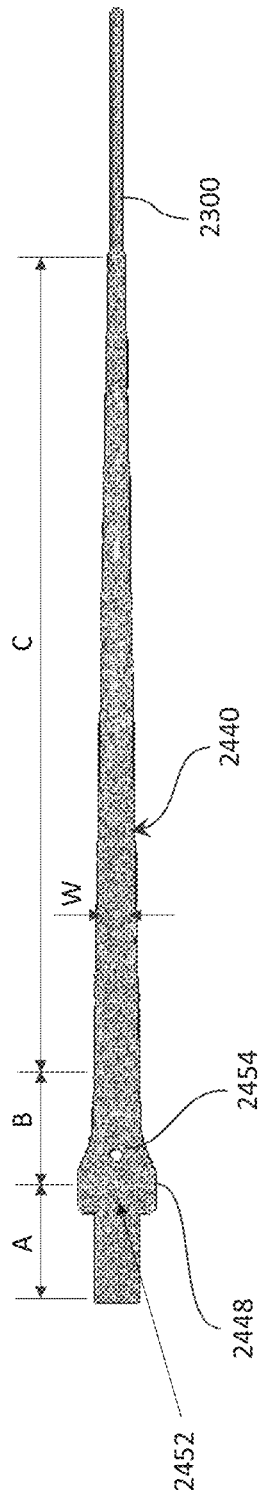
FIG. 86A is a side view of another example embodiment of a braid core.
Figure 86B:
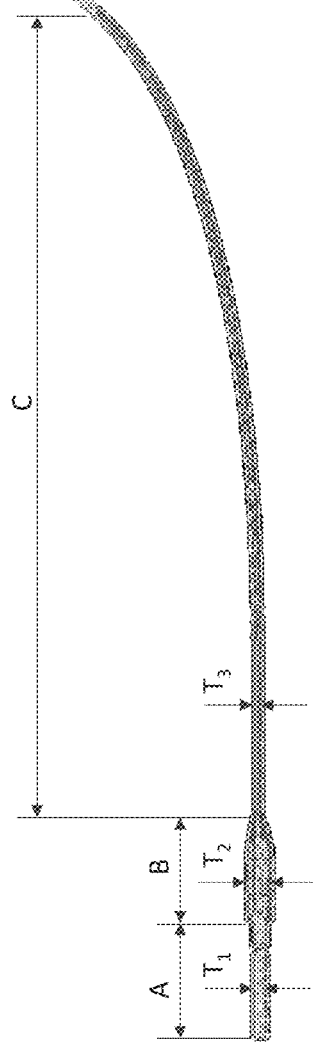
FIG. 86B is a top view of the braid core of FIG. 86A.

FIGS. 86A-86B illustrate another example embodiment of a braid core 2440. The width W of the braid core 2440 of FIGS. 86A-86B has an increased taper toward the free end 2442 compared to the example of FIGS. 84A-84B. The taper can help more evenly distribute loads applied to the filament 2300 along the length of the braid core 2440. A portion of the braid core 2440 at, adjacent, or near the fixed end 2444 can include a geometry 2448 designed to help improve the strength of the mechanical connection between the braid core 2440 and headgear strap. The geometry 2448 can help improve alignment with the overmolding tool. In the illustrated example, the geometry 2448 includes an end portion A that is overmolded within the end of a headgear strap, for example, an intramolded headgear strap. End portion A can include an aperture 2452 that forms part of a mechanical joint between the braid core 2440 and the headgear strap. In the illustrated example, end portion A is rectangular, but portion A can be any suitable shape and/or may include cut-outs, ridges, and/or other features to provide strength to the overmolded joint formed with the headgear strap. A portion B of the braid core 2440 can help align the braid core 2440 within the overmolding tool. As shown, portion B can be adjacent end portion A. Portion B can include an aperture 2454 that receives a protrusion of the overmold tool to prevent, inhibit, or reduce the likelihood of the braid core 2440 from moving when material is injected into the overmold tool. In some embodiments, portion B has an increased thickness T2 compared to thickness T1 and T3 of end portion A and a remainder C (e.g., a portion extending from portion B to the free end 442) of the braid core 2440, as shown in FIG. 86B. The increased thickness T2 can advantageously allow outer surfaces of the braid core 2440 to abut with internal surfaces of a mold cavity within the overmold tool, which can help improve alignment and positioning of the braid core 2440 within the tool.

In some examples, the braid core 2440 can have a width W that is wider or greater than a width of the braid 2302 when the braid 2302 is fully extended. This can allow the braid core 2440 and braid 2302 to provide a soft stop for the adjustment mechanism to minimize or prevent further extension of the adjustment mechanism, and therefore headgear size, when the braid 2302 is extended and reduced in width to a width the same as the width of the braid core 2440. When the braid 2302 is extended such that its width matches the braid core 2440 width, friction between the braid core 2440 and braid 2302 limits further extension of the braid 2302. This soft stop can prevent, inhibit, or reduce the likelihood of the filament 2300 from being pulled out of contact with the washers, which could prevent, inhibit, or reduce the likelihood of the adjustment mechanism from working properly. In some examples, the thickness of the braid core 2440 can be greater than the width of the braid core 2440. This arrangement can provide greater rigidity in a direction that is radial to the user's head in use and/or help reduce side-to-side movement of the mask on the user's face.

In some examples, the braid core 2440 can extend into the end caps 2203 or ends of the yoke 2202 when the headgear is in a neutral (minimum length) position, for example, as shown in FIG. 87. This arrangement can increase the engagement between the braid core 2440 and yoke 2202, which can help improve the stability of the mask. This arrangement can also or alternatively help prevent, inhibit, or reduce the likelihood of the braid 2302 from twisting and/or the yoke 2202 and/or interface 2102 from flipping relative to the headgear 2200, when not in use. The greater the distance the free end 2442 extends into the end cap 2203 or yoke 2202, the more likely it is that the braid core 2440 will be engaged with the yoke 2202 when the headgear is fitted to a user.

Referring to FIGS. 88-97, a nasal seal component 3102 of a further example of nasal mask interface 3100 will be described in further detail. The nasal seal 3102 is flexible and soft, and may be formed of a silicone material or other suitable material.

Figure 88:
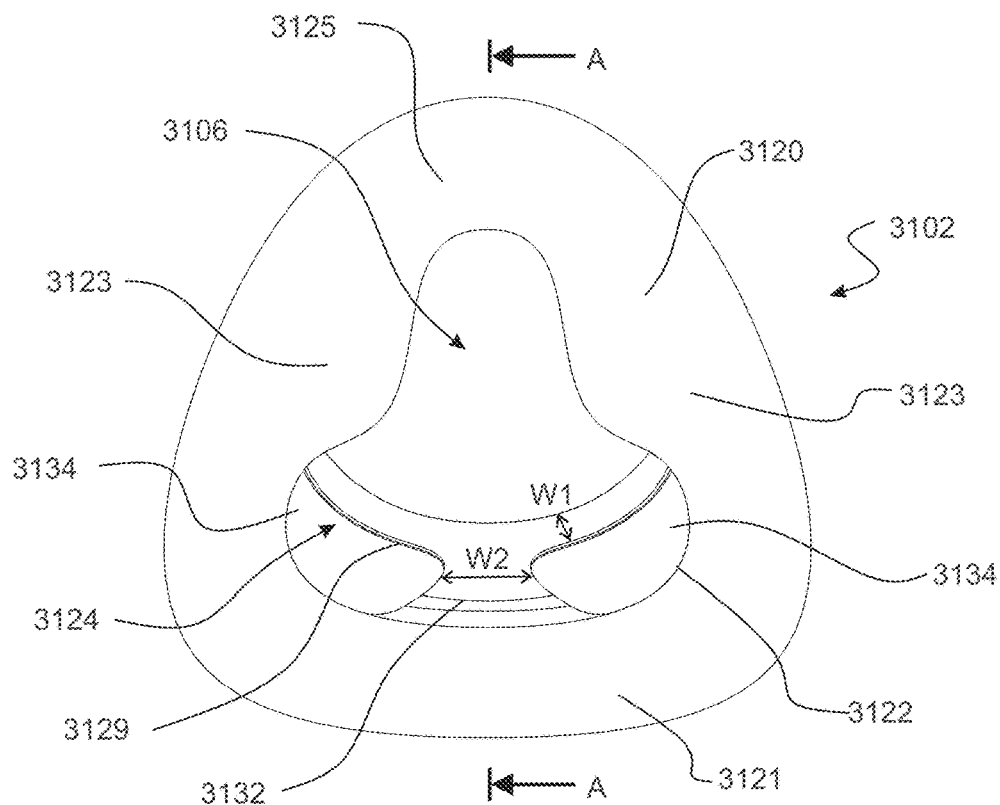
FIG. 88 is a front view from the face-contacting side (or wearer side) of the nasal seal of the nasal mask interface of the first embodiment.

Referring to the face-contacting or wearer side of the nasal seal 3102 shown in FIG. 88, the contacting surface generally indicated at (3120) is configured to seal about the user's nose, including across the bridge of the user's nose. In this example, the contacting surface 3120 circumscribes the nose and seals about the nose of the user. In this embodiment, the contacting surface portion of the nasal seal comprises an upper lip region generally indicated at 3121 that is configured to contact the upper lip region of the face of the user such as at a location above the vermillion border and below the nares. The contacting surface 3120 also comprises left and right cheek or side regions 3123 that extend between the upper lip region 3121 at the bottom of the seal 3102 and a region 3125 corresponding to or proximal to the nasal bridge region at the top of the seal 3102. The cheek regions 3123 of the contacting surface 3120 are configured to contact the medial cheek surface of the user and/or lateral nose surface of the user on either side of the nose. The nasal bridge region 3125 of the contacting surface 3120 is configured to extend over nose and contacts the nasal bridge region of the user's nose and connects the two cheek regions 3123. The overall shape and configuration of the contacting surface 3120 is configured to sealingly conform to the contour of the user's face about the nose and to sealingly engage about the user's nose when secured to the user's head via headgear and when the nasal mask interface receives flow of gases. The nasal seal 3102 can be considered to be of the inflating type as under pressure the seal urges the face-contacting surface 3120 against the face of the user and deforms to substantially seal against the facial contours of the user, including one or more of the upper lip, the medial cheek, the lateral nose and the bridge of the nose.

The contacting surface 3120 of the nasal seal 3102 terminates in an inner peripheral edge 3122 that defines a nose-receiving opening into the mask cavity when the seal 3102 is assembled to the seal housing 3104.

Figure 96:
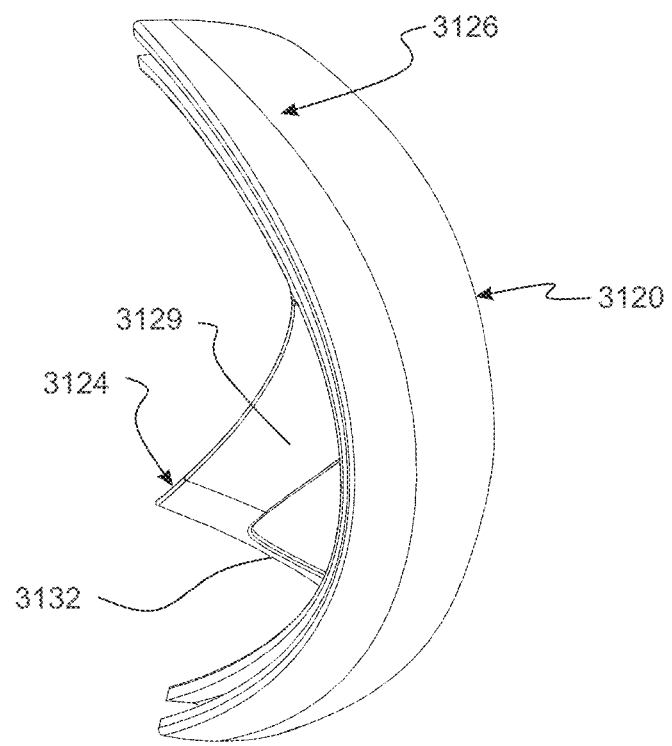
FIG. 96 is a side elevation view of the first embodiment nasal seal.
Figure 97:
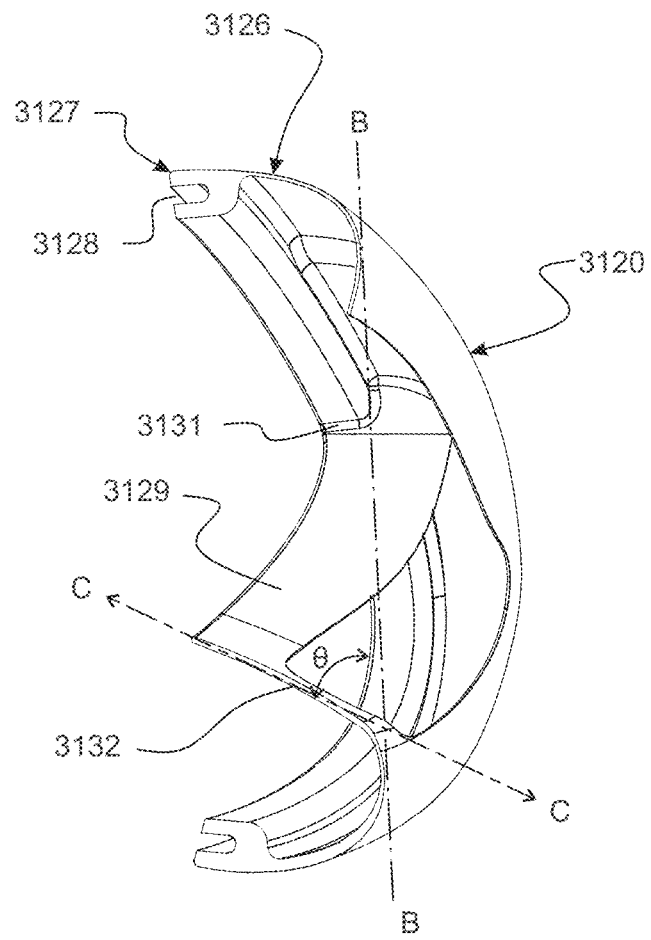

Referring to FIGS. 96 and 97, the nasal seal 3102 is substantially defined by the face-contacting surface portion 3120 and a sidewall portion 3126 that extends rearwardly from the contacting surface 3120 about the periphery of the seal and which terminates at a connecting edge generally indicated at 3127 at the exterior or outer side of the seal that couples or is connectable to the opening 3140 seal housing 3104. As previously described, in this example the nasal seal 3102 is releasably connectable to the seal housing and the terminating edge of the sidewall 3126 comprises a peripheral channel 3128 that is configured to engage with a complimentary peripheral ridge or extension provided at the opening 3140 of the seal housing 3104. As previously discussed, in alternative embodiments, the flexible nasal seal 3102 may be permanently or semi-permanently connected or coupled to the seal housing 3104 such as via overmolding, welding or other connecting methods. In further alternative examples, interface may be provided with a semi-rigid or rigid clip component that is shaped to correspond to the connecting edge 3127 on the exterior or outer side of the nasal seal. In such examples, the connecting edge 3127 of the seal may be overmolded or otherwise permanently connected to the rigid clip component, so as to provide a rigid edge or portion at the outer side of the seal. The rigid clip component may be configured to engage or otherwise connect with a complementary base or housing component to thereby couple the nasal seal to the base or housing.

As shown in FIG. 97, the face-contacting surface 3120 of the nasal seal forms a flange that curls or extends inward from the sidewall 3126 portion of the nasal seal. In this embodiment, the region at or toward the terminating edge 3127 of the sidewall 3126 may be a thickened region relative to the remainder of the sidewall and contacting surface portions of the nasal seal, so as to accommodate the connecting channel 3128 or to otherwise provide some stability at the outerside to the overall shape of the nasal seal.

As discussed, the nasal seal 3102 is formed of a flexible and soft material such that nasal seal 3102 is flexible relative to the rigid housing 3104. By way of example, the seal 3102 may be formed of silicone material or similar.

The nasal seal 3102 comprises an under-nose support 3124 (or nasal sling) that at least extends or is suspended laterally across the nasal seal between the sides of the seal and within the mask cavity 3106 when the nasal seal 3102 is assembled to the seal housing 3104. The under-nose support 3124 is configured to contact at least a portion of the under-nose surface of the user's nose so as to counteract any resultant lift force created when the nasal mask is worn and in use as previously discussed.

In this example, the under-nose support at least extends laterally across the nasal seal between the opposing left and right sides of the nasal seal. As shown, the under-nose support is disposed or located behind or rearward of the nasal seal opening 3106. The under-nose support 3124 is fixedly connected to the nasal seal in that it is not removable. In one form, the under-nose support 3124 is integrally molded within the nasal seal. In alternative forms, it will be appreciated that the under-nose support part or portion of the nasal seal 3102 may be formed separately and then fixedly coupled within the nasal seal such as via an adhesive or welding, or the like, or it could be connected to the seal housing.

Figure 89:
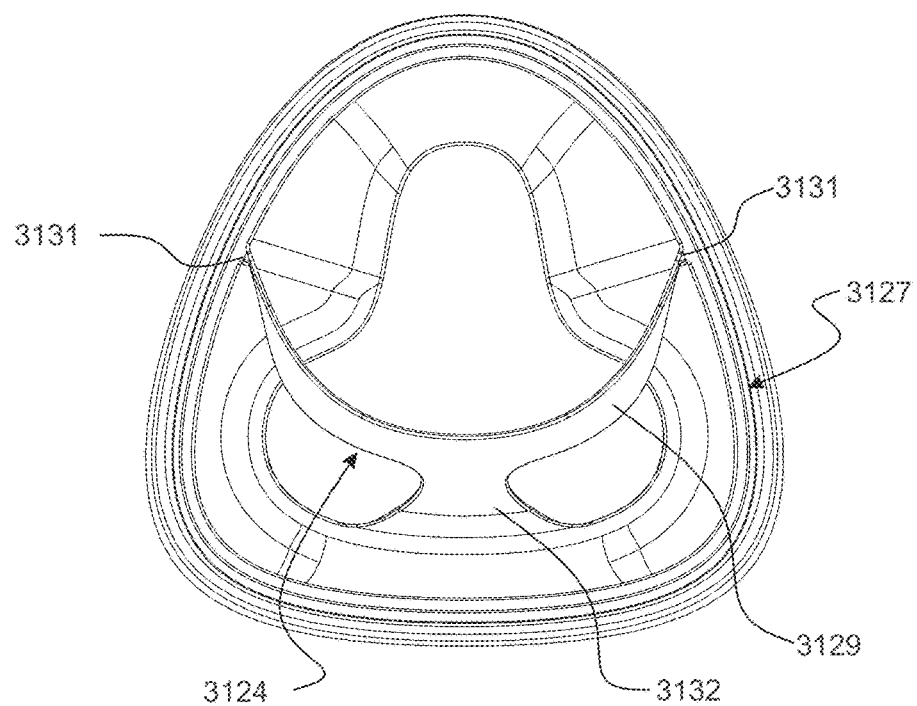
FIG. 89 is a rear view from the outer side of the first embodiment nasal seal.
Figure 90:
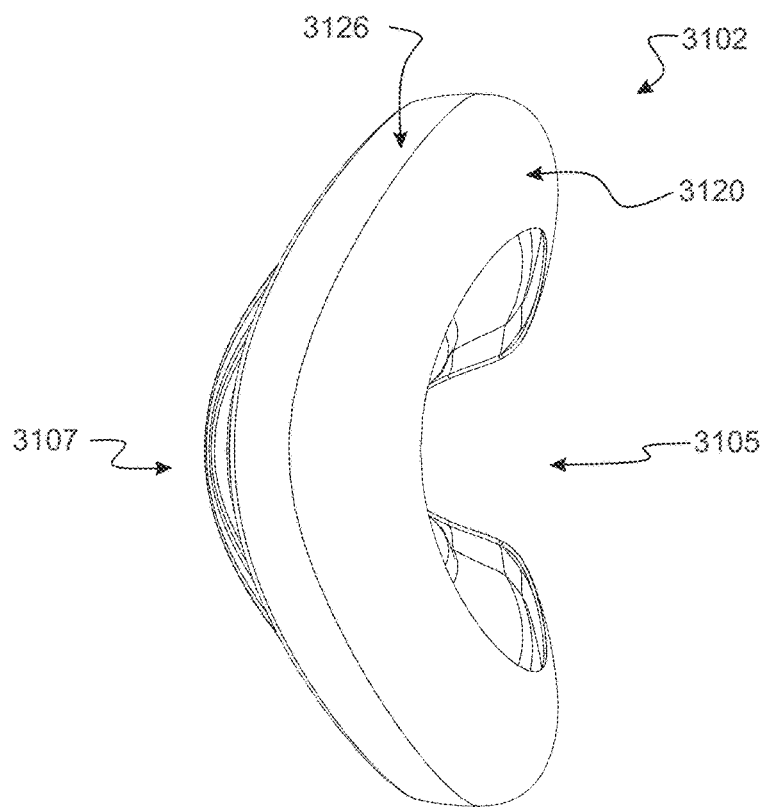
FIG. 90 is a top view of the first embodiment nasal seal.
Figure 91:
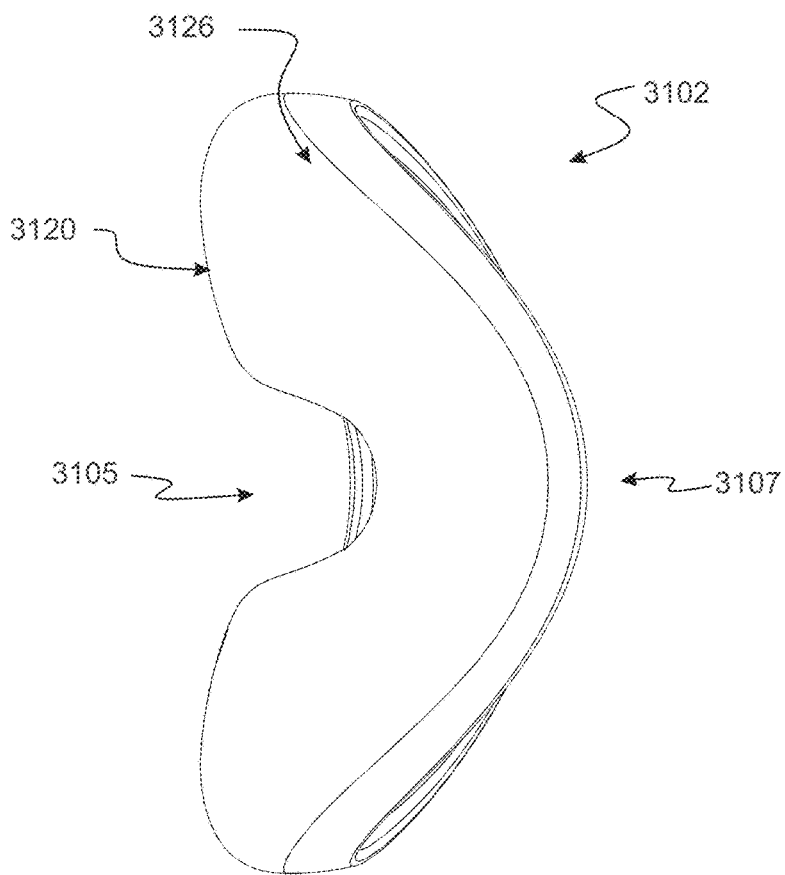
FIG. 91 is an underside view of the first embodiment nasal seal.
Figure 92:
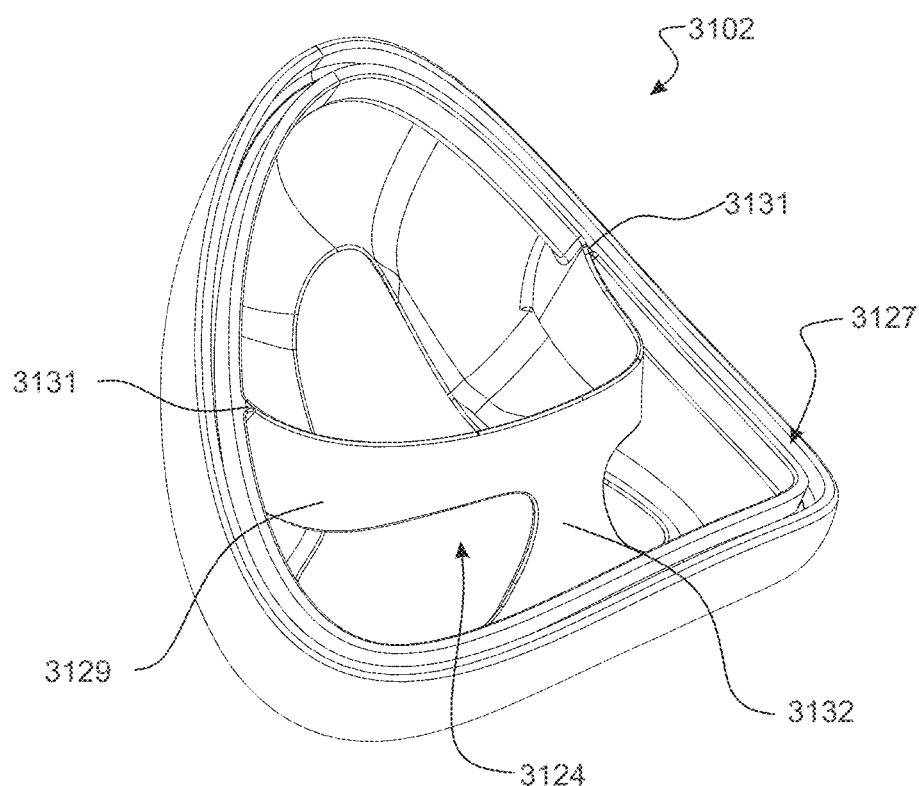
FIG. 92 is a first rear underside perspective view from the outer side of the first embodiment nasal seal.
Figure 93:
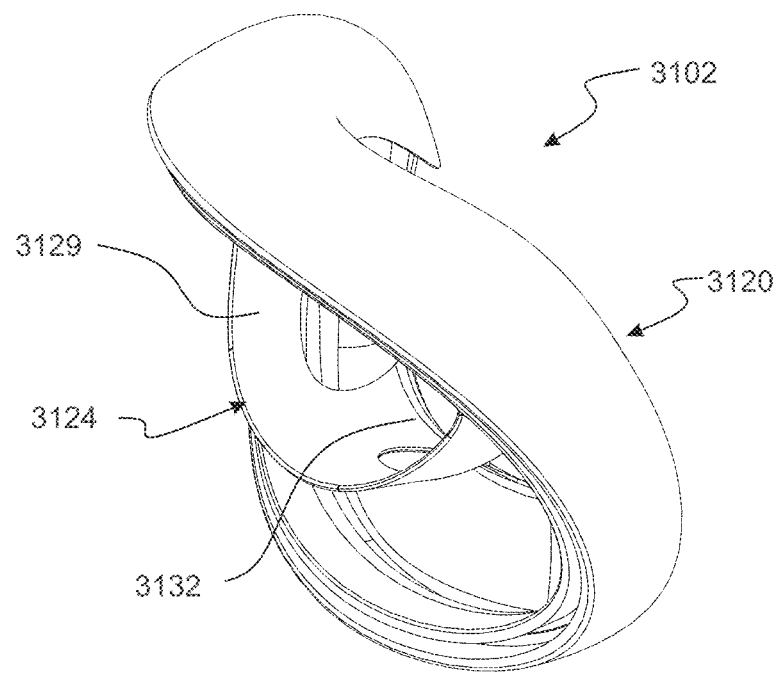
FIG. 93 is a second rear upper perspective view from the outer side of the first embodiment nasal seal.
Figure 94:
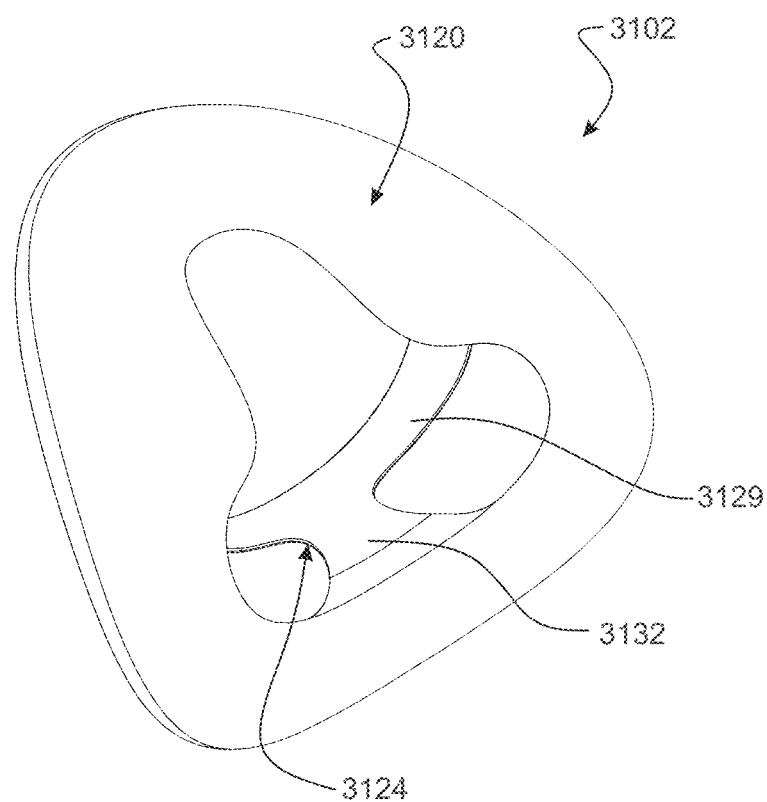
FIG. 94 is a first upper perspective view from the face-contacting side of the first embodiment nasal seal.
Figure 95:
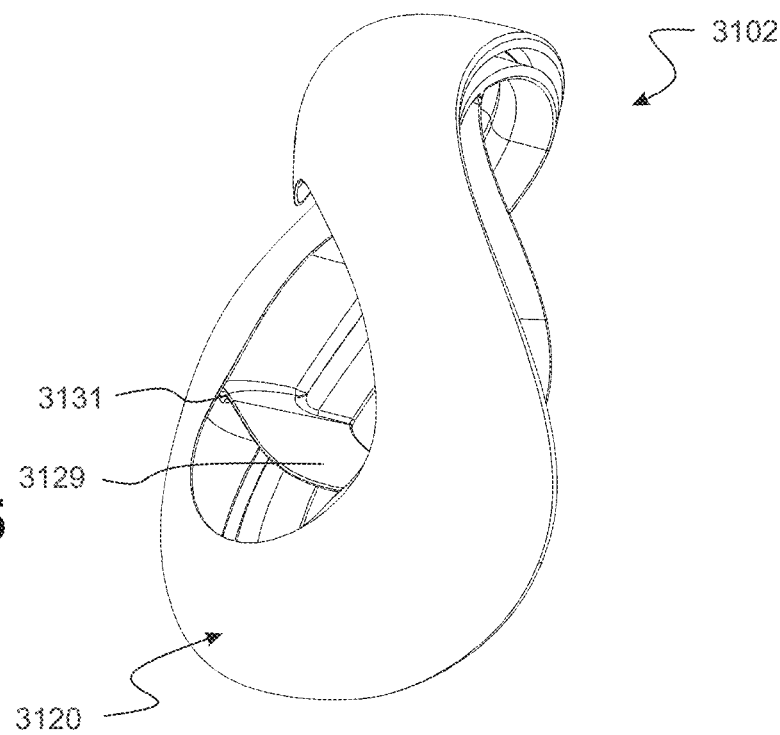
FIG. 95 is a second underside perspective view from the face-contacting side of the first embodiment nasal seal.

In this example, the under-nose support configuration 3124 comprises an elongate main lateral portion or band 3129 that extends across and within the nasal seal, such as suspended between opposing sides of the seal. With reference to FIGS. 89, 92 and 97, the main lateral portion 3129 of the under-nose support is connected or extends from the nasal seal at locations isolated or displaced from at least the peripheral opening edge 3122 of the contacting surface 3120, but also in this example is entirely decoupled or displaced from the contacting surface 3120 such that the lateral portion 3129 does not inhibit or reduce the sealing engagement or deformability of the contacting surface 3120 with the user's face in the cheek and/or lateral nose regions 3123. In this example, the main lateral portion 3129 extends from or is connected at locations 3131 on the inner surfaces of opposing sidewall 3126 portions of the nasal seal rearwardly of the contacting surface 3120. In this example, the connecting locations 3131 correspond with or include the terminating edge 3127 of the sidewall 3126, although this is not essential.

In this example, the under-nose support 3124 further comprises a central extension portion 3132 that extends centrally from the main lateral portion 3129 and is coupled or connected to or at the opening edge 3122 of the contacting surface 3120 in the upper lip region 3121. In alternative examples, the central extension portion 3132 may alternatively be connected to a lower part of the upper lip region 3121 of the contacting surface 3120 below the opening edge 3122 of the seal, or alternatively may be connected at a location at least partially or entirely displaced or isolated from the contacting surface 3121, such as connected to a lower part of the sidewall 3126 of the nasal seal that is rearward of the contacting surface 3120.

The under-nose support 3124 comprising main lateral portion 3129 and central extension portion 3132 provides a contact surface that is configured and/or orientated to contact at least a part of the under-nose surface of the user's nose in use. In this configuration, the main contact surface of the main lateral portion 3129 is configured to engage with at least a portion of the tip of the under-nose surface of the user's nose, which may for example include the tip end of the columella and portions of the alar rim toward the tip of the nose. The central extension portion 3132 is configured to contact the columella region of the under-nose surface of the user's nose, or at least a portion of the columella between the tip and base of the nose, but preferably the majority of the columella extending from the base. The ultimate contact surface area of the under-nose support depends on the shape and size of the user's nose. The configuration of the under-nose support is designed to contact the maximum portion or portions of the under-nose surface without substantially obstructing the user's nostrils which tend to be aligned with the open spaces 3134 on either side of the central extension portion 3132. Depending on the size and shape of the user's nose, the under-nose support 3124 is generally configured to at best completely avoid obstruction of the user's nostrils, but at worst only partially obstruct one or both nostrils.

As shown, the contact surface of the under-nose support 3124 is generally oriented and configured relative to the nasal seal so as to engage the under-nose surface of the user's nose. In this example, the portions of the under-nose support 3124 are integral thin webs or strips of the nasal seal formed during molding of the seal. For example, the thickness of the under-nose support transverse to its contact surface is significantly smaller than the corresponding width of the contacting surface at any location on the under-nose support. In one configuration, the thickness of the under-nose support portions may be substantially similar to the thickness of the seal in the region of the contacting surface 3120 of the nasal seal.

In this example, the width of the main lateral portion 3129 of the under-nose support 3124 may vary along its length between the opposing sides of the nasal seal. In this example, the width W1 of the main lateral portion 3129 may progressively increase from the centre of the nasal seal toward each side. In this example, the width W2 of the central extension portion 3132 of the under-nose support 3124 progressively increases in width W2 as it extends from the main lateral portion 3129 to the contacting surface 3120. In alternative examples, it will be appreciated that the width of either or both of the main lateral portions or central extension portions may be uniform along their length, or have alternative width profiles along their length.

Referring to FIG. 97, a central seal axis BB is defined as extending tangentially between the outer uppermost and lowermost contact points at the center of the contacting surface 3120 when in a relaxed condition (e.g. not in use). As shown in FIG. 97, at least a portion (e.g. indicated by axis CC extending coincident with the contact surface of the under-nose support portion(s) in the central region) of the contact surface of the under-nose support 3124 in a central region of the under-nose support extends at an angle θ relative to seal axis BB such that the contact surface of the under-nose support is not parallel or aligned with the seal axis BB. In this example, the contact surface in the central region of the under-nose support 3124 is oriented at an angle offset from the seal axis BB in the range of approximately 30 to approximately 90 degrees, more preferably approximately 45 to approximately 75 degrees, and more preferably approximately 60 degrees. This angular orientation of at least the main nose contacting portion or surface of the under-nose support in the central region is configured to substantially align with the general or typical angular orientation of the under-nose surface of the user's nose when their nose is within the nasal seal.

As explained above, the under-nose support 3124 is fixedly connected or is otherwise an integral component of the nasal seal 3102. The accompanying drawings depict the nasal seal and its under-nose support 3124 in a rest state, i.e. un-used. Like the contacting surface 3120 of the nasal seal, the under-nose support 3124 is also configured to be soft and flexible or pliable such that its shape and position may conform with a sling-like effect to the under-nose surface of the user's nose when the nasal mask interface is secured to a user's face in use or is otherwise worn. Typically, the under-nose support is non-stretchable in any direction, although may have a degree of stretch in alternative examples.

Referring to FIGS. 98-118, the nasal seal 3202 of the nasal mask interface 3200 will be described in further detail. The nasal seal 3202 is flexible and soft, and may be formed of a silicone material or other suitable material as will be appreciated by a skilled person.

Figure 98:
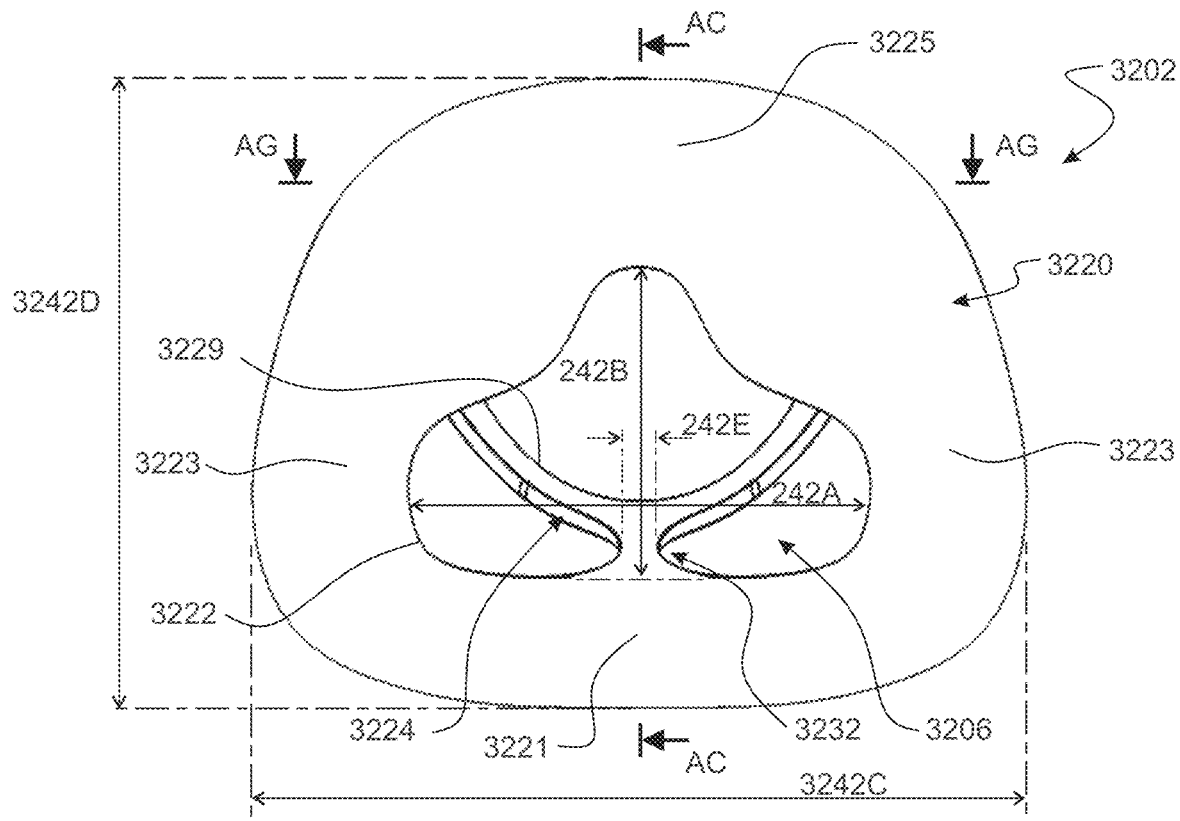

Referring to the face-contacting or wearer side of the nasal seal 3202 shown in FIG. 98, the contacting surface is generally indicated at 3220 and is configured to seal about the user's nose, including across the bridge of the user's nose. In this example, the contacting surface 3220 circumscribes at least a portion of the nose and seals about that portion of the nose of the user. The contacting surface 3220 of the nasal seal comprises an upper lip region generally indicated at 3221 that is configured to contact the upper lip region of the face of the user such as at a location above the vermillion border and below the nares. The contacting surface 3220 also comprises left and right cheek or side regions 3223 that extend between the upper lip region 3221 at the bottom of the seal and an upper region 3225 corresponding to or proximal to the nasal bridge region at the top of the nasal seal 3202. The cheek regions 3223 of the contacting surface 3220 are configured to contact the medial cheek surface of the user and/or lateral nose surface of the user on either side of the nose. The nasal bridge region 3225 of the contacting surface 3220 is configured to extend over the nose and contacts the nasal bridge region of the user's nose, and connects to the two cheek regions 3223. As will be explained in further detail later, in this example the nasal seal 3202 comprises a lower profile height dimension than conventional nasal masks such that the nasal bridge region 3225 of the contacting surface is configured to contact the user's nasal bridge in a middle region of the nasal bridge at a location on the nasal bridge between the lower tip of the user's nose and the upper extremity of the nasal bridge between the user's eyes. In this example, the nasal bridge region 3225 of the contacting surface 3220 is configured to contact the user's nasal bridge in a region of the nasal bridge that is below the user's eyes. In an example, the nasal bridge region 3225 of the nasal seal is configured to contact the user's nasal bridge in the region defined between the nares of the nose and the center of the nasal bridge. In an example, the nasal bridge region 3225 of the nasal seal is configured to contact the bottom half of the user's nose.

Figure 103:
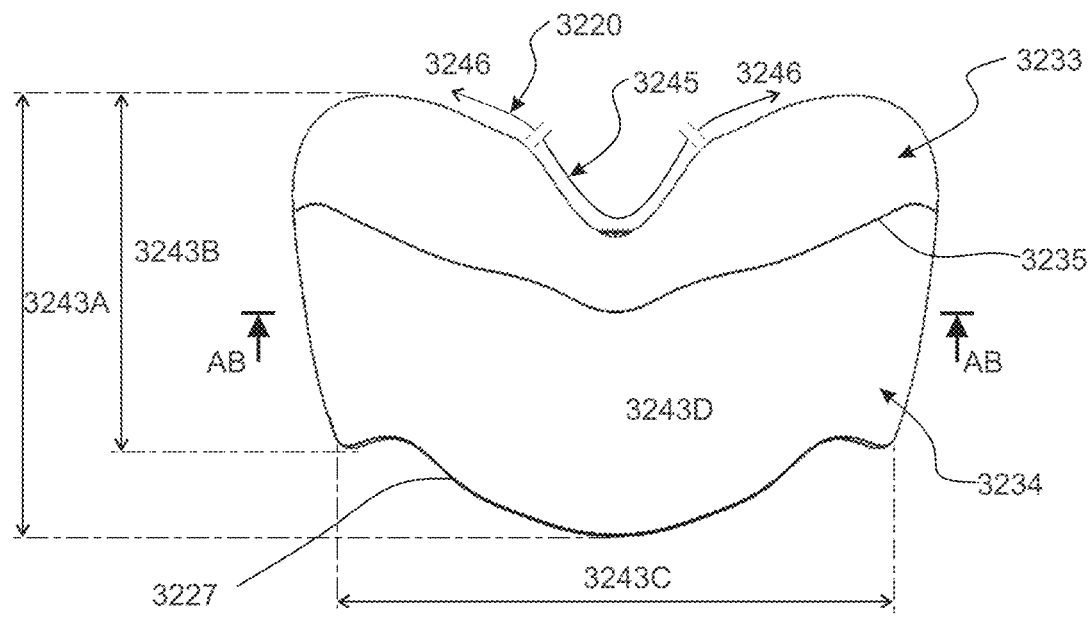

Referring to FIG. 103, in this example the nasal bridge region 3225 of the contacting surface 3220 comprises a central valley region or portion indicated at 3245 that is recessed relative to the remainder of the contacting surface. The valley region 3245 is configured to engage with the user's nasal bridge and is shaped to conform substantially to the nasal bridge of a user.

The overall shape and configuration of the contacting surface 3220 is arranged to sealingly conform to the contour of the user's face about the nose and to sealingly engage about the user's nose when secured to the user's head via headgear and when the nasal mask interface receives a flow of gases. In this example, the nasal seal can be considered to be of the inflating type as under pressure the seal urges the face-contacting surface 3220 against the face of the user and deforms to substantially seal against the facial contours of the user, including one or more of the upper lip, the medial cheek, the lateral nose and the bridge of the nose.

Figure 99:
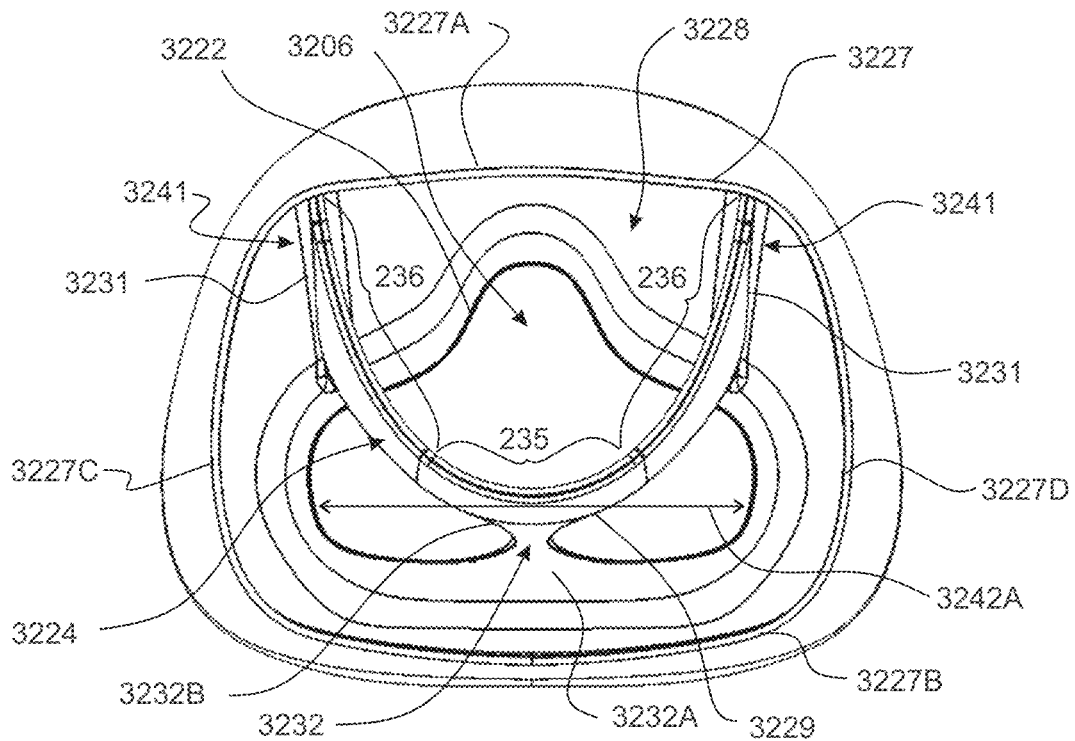
Figure 100:
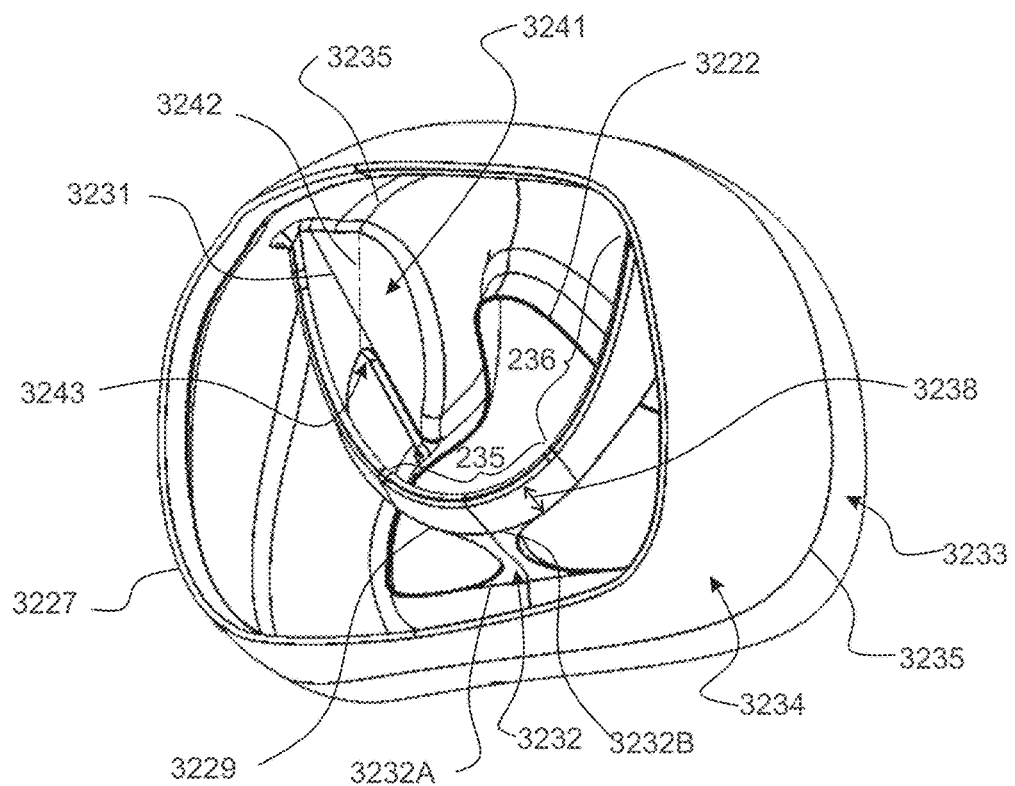
Figure 101:
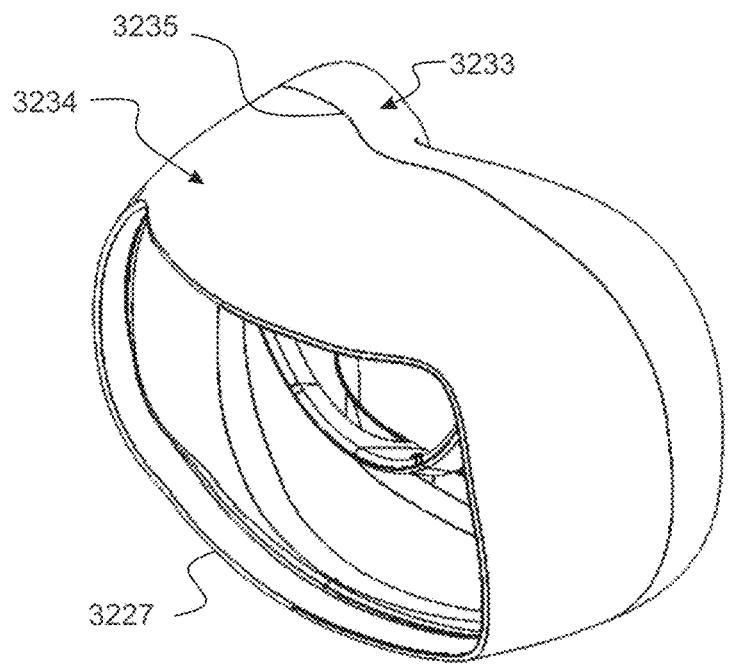

The contacting surface 3220 of the nasal seal 3202 terminates at an inner peripheral edge 3222 that defines the nose-receiving opening or nasal aperture 3206 into the mask cavity. The mask cavity is defined or formed when the nasal seal 3202 is assembled or connected to the seal housing 3204. Referring to FIG. 99, the outer side of the nasal seal opposite to the face-contacting side of FIG. 98 is shown. The outer side of the nasal seal 3202 connects to the seal housing 3204. In this example, the outer side of the nasal seal 202 terminates at a connecting edge 3227 that defines an outer side or housing aperture 3228 for receiving or connecting with the seal housing 3204.

Figure 102:
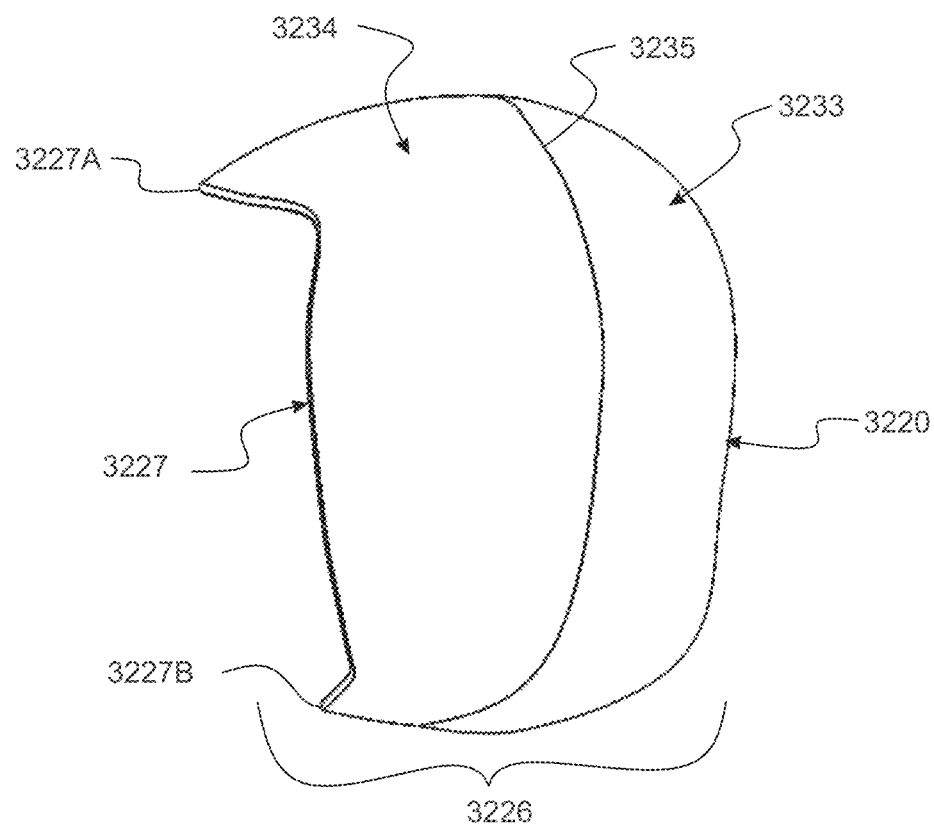
Figure 104:
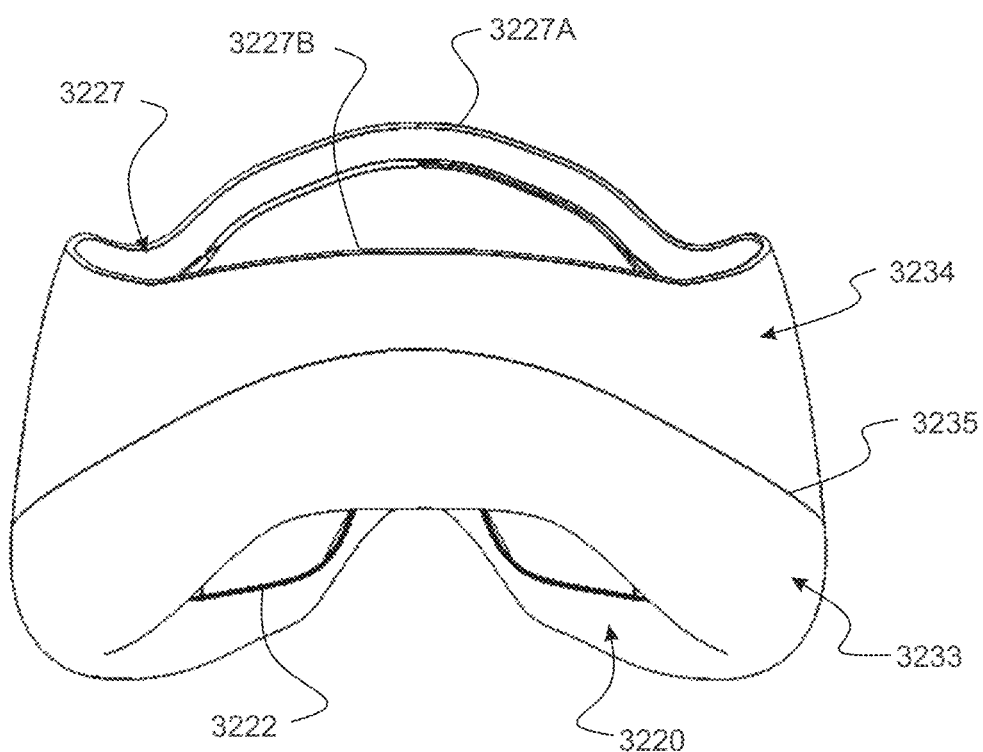

Referring to FIG. 102, the connecting edge 3227 at the outer side of the nasal seal 3202 is not coincident with a single plane or extends in a single plane. Referring to FIGS. 99 and 102, the connecting edge 3227 at the outer side of the nasal seal comprises an upper edge 3227A, a lower edge 3227B and lateral side edges 3227C, 3227D that extend between the upper 3227A and lower 3227B edges. The upper edge 3227A protrudes rearwardly of the side lateral edges 3227C and 3227D. At least a central portion of the lower edge 3227B may also protrude rearwardly of the lateral edges 3227. At least a central portion of the upper connecting edge 3227A protrudes rearwardly beyond both the lateral edges 3227C, 3227D and the lower edge 3227B. As shown in FIG. 104, the upper edge 3227A protrudes or bulges outwardly to an apex at a centre of the nasal seal.

The nasal aperture 3206 formed on the face-contacting side of the nasal seal 3202 is generally or semi triangular in shape to match the natural geometry of a human nose. The housing aperture 3228 on the outer side of the nasal seal 3202 is generally or semi rectangular in shape.

Referring to FIGS. 98 and 99, the under-nose support 3224 can be seen and is generally concave or U-shaped with three connection or attachment points to or within the nasal seal 3202. As shown, the under-nose support 3224 is suspended like a sling or hammock between two upper connection points 3231 located at opposing upper lateral positions or surfaces within the nasal seal 3202. In particular, the upper lateral connections 3231 are located on the inside surface of the nasal seal 3202, one on each side of the central apex region of the nasal aperture 3206. The lateral connections 3231 of the under-nose support 3224 are configured or arranged in a vertical orientation such that the inner or contact surfaces of the under-nose support 3224 substantially face or oppose each other at or toward the lateral connection points 3231. In particular, the lateral contact surfaces of the under-nose support 3224 may be substantially parallel to each other at or toward the lateral connection points 3231. The under-nose support 3224 further comprises a third connection at or toward the centre bottom of the nasal seal. The bottom centre connection point 3232 couples to or at the centre bottom region of the edge 3222 of the contacting surface 3220 of the nasal seal that defines the nasal aperture 206. The under-nose support 3224 and its connections will be explained further in detail later.

Referring to FIGS. 102-104, the nasal seal to 3202 is substantially defined by the face-contacting surface portion 3220 (shown in FIG. 98) and a sidewall portion 3226 (shown in FIG. 102) that extends rearwardly from the contacting surface about the periphery of the seal and which terminates at the connecting edge 3227 at the exterior or outer side of the seal that couples or is connected to the seal housing 3204. The nasal seal 3202 may comprise varying thickness profiles or regions extending from the nasal aperture edge 3222 on the face-contacting side of the nasal seal to the connecting edge 3227 at the outer side of the nasal seal.

The nasal seal 3202 comprises at least a first front region generally indicated at 3233 that extends from the nasal aperture edge 3222 to an intermediate peripheral boundary 3235 located on the side wall portion 3226 and a second rear region 3234 that extends from the intermediate peripheral transition boundary 3235 to the connecting edge 3227 on the outer side of the seal.

The front region 3233 includes the contacting surface 3220 and at least a portion of the side wall portion 3226 of the nasal seal adjacently contact surface 3220. The rear region 3234 comprises the remainder of the side wall portion 3226 extending back from the transition boundary 3235 to the connecting edge 3227.

Referring to FIG. 107, the front region 3233 of the nasal seal comprising the contact surface is thinner or of reduced thickness on average relative to the rear region 3234 of the nasal seal. The nasal seal further comprises an additional third thickness region 3236 within the front region 3233. In particular, the front region 3233 transitions into a thinner edge region 3236 adjacent the nasal aperture edge 3222. The edge region 3236 is thinner than the remaining portion of the front region 3233. The edge region 3236 is a minor portion of the front region 3233.

The described thickness profile provides the nasal seal 3202 with stability and enhances the sealing engagement with the user's nose. In particular, the thicker rear region 3234 provides stability to the overall nasal seal shape, while the reduced thickness of the front region 3233 comprising the contacting surface 3220 encourages conformity of the nasal seal with the user's nose. Furthermore, the edge region 3236 about the periphery of the nasal aperture edge 3222 is the thinnest part of the contacting surface 3220 and provides increased user comfort and sealing conformity. It will be appreciated that the thicknesses of the rear region 3234, front region 3233 and edge region 3236 may be uniform within the respective regions or may have varying thicknesses within the regions. For example, the rear region 3234 gradually reduces in thickness from the contacting edge 3227 to the intermediate transition boundary 3235. The front region 3233 is of substantially uniform thickness in the majority portion and the minor thinned edge portion 3236, with the edge portion 3236 having a uniform thicknesses reduced relative to the majority of the front region. The majority portion of the front region 3233 transitions gradually to the thinner edge region 3236 as shown at the body transition zone 3237 in FIG. 107. As shown in FIG. 107, the face-contacting surface 3220 of the nasal seal forms a flange that curls or extends inward from the side wall portion 3226 of the nasal seal, the flange including the thinned edge portion 3236.

The under-nose support 3224 of the nasal seal 3202 is in the form of a nasal sling or hammock that at least extends or is suspended laterally across a central portion of the nasal seal within the mask cavity. The under-nose support 3224 is configured to contact at least a portion of the under-nose surface of the user's nose so is to counteract any resultant lift force created when the nasal mask is worn and in use with pressurised gases flowing as previously discussed.

The under-nose support 3224 is entirely defined or enclosed within the outer envelope of the nasal seal, i.e. it does not protrude or extend beyond the connecting edge 3227 on the outer side of the nasal seal that connects to the seal housing or the contacting surface edge 3222 of the nasal aperture 3206. However, it will be appreciated that at least a portion of the under-nose support 3224 may protrude beyond the housing aperture defined by the connecting edge 3227 in alternative examples.

The under-nose support 3224 is suspended laterally across a central region of the nasal seal 3202 between left and right sides of the nasal seal. As shown, the under-nose support is disposed or located behind or rearward of the nasal aperture or opening 3206 on the face-contacting side of the nasal seal. The under-nose support 3224 is fixedly connected to the nasal seal in that it is not removable in this embodiment. In one form, the under-nose support is integrally moulded within the nasal seal. In alternative forms, the under-nose support part or portion of the nasal seal may be formed separately and then fixedly coupled within the nasal seal via adhesive or welding or the like, or it could be connected to the seal housing.

The under-nose support configuration 3224 comprises an elongate main lateral portion or band 3229 that extends laterally across at least a portion of the nasal seal and within the nasal seal. With reference to FIGS. 98-99, and 105-107, and 108, the main lateral portion 3229 of the under-nose support 3224 is suspended or connected at each opposite end to a respective upper connection point 3231 located on the upper internal surface of the nasal seal on opposite sides of the seal relative to the apex region of the nasal aperture 3206. The distal ends of the main lateral portion 3229 of the under-nose support 3224 are connected to the inner surface of the nasal seal via respective reinforcing portions or regions, for example in the form of ribs 3241. The ribs 3241 extend in a substantially vertical orientation from the upper lateral positions within the nasal seal inner surface and extend into or connect to a respective distal end of the main lateral portion 3229 at connection locations 3231. The ribs 3241 are integrally moulded with the main lateral portion 3229 of the under-nose support 3224. It will also be appreciated that the ribs 3241 at the ends of the main lateral portion 3229 can be considered to be part of the under-nose support and main lateral portion 3229. In other words, the reinforcing portions or regions 3241 may be considered as extension portions of the main lateral portion, or simply end portions of the main lateral portions. Alternatively, the reinforcing portions or regions may be considered to be separate components or formations that are connected or integrally formed with the ends of the main lateral portions. The functionality and effect of the reinforcing portions or ribs 3241 remains substantially the same under either interpretation.

Figure 106:
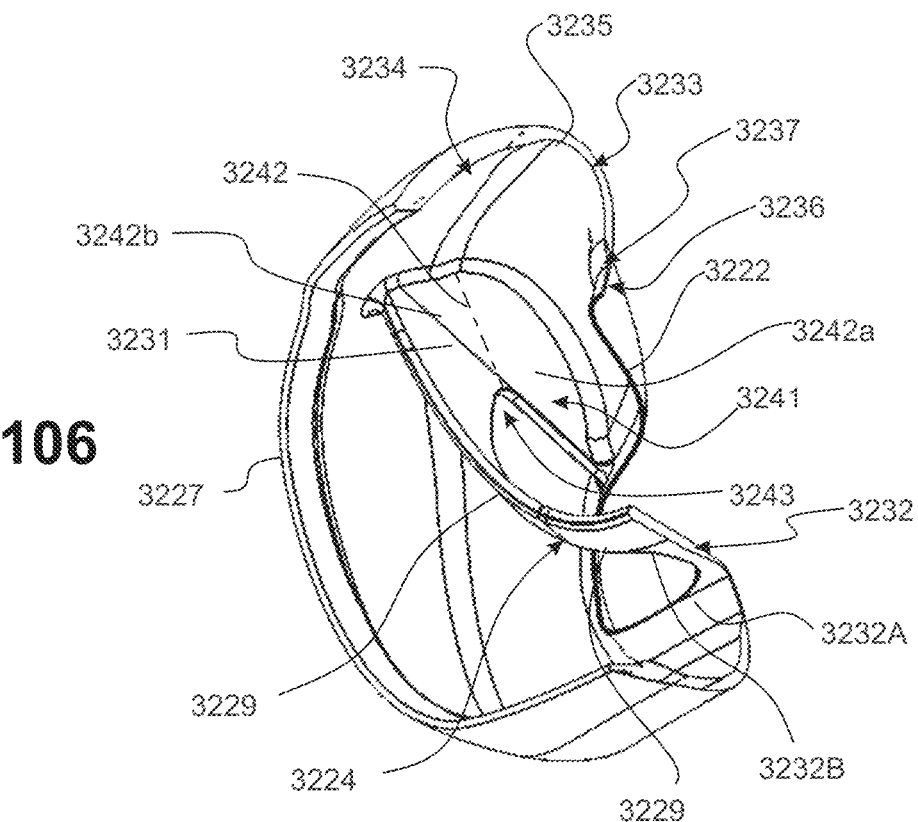

Referring to FIG. 106, the rib 3241 is at a portion of its peripheral edge coupled to or extends from a region of the inner surface of the nasal seal comprising a portion of the rear region 3234 and front region 3233. The ribs extend across a portion of the rear region 3234 and the majority of the front region 3233 comprising the contact surface, but excluding the thinned edge region 3236 adjacent the nasal aperture. However, it will be appreciated that in alternative examples the ribs 3241 may also extend from or contact or extend into at least a portion of the thinned edge region 3236. The main lateral portion 3229 of the under-nose support connects to each respective rib 3241 at a portion of the rib that extends or is coincident with the thicker rear region 3234 of the nasal seal wall. The ribs 3241 provide the main lateral portion 3229 of the under-nose support 3224 with a solid connection within the nasal seal and also provide the dual function of structural support to the nasal seal by increasing the rigidity in that area or region of the nasal seal that contacts the patient on either side of the nose. In particular, the ribs 3241 flank or are located either side of the upper valley region 3245 of the contacting surface 3220 (see FIG. 103) associated with the nasal bridge region of the contacting surface 3220. In particular the ribs or panels 3241 preventing the nasal seal from collapsing under excessive compression force while also allowing for a secure connection between the under-nose support and the inside surface of the nasal seal.

In some forms, the ribs may also function, either directly or indirectly, to give feedback to the user when the mask is overtightened. As described further below, the buckling of the ribs may be configured to deform or change the shape of the under-nose support to squeeze upon the user's nose, and/or to cause portions of the contacting surface adjacent or associated with the ribs to progressively press tighter into the side of the nose under increased compression of the nasal seal, e.g. due to tightening of the headgear. In other words, buckling of the ribs initially provides an increased/improved seal with the interface and minimizes leakages in that portion but, as the headgear is tightened past its intended limit, the buckling ribs provide further squeezing providing feedback indicating the headgear is too tight.

Referring to FIG. 106, a recessed region or zone 3243 is provided or formed between the front portion 3242*a* of the rib 3241 and the rear portion 3242*b* that connects to the main lateral portion 3229 of the under-nose support 3224. This recessed region 3243 creates a buckling zone or axis 3242 in each rib 3241. The buckling axis 3242 extends from between toward the thickness region transition boundary 3235 and the apex of the recessed region 3243.

In some configurations, the buckling axis 3242 enables the rib 3241 to buckle outwardly toward its adjacent inner surface of its associated lateral wall of the nasal seal in use when the nasal seal is compressed in its depth dimension when worn by a user. This buckling of the ribs allows the front regions 3242*a* of the ribs 3241 to bend or compress inwardly toward the user's nose to enhance the seal created in use, and may also lift the under-nose support into the under-nose surface of the user.

In other configurations, the buckling axis 3242 enables the ribs 3241 to buckle inwardly toward each other in use when the nasal seal is compressed in its depth dimension when worn by a user. This inwards buckling of the ribs causes the under-nose support 3224 to tighten or close-up at least in a lateral width direction and this acts to cause the under-nose support squeeze on or tighten onto the surface of the user's nose. In other words, the inwards buckling of the ribs causes the contact surfaces of the lateral regions of the main lateral portion of the under-nose support to move toward each other to effectively narrow or tighten the U-shape of the under-nose support so as to squeeze upon the user's nose.

The recessed region 3243 can also be a region or zone of the rib 3241 that has reduced depth (i.e. distance of the free peripheral edge of the rib from the edge of the rib connected to the inner surface of the seal) or surface area relative to other portions of the rib.

Referring to FIG. 99, the upper connecting locations 3231 of the under-nose support are located in bound of the lateral extremities or sides of the nasal seal. In particular, the vertical connecting ribs 3241 and connection points 3231 are offset relative to the outer lateral width of the nasal seal on their respective sides. The distance between the connection locations 3231 is generally equal to or less than the outermost width of the nasal aperture indicated at 3242A in FIGS. 98 and 99. In particular, the connection points 3231 of the main lateral portion 3229 of the under-nose support are located within the same width zone as the nasal aperture 3206 in the context of the nasal seal. The connecting ribs 3241 extend from the contacting surface 3220 in the upper lateral cheek regions 3223 of the contacting surface at a location that engages with the cheek and/or outer nose or lateral nose surface of a user relative to their nasal bridge.

Figure 108:
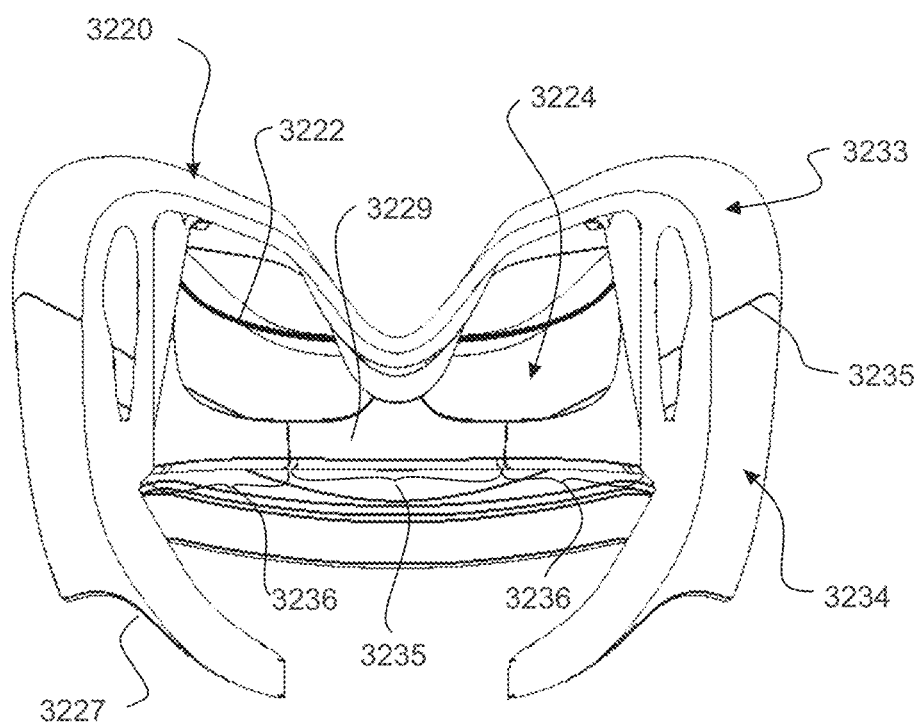

Referring to FIG. 108, the main lateral portion 3229 of the under-nose support 3224 is arranged to extend laterally across the nasal seal 3202 at a depth that is approximately midway or in the centre of the overall depth profile of the nasal seal in the dimension extending from the contacting surface 3220 to the outermost portion of the connecting edge 3227 on the outer side of the nasal seal. However, in alternative forms the main lateral portion may be arranged to extend laterally across the nasal seal at other depths, whether closer or further from the contacting surface, and may also have portions that extend or protrude beyond the outer side connecting edge 3227 or main envelope of the nasal seal.

The under-nose support 3224 also comprises a third connection to nasal seal in addition to the two upper lateral connections 3231. The under-nose support is connected to a central lower or bottom portion of the nasal seal as indicated at 3232. The lower central connection of the under-nose support 3224 is in the form of a central extension or connecting portion 3232 that extends centrally from the main lateral portion 3229 and is coupled or connected to or at the nasal aperture edge 3222 of the contacting surface 3220 in the upper lip region 3221 of the nasal seal. The central connecting portion 3232 has an approximately hour glass width profile. In particular, the width dimension of the central connecting portion 3232 at both the nasal aperture edge 3222 and the interface with the main lateral band 3229 is larger than a width dimension of the central connecting portion 3232 in a middle or intermediate region. For example, the central connecting portion 3232 is an elongate portion that extends from a first end 3232A that is coupled or integrally formed with the nasal aperture edge 3222 of the contacting surface 3220 to a second end 3232B that is coupled or integrally formed to the main lateral band 3229 of the under-nose support 3224 (see FIGS. 99, 100 and 105). The width dimension of the central connecting portion 3232 progressively reduces from each of its ends 3232A, 3232B toward a central or middle region of reduced width to provide an approximately hourglass width dimension profile.

Referring to FIGS. 106 and 107, the central connecting portion 3232 of the under-nose support comprises a varying thickness profile in the direction transverse to the contacting surface of the connection portion 3232. The thickness of the central connecting portion 3232 tapes or reduces in width from its second end 3232B at the main lateral portion 3229 to its first end 3232A at the nasal aperture edge 3222. For example, the thickness of the central connecting portion 3232 at the second end 3232B is substantially equal or uniform with the thickness of the main lateral portion or band 3229 in that region, and the thickness tapers or reduces either from the second end 3232B or at a point in the middle region of the connecting portion 3232 to a reduced thickness at the first end 3232A at the nasal aperture edge 3222. The reduced thickness at the first end 3232A is substantially equal to or uniform with the thickness of the nasal aperture edge 3222 of the contacting surface. For example, the thickness of the central connecting portion 3232 at its first end 3232A may be substantially equal to the thickness of the thinned edge region 3236 of the contacting surface 3220 of the nasal seal.

Figure 105:
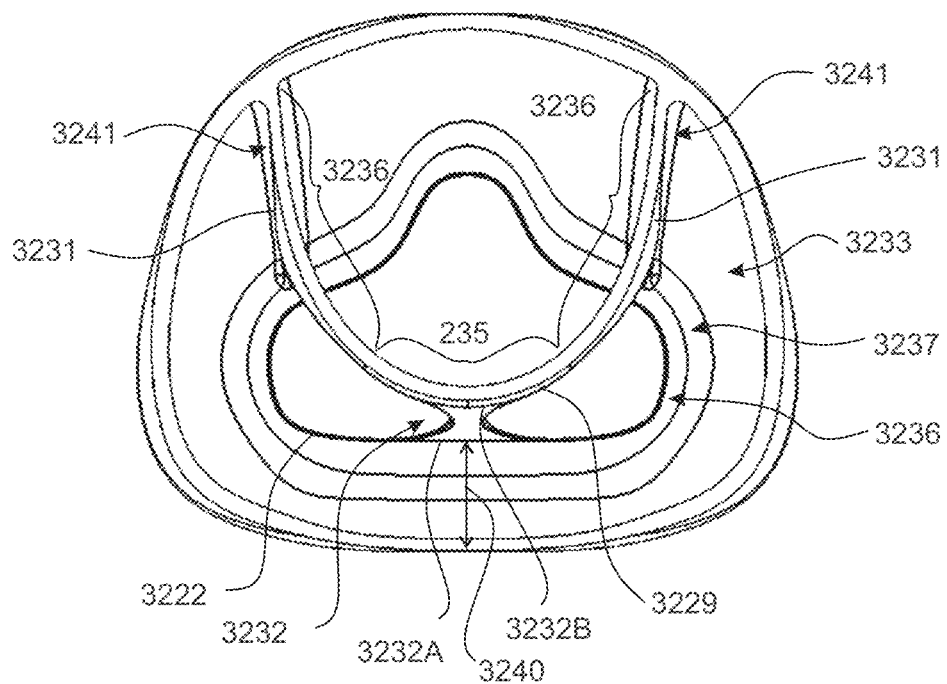

Referring to FIGS. 98-99 and 105 in particular, the under-nose support 3224 is configured with a curved profile across the lateral width of the under-nose support between the upper lateral connections 3231. The curvature profile may vary across the lateral width of the under-nose support in some forms, but alternatively it may have a uniform curvature. As shown, the curvature profile varies. The contacting surface of the main lateral portion 3229 of the under-nose support 3224 has a steeper curved profile in a middle or central region 3235 relative to a flatter curved profile in the remaining lateral or outer regions 3236 that extend to the upper lateral connections 3231. For example, in the central region indicated at 3235 the main lateral portion 3229 is provided with a first radius of curvature that is substantially uniform in the central region 3235. The radius of curvature of the remaining lateral regions 3236 on either side of the central region 3235 may be constant or varying, but generally has a radius of curvature that is larger than the first radius of curvature of the central region 3235 such that it is generally of flatter curvature. The main lateral portion 3229 is or comprises a curved contact surface profile across its entire lateral width without any flat regions.

The width of the contacting surface of the main lateral portion 3229 of the under-nose support 3224 may vary along its length between the opposing sides of the nasal seal. The main lateral portion 3229 comprises a substantially uniform width indicated at 3238 in the central region 3235, with the width then progressively increasing in the outer lateral regions 3236 toward the connection points 3231.

Referring to FIG. 107, a central seal axis AG is defined as extending tangentially between the outermost upper and lower contact points of the central region of the contacting surface 3220 when the nasal seal is in a relaxed condition (e.g. not in use). As shown in FIG. 107, at least a portion of the contact surface of the under-nose support in a central region is indicated by axis AH extends at an angle defined or indicated at 3239 relative to the seal axis AG such that the contact surface of the under-nose support is not parallel or aligned with the seal axis AG. The contact surface in the central region of the under-nose support 3224 is oriented at an angle offset from the seal axis AG in a range of approximately 40°. to approximately 80°, more preferably approximately 45° to approximately 75°, even more preferably approximately 50° to approximately 70°, even more preferably approximately 55° to approximately 65°. As shown, at least a portion of the central connecting portion 3232 also has a corresponding or aligned angular offset.

As explained above, the under-nose support 3224 is fixedly connected or otherwise an integral component of the nasal seal 3202. The drawings depict the nasal seal 3202 and its under-nose support 3224 in a rest state, i.e. un-used. Like the contacting surface 3220 of the nasal seal, the under-nose support 3224 is also configured to be soft and flexible or pliable such that its shape and position may conform in a sling or hammock like manner to the under-nose surface of the user's nose when the nasal mask interface is secured to the user's face or is otherwise worn. The under-nose support is non-stretchable in any direction, although it may have a degree of stretching in same directions in alternative forms.

The main lateral portion 3229 or band of the under-nose support 3224 is generally U-shaped with some curvature across the lateral width of the under-nose support. In alternative forms, the under-nose support may have flat sections or portions, or generally more rectangular or squarish in shape. For example, referring to FIG. 112, the under-nose support indicated at 3224A may have a substantially flat central horizontal portion 3229A, and two substantially vertical or upright portions 3229B extending upwardly from a respective end of the central horizontal portion 3229A and each connecting at connecting points 3229C to an inner surface on each upper later side of the nasal seal either directly or via a rib as with the previous examples.

The ratio of the overall height to overall lateral width of the nasal seal 3202 is in the range of approximately 1:1 to approximately 1:1.4, and in this example embodiment approximately 1:1.2. The ratio of the overall height to overall lateral width to overall depth of the nasal seal is in the range of approximately 1:1:0.6 to approximately 1:1.4:1, and in this example approximately 1:1.2:0.8.

By way of example, the main dimensions of aspects of one nasal seal configuration will be described to provide a sense of scale. Referring to FIG. 98, the height of the nasal aperture defined by contacting surface edge 3222 indicated in the central region at 3242B is in the range of approximately 8 mm to approximately 43 mm, preferably approximately 23 mm and the outermost width of the nasal aperture indicated at 3242A is in the range of approximately 24 mm to approximately 49 mm, preferably approximately 34 mm. The overall height of the nasal seal as indicated at 3242D is in the range of approximately 22 mm to approximately 72 mm, preferably approximately 47 mm, and the overall width as indicated at 3242C is in the range of approximately 47 mm to approximately 87 mm, preferably approximately 57 mm. The width of the central connecting portion 3232 in the reduced width middle region is in the range of approximately 2 mm to approximately 15 mm, preferably approximately 3 mm as indicated at 3242E. Referring to FIG. 103, the overall depth of the nasal seal indicated at 3243A is in the range of approximately 29 mm to approximately 49 mm, preferably approximately 39 mm. The depth of the nasal seal between the lateral contacting surface and lateral edge of the housing aperture as indicated at 3243B is in the range of approximately 21 mm to approximately 36 mm, preferably approximately 31 mm. The depth of the nasal seal between the central nasal bridge valley 3245 of the contacting surface 3220 and the corresponding central housing aperture edge 3227 is in the range of approximately 18 mm to approximately 33 mm, preferably approximately 28 mm. The lateral width of the nasal seal between the outer lateral points of the connecting edge 3227 at the outer side of the nasal seal is in the range of approximately 40 mm to approximately 50 mm, preferably approximately 49 mm. Referring to FIG. 105, the height of the nasal seal between the bottom edge 3222 of the nasal aperture 3206 and the bottom surface of the nasal seal 3202 is in the range of approximately 5 mm to approximately 20 mm.

Referring to FIG. 109, the thickness of the main lateral portion 3229 of the under-nose support 3224 in a direction transverse to the contacting surface of the main lateral portion as indicated at 3244A is in the range of approximately 0.2 mm to approximately 3 mm, preferably approximately 1.1 mm. The central connecting portion 3232 extending from the centre of the main lateral portion 3229 starts with a similar thickness and then transitions to a thinner thickness as shown as it connects to the nasal aperture edge 3222 of the contacting surface 3220. In this example embodiment, the thickness in the edge region 3236 of the contacting surface is approximately 0.2 mm.

The dimensions of various aspects of the nasal seal may be varied to provide for different sized patients. The nasal seal and interface may be provided in a number of different sizes such as small, medium and large, or a larger number of size categories. The nasal seal may be provided in two sizes, such as a small-medium size and a medium-large size. By way of example, dimensional aspects of a small-medium nasal seal compared to a medium-large nasal seal will be provided by way of example, with reference to FIGS. 110-118. Referring to FIGS. 110 and 111, the radius of curvature R of a central region 3235 of the main lateral band 3229 of the under-nose support is in the range of approximately 8 mm to approximately 18 mm, preferably for a small-medium nasal seal is approximately 12.5 mm, and for a medium-large size nasal seal the central region 3235 is longer and comprises a substantially constant larger radius of curvature of approximately 14 mm. Referring to FIGS. 113 and 114, the width of the central connecting portion 3232 in the middle thin region is approximately 2.9 mm for a small-medium size configuration and approximately 4.12 mm for a medium-large size configuration. Referring to FIGS. 115 and 116, the angular offset indicated at 3239 between the axis AH of the central region of the main lateral portion 3229 and the seal tangential axis AG is approximately 64° for a small-medium size configuration and approximately 58° for a medium-large configuration. Referring to FIGS. 117 and 118, the nasal bridge region of the contacting surface of the nasal seal comprises a recessed valley portion 3245 as previously described. In this example, the depth of the valley region 3245 as indicated at 3245B is approximately 7 mm for both the small-medium and medium-large size configurations. The width of the valley region as indicated at 3245A is in the range of approximately 7 mm to approximately 17 mm, preferably approximately 13.8 mm for the small-medium size configuration, and approximately 14.1 mm for the medium-large configuration.

As described, the nasal seal is generally dimensionally and/or configured so as to have a generally rectangular shape when viewed from the outer side as shown in FIG. 99 and from the front or face-contacting side as shown in FIG. 98.

FIGS. 119 to 128 describe a further embodiment of respiratory mask system adapted from earlier examples described above. However, features from the earlier examples can be combined into new combinations with the present embodiment or, indeed, there may be combinations between past examples as already described.

FIG. 119 illustrates an overview, featuring a mask assembly 4100 for the delivery of respiratory therapy to a patient. The assembly includes a mask interface 4102 such as a seal module 4104 and frame assembly 4106, and a headgear assembly 4200. In use, the seal or cushion 4123 seals around a user's nose and/or mouth or inside the user's nares in use. The frame 4106 supports the seal module 4104 and effectively couples the seal 4123 to the headgear 4200 and/or a gas delivery conduit 4110. The seal module 4104 can be removably coupled to the frame 4106 in use, by a yoke 4202. The seal has an undernose sling and is of a similar form to the seal illustrated and described with respect FIGS. 88-118.

Connection features between the yoke 4202 and frame 4106, further supporting/connecting to the seal 4104, are analogous with features discussed in relation to any of the earlier examples, alone or in various combinations. Furthermore, the headgear 4200 preferentially includes adjustment features as outlined above with reference to at least FIGS. 11 to 15, 28 and 74 to 83. As previously described, the side strap of the headgear may employ an elastic portion, such as an elastic braid 4302 to act as a retraction means or biasing element to retract the headgear or cause the headgear to reduce in length after being stretched in combination with an inelastic filament 4300 and a washer configuration as has been detailed above. A clip arrangement 4122 (FIGS. 128A and 128B) removably connects the seal module 4104 to the frame 4106 in an analogous way that previously described, e.g. with reference to earlier examples.

A distinction with earlier examples is the use of a curved support beam or linking member 4444 within the braid of side strap 4302 to direct forces on the headgear and move the straps away from the patient's eyes. By way of example, curved support beam 4444 is substituted for a straight support beam 210 as shown by FIG. 11. The support beam or support beam serves as a core for the braid which is an elastic part of the adjustment mechanism for the headgear.

While the braid serves as an elastic portion, the filament is a non-elastic portion extending therein. A washer configuration or equivalent serves as a restriction mechanism. The curved support beam or support beam, couples to the non-elastic portion and extends along a portion of the headgear. As mentioned, at least part of the support beam is curved along its longitudinal extent. The support beam and elastic portion arrangement preferably form a side strap of the headgear. However, other configurations may be contemplated where the halo portion provides adjustable configurations, such as a restricting mechanism located at the intersection between the side strap and rear halo strap of the headgear.

Referring to FIG. 120, an enlarged perspective view of the seal module 4104, frame 4106, yoke 4202 and side strap 4302 part of the headgear, is shown. Particularly visible is an end cap 4250 of the yoke 4202, analogous to the arrangement illustrated by FIGS. 12 and 28, e.g. where a washer housing 270 is located at each distal end of the yoke 4202 and receives a filament 4220 (FIG. 122) associated with adjustment of the headgear. This mechanism is detailed above with reference to earlier examples.

Also detailed with reference to previous examples is the yoke 4202 which is removably connected to the mask frame 4106, thereby enabling the headgear component 4250 to be separated from the mask frame 4106 and seal module 4104. The seal module 4104 is also demountable from the other side of the mask frame 4106 via a seal clip arrangement, alternatives of which have been previously described above.

The two removable connection aspects allow the assembly to be broken down into three main components, e.g. the mask frame 4106, the seal module 4104 and headgear 4200. Bias vent holes 4445 are visible on the mask frame 4106, proximate the conduit connection.

FIGS. 121 and 122 illustrate side views of the mask and headgear assembly, where FIG. 122 shows a superimposed view of the curved support beam 4444 over braided side strap 4102 (indicating its location within side strap 4102). The support beam is joined with an overmolded connection portion 4207 of the headgear to the headgear strap, the process for which has been described previously by reference to FIGS. 8 to 15.

Also as described previously, the automatic adjustment mechanism and directional locks are configured to resist at least the blow-off force produced by the mask assembly in use and, in some configurations may also resist some amount of hose pull force.

FIG. 122 shows the approximate location of the linking member 4444 within the side strap 4302. In use, the support beam 4444 is positioned inside the strap as a core of the braid and is connected to the headgear strap via overmolding at one end 4447. The small hole 4446 at end 4447 assists positioning of the curved support beam in the mold assembly. A lower end 4458 of the support beam is connected to the headgear adjustment filament 4220, in some embodiments by overmolding.

The lower end of the support beam 4444 serves as a first portion 4458 configured to extend along a first axis 4501 and connected to the non-elastic portion, e.g. filament 4220. Whereas, the headgear connecting end 4447 serves as a second portion configured to extend along a second axis 4502 and connected to a top and/or rear strap. Preferably the second axis 4502 is substantially parallel to the first axis 4501.

The support beam 4444 includes a transition portion 4459 extending along a curve between the first 4458 and second 4447 portions. The transition portion 4459 extends, when in position on a user's head, downwardly from the second portion 4447. The first portion 4458 preferably extends from the transition portion towards a mask.

As best seen by FIG. 122, the second portion 4447 is connected to the headgear 4200 above a user's ear position. Preferably the second portion 4447 connects to a halo strap that provides top and rear straps.

The support beam is somewhat flexible laterally in use against the contour of a user's face, but holds it curved shape longitudinally in the plane pictured so that, in use, forces are reliably directed between the headgear and seal while also maintaining the side strap away from a user's eyes. In other words, the support beam exhibits greater resistance to buckling in a direction perpendicular to the support beam's length than the non-elastic portion in a direction perpendicular to the non-elastic portion's longitudinal axis.

The support beam 4444 may feature an overall vertical drop of approximately 40 mm, e.g. the distance between the axes of the first and second portions respectively, with a horizontal length of approximately 75 mm. The curved support beam 4444 has a height of approximately 3 mm with a thickness of approximately 0.8 mm. It will be apparent that the curve inverts smoothly from its rear connection end 4447, through the transition 4459, toward the first portion 4458 where it is substantially horizontal, in use. As mentioned the axes of first portion 4458 and second portion 4447 are substantially parallel, although alternative configurations may be contemplated depending on force distribution, such as a second portion that follows an axis of the transition portion 4459 or curves backward.

FIGS. 124A and 124B show a comparison of a straight support beam (e.g. of the type pictured by FIG. 11) compared to the curved support beam 4444 of the present embodiment. Alteration of the headgear force vectors, provided by the embodiment of FIG. 124B, serve to stabilize the patient interface while also aligning the blow-off force with the retention force of the headgear.

Consideration of the internal curve and subsequent shape of the support beam enables seals with different blow-off force vectors to be employed with the headgear as described with reference to previous examples. For example, the seal referred to by FIG. 43 may have a different blow-off force vector as well as differing stability issues, compared to other seal configurations, e.g. as pictured by FIGS. 126 to 128. Modifying the side strap and/or support beam shape allows a common headgear type to be used with multiple seal configurations.

While a currently preferred embodiment has been outlined above, the support beam may have a range of possible dimensions; e.g. a vertical drop between 20 and 60 mm, a horizontal length between 50 and 100 mm, a height between 1 and 15 mm and/or a thickness between 0.5 and 1 mm. Preferably the width of the support beam is substantially constant along its length, e.g. at least at the transition portion 4459. Preferably the thickness of the support beam is substantially constant along its length, e.g. at least at the transition portion 4459.

The curved side strap of FIG. 124B compared to FIG. 124A provides a change in angle affecting the force vectors for the headgear that is suited to a particular nasal seal that relies on an under nose sling/hammock for a substantial part of the vertical support of the seal on a user's face, such as the seal illustrated in FIGS. 88-118. However, a curved member and/or curved side strap configuration can be implemented and configured in combination with any of the examples described herein.

FIGS. 125A to 125C illustrate a user sizing guide. The sizing guide is a peripheral device that can be used by a user or advisor to indicate recommendations of the most appropriate seal module size for a particular person, i.e. assisting in choosing an appropriate seal module of the types illustrated by FIG. 88 onwards. Such user interfaces (i.e. the seal component which contacts the patient's face) have two different measurement points for size selection, namely the breadth (width) of the seal, as well as the hammock (sling) angle which can create a more complex decision regarding the best seal module to choose. The sizing guide as pictured is capable of measuring both aspects simultaneously and simplifies the decision making process.

In use, an upper lip contacting portion 4448, in the form of a silicone guard, is placed against a user's upper lip. The guard 4448 projects from a base portion 4449 that should preferably be maintained in a perpendicular orientation to the user's face. A first (breadth) measurement panel 4450 extends perpendicularly from the base portion 4448, however, it is seated in a flexible holder 4451 that serves as a hinge to collapse and pivot the breadth measurement panel 4450 as it contacts a user's nose as pictured by FIG. 125C.

The breadth of the user's nose is determined by covering measurement markings 4452 etched on to the surface of panel 4450. The recommended measurement is the marking still visible while a user's nose covers the panel 4450. At the same time, a pivot angle of the displaced breadth measurement panel 4450 can be taken by a side panel 4453 serving as a protractor or, more generally can be termed an "angle reader". This angular offset measurement can assist the user or advisor to select particular sling characteristics of the seal, for example a high or low sling while the general width of the seal is determined from the breadth measurement markings 4452.

Accordingly, the size guide device can be said to be comprised of a displaceable upstanding face contact panel, hingedly connected to a base portion at a predetermined distance from a user's face. When in contact with a user's nose, the upstanding panel is displaceable angularly from an upright position. The angular displacement is preferably measured by markings upon a second, fixed, upstanding wall arranged perpendicular to an edge of the displaceable panel. Furthermore, preferably markings, e.g. width markings, upon the displaceable panel can be aligned with a user's nose in order to determine a particular characteristic of dimension. The nose width dimensions could be grouped into small, medium and large categories corresponding to sizes of seal modules. Preferably the sizing device is made partially or wholly from a transparent material, particularly so that displacement of the breadth measurement panel is visible through the protractor wall.

FIGS. 126A and 126B illustrate cutaway views of a seal module with an interfacing clip 4122a (e.g. similar in structure to FIG. 45) and a mask frame 4106. This embodiment details the seal module 4104 in the form of a three piece construction comprised of the seal 4123, with an inner clip rigid member 4122a and outer clip rigid member 4122b connected to each other, e.g. via an interference fit connection, with an annular flange 4123a of the seal 4123 clamped therebetween. Connecting together the inner and outer clips is a one-time operation resulting in a completed seal module 4104. Both members of the clip are relatively rigid materials compared to the soft material of the seal 4123. The members 4122a and 4122b can be of a different density or hardness than the seal. The clip members have secondary benefits including aesthetic improvements as well as added support.

FIG. 127 illustrates a seal 4123 molding intermediate where the sling portion 4129 is located on the outside of the seal during molding. The molding intermediate is an intermediate product that is ultimately formed into a seal construction analogous to that of, for example, FIGS. 88 and 89. In the molding intermediate, the sling is connected by its central extension portion to an edge of the seal with the sling arms remaining free of connection.

To form the molding intermediate into the seal construction the sling arms 4129 can be pulled through the opening from where its edge is connected with the central extension portion 4132. The sling arms are subsequently connected into position, e.g. upon the inner surface of the seal and/or internal features of the seal 4123, by suitable means such as overmolding, adhesive, buttons, clips, magnets, welding or other chemical and/or mechanical processes. By forming the sling 4129 outside of the seal body the resultant construction allows for a multitude of connection points and, thus, the angle of the sling can be selected from a range of available angles, while only needing one tool. FIG. 127 shows a possible connection point 4455 upon the sling arm which, when pulled through the seal opening, can be positioned in one of multiple locations 4456. In other words, the sling characteristics such as angle for nose support can be tailored for a particular size of seal.

The seal 4123 from FIG. 127 can be overmolded on to a seal housing without the need for additional manufacturing steps. By molding the sling externally the tool core is able to be removed by deforming the seal (e.g. of silicone) enough to slide the core out of the main opening. In alternative scenarios where the sling is molded in position, removal of the tool core is complicated which makes overmoulding the seal directly onto a seal housing not viable.

FIGS. 128A and 128B provide detail of a three piece seal module assembly according to an embodiment. The assembly includes a seal 4104, a seal housing 4122 and an overmolded connection 4454. This embodiment provides an overmold geometry to bond the seal cushion 4123 to a rigid substrate (i.e. the housing 4122) by means of mechanical adherence. Particularly, as seen in FIG. 128A, a channel 4457 with multiple openings will be located, in the final form of FIG. 128B, underneath the overmould connection 4454. The channel 4457 will become occupied with overmold material, causing the seal housing 4122 to be permanently attached to the seal 4123.

Because of the unique geometry of a seal requiring an internal sling, i.e. it can be difficult to use traditional overmolding methods to mold the seal straight onto a seal housing as the sling/hammock presents difficulties for removing the seal/housing from the tool. By creating the seal assembly in a multi stage process complications can be mitigated or eliminated. Essentially the seal and seal housing are molded separately, the seal and seal housing are then placed in an overmolded tool and locked into place whereupon a separate overmolded material is then injected into the cavity between the seal and seal housing which permanently joins the two components together.

Although this disclosure has been described in the context of certain embodiments and examples, it will be understood by those skilled in the art that the disclosure extends beyond the specifically disclosed examples to other alternative examples and/or uses and obvious modifications and equivalents thereof. In addition, while several variations have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one example can be used with a different example described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An adjustable headgear for a respiratory mask comprising:
    an elastic portion having a longitudinal axis;
    a non-elastic portion that is relatively inelastic compared to the elastic portion and having a longitudinal axis that is aligned with the longitudinal axis of the elastic portion, wherein the elastic portion is configured to provide a retraction force to the non-elastic portion in a direction of the longitudinal axis of the elastic portion;
    a restriction mechanism configured to provide a force resisting movement of the non-elastic portion when the elastic portion is extended in the direction of the longitudinal axis of the elastic portion;
    a support beam coupled to the non-elastic portion and extending along a portion of the adjustable headgear, wherein the support beam exhibits a resistance to buckling that is greater in a direction perpendicular to a length of the support beam than the non-elastic portion in a direction perpendicular to the longitudinal axis of the non-elastic portion; and
    wherein the resistance to buckling of the support beam is greater in a superior-inferior direction than in a medial-lateral direction in use.

2. The adjustable headgear of claim 1, wherein the elastic portion comprises a tube and the support beam is disposed within the tube.

3. The adjustable headgear of claim 1, wherein the support beam comprises inter-engaging rails.

4. The adjustable headgear of claim 1, wherein the support beam comprises telescoping inner and outer members.

5. The adjustable headgear of claim 1, wherein the elastic portion comprises an elastic braid and the support beam comprises a body disposed within the elastic braid.

6. The adjustable headgear of claim 5, wherein the non-elastic portion extends from the body and partially extends within the elastic braid when the elastic braid is extended in the direction of its longitudinal axis.

7. The adjustable headgear of claim 5, wherein the body is tapered.

8. The adjustable headgear of claim 7, wherein an end of the body coupled to the non-elastic portion is narrower than an opposite end of the body.

9. An adjustable headgear for a respiratory mask comprising:
an elastic portion configured to provide a retraction force;
a non-elastic filament that is relatively inelastic compared to an elastic portion;
a restriction mechanism configured to provide a force resisting movement of the non-elastic filament when the elastic portion is extended in a direction of a longitudinal axis;
a core disposed within the elastic portion and coupled to the non-elastic filament, the core configured to limit buckling of the non-elastic filament under retraction forces of the elastic portion;
wherein the core exhibits a resistance to buckling that is greater in a direction perpendicular to a length of the core than the non-elastic filament in a direction perpendicular to the longitudinal axis of the non-elastic filament; and
wherein the resistance to buckling of the core is greater in a superior-inferior direction than in a medial-lateral direction in use.

10. The adjustable headgear of claim 9, wherein the elastic portion comprises an elastic braid.

11. The adjustable headgear of claim 9 further comprising a core and a non-elastic filament, wherein the core is relatively more rigid than the non-elastic filament.

12. The adjustable headgear of claim 9 further comprising a core and a non-elastic filament, wherein the core is tapered.

13. The adjustable headgear of claim 12, wherein an end of the core coupled to the non-elastic filament is narrower than an opposite end of the core.

14. An adjustable headgear for a respiratory mask comprising:
an elastic portion having a longitudinal axis and configured to provide a retraction force in a direction of the longitudinal axis of the elastic portion;
a non-elastic component that is relatively inelastic compared to the elastic portion, the non-elastic component having a first portion and a second portion, the second portion being wider than the first portion, wherein the first portion is a filament and the second portion is a body;
a restriction mechanism configured to provide a force resisting movement to the non-elastic component when the elastic portion is extended in the direction of the longitudinal axis of the elastic portion; and
wherein the body exhibits a resistance to buckling that is greater in a superior-inferior direction than in a medial-lateral direction in use.

15. The adjustable headgear of claim 14, wherein the second portion is substantially contained within the elastic portion when the elastic portion is extended in the direction of the longitudinal axis of the elastic portion and the first portion partially moves into the elastic portion when the elastic portion is extended in the direction of the longitudinal axis of the elastic portion.

16. The adjustable headgear of claim 15, wherein the second portion is joined to the first portion by overmolding.

17. The adjustable headgear of claim 14, wherein the second portion is joined to the first portion.

18. The adjustable headgear of claim 14, wherein the first portion and the second portion are a unitary body.

* * * * *